US006261550B1

(12) United States Patent
Osslund

(10) Patent No.: US 6,261,550 B1
(45) Date of Patent: Jul. 17, 2001

(54) G-CSF HYBRID MOLECULES AND PHARMACEUTICAL COMPOSITIONS

(75) Inventor: Timothy David Osslund, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/304,186

(22) Filed: May 3, 1999

Related U.S. Application Data

(63) Continuation of application No. 09/027,508, filed on Feb. 20, 1998, now abandoned, which is a continuation of application No. 08/956,812, filed on Oct. 23, 1997, now abandoned, which is a division of application No. 08/448,716, filed on May 24, 1995, now Pat. No. 5,790,421, which is a division of application No. 08/010,099, filed on Jan. 28, 1993, now Pat. No. 5,581,476.

(51) Int. Cl.$^7$ .................... A61K 38/19; A61K 38/18; C07K 14/535; C07K 14/52; C07K 21/04

(52) U.S. Cl. ................ 424/85.1; 424/192.1; 435/69.1; 435/69.7; 530/351; 530/402; 536/23.1; 536/23.4

(58) Field of Search ................ 424/85.1, 192.1; 435/69.1, 69.7; 530/351, 402; 536/23.1, 23.4

(56) References Cited

U.S. PATENT DOCUMENTS

| | | | |
|---|---|---|---|
| 4,810,643 | 3/1989 | Souza | 435/68 |
| 4,853,871 | 8/1989 | Pantoliano et al. | 364/496 |
| 4,904,584 | 2/1990 | Shaw | 435/69.4 |
| 4,908,773 | 3/1990 | Pantoliano et al. | 364/496 |
| 5,023,802 | 6/1991 | Fujita | 364/496 |
| 5,025,388 | 6/1991 | Cramer, III et al. | 364/496 |
| 5,109,119 | 4/1992 | Reichert et al. | 530/402 |
| 5,157,736 | 10/1992 | Boyer et al. | 382/10 |
| 5,265,030 | 11/1993 | Skolnick et al. | 364/496 |
| 5,307,287 | 4/1994 | Cramer et al. | 364/496 |
| 5,386,507 | 1/1995 | Teig et al. | 395/161 |
| 5,424,963 | 6/1995 | Turner et al. | 364/578 |
| 5,448,498 | 9/1995 | Namiki et al. | 364/496 |
| 5,555,366 | 9/1996 | Teig et al. | 395/161 |
| 5,597,562 | 1/1997 | Nomura et al. | 424/85.1 |
| 5,738,849 | 4/1998 | Bauer et al. | 424/192.1 |
| 5,772,992 | 6/1998 | Bauer et al. | 424/85.5 |
| 5,817,486 | 10/1998 | Bauer et al. | 435/69.52 |
| 5,858,347 | 1/1999 | Bauer et al. | 424/85.2 |
| 5,883,230 | 3/1999 | Schendel | 530/351 |
| 5,997,860 | 12/1999 | Bauer et al. | 424/93 |
| 6,017,523 | 1/2000 | Bauer et al. | 424/85.2 |
| 6,022,535 | 2/2000 | Bauer et al. | 424/85.2 |
| 6,030,812 | 2/2000 | Bauer et al. | 435/69.7 |
| 6,051,217 | 4/2000 | Bauer et al. | 424/85.2 |
| 6,057,133 | 5/2000 | Bauer et al. | 435/69.7 |
| 6,060,047 | 5/2000 | Bauer et al. | 424/85.2 |
| 6,066,318 | 5/2000 | Feng et al. | 424/93.2 |
| 6,074,639 | 6/2000 | Bauer et al. | 424/93.71 |

FOREIGN PATENT DOCUMENTS

| | | |
|---|---|---|
| 76380 | 11/1991 | (AU) . |
| 10948 | 8/1992 | (AU) . |
| 0 243 153 | 10/1987 | (EP) . |
| 0 256 843 | 2/1988 | (EP) . |
| 0 272 703 | 6/1988 | (EP) . |
| 0370205 | 9/1989 | (EP) . |
| 0 335 423 | 10/1989 | (EP) . |
| 0 344 796 | 12/1989 | (EP) . |
| 0 456 200 | 11/1991 | (EP) . |
| 0 459 630 | 12/1991 | (EP) . |
| 2 213 821 | 8/1989 | (GB) . |
| WO 85/00817 | 1/1985 | (WO) . |
| WO 87/01132 | 2/1987 | (WO) . |
| WO 88/01775 | 3/1988 | (WO) . |
| WO 89/05824 | 6/1989 | (WO) . |
| WO 90/12874 | 11/1990 | (WO) . |
| WO 92/04455 | 3/1992 | (WO) . |
| WO 93/25687 | 12/1993 | (WO) . |
| WO 95/21254 | 8/1995 | (WO) . |
| WO 95/27732 | 10/1995 | (WO) . |
| WO 97/12977 | 4/1997 | (WO) . |
| WO 97/12985 | 4/1997 | (WO) . |
| WO 98/17810 | 4/1998 | (WO) . |
| WO 98/18923 | 5/1998 | (WO) . |
| WO 95/21197 | 9/1999 | (WO) . |

OTHER PUBLICATIONS

Creighton, *Proteins, Structures, & Molecular Principles*, WH Freeman & Co. New York 1984, p. 216.
White et al., *Principles of Biochemistry*, vol. 6, McGraw–Hill, Inc. (1978) pp. 156–158.
Dickerson et al., *The Structure and Action of Proteins*, Benjamin/Cummings Publ. Co., California 1969 p. 19.
Abdel–Meguid et al., PNAS–USA 84: 6434 (1987).
Abrahmsen et al., Biochem. 30: 4151–4159 (1991).
Weber et al., Physical principles of protein crystallization. In: Eisenberg (ed.), Advances in Protein Chemistry 41:1–36 (1991).
Bazan, Immunology Today 11: 350–354 (1990).
Carter and Carter, J. Biol. Chem. 254:12219–12223 (1979).
Carter et al., J.Cryst. Growth 90: 60–73(1988).
Cox and Weber, J.Appl. Crystallogr. 20: 366–373 (1987).
Cox and Weber, J. Cryst. Growth 90: 318–324(1988).
Cunningham and Wells, Science 244: 1081–1084 (1989).
Diederichs et al., Science 254: 1779–1782 (1991).

(List continued on next page.)

Primary Examiner—Yvonne Eyler
Assistant Examiner—Nirmal S. Basi
(74) Attorney, Agent, or Firm—Matthew W. Knight; Ron K. Levy; Steven M. Odre

(57) ABSTRACT

The present invention relates to granulocyte colony-stimulating factor ("G-CSF") analogs and compositions containing such analogs which retain the three-dimensional structure of the internal core of the four alpha helical bundle of G-CSF. In another aspect, such G-CSF analogs can also be attached with biologically active proteins to form hybrid molecules and still retain G-CSF structural integrity. Also provided are methods for determining and preparing analog or hybrid molecules and modifications.

25 Claims, 55 Drawing Sheets

OTHER PUBLICATIONS

Francis, Focus on Growth Factors 3: 4–10 (May 1992)(published by Mediscript, Mountview Court, Friern Barnet Lane, London N20 OLD, UK).
Gabrilove, J. Seminars in Hematology 26: (2) 1–14 (1989).
Hill et al., Proceedings of the National Acad. of Sciences of USA, 90: 5167–5171 (1993).
Hill, et al., PNAS 90: 5167–71 (1993).
Huse et al., Science 246:1275 (1989).
Ishikawa et al., Cell Structure and Function, 17: 61–65 (1992).
Jancarik and Kim, J. Appl. Crystallogr. 24: 409 (1991).
Jones et al., Bailliere's Clinical Hematology 2 (1): 83–111 (1989).
Karplus, Protein Engineering, p. 35–44 (1987).
Kuga et al., Biochem. Biophy. Res. Comm 159: 103–111 (1989).
Layton et al., J.B.C. 266: 23815–23823 (1991).
Layton et al., J. of Cell. Biochem. Suppl. 17B: 78 (1993).
Layton, et al. JBC 266(35) 23815–23 (1991).
Li, et al., JBC 268(30) 22377–84 (1993).
Lieshke and Burgess, N.Engl.J.Med. 327: 28–34 and 99–106 (1992).
Lonejay, et al., J.Mol.Biol.234: 640–53 (1993).
Lu et al., Arch. Biochem. Biophys. 268: 81–92 (1989).
McKay Science 257: 1673–1677 (1992).
Moore et al., PNAS–USA 84: 7134–7138 (1987).
Nagata et al., EMBO J 5: 575–581 (1986).
Najahara, et al., J.Mol.Biol. 214: 25–26 (1990).
Nicola, Annu. Rev. Biochem. 58: 45–77 (1989).
Nicola, et al., Blood 54: 614–27 (1979).
Olson et al., Pour La Science, 183: 76–82 (1993).
Osslund et al., Dissertation Abstracts International B., 54: 1239 (1993).
Pandit et al., Science, 258: 1358–1362 (1992).
Parry et al., J. Molecular Recognition 8: 107–110 (1988).
Powers et al., Science 256: 1673–1677 (1992).
Rastetter, Trends in Biotechnology, 1(3) 80–84 (1983).
Remington's Pharmaceutical Sciences, 18th Ed. (1990, Mack Publishing Co., Easton, Pennsylvania 18042) pp. 1435–1712.
Senda et al., EMBO J. 11: 3193–3201 (1992).
Smith et al., J. Mol. Biol. 224: 899–904 (1992).
Souza et al., Science 232: 61–65 (1986).
Stryer, Biochemistry, 3d Ed., W.H. Freeman and Company, N.Y. 1988, inside back cover).
Vos et al., Science 255: 305–312 (1992).
Weber, J.Appl.Crystallogr. 20: 366–373 (1987).
Welte et al., PNAS–USA 82: 1526–1530 (1985).
McWherter et al. Circular Permutation of the Granulocyte Colony–Stimulating Factor Receptor Agonist Domain of Myelopoietin, Biochemistry, 38(14): 4564–4571 (1999).
Feng et al., Circular Permutation of Granulocyte Colony-Stimulating Factor, Biochemistry, 38(14): 4553–4563 (1999).

FIG. 1

```
                                      Met Thr Pro Leu Gly Pro Ala
TCTAGAAAAAAACCAAGGAGGTAATAAATA ATG ACT CCA TTA GGT CCT GCT

Ser Ser Leu Pro Gln Ser Phe Leu Leu Lys Cys Leu Glu Gln
TCT TCT CTG CCG CAA AGC TTT CTG CTG AAA TGT CTG GAA CAG

Val Arg Lys Ile Gln Gly Asp Gly Ala Ala Leu Gln Glu Lys Leu
GTT CGT AAA ATC CAG GGT GAC GGT GCT GCA CTG CAA GAA AAA CTG

Cys Ala Thr Tyr Lys Leu Cys His Pro Glu Glu Leu Val Leu Leu
TGC GCT ACT TAC AAA CTG TGC CAT CCG GAA GAG CTG GTA CTG CTG

Gly His Ser Leu Gly Ile Pro Trp Ala Pro Leu Ser Ser Cys Pro
GGT CAT TCT CTT GGG ATC CCG TGG GCT CCG CTG TCT TCT TGT CCA

Ser Gln Ala Leu Gln Leu Ala Gly Cys Leu Ser Gln Leu His Ser
TCT CAA GCT CTT CAG CTG GCT GGT TGT CTG TCT CAA CTG CAT TCT

Gly Leu Phe Leu Tyr Gln Gly Leu Leu Gln Ala Leu Glu Gly Ile
GGT CTG TTC CTG TAT CAG GGT CTT CTG CAA GCT CTG GAA GGT ATC

Ser Pro Glu Leu Gly Pro Thr Leu Asp Thr Leu Gln Leu Asp Val
TCT CCG GAA CTG GGT CCG ACT CTG GAC ACT CTG CAG CTA GAT GTA

Ala Asp Phe Ala Thr Thr Ile Trp Gln Gln Met Glu Glu Leu Gly
GCT GAC TTT GCT ACT ACT ATT TGG CAA CAG ATG GAA GAG CTC GGT

Met Ala Pro Ala Leu Gln Pro Thr Gln Gly Ala Met Pro Ala Phe
ATG GCA CCA GCT CTG CAA CCG ACT CAA GGT GCT ATG CCG GCA TTC

Ala Ser Ala Phe Gln Arg Arg Ala Gly Gly Val Leu Val Ala Ser
GCT TCT GCA TTC CAG CGT CGT GCA GGA GGT GTA CTG GTT GCT TCT

His Leu Gln Ser Phe Leu Glu Val Ser Tyr Arg Val Leu Arg His
CAT CTG CAA TCT TTC CTG GAA GTA TCT TAC CGT GTT CTG CGT CAT

Leu Ala Gln Pro OC  AM
CTG GCT CAG CCG TAA TAG AATTC
``` rhG-CSF hGH

IL-2

IL-4

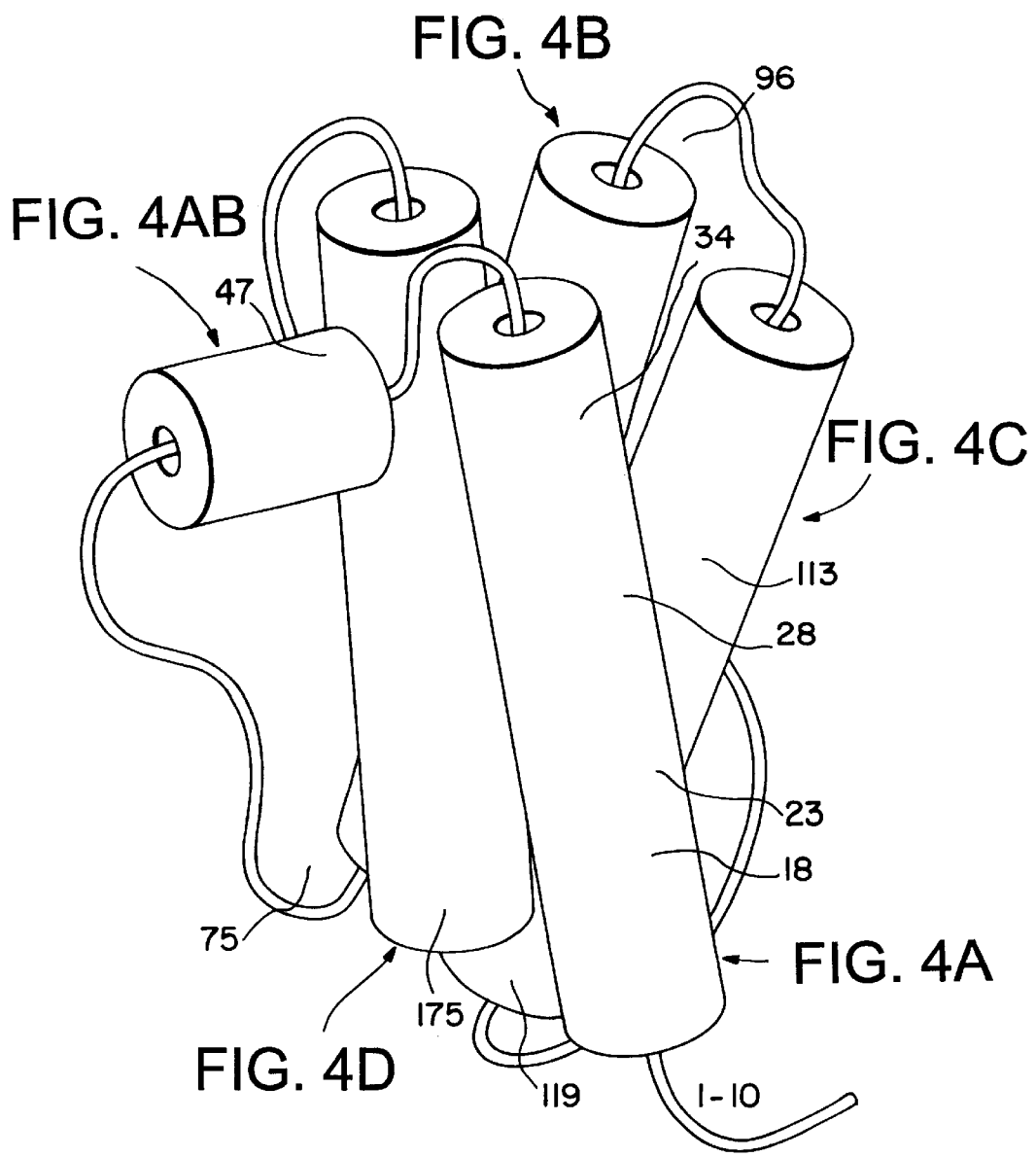

FIG. 5A

```
ATOM   1 CB   LEU  10   58.751 58.191 -14.868 1.00 61.22 A1
ATOM   2 CG   LEU  10   58.360 59.271 -13.939 1.00 60.19 A1
ATOM   3 CD1  LEU  10   59.307 60.461 -14.022 1.00 60.14 A1
ATOM   4 CD2  LEU  10   56.954 59.658 -14.335 1.00 60.68 A1
ATOM   5 C    LEU  10   60.544 56.734 -13.849 1.00 62.85 A1
ATOM   6 O    LEU  10   60.079 55.595 -14.041 1.00 63.08 A1
ATOM   7 HT1  LEU  10   59.876 56.135 -15.998 1.00  0.00 A1
ATOM   8 HT2  LEU  10   61.323 56.887 -16.434 1.00  0.00 A1
ATOM   9 N    LEU  10   60.328 57.059 -16.204 1.00 62.24 A1
ATOM  10 HT3  LEU  10   59.817 57.535 -16.971 1.00  0.00 A1
ATOM  11 CA   LEU  10   60.183 57.758 -14.941 1.00 62.58 A1
ATOM  12 N    PRO  11   61.357 56.962 -12.780 1.00 61.96 A1
ATOM  13 CD   PRO  11   61.960 58.238 -12.383 1.00 61.21 A1
ATOM  14 CA   PRO  11   61.832 55.889 -11.906 1.00 61.34 A1
ATOM  15 CB   PRO  11   62.915 56.547 -11.043 1.00 59.77 A1
ATOM  16 CG   PRO  11   62.511 57.983 -10.975 1.00 59.16 A1
ATOM  17 C    PRO  11   60.712 55.225 -11.109 1.00 60.68 A1
ATOM  18 O    PRO  11   60.075 55.843 -10.250 1.00 61.73 A1
ATOM  19 N    GLN  12   60.466 53.946 -11.407 1.00 59.31 A1
ATOM  20 H    GLN  12   60.944 53.573 -12.175 1.00  0.00 A1
ATOM  21 CA   GLN  12   59.468 53.121 -10.743 1.00 57.22 A1
ATOM  22 CB   GLN  12   59.779 51.646 -10.970 1.00 59.27 A1
ATOM  23 CG   GLN  12   58.620 50.714 -10.591 1.00 59.70 A1
ATOM  24 CD   GLN  12   57.604 50.575 -11.702 1.00 61.71 A1
ATOM  25 OE1  GLN  12   57.170 49.465 -11.970 1.00 65.82 A1
ATOM  26 NE2  GLN  12   57.227 51.534 -12.541 1.00 63.02 A1
ATOM  27 HE21 GLN  12   57.639 52.419 -12.489 1.00  0.00 A1
ATOM  28 HE22 GLN  12   56.500 51.308 -13.156 1.00  0.00 A1
ATOM  29 C    GLN  12   59.336 53.347  -9.245 1.00 55.34 A1
ATOM  30 O    GLN  12   58.242 53.196  -8.708 1.00 54.56 A1
ATOM  31 N    SER  13   60.423 53.732  -8.576 1.00 53.44 A1
ATOM  32 H    SER  13   61.276 53.839  -9.033 1.00  0.00 A1
ATOM  33 CA   SER  13   60.335 53.974  -7.168 1.00 52.86 A1
ATOM  34 CB   SER  13   61.704 54.144  -6.626 1.00 52.24 A1
ATOM  35 OG   SER  13   61.702 53.493  -5.362 1.00 56.64 A1
ATOM  36 HG   SER  13   61.534 52.551  -5.477 1.00  0.00 A1
ATOM  37 C    SER  13   59.497 55.214  -6.900 1.00 52.58 A1
ATOM  38 O    SER  13   58.509 55.144  -6.160 1.00 53.55 A1
ATOM  39 N    PHE  14   59.791 56.333  -7.577 1.00 50.84 A1
ATOM  40 H    PHE  14   60.469 56.292  -8.279 1.00  0.00 A1
ATOM  41 CA   PHE  14   59.067 57.590  -7.423 1.00 47.21 A1
ATOM  42 CB   PHE  14   59.611 58.590  -8.454 1.00 44.68 A1
ATOM  43 CG   PHE  14   58.618 59.669  -8.866 1.00 42.88 A1
ATOM  44 CD1  PHE  14   58.052 59.594 -10.123 1.00 40.40 A1
ATOM  45 CD2  PHE  14   58.264 60.673  -7.978 1.00 40.30 A1
ATOM  46 CE1  PHE  14   57.114 60.518 -10.507 1.00 39.59 A1
ATOM  47 CE2  PHE  14   57.329 61.587  -8.380 1.00 41.82 A1
ATOM  48 CZ   PHE  14   56.751 61.515  -9.635 1.00 41.56 A1
ATOM  49 C    PHE  14   57.605 57.263  -7.661 1.00 45.83 A1
ATOM  50 O    PHE  14   56.789 57.588  -6.805 1.00 46.07 A1
ATOM  51 N    LEU  15   57.298 56.509  -8.718 1.00 44.64 A1
ATOM  52 H    LEU  15   58.024 56.183  -9.287 1.00  0.00 A1
ATOM  53 CA   LEU  15   55.940 56.181  -9.038 1.00 44.53 A1
ATOM  54 CB   LEU  15   55.858 55.402 -10.300 1.00 48.74 A1
ATOM  55 CG   LEU  15   54.853 56.013 -11.289 1.00 51.65 A1
ATOM  56 CD1  LEU  15   55.525 57.121 -12.105 1.00 50.33 A1
ATOM  57 CD2  LEU  15   54.320 54.906 -12.204 1.00 53.77 A1
ATOM  58 C    LEU  15   55.169 55.410  -8.014 1.00 44.07 A1
ATOM  59 O    LEU  15   53.945 55.567  -7.959 1.00 45.46 A1
ATOM  60 N    LEU  16   55.809 54.620  -7.166 1.00 43.18 A1
ATOM  61 H    LEU  16   56.781 54.503  -7.251 1.00  0.00 A1
ATOM  62 CA   LYS  16   55.110 53.913  -6.095 1.00 42.96 A1
ATOM  63 CB   LEU  16   55.866 52.623  -5.751 1.00 43.34 A1
ATOM  64 CG   LEU  16   55.840 51.608  -6.868 1.00 42.25 A1
ATOM  65 CD1  LEU  16   56.889 50.567  -6.596 1.00 43.68 A1
ATOM  66 CD2  LEU  16   54.413 51.068  -7.030 1.00 42.75 A1
ATOM  67 C    LEU  16   54.963 54.778  -4.852 1.00 42.35 A1
ATOM  68 O    LEU  16   54.077 54.579  -4.018 1.00 42.65 A1
ATOM  69 N    LYS  17   55.823 55.779  -4.703 1.00 42.47 A1
ATOM  70 H    LYS  17   56.587 55.840  -5.320 1.00  0.00 A1
ATOM  71 CA   LYS  17   55.681 56.767  -3.650 1.00 42.07 A1
ATOM  72 CB   LYS  17   56.995 57.554  -3.573 1.00 44.14 A1
ATOM  73 CG   LYS  17   57.214 58.197  -2.223 1.00 49.61 A1
ATOM  74 CD   LYS  17   57.114 57.164  -1.086 1.00 55.15 A1
ATOM  75 CE   LYS  17   56.747 57.804   0.293 1.00 62.05 A1
ATOM  76 NZ   LYS  17   55.462 58.533   0.331 1.00 65.43 A1
ATOM  77 HZ1  LYS  17   54.684 57.884   0.098 1.00  0.00 A1
ATOM  78 HZ2  LYS  17   55.482 59.308  -0.362 1.00  0.00 A1
ATOM  79 HZ3  LYS  17   55.312 58.926   1.282 1.00  0.00 A1
ATOM  80 C    LYS  17   54.463 57.640  -4.051 1.00 41.20 A1
ATOM  81 O    LYS  17   53.648 57.999  -3.186 1.00 40.66 A1
ATOM  82 N    CYS  18   54.272 57.992  -5.346 1.00 39.13 A1
ATOM  83 H    CYS  18   54.998 57.809  -5.981 1.00  0.00 A1
ATOM  84 CA   CYS  18   53.080 58.656  -5.802 1.00 37.42 A1
ATOM  85 CB   CYS  18   53.092 58.891  -7.261 1.00 35.02 A1
```

FIG. 5B

| | | | | | | | | | | | | | | | | |
|---|---|---|---|---|---|---|---|---|---|---|---|---|---|---|---|---|
| ATOM | 86 | SG | CYS | 18 | 54.421 | 60.026 | -7.681 | 1.00 | 40.40 | A1 | ATOM | 129 | H | ARG | 23 | 47.440 56.819 -3.056 1.00 0.00 A1 |
| ATOM | 87 | C | CYS | 18 | 51.859 | 57.789 | -5.502 | 1.00 | 39.33 | A1 | ATOM | 130 | CA | ARG | 23 | 45.667 56.593 -1.892 1.00 20.67 A1 |
| ATOM | 88 | O | CYS | 18 | 50.959 | 58.346 | -4.847 | 1.00 | 40.83 | A1 | ATOM | 131 | CB | ARG | 23 | 46.104 55.135 -1.635 1.00 20.45 A1 |
| ATOM | 89 | N | LEU | 19 | 51.738 | 56.475 | -5.842 | 1.00 | 37.15 | A1 | ATOM | 132 | CG | ARG | 23 | 46.325 54.321 -2.904 1.00 17.51 A1 |
| ATOM | 90 | H | LEU | 19 | 52.462 | 56.038 | -6.341 | 1.00 | 0.00 | A1 | ATOM | 133 | CD | ARG | 23 | 45.095 54.446 -3.769 1.00 21.54 A1 |
| ATOM | 91 | CA | LEU | 19 | 50.521 | 55.702 | -5.534 | 1.00 | 36.00 | A1 | ATOM | 134 | NE | ARG | 23 | 45.076 53.437 -4.809 1.00 24.82 A1 |
| ATOM | 92 | CB | LEU | 19 | 50.644 | 54.204 | -5.947 | 1.00 | 38.31 | A1 | ATOM | 135 | HE | ARG | 23 | 45.642 52.647 -4.701 1.00 0.00 A1 |
| ATOM | 93 | CG | LEU | 19 | 49.410 | 53.271 | -5.657 | 1.00 | 40.86 | A1 | ATOM | 136 | CZ | ARG | 23 | 44.323 53.556 -5.904 1.00 27.69 A1 |
| ATOM | 94 | CD1 | LEU | 19 | 48.208 | 53.684 | -6.467 | 1.00 | 39.71 | A1 | ATOM | 137 | NH1 | ARG | 23 | 43.567 54.669 -6.006 1.00 29.51 A1 |
| ATOM | 95 | CD2 | LEU | 19 | 49.692 | 51.833 | -6.113 | 1.00 | 45.71 | A1 | ATOM | 138 | HH11 | ARG | 23 | 43.562 55.377 -5.303 1.00 0.00 A1 |
| ATOM | 96 | C | LEU | 19 | 50.102 | 55.736 | -4.076 | 1.00 | 33.52 | A1 | ATOM | 139 | HH12 | ARG | 23 | 42.956 54.730 -6.789 1.00 0.00 A1 |
| ATOM | 97 | O | LEU | 19 | 48.930 | 55.949 | -3.766 | 1.00 | 32.75 | A1 | ATOM | 140 | NH2 | ARG | 23 | 44.345 52.604 -6.891 1.00 24.22 A1 |
| ATOM | 98 | N | GLU | 20 | 51.030 | 55.576 | -3.166 | 1.00 | 31.88 | A1 | ATOM | 141 | HH21 | ARG | 23 | 43.780 52.713 -7.709 1.00 0.00 A1 |
| ATOM | 99 | H | GLU | 20 | 51.940 | 55.338 | -3.455 | 1.00 | 0.00 | A1 | ATOM | 142 | HH22 | ARG | 23 | 44.936 51.802 -6.793 1.00 0.00 A1 |
| ATOM | 100 | CA | GLU | 20 | 50.750 | 55.710 | -1.748 | 1.00 | 33.40 | A1 | ATOM | 143 | C | ARG | 23 | 45.458 57.285 -0.560 1.00 20.56 A1 |
| ATOM | 101 | CB | GLU | 20 | 52.053 | 55.334 | -1.167 | 1.00 | 35.25 | A1 | ATOM | 144 | O | ARG | 23 | 44.374 57.254 0.042 1.00 20.04 A1 |
| ATOM | 102 | CG | GLU | 20 | 52.508 | 55.504 | 0.260 | 1.00 | 43.21 | A1 | ATOM | 145 | N | LYS | 24 | 46.485 58.015 -0.118 1.00 22.67 A1 |
| ATOM | 103 | CD | GLU | 20 | 53.948 | 54.947 | 0.407 | 1.00 | 51.06 | A1 | ATOM | 146 | H | LYS | 24 | 47.291 58.105 -0.668 1.00 0.00 A1 |
| ATOM | 104 | OE1 | GLU | 20 | 54.320 | 54.660 | 1.546 | 1.00 | 56.78 | A1 | ATOM | 147 | CA | LYS | 24 | 46.431 58.729 1.166 1.00 22.85 A1 |
| ATOM | 105 | OE2 | GLU | 20 | 54.708 | 54.766 | -0.570 | 1.00 | 51.57 | A1 | ATOM | 148 | CB | LYS | 24 | 47.811 59.255 1.506 1.00 26.86 A1 |
| ATOM | 106 | C | GLU | 20 | 50.230 | 57.117 | -1.326 | 1.00 | 33.25 | A1 | ATOM | 149 | CG | LYS | 24 | 47.821 59.661 2.971 1.00 33.79 A1 |
| ATOM | 107 | O | GLU | 20 | 49.432 | 57.291 | -0.380 | 1.00 | 32.37 | A1 | ATOM | 150 | CD | LYS | 24 | 49.121 60.265 3.404 1.00 40.73 A1 |
| ATOM | 108 | N | GLN | 21 | 50.660 | 58.167 | -2.044 | 1.00 | 32.33 | A1 | ATOM | 151 | CE | LYS | 24 | 50.258 59.258 3.335 1.00 46.19 A1 |
| ATOM | 109 | H | GLN | 21 | 51.270 | 58.004 | -2.794 | 1.00 | 0.00 | A1 | ATOM | 152 | NZ | LYS | 24 | 51.532 59.975 3.333 1.00 51.19 A1 |
| ATOM | 110 | CA | GLN | 21 | 50.275 | 59.538 | -1.742 | 1.00 | 31.00 | A1 | ATOM | 153 | HZ1 | LYS | 24 | 51.637 60.498 4.225 1.00 0.00 A1 |
| ATOM | 111 | CB | GLN | 21 | 51.326 | 60.489 | -2.340 | 1.00 | 32.37 | A1 | ATOM | 154 | HZ2 | LYS | 24 | 51.539 60.651 2.539 1.00 0.00 A1 |
| ATOM | 112 | CG | GLN | 21 | 52.436 | 60.530 | -1.272 | 1.00 | 38.01 | A1 | ATOM | 155 | HZ3 | LYS | 24 | 52.317 59.303 3.216 1.00 0.00 A1 |
| ATOM | 113 | CD | GLN | 21 | 53.622 | 61.460 | -1.504 | 1.00 | 42.67 | A1 | ATOM | 156 | C | LYS | 24 | 45.455 59.893 1.101 1.00 21.66 A1 |
| ATOM | 114 | OE1 | GLN | 21 | 54.008 | 62.236 | -0.615 | 1.00 | 43.63 | A1 | ATOM | 157 | O | LYS | 24 | 44.588 60.068 1.962 1.00 20.90 A1 |
| ATOM | 115 | NE2 | GLN | 21 | 54.256 | 61.448 | -2.678 | 1.00 | 42.31 | A1 | ATOM | 158 | N | ILE | 25 | 45.549 60.696 0.044 1.00 21.66 A1 |
| ATOM | 116 | HE21 | GLN | 21 | 53.965 | 60.840 | -3.384 | 1.00 | 0.00 | A1 | ATOM | 159 | H | ILE | 25 | 46.242 60.509 -0.629 1.00 0.00 A1 |
| ATOM | 117 | HE22 | GLN | 21 | 55.026 | 62.052 | -2.730 | 1.00 | 0.00 | A1 | ATOM | 160 | CA | ILE | 25 | 44.667 61.841 -0.115 1.00 22.53 A1 |
| ATOM | 118 | C | GLN | 21 | 48.894 | 59.765 | -2.288 | 1.00 | 28.51 | A1 | ATOM | 161 | CB | ILE | 25 | 45.075 62.694 -1.307 1.00 22.15 A1 |
| ATOM | 119 | O | GLN | 21 | 48.027 | 60.242 | -1.563 | 1.00 | 28.65 | A1 | ATOM | 162 | CG2 | ILE | 25 | 44.097 63.834 -1.439 1.00 20.44 A1 |
| ATOM | 120 | N | VAL | 22 | 48.682 | 59.319 | -3.521 | 1.00 | 25.85 | A1 | ATOM | 163 | CG1 | ILE | 25 | 46.475 63.230 -1.136 1.00 21.03 A1 |
| ATOM | 121 | H | VAL | 22 | 49.448 | 58.980 | -4.013 | 1.00 | 0.00 | A1 | ATOM | 164 | CD | ILE | 25 | 47.188 63.281 -2.497 1.00 20.03 A1 |
| ATOM | 122 | CA | VAL | 22 | 47.382 | 59.303 | -4.161 | 1.00 | 24.94 | A1 | ATOM | 165 | C | ILE | 25 | 43.263 61.308 -0.352 1.00 24.75 A1 |
| ATOM | 123 | CB | VAL | 22 | 47.508 | 58.614 | -5.526 | 1.00 | 24.09 | A1 | ATOM | 166 | O | ILE | 25 | 42.339 61.839 0.301 1.00 26.13 A1 |
| ATOM | 124 | CG1 | VAL | 22 | 46.154 | 58.378 | -6.096 | 1.00 | 19.97 | A1 | ATOM | 167 | N | GLN | 26 | 43.065 60.289 -1.244 1.00 22.79 A1 |
| ATOM | 125 | CG2 | VAL | 22 | 48.252 | 59.479 | -6.498 | 1.00 | 25.82 | A1 | ATOM | 168 | H | GLN | 26 | 43.842 59.926 -1.726 1.00 0.00 A1 |
| ATOM | 126 | C | VAL | 22 | 46.418 | 58.549 | -3.226 | 1.00 | 25.65 | A1 | ATOM | 169 | CA | GLN | 26 | 41.737 59.713 -1.437 1.00 20.12 A1 |
| ATOM | 127 | O | VAL | 22 | 45.428 | 59.190 | -2.800 | 1.00 | 29.31 | A1 | ATOM | 170 | CB | GLN | 26 | 41.729 58.539 -2.341 1.00 18.89 A1 |
| ATOM | 128 | N | ARG | 23 | 46.643 | 57.291 | -2.759 | 1.00 | 23.93 | A1 | ATOM | 171 | CG | GLN | 26 | 42.203 59.042 -3.627 1.00 19.77 A1 |

FIG. 5C

| | | | | | | | | | |
|---|---|---|---|---|---|---|---|---|---|
| ATOM | 172 | CD | GLN | 26 | 42.163 | 57.996 | -4.684 | 1.00 24.26 | A1 |
| ATOM | 173 | OE1 | GLN | 26 | 42.550 | 56.853 | -4.465 | 1.00 26.82 | A1 |
| ATOM | 174 | NE2 | GLN | 26 | 41.732 | 58.351 | -5.890 | 1.00 27.68 | A1 |
| ATOM | 175 | HE21 | GLN | 26 | 41.421 | 59.265 | -6.042 | 1.00 0.00 | A1 |
| ATOM | 176 | HE22 | GLN | 26 | 41.743 | 57.649 | -6.552 | 1.00 0.00 | A1 |
| ATOM | 177 | C | GLN | 26 | 41.207 | 59.239 | -0.111 | 1.00 21.88 | A1 |
| ATOM | 178 | O | GLN | 26 | 40.067 | 59.550 | 0.220 | 1.00 27.02 | A1 |
| ATOM | 179 | N | GLY | 27 | 41.952 | 58.622 | 0.773 | 1.00 22.54 | A1 |
| ATOM | 180 | H | GLY | 27 | 42.891 | 58.420 | 0.576 | 1.00 0.00 | A1 |
| ATOM | 181 | CA | GLY | 27 | 41.386 | 58.191 | 2.037 | 1.00 25.55 | A1 |
| ATOM | 182 | C | GLY | 27 | 40.936 | 59.352 | 2.890 | 1.00 27.80 | A1 |
| ATOM | 183 | O | GLY | 27 | 39.889 | 59.251 | 3.526 | 1.00 29.95 | A1 |
| ATOM | 184 | N | ASP | 28 | 41.683 | 60.460 | 2.915 | 1.00 29.39 | A1 |
| ATOM | 185 | H | ASP | 28 | 42.547 | 60.454 | 2.448 | 1.00 0.00 | A1 |
| ATOM | 186 | CA | ASP | 28 | 41.257 | 61.680 | 3.624 | 1.00 28.45 | A1 |
| ATOM | 187 | CB | ASP | 28 | 42.266 | 62.789 | 3.552 | 1.00 30.13 | A1 |
| ATOM | 188 | CG | ASP | 28 | 43.737 | 62.502 | 3.777 | 1.00 31.72 | A1 |
| ATOM | 189 | OD1 | ASP | 28 | 44.539 | 63.024 | 2.995 | 1.00 31.95 | A1 |
| ATOM | 190 | OD2 | ASP | 28 | 44.063 | 61.811 | 4.741 | 1.00 32.00 | A1 |
| ATOM | 191 | C | ASP | 28 | 39.994 | 62.264 | 2.960 | 1.00 25.81 | A1 |
| ATOM | 192 | O | ASP | 28 | 39.101 | 62.699 | 3.655 | 1.00 26.21 | A1 |
| ATOM | 193 | N | GLY | 29 | 39.882 | 62.270 | 1.631 | 1.00 23.93 | A1 |
| ATOM | 194 | H | GLY | 29 | 40.660 | 61.950 | 1.135 | 1.00 0.00 | A1 |
| ATOM | 195 | CA | GLY | 29 | 38.729 | 62.694 | 0.886 | 1.00 25.69 | A1 |
| ATOM | 196 | C | GLY | 29 | 37.528 | 61.961 | 1.418 | 1.00 27.36 | A1 |
| ATOM | 197 | O | GLY | 29 | 36.648 | 62.558 | 2.061 | 1.00 28.14 | A1 |
| ATOM | 198 | N | ALA | 30 | 37.646 | 60.628 | 1.295 | 1.00 27.85 | A1 |
| ATOM | 199 | H | ALA | 30 | 38.442 | 60.288 | 0.843 | 1.00 0.00 | A1 |
| ATOM | 200 | CA | ALA | 30 | 36.683 | 59.655 | 1.814 | 1.00 25.94 | A1 |
| ATOM | 201 | CB | ALA | 30 | 37.269 | 58.303 | 1.556 | 1.00 22.15 | A1 |
| ATOM | 202 | C | ALA | 30 | 36.356 | 59.842 | 3.308 | 1.00 27.18 | A1 |
| ATOM | 203 | O | ALA | 30 | 35.194 | 59.772 | 3.754 | 1.00 28.82 | A1 |
| ATOM | 204 | N | ALA | 31 | 37.340 | 60.105 | 4.150 | 1.00 27.16 | A1 |
| ATOM | 205 | H | ALA | 31 | 38.253 | 60.114 | 3.809 | 1.00 0.00 | A1 |
| ATOM | 206 | CA | ALA | 31 | 37.113 | 60.470 | 5.531 | 1.00 27.70 | A1 |
| ATOM | 207 | CB | ALA | 31 | 38.383 | 60.881 | 6.177 | 1.00 27.65 | A1 |
| ATOM | 208 | C | ALA | 31 | 36.178 | 61.675 | 5.660 | 1.00 30.01 | A1 |
| ATOM | 209 | O | ALA | 31 | 35.195 | 61.624 | 6.413 | 1.00 32.91 | A1 |
| ATOM | 210 | N | LEU | 32 | 36.397 | 62.744 | 4.895 | 1.00 27.63 | A1 |
| ATOM | 211 | H | LEU | 32 | 37.133 | 62.734 | 4.242 | 1.00 0.00 | A1 |
| ATOM | 212 | CA | LEU | 32 | 35.560 | 63.898 | 4.997 | 1.00 28.52 | A1 |
| ATOM | 213 | CB | LEU | 32 | 36.226 | 65.019 | 4.167 | 1.00 32.94 | A1 |
| ATOM | 214 | CG | LEU | 32 | 35.658 | 66.472 | 4.091 | 1.00 32.54 | A1 |
| ATOM | 215 | CD1 | LEU | 32 | 35.516 | 67.082 | 5.499 | 1.00 32.87 | A1 |
| ATOM | 216 | CD2 | LEU | 32 | 36.555 | 67.267 | 3.181 | 1.00 30.97 | A1 |
| ATOM | 217 | C | LEU | 32 | 34.133 | 63.597 | 4.518 | 1.00 27.87 | A1 |
| ATOM | 218 | O | LEU | 32 | 33.169 | 63.889 | 5.250 | 1.00 25.93 | A1 |
| ATOM | 219 | N | GLN | 33 | 33.977 | 63.028 | 3.315 | 1.00 27.51 | A1 |
| ATOM | 220 | H | GLN | 33 | 34.787 | 62.826 | 2.802 | 1.00 0.00 | A1 |
| ATOM | 221 | CA | GLN | 33 | 32.687 | 62.671 | 2.775 | 1.00 30.40 | A1 |
| ATOM | 222 | CB | GLN | 33 | 32.737 | 61.721 | 1.614 | 1.00 29.47 | A1 |
| ATOM | 223 | CG | GLN | 33 | 32.888 | 62.584 | 0.436 | 1.00 29.26 | A1 |
| ATOM | 224 | CD | GLN | 33 | 33.015 | 61.869 | -0.887 | 1.00 30.21 | A1 |
| ATOM | 225 | OE1 | GLN | 33 | 34.064 | 61.495 | -1.452 | 1.00 29.61 | A1 |
| ATOM | 226 | NE2 | GLN | 33 | 31.823 | 61.759 | -1.426 | 1.00 33.19 | A1 |
| ATOM | 227 | HE21 | GLN | 33 | 31.781 | 61.328 | -2.302 | 1.00 0.00 | A1 |
| ATOM | 228 | HE22 | GLN | 33 | 31.042 | 62.060 | -0.914 | 1.00 0.00 | A1 |
| ATOM | 229 | C | GLN | 33 | 31.839 | 61.963 | 3.788 | 1.00 35.60 | A1 |
| ATOM | 230 | O | GLN | 33 | 30.715 | 62.416 | 4.073 | 1.00 36.49 | A1 |
| ATOM | 231 | N | GLU | 34 | 32.386 | 60.925 | 4.438 | 1.00 39.81 | A1 |
| ATOM | 232 | H | GLU | 34 | 33.340 | 60.707 | 4.328 | 1.00 0.00 | A1 |
| ATOM | 233 | CA | GLU | 34 | 31.541 | 60.131 | 5.304 | 1.00 43.24 | A1 |
| ATOM | 234 | CB | GLU | 34 | 32.228 | 58.792 | 5.571 | 1.00 46.46 | A1 |
| ATOM | 235 | CG | GLU | 34 | 33.274 | 58.721 | 6.624 | 1.00 55.01 | A1 |
| ATOM | 236 | CD | GLU | 34 | 32.777 | 58.092 | 7.930 | 1.00 60.29 | A1 |
| ATOM | 237 | OE1 | GLU | 34 | 33.483 | 57.186 | 8.412 | 1.00 63.26 | A1 |
| ATOM | 238 | OE2 | GLU | 34 | 31.724 | 58.504 | 8.459 | 1.00 60.44 | A1 |
| ATOM | 239 | C | GLU | 34 | 31.218 | 60.877 | 6.564 | 1.00 43.59 | A1 |
| ATOM | 240 | O | GLU | 34 | 30.175 | 60.631 | 7.161 | 1.00 44.87 | A1 |
| ATOM | 241 | N | LYS | 35 | 32.045 | 61.811 | 6.998 | 1.00 44.80 | A1 |
| ATOM | 242 | H | LYS | 35 | 32.923 | 61.931 | 6.569 | 1.00 0.00 | A1 |
| ATOM | 243 | CA | LYS | 35 | 31.674 | 62.634 | 8.134 | 1.00 45.43 | A1 |
| ATOM | 244 | CB | LYS | 35 | 32.881 | 63.364 | 8.686 | 1.00 47.67 | A1 |
| ATOM | 245 | CG | LYS | 35 | 33.701 | 62.414 | 9.510 | 1.00 52.75 | A1 |
| ATOM | 246 | CD | LYS | 35 | 35.084 | 63.021 | 9.548 | 1.00 57.55 | A1 |
| ATOM | 247 | CE | LYS | 35 | 36.067 | 62.099 | 10.238 | 1.00 60.35 | A1 |
| ATOM | 248 | NZ | LYS | 35 | 35.810 | 62.064 | 11.669 | 1.00 62.91 | A1 |
| ATOM | 249 | HZ1 | LYS | 35 | 34.838 | 61.733 | 11.840 | 1.00 0.00 | A1 |
| ATOM | 250 | HZ2 | LYS | 35 | 35.930 | 63.011 | 12.078 | 1.00 0.00 | A1 |
| ATOM | 251 | HZ3 | LYS | 35 | 36.477 | 61.405 | 12.119 | 1.00 0.00 | A1 |
| ATOM | 252 | C | LYS | 35 | 30.630 | 63.660 | 7.697 | 1.00 44.45 | A1 |
| ATOM | 253 | O | LYS | 35 | 29.730 | 63.999 | 8.478 | 1.00 44.61 | A1 |
| ATOM | 254 | N | LEU | 36 | 30.652 | 64.190 | 6.480 | 1.00 41.21 | A1 |
| ATOM | 255 | H | LEU | 36 | 31.343 | 63.930 | 5.836 | 1.00 0.00 | A1 |
| ATOM | 256 | CA | LEU | 36 | 29.647 | 65.157 | 6.144 | 1.00 40.25 | A1 |
| ATOM | 257 | CB | LEU | 36 | 30.070 | 65.899 | 4.889 | 1.00 39.03 | A1 |

FIG. 5D

| ATOM | 258 | CG | LEU | 36 | 31.253 | 66.834 | 4.935 | 1.00 | 33.99 | A1 |
|---|---|---|---|---|---|---|---|---|---|---|
| ATOM | 259 | CD1 | LEU | 36 | 31.438 | 67.404 | 3.571 | 1.00 | 32.08 | A1 |
| ATOM | 260 | CD2 | LEU | 36 | 31.034 | 67.939 | 5.928 | 1.00 | 35.05 | A1 |
| ATOM | 261 | C | LEU | 36 | 28.332 | 64.414 | 5.941 | 1.00 | 41.90 | A1 |
| ATOM | 262 | O | LEU | 36 | 27.267 | 64.828 | 6.431 | 1.00 | 42.30 | A1 |
| ATOM | 263 | N | CYS | 37 | 28.392 | 63.251 | 5.309 | 1.00 | 42.63 | A1 |
| ATOM | 264 | H | CYS | 37 | 29.250 | 62.904 | 5.020 | 1.00 | 0.00 | A1 |
| ATOM | 265 | CA | CYS | 37 | 27.216 | 62.469 | 5.084 | 1.00 | 43.53 | A1 |
| ATOM | 266 | C | CYS | 37 | 26.638 | 62.026 | 6.362 | 1.00 | 44.65 | A1 |
| ATOM | 267 | O | CYS | 37 | 25.426 | 61.997 | 6.459 | 1.00 | 46.40 | A1 |
| ATOM | 268 | CB | CYS | 37 | 27.474 | 61.240 | 4.313 | 1.00 | 44.60 | A1 |
| ATOM | 269 | SG | CYS | 37 | 26.133 | 60.038 | 4.530 | 1.00 | 43.86 | A1 |
| ATOM | 270 | N | ALA | 38 | 27.465 | 61.734 | 7.342 | 1.00 | 45.96 | A1 |
| ATOM | 271 | H | ALA | 38 | 28.433 | 61.707 | 7.202 | 1.00 | 0.00 | A1 |
| ATOM | 272 | CA | ALA | 38 | 26.932 | 61.261 | 8.592 | 1.00 | 48.03 | A1 |
| ATOM | 273 | CB | ALA | 38 | 27.869 | 60.140 | 9.108 | 1.00 | 48.64 | A1 |
| ATOM | 274 | C | ALA | 38 | 26.748 | 62.358 | 9.624 | 1.00 | 48.89 | A1 |
| ATOM | 275 | O | ALA | 38 | 26.103 | 62.085 | 10.621 | 1.00 | 50.72 | A1 |
| ATOM | 276 | N | THR | 39 | 27.256 | 63.590 | 9.512 | 1.00 | 50.66 | A1 |
| ATOM | 277 | H | THR | 39 | 27.858 | 63.780 | 8.770 | 1.00 | 0.00 | A1 |
| ATOM | 278 | CA | THR | 39 | 26.976 | 64.638 | 10.503 | 1.00 | 51.54 | A1 |
| ATOM | 279 | CB | THR | 39 | 28.179 | 65.593 | 10.690 | 1.00 | 51.76 | A1 |
| ATOM | 280 | OG1 | THR | 39 | 29.294 | 64.826 | 11.126 | 1.00 | 52.65 | A1 |
| ATOM | 281 | HG1 | THR | 39 | 29.749 | 64.481 | 10.355 | 1.00 | 0.00 | A1 |
| ATOM | 282 | CG2 | THR | 39 | 27.900 | 66.655 | 11.729 | 1.00 | 51.62 | A1 |
| ATOM | 283 | C | THR | 39 | 25.775 | 65.466 | 10.037 | 1.00 | 52.17 | A1 |
| ATOM | 284 | O | THR | 39 | 24.886 | 65.882 | 10.781 | 1.00 | 52.15 | A1 |
| ATOM | 285 | N | TYR | 40 | 25.751 | 65.720 | 8.738 | 1.00 | 52.83 | A1 |
| ATOM | 286 | H | TYR | 40 | 26.420 | 65.331 | 8.139 | 1.00 | 0.00 | A1 |
| ATOM | 287 | CA | TYR | 40 | 24.729 | 66.561 | 8.165 | 1.00 | 52.53 | A1 |
| ATOM | 288 | CB | TYR | 40 | 25.314 | 67.872 | 7.696 | 1.00 | 52.15 | A1 |
| ATOM | 289 | CG | TYR | 40 | 26.399 | 68.458 | 8.552 | 1.00 | 54.11 | A1 |
| ATOM | 290 | CD1 | TYR | 40 | 27.678 | 68.341 | 8.062 | 1.00 | 56.50 | A1 |
| ATOM | 291 | CE1 | TYR | 40 | 28.719 | 68.934 | 8.724 | 1.00 | 58.28 | A1 |
| ATOM | 292 | CD2 | TYR | 40 | 26.122 | 69.144 | 9.714 | 1.00 | 54.86 | A1 |
| ATOM | 293 | CE2 | TYR | 40 | 27.170 | 69.746 | 10.378 | 1.00 | 56.20 | A1 |
| ATOM | 294 | CZ | TYR | 40 | 28.453 | 69.642 | 9.872 | 1.00 | 58.26 | A1 |
| ATOM | 295 | OH | TYR | 40 | 29.513 | 70.310 | 10.463 | 1.00 | 61.00 | A1 |
| ATOM | 296 | HH | TYR | 40 | 30.179 | 70.443 | 9.782 | 1.00 | 0.00 | A1 |
| ATOM | 297 | C | TYR | 40 | 24.035 | 65.911 | 6.981 | 1.00 | 51.75 | A1 |
| ATOM | 298 | O | TYR | 40 | 23.662 | 66.578 | 6.024 | 1.00 | 52.52 | A1 |
| ATOM | 299 | N | LYS | 41 | 23.941 | 64.600 | 6.965 | 1.00 | 50.54 | A1 |
| ATOM | 300 | H | LYS | 41 | 24.474 | 64.064 | 7.583 | 1.00 | 0.00 | A1 |
| ATOM | 301 | CA | LYS | 41 | 23.112 | 63.885 | 6.029 | 1.00 | 50.48 | A1 |
| ATOM | 302 | CB | LYS | 41 | 21.641 | 63.989 | 6.540 | 1.00 | 50.62 | A1 |
| ATOM | 303 | CG | LYS | 41 | 21.387 | 63.326 | 7.911 | 1.00 | 52.11 | A1 |
| ATOM | 304 | CD | LYS | 41 | 20.112 | 63.878 | 8.574 | 1.00 | 55.54 | A1 |
| ATOM | 305 | CE | LYS | 41 | 19.578 | 63.087 | 9.820 | 1.00 | 58.79 | A1 |
| ATOM | 306 | NZ | LYS | 41 | 18.374 | 63.648 | 10.457 | 1.00 | 58.31 | A1 |
| ATOM | 307 | HZ1 | LYS | 41 | 17.605 | 63.688 | 9.757 | 1.00 | 0.00 | A1 |
| ATOM | 308 | HZ2 | LYS | 41 | 18.578 | 64.607 | 10.803 | 1.00 | 0.00 | A1 |
| ATOM | 309 | HZ3 | LYS | 41 | 18.084 | 63.043 | 11.252 | 1.00 | 0.00 | A1 |
| ATOM | 310 | C | LYS | 41 | 23.251 | 64.318 | 4.588 | 1.00 | 49.92 | A1 |
| ATOM | 311 | O | LYS | 41 | 22.312 | 64.124 | 3.793 | 1.00 | 51.49 | A1 |
| ATOM | 312 | N | LEU | 42 | 24.432 | 64.893 | 4.246 | 1.00 | 48.28 | A1 |
| ATOM | 313 | H | LEU | 42 | 25.103 | 65.050 | 4.937 | 1.00 | 0.00 | A1 |
| ATOM | 314 | CA | LEU | 42 | 24.742 | 65.286 | 2.859 | 1.00 | 46.61 | A1 |
| ATOM | 315 | CB | LEU | 42 | 25.565 | 66.574 | 2.757 | 1.00 | 44.69 | A1 |
| ATOM | 316 | CG | LEU | 42 | 24.807 | 67.802 | 3.218 | 1.00 | 42.63 | A1 |
| ATOM | 317 | CD1 | LEU | 42 | 25.718 | 68.580 | 4.097 | 1.00 | 43.29 | A1 |
| ATOM | 318 | CD2 | LEU | 42 | 24.283 | 68.590 | 2.045 | 1.00 | 41.26 | A1 |
| ATOM | 319 | C | LEU | 42 | 25.580 | 64.124 | 2.397 | 1.00 | 45.46 | A1 |
| ATOM | 320 | O | LEU | 42 | 26.766 | 64.017 | 2.711 | 1.00 | 46.32 | A1 |
| ATOM | 321 | N | CYS | 43 | 24.882 | 63.193 | 1.754 | 1.00 | 44.09 | A1 |
| ATOM | 322 | H | CYS | 43 | 23.925 | 63.353 | 1.619 | 1.00 | 0.00 | A1 |
| ATOM | 323 | CA | CYS | 43 | 25.480 | 61.951 | 1.358 | 1.00 | 42.87 | A1 |
| ATOM | 324 | C | CYS | 43 | 25.448 | 61.846 | -0.123 | 1.00 | 41.62 | A1 |
| ATOM | 325 | O | CYS | 43 | 25.762 | 60.805 | -0.666 | 1.00 | 41.99 | A1 |
| ATOM | 326 | CB | CYS | 43 | 24.716 | 60.796 | 2.026 | 1.00 | 41.77 | A1 |
| ATOM | 327 | SG | CYS | 43 | 24.523 | 61.011 | 3.835 | 1.00 | 45.91 | A1 |
| ATOM | 328 | N | HIS | 44 | 25.057 | 62.846 | -0.882 | 1.00 | 42.90 | A1 |
| ATOM | 329 | H | HIS | 44 | 24.841 | 63.721 | -0.491 | 1.00 | 0.00 | A1 |
| ATOM | 330 | CA | HIS | 44 | 25.069 | 62.680 | -2.320 | 1.00 | 44.60 | A1 |
| ATOM | 331 | CB | HIS | 44 | 23.653 | 62.264 | -2.825 | 1.00 | 48.40 | A1 |
| ATOM | 332 | CG | HIS | 44 | 23.085 | 60.935 | -2.310 | 1.00 | 50.37 | A1 |
| ATOM | 333 | CD2 | HIS | 44 | 22.178 | 60.844 | -1.272 | 1.00 | 50.52 | A1 |
| ATOM | 334 | ND1 | HIS | 44 | 23.358 | 59.689 | -2.713 | 1.00 | 52.28 | A1 |
| ATOM | 335 | HD1 | HIS | 44 | 24.130 | 59.394 | -3.251 | 1.00 | 0.00 | A1 |
| ATOM | 336 | CE1 | HIS | 44 | 22.652 | 58.873 | -1.955 | 1.00 | 51.92 | A1 |
| ATOM | 337 | NE2 | HIS | 44 | 21.947 | 59.565 | -1.091 | 1.00 | 50.53 | A1 |
| ATOM | 338 | HE2 | HIS | 44 | 21.290 | 59.189 | -0.466 | 1.00 | 0.00 | A1 |
| ATOM | 339 | C | HIS | 44 | 25.522 | 63.941 | -3.047 | 1.00 | 43.69 | A1 |
| ATOM | 340 | O | HIS | 44 | 24.765 | 64.906 | -3.108 | 1.00 | 43.00 | A1 |
| ATOM | 341 | N | PRO | 45 | 26.710 | 63.978 | -3.667 | 1.00 | 43.07 | A1 |
| ATOM | 342 | CD | PRO | 45 | 27.785 | 62.995 | -3.501 | 1.00 | 42.17 | A1 |
| ATOM | 343 | CA | PRO | 45 | 27.133 | 65.024 | -4.570 | 1.00 | 42.50 | A1 |

FIG. 5E

| ATOM | 344 | CB | PRO | 45 | 28.380 | 64.466 | -5.217 | 1.00 | 39.76 | A1 |
|------|-----|----|----|---|--------|--------|--------|------|-------|-----|
| ATOM | 345 | CG | PRO | 45 | 28.995 | 63.680 | -4.123 | 1.00 | 39.09 | A1 |
| ATOM | 346 | C | PRO | 45 | 26.071 | 65.423 | -5.585 | 1.00 | 44.49 | A1 |
| ATOM | 347 | O | PRO | 45 | 25.876 | 66.612 | -5.801 | 1.00 | 45.36 | A1 |
| ATOM | 348 | N | GLU | 46 | 25.334 | 64.501 | -6.225 | 1.00 | 45.36 | A1 |
| ATOM | 349 | H | GLU | 46 | 25.464 | 63.561 | -5.996 | 1.00 | 0.00 | A1 |
| ATOM | 350 | CA | GLU | 46 | 24.406 | 64.806 | -7.319 | 1.00 | 45.46 | A1 |
| ATOM | 351 | CB | GLU | 46 | 23.952 | 63.515 | -7.997 | 1.00 | 50.54 | A1 |
| ATOM | 352 | CG | GLU | 46 | 24.462 | 63.460 | -9.445 | 1.00 | 58.48 | A1 |
| ATOM | 353 | CD | GLU | 46 | 23.637 | 64.215 | -10.502 | 1.00 | 64.93 | A1 |
| ATOM | 354 | OE1 | GLU | 46 | 23.642 | 65.455 | -10.516 | 1.00 | 68.55 | A1 |
| ATOM | 355 | OE2 | GLU | 46 | 22.995 | 63.554 | -11.332 | 1.00 | 68.31 | A1 |
| ATOM | 356 | C | GLU | 46 | 23.181 | 65.584 | -6.937 | 1.00 | 42.96 | A1 |
| ATOM | 357 | O | GLU | 46 | 22.552 | 66.223 | -7.748 | 1.00 | 41.71 | A1 |
| ATOM | 358 | N | GLU | 47 | 22.919 | 65.563 | -5.654 | 1.00 | 41.96 | A1 |
| ATOM | 359 | H | GLU | 47 | 23.507 | 65.098 | -5.028 | 1.00 | 0.00 | A1 |
| ATOM | 360 | CA | GLU | 47 | 21.818 | 66.301 | -5.144 | 1.00 | 43.21 | A1 |
| ATOM | 361 | CB | GLU | 47 | 21.294 | 65.487 | -3.963 | 1.00 | 43.24 | A1 |
| ATOM | 362 | CG | GLU | 47 | 21.409 | 65.925 | -2.515 | 1.00 | 46.07 | A1 |
| ATOM | 363 | CD | GLU | 47 | 20.812 | 64.907 | -1.547 | 1.00 | 47.86 | A1 |
| ATOM | 364 | OE1 | GLU | 47 | 19.847 | 64.225 | -1.910 | 1.00 | 50.99 | A1 |
| ATOM | 365 | OE2 | GLU | 47 | 21.313 | 64.780 | -0.427 | 1.00 | 49.47 | A1 |
| ATOM | 366 | C | GLU | 47 | 22.295 | 67.718 | -4.809 | 1.00 | 44.04 | A1 |
| ATOM | 367 | O | GLU | 47 | 21.532 | 68.547 | -4.292 | 1.00 | 44.60 | A1 |
| ATOM | 368 | N | LEU | 48 | 23.567 | 68.015 | -5.121 | 1.00 | 43.05 | A1 |
| ATOM | 369 | H | LEU | 48 | 24.140 | 67.310 | -5.465 | 1.00 | 0.00 | A1 |
| ATOM | 370 | CA | LEU | 48 | 24.166 | 69.318 | -4.904 | 1.00 | 42.42 | A1 |
| ATOM | 371 | CB | LEU | 48 | 25.223 | 69.201 | -3.858 | 1.00 | 40.53 | A1 |
| ATOM | 372 | CG | LEU | 48 | 24.920 | 68.695 | -2.489 | 1.00 | 41.87 | A1 |
| ATOM | 373 | CD1 | LEU | 48 | 26.277 | 68.424 | -1.892 | 1.00 | 41.71 | A1 |
| ATOM | 374 | CD2 | LEU | 48 | 24.096 | 69.670 | -1.633 | 1.00 | 41.13 | A1 |
| ATOM | 375 | C | LEU | 48 | 24.792 | 69.937 | -6.166 | 1.00 | 42.37 | A1 |
| ATOM | 376 | O | LEU | 48 | 25.439 | 70.994 | -6.098 | 1.00 | 42.37 | A1 |
| ATOM | 377 | N | VAL | 49 | 24.566 | 69.366 | -7.347 | 1.00 | 41.52 | A1 |
| ATOM | 378 | H | VAL | 49 | 23.951 | 68.602 | -7.362 | 1.00 | 0.00 | A1 |
| ATOM | 379 | CA | VAL | 49 | 25.191 | 69.822 | -8.578 | 1.00 | 43.34 | A1 |
| ATOM | 380 | CB | VAL | 49 | 24.890 | 68.761 | -9.636 | 1.00 | 44.29 | A1 |
| ATOM | 381 | CG1 | VAL | 49 | 23.381 | 68.709 | -9.830 | 1.00 | 47.50 | A1 |
| ATOM | 382 | CG2 | VAL | 49 | 25.540 | 69.086 | -10.975 | 1.00 | 45.25 | A1 |
| ATOM | 383 | C | VAL | 49 | 24.740 | 71.214 | -9.028 | 1.00 | 44.98 | A1 |
| ATOM | 384 | O | VAL | 49 | 25.401 | 71.901 | -9.814 | 1.00 | 46.03 | A1 |
| ATOM | 385 | N | LEU | 50 | 23.565 | 71.602 | -8.530 | 1.00 | 46.16 | A1 |
| ATOM | 386 | H | LEU | 50 | 23.081 | 70.953 | -8.006 | 1.00 | 0.00 | A1 |
| ATOM | 387 | CA | LEU | 50 | 22.908 | 72.895 | -8.729 | 1.00 | 46.03 | A1 |
| ATOM | 388 | CB | LEU | 50 | 21.469 | 72.769 | -8.264 | 1.00 | 46.43 | A1 |
| ATOM | 389 | CG | LEU | 50 | 20.443 | 73.718 | -8.760 | 1.00 | 44.16 | A1 |
| ATOM | 390 | CD1 | LEU | 50 | 20.259 | 73.558 | -10.243 | 1.00 | 44.79 | A1 |
| ATOM | 391 | CD2 | LEU | 50 | 19.159 | 73.400 | -8.079 | 1.00 | 44.66 | A1 |
| ATOM | 392 | C | LEU | 50 | 23.632 | 73.968 | -7.917 | 1.00 | 45.85 | A1 |
| ATOM | 393 | O | LEU | 50 | 23.996 | 74.989 | -8.484 | 1.00 | 44.52 | A1 |
| ATOM | 394 | N | LEU | 51 | 23.853 | 73.764 | -6.606 | 1.00 | 45.44 | A1 |
| ATOM | 395 | H | LEU | 51 | 23.489 | 72.958 | -6.189 | 1.00 | 0.00 | A1 |
| ATOM | 396 | CA | LEU | 51 | 24.676 | 74.656 | -5.805 | 1.00 | 46.04 | A1 |
| ATOM | 397 | CB | LEU | 51 | 24.860 | 74.084 | -4.435 | 1.00 | 45.53 | A1 |
| ATOM | 398 | CG | LEU | 51 | 25.741 | 74.931 | -3.535 | 1.00 | 47.78 | A1 |
| ATOM | 399 | CD1 | LEU | 51 | 25.148 | 76.320 | -3.322 | 1.00 | 47.13 | A1 |
| ATOM | 400 | CD2 | LEU | 51 | 25.902 | 74.202 | -2.219 | 1.00 | 48.33 | A1 |
| ATOM | 401 | C | LEU | 51 | 26.064 | 74.845 | -6.436 | 1.00 | 46.27 | A1 |
| ATOM | 402 | O | LEU | 51 | 26.551 | 75.966 | -6.612 | 1.00 | 47.62 | A1 |
| ATOM | 403 | N | GLY | 52 | 26.702 | 73.736 | -6.809 | 1.00 | 44.84 | A1 |
| ATOM | 404 | H | GLY | 52 | 26.306 | 72.869 | -6.578 | 1.00 | 0.00 | A1 |
| ATOM | 405 | CA | GLY | 52 | 27.989 | 73.758 | -7.453 | 1.00 | 42.91 | A1 |
| ATOM | 406 | C | GLY | 52 | 27.984 | 74.533 | -8.750 | 1.00 | 42.47 | A1 |
| ATOM | 407 | O | GLY | 52 | 28.853 | 75.364 | -8.983 | 1.00 | 42.06 | A1 |
| ATOM | 408 | N | HIS | 53 | 27.047 | 74.307 | -9.653 | 1.00 | 42.02 | A1 |
| ATOM | 409 | H | HIS | 53 | 26.366 | 73.624 | -9.471 | 1.00 | 0.00 | A1 |
| ATOM | 410 | CA | HIS | 53 | 27.009 | 75.104 | -10.861 | 1.00 | 42.23 | A1 |
| ATOM | 411 | CB | HIS | 53 | 25.842 | 74.689 | -11.706 | 1.00 | 42.21 | A1 |
| ATOM | 412 | CG | HIS | 53 | 26.076 | 73.399 | -12.460 | 1.00 | 44.60 | A1 |
| ATOM | 413 | CD2 | HIS | 53 | 25.112 | 72.774 | -13.200 | 1.00 | 47.49 | A1 |
| ATOM | 414 | ND1 | HIS | 53 | 27.180 | 72.669 | -12.578 | 1.00 | 46.76 | A1 |
| ATOM | 415 | HD1 | HIS | 53 | 28.039 | 72.853 | -12.139 | 1.00 | 0.00 | A1 |
| ATOM | 416 | CE1 | HIS | 53 | 26.954 | 71.641 | -13.346 | 1.00 | 46.90 | A1 |
| ATOM | 417 | NE2 | HIS | 53 | 25.704 | 71.725 | -13.707 | 1.00 | 50.22 | A1 |
| ATOM | 418 | HE2 | HIS | 53 | 25.237 | 71.033 | -14.239 | 1.00 | 0.00 | A1 |
| ATOM | 419 | C | HIS | 53 | 26.893 | 76.585 | -10.536 | 1.00 | 42.72 | A1 |
| ATOM | 420 | O | HIS | 53 | 27.622 | 77.399 | -11.068 | 1.00 | 42.03 | A1 |
| ATOM | 421 | N | SER | 54 | 26.099 | 76.920 | -9.535 | 1.00 | 45.08 | A1 |
| ATOM | 422 | H | SER | 54 | 25.673 | 76.218 | -9.001 | 1.00 | 0.00 | A1 |
| ATOM | 423 | CA | SER | 54 | 25.792 | 78.278 | -9.177 | 1.00 | 46.92 | A1 |
| ATOM | 424 | CB | SER | 54 | 24.576 | 78.181 | -8.289 | 1.00 | 48.86 | A1 |
| ATOM | 425 | OG | SER | 54 | 23.521 | 77.616 | -9.112 | 1.00 | 53.06 | A1 |
| ATOM | 426 | HG | SER | 54 | 23.465 | 76.677 | -8.918 | 1.00 | 0.00 | A1 |
| ATOM | 427 | C | SER | 54 | 26.939 | 79.033 | -8.549 | 1.00 | 47.92 | A1 |
| ATOM | 428 | O | SER | 54 | 27.038 | 80.264 | -8.655 | 1.00 | 49.60 | A1 |
| ATOM | 429 | N | LEU | 55 | 27.837 | 78.273 | -7.933 | 1.00 | 47.59 | A1 |

FIG. 5F

| ATOM | 430 | H | LEU | 55 | 27.638 | 77.322 | -7.791 | 1.00 | 0.00 | A1 |
|---|---|---|---|---|---|---|---|---|---|---|
| ATOM | 431 | CA | LEU | 55 | 29.075 | 78.810 | -7.401 | 1.00 | 45.27 | A1 |
| ATOM | 432 | CB | LEU | 55 | 29.552 | 77.913 | -6.243 | 1.00 | 45.49 | A1 |
| ATOM | 433 | CG | LEU | 55 | 28.840 | 77.992 | -4.874 | 1.00 | 47.30 | A1 |
| ATOM | 434 | CD1 | LEU | 55 | 28.876 | 76.596 | -4.299 | 1.00 | 49.52 | A1 |
| ATOM | 435 | CD2 | LEU | 55 | 29.530 | 78.921 | -3.862 | 1.00 | 45.69 | A1 |
| ATOM | 436 | C | LEU | 55 | 30.133 | 78.889 | -8.492 | 1.00 | 43.63 | A1 |
| ATOM | 437 | O | LEU | 55 | 31.247 | 79.350 | -8.272 | 1.00 | 43.24 | A1 |
| ATOM | 438 | N | GLY | 56 | 29.855 | 78.383 | -9.675 | 1.00 | 43.55 | A1 |
| ATOM | 439 | H | GLY | 56 | 28.984 | 77.975 | -9.828 | 1.00 | 0.00 | A1 |
| ATOM | 440 | CA | GLY | 56 | 30.814 | 78.390 | -10.753 | 1.00 | 45.59 | A1 |
| ATOM | 441 | C | GLY | 56 | 32.182 | 77.811 | -10.392 | 1.00 | 46.76 | A1 |
| ATOM | 442 | O | GLY | 56 | 33.171 | 78.213 | -11.015 | 1.00 | 47.31 | A1 |
| ATOM | 443 | N | ILE | 57 | 32.247 | 76.885 | -9.412 | 1.00 | 47.49 | A1 |
| ATOM | 444 | H | ILE | 57 | 31.392 | 76.594 | -9.042 | 1.00 | 0.00 | A1 |
| ATOM | 445 | CA | ILE | 57 | 33.486 | 76.249 | -8.950 | 1.00 | 48.28 | A1 |
| ATOM | 446 | CB | ILE | 57 | 33.144 | 75.172 | -7.863 | 1.00 | 47.79 | A1 |
| ATOM | 447 | CG2 | ILE | 57 | 34.457 | 74.591 | -7.348 | 1.00 | 46.85 | A1 |
| ATOM | 448 | CG1 | ILE | 57 | 32.338 | 75.764 | -6.701 | 1.00 | 45.09 | A1 |
| ATOM | 449 | CD | ILE | 57 | 31.859 | 74.739 | -5.659 | 1.00 | 41.23 | A1 |
| ATOM | 450 | C | ILE | 57 | 34.276 | 75.602 | -10.115 | 1.00 | 49.15 | A1 |
| ATOM | 451 | O | ILE | 57 | 33.678 | 74.935 | -10.968 | 1.00 | 49.04 | A1 |
| ATOM | 452 | N | PRO | 58 | 35.596 | 75.817 | -10.248 | 1.00 | 49.75 | A1 |
| ATOM | 453 | CD | PRO | 58 | 36.402 | 76.743 | -9.433 | 1.00 | 50.94 | A1 |
| ATOM | 454 | CA | PRO | 58 | 36.421 | 75.228 | -11.302 | 1.00 | 50.72 | A1 |
| ATOM | 455 | CB | PRO | 58 | 37.525 | 76.241 | -11.488 | 1.00 | 50.92 | A1 |
| ATOM | 456 | CG | PRO | 58 | 37.814 | 76.663 | -10.041 | 1.00 | 50.82 | A1 |
| ATOM | 457 | C | PRO | 58 | 36.916 | 73.845 | -10.875 | 1.00 | 50.36 | A1 |
| ATOM | 458 | O | PRO | 58 | 37.187 | 73.599 | -9.691 | 1.00 | 49.75 | A1 |
| ATOM | 459 | N | TRP | 59 | 37.030 | 72.927 | -11.816 | 1.00 | 50.37 | A1 |
| ATOM | 460 | H | TRP | 59 | 36.888 | 73.141 | -12.760 | 1.00 | 0.00 | A1 |
| ATOM | 461 | CA | TRP | 59 | 37.524 | 71.595 | -11.482 | 1.00 | 51.78 | A1 |
| ATOM | 462 | CB | TRP | 59 | 36.435 | 70.562 | -11.857 | 1.00 | 49.06 | A1 |
| ATOM | 463 | CG | TRP | 59 | 35.254 | 70.712 | -10.889 | 1.00 | 46.37 | A1 |
| ATOM | 464 | CD2 | TRP | 59 | 35.320 | 70.845 | -9.521 | 1.00 | 44.06 | A1 |
| ATOM | 465 | CE2 | TRP | 59 | 33.998 | 71.027 | -9.205 | 1.00 | 44.18 | A1 |
| ATOM | 466 | CE3 | TRP | 59 | 36.274 | 70.842 | -8.538 | 1.00 | 44.03 | A1 |
| ATOM | 467 | CD1 | TRP | 59 | 33.972 | 70.794 | -11.354 | 1.00 | 45.17 | A1 |
| ATOM | 468 | NE1 | TRP | 59 | 33.229 | 70.994 | -10.297 | 1.00 | 43.17 | A1 |
| ATOM | 469 | HE1 | TRP | 59 | 32.301 | 71.312 | -10.332 | 1.00 | 0.00 | A1 |
| ATOM | 470 | CZ2 | TRP | 59 | 33.598 | 71.215 | -7.916 | 1.00 | 45.60 | A1 |
| ATOM | 471 | CZ3 | TRP | 59 | 35.893 | 71.028 | -7.243 | 1.00 | 45.25 | A1 |
| ATOM | 472 | CH2 | TRP | 59 | 34.565 | 71.214 | -6.938 | 1.00 | 46.43 | A1 |
| ATOM | 473 | C | TRP | 59 | 38.815 | 71.435 | -12.256 | 1.00 | 52.84 | A1 |
| ATOM | 474 | O | TRP | 59 | 38.842 | 71.972 | -13.372 | 1.00 | 54.96 | A1 |
| ATOM | 475 | N | ALA | 60 | 39.912 | 70.834 | -11.777 | 1.00 | 51.97 | A1 |
| ATOM | 476 | H | ALA | 60 | 39.857 | 70.269 | -10.977 | 1.00 | 0.00 | A1 |
| ATOM | 477 | CA | ALA | 60 | 41.108 | 70.870 | -12.609 | 1.00 | 52.18 | A1 |
| ATOM | 478 | CB | ALA | 60 | 42.303 | 70.610 | -11.748 | 1.00 | 51.75 | A1 |
| ATOM | 479 | C | ALA | 60 | 41.055 | 69.857 | -13.746 | 1.00 | 52.16 | A1 |
| ATOM | 480 | O | ALA | 60 | 40.545 | 68.760 | -13.530 | 1.00 | 52.17 | A1 |
| ATOM | 481 | N | PRO | 61 | 41.435 | 70.145 | -14.986 | 1.00 | 53.34 | A1 |
| ATOM | 482 | CD | PRO | 61 | 41.370 | 71.458 | -15.622 | 1.00 | 54.76 | A1 |
| ATOM | 483 | CA | PRO | 61 | 41.691 | 69.145 | -15.993 | 1.00 | 55.57 | A1 |
| ATOM | 484 | CB | PRO | 61 | 41.792 | 69.918 | -17.310 | 1.00 | 54.95 | A1 |
| ATOM | 485 | CG | PRO | 61 | 42.211 | 71.297 | -16.901 | 1.00 | 54.05 | A1 |
| ATOM | 486 | C | PRO | 61 | 42.934 | 68.333 | -15.690 | 1.00 | 57.54 | A1 |
| ATOM | 487 | O | PRO | 61 | 43.757 | 68.661 | -14.834 | 1.00 | 57.20 | A1 |
| ATOM | 488 | N | LEU | 62 | 43.040 | 67.271 | -16.486 | 1.00 | 59.98 | A1 |
| ATOM | 489 | H | LEU | 62 | 42.285 | 67.067 | -17.077 | 1.00 | 0.00 | A1 |
| ATOM | 490 | CA | LEU | 62 | 44.184 | 66.370 | -16.471 | 1.00 | 63.64 | A1 |
| ATOM | 491 | CB | LEU | 62 | 44.062 | 65.417 | -15.260 | 1.00 | 63.72 | A1 |
| ATOM | 492 | CG | LEU | 62 | 45.323 | 64.691 | -14.865 | 1.00 | 64.43 | A1 |
| ATOM | 493 | CD1 | LEU | 62 | 46.394 | 65.704 | -14.488 | 1.00 | 64.02 | A2 |
| ATOM | 494 | CD2 | LEU | 62 | 45.016 | 63.764 | -13.717 | 1.00 | 64.98 | A2 |
| ATOM | 495 | C | LEU | 62 | 44.214 | 65.611 | -17.812 | 1.00 | 65.69 | A2 |
| ATOM | 496 | OT1 | LEU | 62 | 44.256 | 66.302 | -18.844 | 1.00 | 68.47 | A2 |
| ATOM | 497 | OT2 | LEU | 62 | 44.194 | 64.371 | -17.845 | 1.00 | 66.57 | A2 |
| ATOM | 498 | CB | LEU | 72 | 57.448 | 63.159 | -19.422 | 1.00 | 63.44 | A2 |
| ATOM | 499 | CG | LEU | 72 | 57.716 | 62.495 | -18.117 | 1.00 | 63.40 | A2 |
| ATOM | 500 | HT3 | LEU | 72 | 56.719 | 61.408 | -17.913 | 1.00 | 61.50 | A2 |
| ATOM | 501 | CD2 | LEU | 72 | 59.107 | 61.901 | -18.121 | 1.00 | 63.22 | A2 |
| ATOM | 502 | C | LEU | 72 | 55.897 | 65.084 | -18.876 | 1.00 | 65.40 | A2 |
| ATOM | 503 | O | LEU | 72 | 54.827 | 65.301 | -18.316 | 1.00 | 67.30 | A2 |
| ATOM | 504 | HT1 | LEU | 72 | 56.469 | 64.683 | -21.261 | 1.00 | 0.00 | A2 |
| ATOM | 505 | HT2 | LEU | 72 | 54.827 | 64.355 | -20.951 | 1.00 | 0.00 | A2 |
| ATOM | 506 | N | LEU | 72 | 55.795 | 63.983 | -20.899 | 1.00 | 66.29 | A2 |
| ATOM | 507 | HT3 | LEU | 72 | 55.866 | 63.098 | -21.439 | 1.00 | 0.00 | A2 |
| ATOM | 508 | CA | LEU | 72 | 56.064 | 63.714 | -19.512 | 1.00 | 64.91 | A2 |
| ATOM | 509 | N | ALA | 73 | 56.807 | 66.046 | -19.086 | 1.00 | 64.54 | A2 |
| ATOM | 510 | H | ALA | 73 | 57.690 | 65.804 | -19.432 | 1.00 | 0.00 | A2 |
| ATOM | 511 | CA | ALA | 73 | 56.707 | 67.433 | -18.615 | 1.00 | 62.55 | A2 |
| ATOM | 512 | CB | ALA | 73 | 57.553 | 68.314 | -19.529 | 1.00 | 64.84 | A2 |
| ATOM | 513 | C | ALA | 73 | 55.319 | 68.024 | -18.539 | 1.00 | 60.37 | A2 |
| ATOM | 514 | O | ALA | 73 | 54.801 | 68.180 | -17.456 | 1.00 | 59.42 | A2 |
| ATOM | 515 | N | GLY | 74 | 54.693 | 68.226 | -19.691 | 1.00 | 59.72 | A2 |

FIG. 5G

| | | | | | | | | | |
|---|---|---|---|---|---|---|---|---|---|
| ATOM | 516 | H | GLY | 74 | 55.212 | 68.174 | -20.514 | 1.00 0.00 | A2 |
| ATOM | 517 | CA | GLY | 74 | 53.336 | 68.728 | -19.816 | 1.00 59.99 | A2 |
| ATOM | 518 | C | GLY | 74 | 52.327 | 68.114 | -18.865 | 1.00 60.27 | A2 |
| ATOM | 519 | O | GLY | 74 | 51.880 | 68.796 | -17.935 | 1.00 60.80 | A2 |
| ATOM | 520 | N | CYS | 75 | 51.945 | 66.850 | -19.030 | 1.00 59.60 | A2 |
| ATOM | 521 | H | CYS | 75 | 52.160 | 66.358 | -19.839 | 1.00 0.00 | A2 |
| ATOM | 522 | CA | CYS | 75 | 51.002 | 66.276 | -18.078 | 1.00 60.17 | A2 |
| ATOM | 523 | CB | CYS | 75 | 50.670 | 64.801 | -18.464 | 1.00 64.08 | A2 |
| ATOM | 524 | SG | CYS | 75 | 49.832 | 64.732 | -20.096 | 1.00 73.47 | A2 |
| ATOM | 525 | C | CYS | 75 | 51.502 | 66.346 | -16.642 | 1.00 56.73 | A2 |
| ATOM | 526 | O | CYS | 75 | 50.734 | 66.748 | -15.765 | 1.00 55.82 | A2 |
| ATOM | 527 | N | LEU | 76 | 52.795 | 66.142 | -16.396 | 1.00 53.93 | A2 |
| ATOM | 528 | H | LEU | 76 | 53.423 | 66.043 | -17.137 | 1.00 0.00 | A2 |
| ATOM | 529 | CA | LEU | 76 | 53.325 | 66.156 | -15.044 | 1.00 52.94 | A2 |
| ATOM | 530 | CB | LEU | 76 | 54.798 | 65.754 | -15.181 | 1.00 50.81 | A2 |
| ATOM | 531 | CG | LEU | 76 | 55.575 | 65.011 | -14.090 | 1.00 49.02 | A2 |
| ATOM | 532 | CD1 | LEU | 76 | 54.852 | 63.740 | -13.698 | 1.00 46.76 | A2 |
| ATOM | 533 | CD2 | LEU | 76 | 56.951 | 64.633 | -14.623 | 1.00 47.67 | A2 |
| ATOM | 534 | C | LEU | 76 | 53.093 | 67.545 | -14.425 | 1.00 53.65 | A2 |
| ATOM | 535 | O | LEU | 76 | 52.731 | 67.716 | -13.244 | 1.00 53.50 | A2 |
| ATOM | 536 | N | SER | 77 | 53.137 | 68.553 | -15.301 | 1.00 53.91 | A2 |
| ATOM | 537 | H | SER | 77 | 53.322 | 68.361 | -16.242 | 1.00 0.00 | A2 |
| ATOM | 538 | CA | SER | 77 | 52.882 | 69.932 | -14.942 | 1.00 54.93 | A2 |
| ATOM | 539 | CB | SER | 77 | 53.425 | 70.835 | -16.040 | 1.00 58.32 | A2 |
| ATOM | 540 | OG | SER | 77 | 54.806 | 70.587 | -16.310 | 1.00 63.35 | A2 |
| ATOM | 541 | HG | SER | 77 | 54.949 | 69.637 | -16.315 | 1.00 0.00 | A2 |
| ATOM | 542 | C | SER | 77 | 51.382 | 70.172 | -14.759 | 1.00 53.47 | A2 |
| ATOM | 543 | O | SER | 77 | 50.982 | 70.965 | -13.899 | 1.00 53.54 | A2 |
| ATOM | 544 | N | GLN | 78 | 50.509 | 69.501 | -15.512 | 1.00 51.82 | A2 |
| ATOM | 545 | H | GLN | 78 | 50.857 | 68.901 | -16.207 | 1.00 0.00 | A2 |
| ATOM | 546 | CA | GLN | 78 | 49.074 | 69.619 | -15.349 | 1.00 50.74 | A2 |
| ATOM | 547 | CB | GLN | 78 | 48.402 | 68.877 | -16.451 | 1.00 54.31 | A2 |
| ATOM | 548 | CG | GLN | 78 | 47.420 | 69.784 | -17.160 | 1.00 58.59 | A2 |
| ATOM | 549 | CD | GLN | 78 | 46.557 | 68.940 | -18.071 | 1.00 62.32 | A2 |
| ATOM | 550 | OE1 | GLN | 78 | 47.005 | 68.260 | -18.998 | 1.00 65.94 | A2 |
| ATOM | 551 | NE2 | GLN | 78 | 45.269 | 68.889 | -17.800 | 1.00 63.17 | A2 |
| ATOM | 552 | HE21 | GLN | 78 | 44.973 | 69.327 | -16.972 | 1.00 0.00 | A2 |
| ATOM | 553 | HE22 | GLN | 78 | 44.704 | 68.444 | -18.456 | 1.00 0.00 | A2 |
| ATOM | 554 | C | GLN | 78 | 48.591 | 69.065 | -14.011 | 1.00 48.17 | A2 |
| ATOM | 555 | O | GLN | 78 | 47.691 | 69.618 | -13.368 | 1.00 46.31 | A2 |
| ATOM | 556 | N | LEU | 79 | 49.236 | 67.988 | -13.564 | 1.00 45.89 | A2 |
| ATOM | 557 | H | LEU | 79 | 49.920 | 67.584 | -14.140 | 1.00 0.00 | A2 |
| ATOM | 558 | CA | LEU | 79 | 48.919 | 67.359 | -12.294 | 1.00 44.54 | A2 |
| ATOM | 559 | CB | LEU | 79 | 49.617 | 66.015 | -12.259 | 1.00 45.06 | A2 |
| ATOM | 560 | CG | LEU | 79 | 49.154 | 64.895 | -11.351 | 1.00 45.18 | A2 |
| ATOM | 561 | CD1 | LEU | 79 | 49.634 | 63.594 | -11.957 | 1.00 48.06 | A2 |
| ATOM | 562 | CD2 | LEU | 79 | 49.766 | 64.986 | -9.969 | 1.00 46.03 | A2 |
| ATOM | 563 | C | LEU | 79 | 49.366 | 68.265 | -11.170 | 1.00 43.49 | A2 |
| ATOM | 564 | O | LEU | 79 | 48.645 | 68.509 | -10.199 | 1.00 43.20 | A2 |
| ATOM | 565 | N | HIS | 80 | 50.556 | 68.834 | -11.329 | 1.00 43.83 | A2 |
| ATOM | 566 | H | HIS | 80 | 51.115 | 68.548 | -12.085 | 1.00 0.00 | A2 |
| ATOM | 567 | CA | HIS | 80 | 51.060 | 69.788 | -10.360 | 1.00 43.79 | A2 |
| ATOM | 568 | CB | HIS | 80 | 52.456 | 70.221 | -10.810 | 1.00 43.58 | A2 |
| ATOM | 569 | CG | HIS | 80 | 53.030 | 71.031 | -9.690 | 1.00 43.75 | A2 |
| ATOM | 570 | CD2 | HIS | 80 | 53.484 | 70.497 | -8.517 | 1.00 47.48 | A2 |
| ATOM | 571 | ND1 | HIS | 80 | 53.083 | 72.343 | -9.567 | 1.00 44.24 | A2 |
| ATOM | 572 | HD1 | HIS | 80 | 52.842 | 73.004 | -10.255 | 1.00 0.00 | A2 |
| ATOM | 573 | CE1 | HIS | 80 | 53.530 | 72.641 | -8.376 | 1.00 44.47 | A2 |
| ATOM | 574 | NE2 | HIS | 80 | 53.772 | 71.520 | -7.748 | 1.00 48.16 | A2 |
| ATOM | 575 | HE2 | HIS | 80 | 54.103 | 71.444 | -6.824 | 1.00 0.00 | A2 |
| ATOM | 576 | C | HIS | 80 | 50.094 | 70.978 | -10.229 | 1.00 44.40 | A2 |
| ATOM | 577 | O | HIS | 80 | 49.643 | 71.294 | -9.131 | 1.00 44.28 | A2 |
| ATOM | 578 | N | SER | 81 | 49.733 | 71.670 | -11.309 | 1.00 45.13 | A2 |
| ATOM | 579 | H | SER | 81 | 50.136 | 71.459 | -12.176 | 1.00 0.00 | A2 |
| ATOM | 580 | CA | SER | 81 | 48.738 | 72.742 | -11.296 | 1.00 45.41 | A2 |
| ATOM | 581 | CB | SER | 81 | 48.612 | 73.347 | -12.682 | 1.00 45.59 | A2 |
| ATOM | 582 | OG | SER | 81 | 49.894 | 73.444 | -13.292 | 1.00 49.27 | A2 |
| ATOM | 583 | HG | SER | 81 | 50.058 | 72.670 | -13.843 | 1.00 0.00 | A2 |
| ATOM | 584 | C | SER | 81 | 47.344 | 72.266 | -10.856 | 1.00 44.85 | A2 |
| ATOM | 585 | O | SER | 81 | 46.604 | 73.064 | -10.256 | 1.00 46.83 | A2 |
| ATOM | 586 | N | GLY | 82 | 46.946 | 71.010 | -11.092 | 1.00 42.16 | A2 |
| ATOM | 587 | H | GLY | 82 | 47.513 | 70.411 | -11.614 | 1.00 0.00 | A2 |
| ATOM | 588 | CA | GLY | 82 | 45.663 | 70.500 | -10.650 | 1.00 39.39 | A2 |
| ATOM | 589 | C | GLY | 82 | 45.569 | 70.461 | -9.139 | 1.00 39.30 | A2 |
| ATOM | 590 | O | GLY | 82 | 44.542 | 70.843 | -8.544 | 1.00 39.64 | A2 |
| ATOM | 591 | N | LEU | 83 | 46.676 | 70.032 | -8.521 | 1.00 37.57 | A2 |
| ATOM | 592 | H | LEU | 83 | 47.413 | 69.695 | -9.075 | 1.00 0.00 | A2 |
| ATOM | 593 | CA | LEU | 83 | 46.826 | 70.007 | -7.057 | 1.00 38.07 | A2 |
| ATOM | 594 | CB | LEU | 83 | 48.133 | 69.202 | -6.748 | 1.00 35.67 | A2 |
| ATOM | 595 | CG | LEU | 83 | 48.071 | 67.736 | -7.225 | 1.00 32.51 | A2 |
| ATOM | 596 | CD1 | LEU | 83 | 49.442 | 67.145 | -7.319 | 1.00 29.77 | A2 |
| ATOM | 597 | CD2 | LEU | 83 | 47.180 | 66.973 | -6.288 | 1.00 28.71 | A2 |
| ATOM | 598 | C | LEU | 83 | 46.836 | 71.386 | -6.354 | 1.00 38.48 | A2 |
| ATOM | 599 | O | LEU | 83 | 46.392 | 71.627 | -5.219 | 1.00 38.05 | A2 |
| ATOM | 600 | N | PHE | 84 | 47.366 | 72.338 | -7.108 | 1.00 40.34 | A2 |
| ATOM | 601 | H | PHE | 84 | 47.804 | 72.078 | -7.944 | 1.00 0.00 | A2 |

FIG. 5H

| | | | | | | | | | | | | | | | | | | | | |
|---|---|---|---|---|---|---|---|---|---|---|---|---|---|---|---|---|---|---|---|---|
| ATOM | 602 | CA | PHE | 84 | 47.414 | 73.703 | -6.688 | 1.00 | 41.54 | A2 | ATOM | 645 | C | GLN | 87 | 43.941 | 74.652 | -2.013 | 1.00 34.36 | A2 |
| ATOM | 603 | CB | PHE | 84 | 48.163 | 74.531 | -7.693 | 1.00 | 46.88 | A2 | ATOM | 646 | O | GLN | 87 | 43.414 | 74.990 | -0.935 | 1.00 31.55 | A2 |
| ATOM | 604 | CG | PHE | 84 | 48.715 | 75.777 | -6.988 | 1.00 | 55.09 | A2 | ATOM | 647 | N | GLY | 88 | 43.740 | 75.335 | -3.159 | 1.00 32.73 | A2 |
| ATOM | 605 | CD1 | PHE | 84 | 49.521 | 75.622 | -5.849 | 1.00 | 55.31 | A2 | ATOM | 648 | H | GLY | 88 | 44.165 | 75.005 | -3.981 | 1.00 0.00 | A2 |
| ATOM | 606 | CD2 | PHE | 84 | 48.396 | 77.053 | -7.469 | 1.00 | 55.79 | A2 | ATOM | 649 | CA | GLY | 88 | 42.948 | 76.546 | -3.232 | 1.00 30.81 | A2 |
| ATOM | 607 | CE1 | PHE | 84 | 50.004 | 76.737 | -5.195 | 1.00 | 57.60 | A2 | ATOM | 650 | C | GLY | 88 | 41.540 | 76.275 | -2.731 | 1.00 30.47 | A2 |
| ATOM | 608 | CE2 | PHE | 84 | 48.892 | 78.156 | -6.796 | 1.00 | 57.25 | A2 | ATOM | 651 | O | GLY | 88 | 41.130 | 76.819 | -1.703 | 1.00 30.27 | A2 |
| ATOM | 609 | CZ | PHE | 84 | 49.688 | 78.002 | -5.667 | 1.00 | 58.34 | A2 | ATOM | 652 | N | LEU | 89 | 40.802 | 75.387 | -3.406 | 1.00 29.01 | A2 |
| ATOM | 610 | C | PHE | 84 | 45.994 | 74.191 | -6.591 | 1.00 | 40.47 | A2 | ATOM | 653 | H | LEU | 89 | 41.220 | 74.912 | -4.154 | 1.00 0.00 | A2 |
| ATOM | 611 | O | PHE | 84 | 45.609 | 74.749 | -5.558 | 1.00 | 42.71 | A2 | ATOM | 654 | CA | LEU | 89 | 39.447 | 75.102 | -3.009 | 1.00 27.60 | A2 |
| ATOM | 612 | N | LEU | 85 | 45.190 | 73.953 | -7.622 | 1.00 | 38.64 | A2 | ATOM | 655 | CB | LEU | 89 | 38.922 | 74.073 | -3.935 | 1.00 28.13 | A2 |
| ATOM | 613 | H | LEU | 85 | 45.555 | 73.527 | -8.429 | 1.00 | 0.00 | A2 | ATOM | 656 | CG | LEU | 89 | 38.764 | 74.583 | -5.340 | 1.00 29.51 | A2 |
| ATOM | 614 | CA | LEU | 85 | 43.794 | 74.335 | -7.584 | 1.00 | 38.81 | A2 | ATOM | 657 | CD1 | LEU | 89 | 38.363 | 73.530 | -6.364 | 1.00 24.13 | A2 |
| ATOM | 615 | CB | LEU | 85 | 43.101 | 73.886 | -8.839 | 1.00 | 41.27 | A2 | ATOM | 658 | CD2 | LEU | 89 | 37.673 | 75.637 | -5.220 | 1.00 32.87 | A2 |
| ATOM | 616 | CG | LEU | 85 | 41.673 | 74.403 | -9.017 | 1.00 | 46.45 | A2 | ATOM | 659 | C | LEU | 89 | 39.352 | 74.629 | -1.583 | 1.00 29.88 | A2 |
| ATOM | 617 | CD1 | LEU | 85 | 41.702 | 75.784 | -9.719 | 1.00 | 47.80 | A2 | ATOM | 660 | O | LEU | 89 | 38.427 | 75.012 | -0.860 | 1.00 30.81 | A2 |
| ATOM | 618 | CD2 | LEU | 85 | 40.860 | 73.359 | -9.787 | 1.00 | 48.25 | A2 | ATOM | 661 | N | LEU | 90 | 40.317 | 73.839 | -1.094 | 1.00 32.59 | A2 |
| ATOM | 619 | C | LEU | 85 | 43.079 | 73.731 | -6.386 | 1.00 | 38.20 | A2 | ATOM | 662 | H | LEU | 90 | 41.101 | 73.626 | -1.643 | 1.00 0.00 | A2 |
| ATOM | 620 | O | LEU | 85 | 42.498 | 74.469 | -5.582 | 1.00 | 38.36 | A2 | ATOM | 663 | CA | LEU | 90 | 40.182 | 73.274 | 0.235 | 1.00 33.41 | A2 |
| ATOM | 621 | N | TYR | 86 | 43.150 | 72.405 | -6.198 | 1.00 | 37.92 | A2 | ATOM | 664 | CB | LEU | 90 | 41.207 | 72.234 | 0.503 | 1.00 36.15 | A2 |
| ATOM | 622 | H | TYR | 86 | 43.637 | 71.850 | -6.845 | 1.00 | 0.00 | A2 | ATOM | 665 | CG | LEU | 90 | 41.075 | 70.971 | -0.343 | 1.00 38.76 | A2 |
| ATOM | 623 | CA | TYR | 86 | 42.501 | 71.801 | -5.057 | 1.00 | 37.15 | A2 | ATOM | 666 | CD1 | LEU | 90 | 42.431 | 70.267 | -0.456 | 1.00 37.21 | A2 |
| ATOM | 624 | CB | TYR | 86 | 42.598 | 70.255 | -5.102 | 1.00 | 36.73 | A2 | ATOM | 667 | CD2 | LEU | 90 | 39.995 | 70.099 | 0.279 | 1.00 40.54 | A2 |
| ATOM | 625 | CG | TYR | 86 | 41.561 | 69.685 | -6.081 | 1.00 | 33.66 | A2 | ATOM | 668 | C | LEU | 90 | 40.342 | 74.319 | 1.255 | 1.00 34.24 | A2 |
| ATOM | 626 | CD1 | TYR | 86 | 41.946 | 69.312 | -7.374 | 1.00 | 30.03 | A2 | ATOM | 669 | O | LEU | 90 | 39.711 | 74.256 | 2.313 | 1.00 35.57 | A2 |
| ATOM | 627 | CE1 | TYR | 86 | 40.991 | 68.885 | -8.280 | 1.00 | 30.08 | A2 | ATOM | 670 | N | GLN | 91 | 41.188 | 75.291 | 0.940 | 1.00 35.24 | A2 |
| ATOM | 628 | CD2 | TYR | 86 | 40.224 | 69.623 | -5.666 | 1.00 | 32.61 | A2 | ATOM | 671 | H | GLN | 91 | 41.663 | 75.284 | 0.078 | 1.00 0.00 | A2 |
| ATOM | 629 | CE2 | TYR | 86 | 39.263 | 69.203 | -6.574 | 1.00 | 31.66 | A2 | ATOM | 672 | CA | GLN | 91 | 41.397 | 76.373 | 1.883 | 1.00 37.60 | A2 |
| ATOM | 630 | CZ | TYR | 86 | 39.656 | 68.838 | -7.868 | 1.00 | 30.57 | A2 | ATOM | 673 | CB | GLN | 91 | 42.557 | 77.182 | 1.363 | 1.00 39.65 | A2 |
| ATOM | 631 | OH | TYR | 86 | 38.670 | 68.428 | -8.751 | 1.00 | 28.18 | A2 | ATOM | 674 | CG | GLN | 91 | 43.155 | 78.237 | 2.284 | 1.00 44.32 | A2 |
| ATOM | 632 | HH | TYR | 86 | 39.107 | 67.994 | -9.485 | 1.00 | 0.00 | A2 | ATOM | 675 | CD | GLN | 91 | 44.348 | 78.799 | 1.542 | 1.00 46.96 | A2 |
| ATOM | 633 | C | TYR | 86 | 43.054 | 72.318 | -3.746 | 1.00 | 37.75 | A2 | ATOM | 676 | OE1 | GLN | 91 | 45.235 | 78.083 | 1.068 | 1.00 47.42 | A2 |
| ATOM | 634 | O | TYR | 86 | 42.173 | 72.469 | -2.889 | 1.00 | 39.52 | A2 | ATOM | 677 | NE2 | GLN | 91 | 44.376 | 80.092 | 1.341 | 1.00 46.82 | A2 |
| ATOM | 635 | N | GLN | 87 | 44.347 | 72.655 | -3.478 | 1.00 | 36.93 | A2 | ATOM | 678 | HE21 | GLN | 91 | 43.690 | 80.685 | 1.700 | 1.00 0.00 | A2 |
| ATOM | 636 | H | GLN | 87 | 45.044 | 72.463 | -4.140 | 1.00 | 0.00 | A2 | ATOM | 679 | HE22 | GLN | 91 | 45.108 | 80.331 | 0.741 | 1.00 0.00 | A2 |
| ATOM | 637 | CA | GLN | 87 | 44.749 | 73.332 | -2.205 | 1.00 | 36.40 | A2 | ATOM | 680 | C | GLN | 91 | 40.129 | 77.231 | 2.061 | 1.00 37.22 | A2 |
| ATOM | 638 | CB | GLN | 87 | 46.210 | 73.668 | -2.255 | 1.00 | 39.56 | A2 | ATOM | 681 | O | GLN | 91 | 39.718 | 77.530 | 3.186 | 1.00 36.21 | A2 |
| ATOM | 639 | CG | GLN | 87 | 47.126 | 72.993 | -1.237 | 1.00 | 46.99 | A2 | ATOM | 682 | N | ALA | 92 | 39.456 | 77.570 | 0.943 | 1.00 38.63 | A2 |
| ATOM | 640 | CD | GLN | 87 | 48.641 | 73.062 | -1.576 | 1.00 | 50.96 | A2 | ATOM | 683 | H | ALA | 92 | 39.808 | 77.205 | 0.098 | 1.00 0.00 | A2 |
| ATOM | 641 | OE1 | GLN | 87 | 49.144 | 72.623 | -2.627 | 1.00 | 52.15 | A2 | ATOM | 684 | CA | ALA | 92 | 38.243 | 78.402 | 0.880 | 1.00 38.10 | A2 |
| ATOM | 642 | NE2 | GLN | 87 | 49.446 | 73.608 | -0.663 | 1.00 | 52.96 | A2 | ATOM | 685 | CB | ALA | 92 | 37.657 | 78.436 | -0.511 | 1.00 36.76 | A2 |
| ATOM | 643 | HE21 | GLN | 87 | 49.055 | 73.957 | 0.164 | 1.00 | 0.00 | A2 | ATOM | 686 | C | ALA | 92 | 37.139 | 77.905 | 1.770 | 1.00 38.95 | A2 |
| ATOM | 644 | HE22 | GLN | 87 | 50.396 | 73.621 | -0.888 | 1.00 | 0.00 | A2 | ATOM | 687 | O | ALA | 92 | 36.294 | 78.687 | 2.194 | 1.00 42.45 | A2 |

| | | | | | | | | | |
|---|---|---|---|---|---|---|---|---|---|
| ATOM | 688 | N | LEU | 93 | 37.151 | 76.618 | 2.123 | 1.00 38.34 | A2 |
| ATOM | 689 | H | LEU | 93 | 37.855 | 76.040 | 1.759 | 1.00 0.00 | A2 |
| ATOM | 690 | CA | LEU | 93 | 36.111 | 76.018 | 2.972 | 1.00 36.90 | A2 |
| ATOM | 691 | CB | LEU | 93 | 36.088 | 74.463 | 2.794 | 1.00 35.34 | A2 |
| ATOM | 692 | CG | LEU | 93 | 35.725 | 73.992 | 1.378 | 1.00 33.55 | A2 |
| ATOM | 693 | CD1 | LEU | 93 | 36.159 | 72.583 | 1.129 | 1.00 33.26 | A2 |
| ATOM | 694 | CD2 | LEU | 93 | 34.254 | 74.167 | 1.215 | 1.00 32.18 | A2 |
| ATOM | 695 | C | LEU | 93 | 36.264 | 76.353 | 4.426 | 1.00 36.44 | A2 |
| ATOM | 696 | O | LEU | 93 | 35.473 | 75.917 | 5.256 | 1.00 35.17 | A2 |
| ATOM | 697 | N | GLU | 93 | 37.357 | 77.019 | 4.736 | 1.00 38.19 | A2 |
| ATOM | 698 | H | GLU | 94 | 38.022 | 77.167 | 4.035 | 1.00 0.00 | A2 |
| ATOM | 699 | CA | GLU | 94 | 37.627 | 77.573 | 6.038 | 1.00 42.71 | A2 |
| ATOM | 700 | CB | GLU | 94 | 36.931 | 78.947 | 6.165 | 1.00 47.38 | A2 |
| ATOM | 701 | CG | GLU | 94 | 37.418 | 80.011 | 5.131 | 1.00 56.10 | A2 |
| ATOM | 702 | CD | GLU | 94 | 36.423 | 81.153 | 4.862 | 1.00 60.26 | A2 |
| ATOM | 703 | OE1 | GLU | 94 | 35.728 | 81.109 | 3.823 | 1.00 60.76 | A2 |
| ATOM | 704 | OE2 | GLU | 94 | 36.331 | 82.054 | 5.721 | 1.00 61.64 | A2 |
| ATOM | 705 | C | GLU | 94 | 37.245 | 76.701 | 7.198 | 1.00 43.90 | A2 |
| ATOM | 706 | O | GLU | 94 | 36.624 | 77.172 | 8.167 | 1.00 45.70 | A2 |
| ATOM | 707 | N | GLY | 95 | 37.641 | 75.410 | 7.001 | 1.00 44.03 | A2 |
| ATOM | 708 | H | GLY | 95 | 38.024 | 75.192 | 6.127 | 1.00 0.00 | A2 |
| ATOM | 709 | CA | GLY | 95 | 37.519 | 74.310 | 7.981 | 1.00 42.49 | A2 |
| ATOM | 710 | C | GLY | 95 | 36.162 | 73.612 | 8.061 | 1.00 42.24 | A2 |
| ATOM | 711 | O | GLY | 95 | 36.028 | 72.596 | 8.739 | 1.00 40.02 | A2 |
| ATOM | 712 | N | ILE | 96 | 35.160 | 74.123 | 7.328 | 1.00 42.82 | A2 |
| ATOM | 713 | H | ILE | 96 | 35.357 | 74.944 | 6.841 | 1.00 0.00 | A2 |
| ATOM | 714 | CA | ILE | 96 | 33.760 | 73.692 | 7.312 | 1.00 42.12 | A2 |
| ATOM | 715 | CB | ILE | 96 | 33.665 | 72.233 | 6.800 | 1.00 36.33 | A2 |
| ATOM | 716 | CG2 | ILE | 96 | 32.248 | 71.768 | 6.789 | 1.00 34.79 | A2 |
| ATOM | 717 | CG1 | ILE | 96 | 34.091 | 72.157 | 5.374 | 1.00 35.35 | A2 |
| ATOM | 718 | CD | ILE | 96 | 34.051 | 70.743 | 4.738 | 1.00 33.64 | A2 |
| ATOM | 719 | C | ILE | 96 | 33.106 | 73.863 | 8.709 | 1.00 44.74 | A2 |
| ATOM | 720 | O | ILE | 96 | 32.220 | 74.716 | 8.841 | 1.00 44.29 | A2 |
| ATOM | 721 | N | SER | 97 | 33.467 | 73.154 | 9.780 | 1.00 46.84 | A2 |
| ATOM | 722 | H | SER | 97 | 34.243 | 72.553 | 9.706 | 1.00 0.00 | A2 |
| ATOM | 723 | CA | SER | 97 | 32.900 | 73.359 | 11.105 | 1.00 48.91 | A2 |
| ATOM | 724 | CB | SER | 97 | 31.804 | 72.343 | 11.347 | 1.00 49.60 | A2 |
| ATOM | 725 | OG | SER | 97 | 32.211 | 71.120 | 11.954 | 1.00 52.85 | A2 |
| ATOM | 726 | HG | SER | 97 | 31.406 | 70.573 | 11.942 | 1.00 0.00 | A2 |
| ATOM | 727 | C | SER | 97 | 34.045 | 73.143 | 12.077 | 1.00 50.64 | A2 |
| ATOM | 728 | O | SER | 97 | 35.035 | 72.538 | 11.678 | 1.00 52.78 | A2 |
| ATOM | 729 | N | PRO | 98 | 34.063 | 73.474 | 13.348 | 1.00 52.12 | A2 |
| ATOM | 730 | CD | PRO | 98 | 33.002 | 74.170 | 14.016 | 1.00 52.90 | A2 |
| ATOM | 731 | CA | PRO | 98 | 35.195 | 73.200 | 14.257 | 1.00 54.94 | A2 |
| ATOM | 732 | CB | PRO | 98 | 34.750 | 73.717 | 15.600 | 1.00 54.78 | A2 |
| ATOM | 733 | CG | PRO | 98 | 33.772 | 74.777 | 15.182 | 1.00 55.48 | A2 |
| ATOM | 734 | C | PRO | 98 | 35.591 | 71.723 | 14.336 | 1.00 56.75 | A2 |
| ATOM | 735 | O | PRO | 98 | 36.738 | 71.274 | 14.468 | 1.00 57.85 | A2 |
| ATOM | 736 | N | GLU | 99 | 34.509 | 70.971 | 14.214 | 1.00 58.21 | A2 |
| ATOM | 737 | H | GLU | 99 | 33.652 | 71.400 | 14.028 | 1.00 0.00 | A2 |
| ATOM | 738 | CA | GLU | 99 | 34.543 | 69.537 | 14.281 | 1.00 58.48 | A2 |
| ATOM | 739 | CB | GLU | 99 | 33.111 | 69.104 | 14.304 | 1.00 63.30 | A2 |
| ATOM | 740 | CG | GLU | 99 | 32.958 | 67.702 | 14.852 | 1.00 71.04 | A2 |
| ATOM | 741 | CD | GLU | 99 | 32.076 | 66.838 | 13.962 | 1.00 76.95 | A2 |
| ATOM | 742 | OE1 | GLU | 99 | 32.209 | 65.608 | 14.079 | 1.00 80.63 | A2 |
| ATOM | 743 | OE2 | GLU | 99 | 31.295 | 67.382 | 13.153 | 1.00 77.99 | A2 |
| ATOM | 744 | C | GLU | 99 | 35.298 | 69.025 | 13.074 | 1.00 55.31 | A2 |
| ATOM | 745 | O | GLU | 99 | 36.251 | 68.270 | 13.210 | 1.00 55.96 | A2 |
| ATOM | 746 | N | LEU | 100 | 34.916 | 69.475 | 11.891 | 1.00 51.23 | A2 |
| ATOM | 747 | H | LEU | 100 | 34.214 | 70.159 | 11.841 | 1.00 0.00 | A2 |
| ATOM | 748 | CA | LEU | 100 | 35.577 | 69.052 | 10.678 | 1.00 48.08 | A2 |
| ATOM | 749 | CB | LEU | 100 | 34.627 | 69.341 | 9.574 | 1.00 45.52 | A2 |
| ATOM | 750 | CG | LEU | 100 | 33.544 | 68.337 | 9.674 | 1.00 45.39 | A2 |
| ATOM | 751 | CD1 | LEU | 100 | 32.207 | 68.972 | 9.458 | 1.00 46.40 | A2 |
| ATOM | 752 | CD2 | LEU | 100 | 33.851 | 67.245 | 8.677 | 1.00 47.48 | A2 |
| ATOM | 753 | C | LEU | 100 | 36.956 | 69.629 | 10.368 | 1.00 46.77 | A2 |
| ATOM | 754 | O | LEU | 100 | 37.578 | 69.244 | 9.357 | 1.00 46.62 | A2 |
| ATOM | 755 | N | GLY | 101 | 37.441 | 70.505 | 11.272 | 1.00 45.40 | A2 |
| ATOM | 756 | H | GLY | 101 | 36.893 | 70.704 | 12.056 | 1.00 0.00 | A2 |
| ATOM | 757 | CA | GLY | 101 | 38.703 | 71.238 | 11.126 | 1.00 42.52 | A2 |
| ATOM | 758 | C | GLY | 101 | 39.885 | 70.334 | 10.798 | 1.00 40.73 | A2 |
| ATOM | 759 | O | GLY | 101 | 40.475 | 70.402 | 9.710 | 1.00 40.69 | A2 |
| ATOM | 760 | N | PRO | 102 | 40.250 | 69.441 | 11.708 | 1.00 38.61 | A2 |
| ATOM | 761 | CD | PRO | 102 | 39.676 | 69.350 | 13.027 | 1.00 39.26 | A2 |
| ATOM | 762 | CA | PRO | 102 | 41.390 | 68.566 | 11.606 | 1.00 37.30 | A2 |
| ATOM | 763 | CB | PRO | 102 | 41.294 | 67.690 | 12.775 | 1.00 39.36 | A2 |
| ATOM | 764 | CG | PRO | 102 | 40.799 | 68.687 | 13.776 | 1.00 41.02 | A2 |
| ATOM | 765 | C | PRO | 102 | 41.364 | 67.795 | 10.331 | 1.00 37.15 | A2 |
| ATOM | 766 | O | PRO | 102 | 42.358 | 67.854 | 9.600 | 1.00 38.88 | A2 |
| ATOM | 767 | N | THR | 103 | 40.223 | 67.167 | 10.045 | 1.00 35.36 | A2 |
| ATOM | 768 | H | THR | 103 | 39.466 | 67.223 | 10.662 | 1.00 0.00 | A2 |
| ATOM | 769 | CA | THR | 103 | 40.051 | 66.386 | 8.843 | 1.00 34.62 | A2 |
| ATOM | 770 | CB | THR | 103 | 38.592 | 65.888 | 8.715 | 1.00 34.07 | A2 |
| ATOM | 771 | OG1 | THR | 103 | 38.356 | 65.240 | 9.936 | 1.00 35.43 | A2 |
| ATOM | 772 | HG1 | THR | 103 | 38.011 | 65.896 | 10.548 | 1.00 0.00 | A2 |
| ATOM | 773 | CG2 | THR | 103 | 38.312 | 64.896 | 7.594 | 1.00 31.29 | A2 |

FIG. 51

| | | | | | | | | | |
|---|---|---|---|---|---|---|---|---|---|
| ATOM | 774 | C | THR | 103 | 40.417 | 67.215 | 7.625 | 1.00 34.61 | A2 |
| ATOM | 775 | O | THR | 103 | 41.091 | 66.665 | 6.738 | 1.00 38.16 | A2 |
| ATOM | 776 | N | LEU | 104 | 40.054 | 68.498 | 7.529 | 1.00 32.49 | A2 |
| ATOM | 777 | H | LEU | 104 | 39.504 | 68.923 | 8.229 | 1.00 0.00 | A2 |
| ATOM | 778 | CA | LEU | 104 | 40.471 | 69.267 | 6.370 | 1.00 30.49 | A2 |
| ATOM | 779 | CB | LEU | 104 | 39.616 | 70.430 | 6.242 | 1.00 33.51 | A2 |
| ATOM | 780 | CG | LEU | 104 | 38.356 | 69.996 | 5.611 | 1.00 36.61 | A2 |
| ATOM | 781 | CD1 | LEU | 104 | 37.222 | 70.621 | 6.381 | 1.00 39.43 | A2 |
| ATOM | 782 | CD2 | LEU | 104 | 38.418 | 70.294 | 4.132 | 1.00 37.89 | A2 |
| ATOM | 783 | C | LEU | 104 | 41.904 | 69.727 | 6.414 | 1.00 28.48 | A2 |
| ATOM | 784 | O | LEU | 104 | 42.583 | 69.825 | 5.398 | 1.00 28.47 | A2 |
| ATOM | 785 | N | ASP | 105 | 42.449 | 69.949 | 7.574 | 1.00 26.99 | A2 |
| ATOM | 786 | H | ASP | 105 | 41.903 | 69.912 | 8.388 | 1.00 0.00 | A2 |
| ATOM | 787 | CA | ASP | 105 | 43.822 | 70.307 | 7.613 | 1.00 28.67 | A2 |
| ATOM | 788 | CB | ASP | 105 | 44.139 | 70.584 | 9.038 | 1.00 33.06 | A2 |
| ATOM | 789 | CG | ASP | 105 | 43.438 | 71.808 | 9.593 | 1.00 35.46 | A2 |
| ATOM | 790 | OD1 | ASP | 105 | 43.085 | 72.726 | 8.836 | 1.00 38.42 | A2 |
| ATOM | 791 | OD2 | ASP | 105 | 43.244 | 71.816 | 10.808 | 1.00 39.10 | A2 |
| ATOM | 792 | C | ASP | 105 | 44.701 | 69.206 | 7.032 | 1.00 28.90 | A2 |
| ATOM | 793 | O | ASP | 105 | 45.551 | 69.479 | 6.175 | 1.00 29.62 | A2 |
| ATOM | 794 | N | THR | 106 | 44.415 | 67.950 | 7.401 | 1.00 26.86 | A2 |
| ATOM | 795 | H | THR | 106 | 43.674 | 67.826 | 8.029 | 1.00 0.00 | A2 |
| ATOM | 796 | CA | THR | 106 | 45.143 | 66.770 | 6.935 | 1.00 24.81 | A2 |
| ATOM | 797 | CB | THR | 106 | 44.558 | 65.456 | 7.477 | 1.00 26.03 | A2 |
| ATOM | 798 | OG1 | THR | 106 | 44.680 | 65.566 | 8.894 | 1.00 31.53 | A2 |
| ATOM | 799 | HG1 | THR | 106 | 44.069 | 66.223 | 9.242 | 1.00 0.00 | A2 |
| ATOM | 800 | CG2 | THR | 106 | 45.258 | 64.220 | 7.011 | 1.00 20.90 | A2 |
| ATOM | 801 | C | THR | 106 | 45.073 | 66.684 | 5.460 | 1.00 23.75 | A2 |
| ATOM | 802 | O | THR | 106 | 46.065 | 66.411 | 4.812 | 1.00 24.68 | A2 |
| ATOM | 803 | N | LEU | 107 | 43.887 | 66.917 | 4.946 | 1.00 24.30 | A2 |
| ATOM | 804 | H | LEU | 107 | 43.145 | 67.176 | 5.528 | 1.00 0.00 | A2 |
| ATOM | 805 | CA | LEU | 107 | 43.668 | 66.783 | 3.531 | 1.00 27.29 | A2 |
| ATOM | 806 | CB | LEU | 107 | 42.158 | 66.913 | 3.273 | 1.00 25.45 | A2 |
| ATOM | 807 | CG | LEU | 107 | 41.642 | 66.888 | 1.863 | 1.00 26.24 | A2 |
| ATOM | 808 | CD1 | LEU | 107 | 42.095 | 65.649 | 1.158 | 1.00 26.41 | A2 |
| ATOM | 809 | CD2 | LEU | 107 | 40.140 | 66.925 | 1.914 | 1.00 27.62 | A2 |
| ATOM | 810 | C | LEU | 107 | 44.485 | 67.848 | 2.819 | 1.00 28.01 | A2 |
| ATOM | 811 | O | LEU | 107 | 45.154 | 67.555 | 1.823 | 1.00 30.72 | A2 |
| ATOM | 812 | N | GLN | 108 | 44.540 | 69.055 | 3.373 | 1.00 28.52 | A2 |
| ATOM | 813 | H | GLN | 108 | 44.030 | 69.221 | 4.194 | 1.00 0.00 | A2 |
| ATOM | 814 | CA | GLN | 108 | 45.343 | 70.132 | 2.792 | 1.00 28.38 | A2 |
| ATOM | 815 | CB | GLN | 108 | 45.138 | 71.363 | 3.630 | 1.00 30.15 | A2 |
| ATOM | 816 | CG | GLN | 108 | 43.711 | 71.787 | 3.542 | 1.00 32.67 | A2 |
| ATOM | 817 | CD | GLN | 108 | 43.606 | 73.192 | 4.048 | 1.00 35.24 | A2 |
| ATOM | 818 | OE1 | GLN | 108 | 43.085 | 73.484 | 5.125 | 1.00 36.07 | A2 |
| ATOM | 819 | NE2 | GLN | 108 | 44.189 | 74.044 | 3.213 | 1.00 33.58 | A2 |
| ATOM | 820 | HE21 | GLN | 108 | 44.582 | 73.701 | 2.386 | 1.00 0.00 | A2 |
| ATOM | 821 | HE22 | GLN | 108 | 44.195 | 74.986 | 3.471 | 1.00 0.00 | A2 |
| ATOM | 822 | C | GLN | 108 | 46.840 | 69.842 | 2.675 | 1.00 26.40 | A2 |
| ATOM | 823 | O | GLN | 108 | 47.450 | 69.955 | 1.597 | 1.00 27.57 | A2 |
| ATOM | 824 | N | LEU | 109 | 47.388 | 69.473 | 3.833 | 1.00 25.81 | A2 |
| ATOM | 825 | H | LEU | 109 | 46.795 | 69.495 | 4.615 | 1.00 0.00 | A2 |
| ATOM | 826 | CA | LEU | 109 | 48.764 | 69.003 | 4.043 | 1.00 27.96 | A2 |
| ATOM | 827 | CB | LEU | 109 | 48.951 | 68.637 | 5.513 | 1.00 29.41 | A2 |
| ATOM | 828 | CG | LEU | 109 | 48.712 | 69.771 | 6.520 | 1.00 31.78 | A2 |
| ATOM | 829 | CD1 | LEU | 109 | 48.750 | 69.188 | 7.933 | 1.00 29.16 | A2 |
| ATOM | 830 | CD2 | LEU | 109 | 49.724 | 70.889 | 6.285 | 1.00 32.19 | A2 |
| ATOM | 831 | C | LEU | 109 | 49.168 | 67.790 | 3.186 | 1.00 26.80 | A2 |
| ATOM | 832 | O | LEU | 109 | 50.214 | 67.721 | 2.544 | 1.00 26.81 | A2 |
| ATOM | 833 | N | ASP | 110 | 48.305 | 66.807 | 3.090 | 1.00 25.98 | A2 |
| ATOM | 834 | H | ASP | 110 | 47.471 | 66.835 | 3.600 | 1.00 0.00 | A2 |
| ATOM | 835 | CA | ASP | 110 | 48.590 | 65.684 | 2.250 | 1.00 23.32 | A2 |
| ATOM | 836 | CB | ASP | 110 | 47.577 | 64.570 | 2.553 | 1.00 26.34 | A2 |
| ATOM | 837 | CG | ASP | 110 | 47.905 | 63.878 | 3.894 | 1.00 31.10 | A2 |
| ATOM | 838 | OD1 | ASP | 110 | 47.070 | 63.093 | 4.323 | 1.00 34.98 | A2 |
| ATOM | 839 | OD2 | ASP | 110 | 48.958 | 64.107 | 4.535 | 1.00 34.06 | A2 |
| ATOM | 840 | C | ASP | 110 | 48.557 | 66.138 | 0.842 | 1.00 21.31 | A2 |
| ATOM | 841 | O | ASP | 111 | 49.493 | 65.711 | 0.165 | 1.00 20.63 | A2 |
| ATOM | 842 | N | VAL | 111 | 47.627 | 66.998 | 0.363 | 1.00 20.80 | A2 |
| ATOM | 843 | H | VAL | 111 | 46.900 | 67.310 | 0.944 | 1.00 0.00 | A2 |
| ATOM | 844 | CA | VAL | 111 | 47.711 | 67.454 | -1.019 | 1.00 20.44 | A2 |
| ATOM | 845 | CB | VAL | 111 | 46.531 | 68.364 | -1.376 | 1.00 23.60 | A2 |
| ATOM | 846 | CG1 | VAL | 111 | 46.615 | 68.946 | -2.808 | 1.00 23.04 | A2 |
| ATOM | 847 | CG2 | VAL | 111 | 45.289 | 67.497 | -1.371 | 1.00 24.30 | A2 |
| ATOM | 848 | C | VAL | 111 | 49.006 | 68.224 | -1.245 | 1.00 20.82 | A2 |
| ATOM | 849 | O | VAL | 111 | 49.617 | 68.006 | -2.303 | 1.00 19.22 | A2 |
| ATOM | 850 | N | ALA | 112 | 49.442 | 69.063 | -0.267 | 1.00 21.84 | A2 |
| ATOM | 851 | H | ALA | 112 | 48.839 | 69.190 | 0.492 | 1.00 0.00 | A2 |
| ATOM | 852 | CA | ALA | 112 | 50.708 | 69.805 | -0.295 | 1.00 24.16 | A2 |
| ATOM | 853 | CB | ALA | 112 | 50.861 | 70.561 | 1.011 | 1.00 22.69 | A2 |
| ATOM | 854 | C | ALA | 112 | 51.931 | 68.878 | -0.486 | 1.00 28.58 | A2 |
| ATOM | 855 | O | ALA | 112 | 52.778 | 69.026 | -1.390 | 1.00 32.53 | A2 |
| ATOM | 856 | N | ASP | 113 | 52.086 | 67.852 | 0.343 | 1.00 30.21 | A2 |
| ATOM | 857 | H | ASP | 113 | 51.507 | 67.817 | 1.130 | 1.00 0.00 | A2 |
| ATOM | 858 | CA | ASP | 113 | 53.084 | 66.846 | 0.166 | 1.00 31.70 | A2 |
| ATOM | 859 | CB | ASP | 113 | 52.706 | 65.659 | 0.953 | 1.00 36.31 | A2 |

| ATOM | 860 | CG | ASP | 113 | 53.170 | 65.758 | 2.357 | 1.00 | 42.27 | A2 |
|---|---|---|---|---|---|---|---|---|---|---|
| ATOM | 861 | OD1 | ASP | 113 | 52.559 | 65.109 | 3.203 | 1.00 | 46.37 | A2 |
| ATOM | 862 | OD2 | ASP | 113 | 54.160 | 66.461 | 2.589 | 1.00 | 48.93 | A2 |
| ATOM | 863 | C | ASP | 113 | 53.315 | 66.361 | -1.239 | 1.00 | 32.82 | A2 |
| ATOM | 864 | O | ASP | 113 | 54.433 | 66.308 | -1.754 | 1.00 | 36.25 | A2 |
| ATOM | 865 | N | PHE | 114 | 52.187 | 65.978 | -1.830 | 1.00 | 30.94 | A2 |
| ATOM | 866 | H | PHE | 114 | 51.344 | 66.164 | -1.361 | 1.00 | 0.00 | A2 |
| ATOM | 867 | CA | PHE | 114 | 52.109 | 65.328 | -3.103 | 1.00 | 27.84 | A2 |
| ATOM | 868 | CB | PHE | 114 | 50.708 | 64.794 | -3.224 | 1.00 | 23.18 | A2 |
| ATOM | 869 | CG | PHE | 114 | 50.565 | 63.928 | -4.420 | 1.00 | 21.04 | A2 |
| ATOM | 870 | CD1 | PHE | 114 | 51.623 | 63.225 | -4.938 | 1.00 | 24.05 | A2 |
| ATOM | 871 | CD2 | PHE | 114 | 49.369 | 63.914 | -5.046 | 1.00 | 22.37 | A2 |
| ATOM | 872 | CE1 | PHE | 114 | 51.476 | 62.514 | -6.102 | 1.00 | 24.54 | A2 |
| ATOM | 873 | CE2 | PHE | 114 | 49.211 | 63.207 | -6.212 | 1.00 | 21.33 | A2 |
| ATOM | 874 | CZ | PHE | 114 | 50.263 | 62.509 | -6.741 | 1.00 | 24.71 | A2 |
| ATOM | 875 | C | PHE | 114 | 52.453 | 66.291 | -4.190 | 1.00 | 29.20 | A2 |
| ATOM | 876 | O | PHE | 114 | 53.072 | 65.883 | -5.158 | 1.00 | 30.84 | A2 |
| ATOM | 877 | N | ALA | 115 | 52.057 | 67.554 | -4.058 | 1.00 | 31.99 | A2 |
| ATOM | 878 | H | ALA | 115 | 51.446 | 67.768 | -3.317 | 1.00 | 0.00 | A2 |
| ATOM | 879 | CA | ALA | 115 | 52.423 | 68.655 | -4.952 | 1.00 | 31.29 | A2 |
| ATOM | 880 | CB | ALA | 115 | 51.824 | 69.939 | -4.420 | 1.00 | 30.65 | A2 |
| ATOM | 881 | C | ALA | 115 | 53.936 | 68.787 | -4.976 | 1.00 | 31.31 | A2 |
| ATOM | 882 | O | ALA | 115 | 54.539 | 68.823 | -6.044 | 1.00 | 30.36 | A2 |
| ATOM | 883 | N | THR | 116 | 54.551 | 68.846 | -3.813 | 1.00 | 32.20 | A2 |
| ATOM | 884 | H | THR | 116 | 54.013 | 68.910 | -2.992 | 1.00 | 0.00 | A2 |
| ATOM | 885 | CA | THR | 116 | 55.998 | 68.897 | -3.656 | 1.00 | 34.91 | A2 |
| ATOM | 886 | CB | THR | 116 | 56.325 | 68.953 | -2.150 | 1.00 | 35.78 | A2 |
| ATOM | 887 | OG1 | THR | 116 | 55.564 | 70.038 | -1.576 | 1.00 | 35.58 | A2 |
| ATOM | 888 | HG1 | THR | 116 | 54.942 | 69.644 | -0.939 | 1.00 | 0.00 | A2 |
| ATOM | 889 | CG2 | THR | 116 | 57.816 | 69.050 | -1.921 | 1.00 | 35.38 | A2 |
| ATOM | 890 | C | THR | 116 | 56.714 | 67.726 | -4.304 | 1.00 | 37.14 | A2 |
| ATOM | 891 | O | THR | 116 | 57.641 | 67.937 | -5.066 | 1.00 | 39.27 | A2 |
| ATOM | 892 | N | THR | 117 | 56.318 | 66.485 | -4.045 | 1.00 | 39.05 | A2 |
| ATOM | 893 | H | THR | 117 | 55.615 | 66.383 | -3.369 | 1.00 | 0.00 | A2 |
| ATOM | 894 | CA | THR | 117 | 56.840 | 65.269 | -4.630 | 1.00 | 40.23 | A2 |
| ATOM | 895 | CB | THR | 117 | 55.909 | 64.090 | -4.216 | 1.00 | 39.99 | A2 |
| ATOM | 896 | OG1 | THR | 117 | 56.149 | 63.920 | -2.820 | 1.00 | 41.66 | A2 |
| ATOM | 897 | HG1 | THR | 117 | 55.653 | 64.559 | -2.286 | 1.00 | 0.00 | A2 |
| ATOM | 898 | CG2 | THR | 117 | 56.110 | 62.781 | -4.981 | 1.00 | 38.23 | A2 |
| ATOM | 899 | C | THR | 117 | 56.882 | 65.417 | -6.134 | 1.00 | 43.42 | A2 |
| ATOM | 900 | O | THR | 117 | 57.934 | 65.253 | -6.749 | 1.00 | 46.29 | A2 |
| ATOM | 901 | N | ILE | 118 | 55.763 | 65.777 | -6.741 | 1.00 | 45.87 | A2 |
| ATOM | 902 | H | ILE | 118 | 54.962 | 65.942 | -6.200 | 1.00 | 0.00 | A2 |
| ATOM | 903 | CA | ILE | 118 | 55.659 | 65.914 | -8.182 | 1.00 | 47.97 | A2 |
| ATOM | 904 | CB | ILE | 118 | 54.170 | 66.271 | -8.452 | 1.00 | 47.69 | A2 |
| ATOM | 905 | CG2 | ILE | 118 | 54.041 | 66.930 | -9.835 | 1.00 | 47.03 | A2 |
| ATOM | 906 | CG1 | ILE | 118 | 53.302 | 65.011 | -8.244 | 1.00 | 44.00 | A2 |
| ATOM | 907 | CD | ILE | 118 | 53.651 | 63.883 | -9.236 | 1.00 | 43.71 | A2 |
| ATOM | 908 | C | ILE | 118 | 56.647 | 66.932 | -8.724 | 1.00 | 50.69 | A2 |
| ATOM | 909 | O | ILE | 118 | 57.390 | 66.676 | -9.681 | 1.00 | 49.98 | A2 |
| ATOM | 910 | N | TRP | 119 | 56.697 | 68.061 | -8.015 | 1.00 | 54.68 | A2 |
| ATOM | 911 | H | TRP | 119 | 56.164 | 68.135 | -7.197 | 1.00 | 0.00 | A2 |
| ATOM | 912 | CA | TRP | 119 | 57.575 | 69.142 | -8.399 | 1.00 | 58.98 | A2 |
| ATOM | 913 | CB | TRP | 119 | 57.392 | 70.367 | -7.477 | 1.00 | 59.84 | A2 |
| ATOM | 914 | CG | TRP | 119 | 58.051 | 71.529 | -8.196 | 1.00 | 62.64 | A2 |
| ATOM | 915 | CD2 | TRP | 119 | 57.596 | 72.211 | -9.307 | 1.00 | 63.78 | A2 |
| ATOM | 916 | CE2 | TRP | 119 | 58.699 | 72.955 | -9.643 | 1.00 | 62.55 | A2 |
| ATOM | 917 | CE3 | TRP | 119 | 56.465 | 72.314 | -10.080 | 1.00 | 66.02 | A2 |
| ATOM | 918 | CD1 | TRP | 119 | 59.322 | 71.870 | -7.863 | 1.00 | 64.12 | A2 |
| ATOM | 919 | NE1 | TRP | 119 | 59.680 | 72.727 | -8.784 | 1.00 | 65.00 | A2 |
| ATOM | 920 | HE1 | TRP | 119 | 60.568 | 73.140 | -8.828 | 1.00 | 0.00 | A2 |
| ATOM | 921 | CZ2 | TRP | 119 | 58.726 | 73.794 | -10.714 | 1.00 | 62.90 | A2 |
| ATOM | 922 | CZ3 | TRP | 119 | 56.469 | 73.157 | -11.170 | 1.00 | 65.18 | A2 |
| ATOM | 923 | CH2 | TRP | 119 | 57.591 | 73.887 | -11.481 | 1.00 | 64.40 | A2 |
| ATOM | 924 | C | TRP | 119 | 59.021 | 68.664 | -8.352 | 1.00 | 61.26 | A2 |
| ATOM | 925 | O | TRP | 119 | 59.748 | 68.788 | -9.343 | 1.00 | 62.12 | A2 |
| ATOM | 926 | N | GLN | 120 | 59.447 | 68.065 | -7.249 | 1.00 | 62.91 | A2 |
| ATOM | 927 | H | GLN | 120 | 58.811 | 67.961 | -6.519 | 1.00 | 0.00 | A2 |
| ATOM | 928 | CA | GLN | 120 | 60.786 | 67.504 | -7.113 | 1.00 | 65.16 | A2 |
| ATOM | 929 | CB | GLN | 120 | 60.900 | 66.800 | -5.780 | 1.00 | 66.56 | A2 |
| ATOM | 930 | CG | GLN | 120 | 60.627 | 67.678 | -4.582 | 1.00 | 67.18 | A2 |
| ATOM | 931 | CD | GLN | 120 | 60.725 | 66.907 | -3.284 | 1.00 | 67.77 | A2 |
| ATOM | 932 | OE1 | GLN | 120 | 61.221 | 67.465 | -2.319 | 1.00 | 69.31 | A2 |
| ATOM | 933 | NE2 | GLN | 120 | 60.305 | 65.654 | -3.129 | 1.00 | 69.39 | A2 |
| ATOM | 934 | HE21 | GLN | 120 | 59.903 | 65.174 | -3.877 | 1.00 | 0.00 | A2 |
| ATOM | 935 | HE22 | GLN | 120 | 60.441 | 65.282 | -2.234 | 1.00 | 0.00 | A2 |
| ATOM | 936 | C | GLN | 120 | 61.169 | 66.509 | -8.222 | 1.00 | 66.22 | A2 |
| ATOM | 937 | O | GLN | 120 | 62.326 | 66.421 | -8.662 | 1.00 | 66.50 | A2 |
| ATOM | 938 | N | GLN | 121 | 60.202 | 65.745 | -8.706 | 1.00 | 67.10 | A2 |
| ATOM | 939 | H | GLN | 121 | 59.307 | 65.754 | -8.303 | 1.00 | 0.00 | A2 |
| ATOM | 940 | CA | GLN | 121 | 60.480 | 64.878 | -9.812 | 1.00 | 68.66 | A2 |
| ATOM | 941 | CB | GLN | 121 | 59.292 | 63.971 | -10.070 | 1.00 | 67.96 | A2 |
| ATOM | 942 | CG | GLN | 121 | 59.614 | 62.937 | -11.128 | 1.00 | 68.89 | A2 |
| ATOM | 943 | CD | GLN | 121 | 60.940 | 62.236 | -10.852 | 1.00 | 71.37 | A2 |
| ATOM | 944 | OE1 | GLN | 121 | 61.212 | 61.706 | -9.777 | 1.00 | 71.70 | A2 |
| ATOM | 945 | NE2 | GLN | 121 | 61.879 | 62.262 | -11.786 | 1.00 | 74.41 | A2 |

FIG. 5L

| | | | | | | | | |
|---|---|---|---|---|---|---|---|---|
| ATOM | 946 | HE21 | GLN | 121 | 61.707 | 62.729 | -12.627 | 1.00 0.00 | A2 |
| ATOM | 947 | HE22 | GLN | 121 | 62.736 | 61.859 | -11.541 | 1.00 0.00 | A2 |
| ATOM | 948 | C | GLN | 121 | 60.760 | 65.743 | -11.045 | 1.00 70.48 | A2 |
| ATOM | 949 | O | GLN | 121 | 61.671 | 65.436 | -11.827 | 1.00 70.94 | A2 |
| ATOM | 950 | N | MET | 122 | 60.019 | 66.846 | -11.236 | 1.00 71.67 | A2 |
| ATOM | 951 | H | MET | 122 | 59.351 | 67.087 | -10.555 | 1.00 0.00 | A2 |
| ATOM | 952 | CA | MET | 122 | 60.190 | 67.688 | -12.412 | 1.00 72.62 | A2 |
| ATOM | 953 | CB | MET | 122 | 59.173 | 68.819 | -12.448 | 1.00 73.12 | A2 |
| ATOM | 954 | CG | MET | 122 | 57.880 | 68.343 | -13.083 | 1.00 73.64 | A2 |
| ATOM | 955 | SD | MET | 122 | 56.669 | 69.662 | -13.295 | 1.00 75.44 | A2 |
| ATOM | 956 | CE | MET | 122 | 55.695 | 69.349 | -11.861 | 1.00 76.43 | A2 |
| ATOM | 957 | C | MET | 122 | 61.566 | 68.281 | -12.411 | 1.00 73.22 | A2 |
| ATOM | 958 | O | MET | 122 | 62.240 | 68.287 | -13.441 | 1.00 73.03 | A2 |
| ATOM | 959 | N | GLU | 123 | 61.991 | 68.697 | -11.223 | 1.00 74.74 | A2 |
| ATOM | 960 | H | GLU | 123 | 61.372 | 68.617 | -10.466 | 1.00 0.00 | A2 |
| ATOM | 961 | CA | GLU | 123 | 63.305 | 69.262 | -11.018 | 1.00 75.95 | A2 |
| ATOM | 962 | CB | GLU | 123 | 63.484 | 69.665 | -9.597 | 1.00 75.72 | A2 |
| ATOM | 963 | CG | GLU | 123 | 62.644 | 70.906 | -9.500 | 1.00 79.11 | A2 |
| ATOM | 964 | CD | GLU | 123 | 62.651 | 71.529 | -8.122 | 1.00 83.02 | A2 |
| ATOM | 965 | OE1 | GLU | 123 | 62.741 | 72.763 | -8.057 | 1.00 84.15 | A2 |
| ATOM | 966 | OE2 | GLU | 123 | 62.543 | 70.789 | -7.133 | 1.00 84.45 | A2 |
| ATOM | 967 | C | GLU | 123 | 64.381 | 68.280 | -11.386 | 1.00 77.17 | A2 |
| ATOM | 968 | O | GLU | 123 | 65.092 | 68.558 | -12.356 | 1.00 78.22 | A2 |
| ATOM | 969 | N | GLU | 124 | 64.504 | 67.110 | -10.765 | 1.00 77.66 | A2 |
| ATOM | 970 | H | GLU | 124 | 63.867 | 66.852 | -10.060 | 1.00 0.00 | A2 |
| ATOM | 971 | CA | GLU | 124 | 65.574 | 66.215 | -11.167 | 1.00 78.47 | A2 |
| ATOM | 972 | CB | GLU | 124 | 65.600 | 65.051 | -10.195 | 1.00 80.79 | A2 |
| ATOM | 973 | CG | GLU | 124 | 64.387 | 64.132 | -10.150 | 1.00 83.29 | A2 |
| ATOM | 974 | CD | GLU | 124 | 64.375 | 63.248 | -8.908 | 1.00 85.51 | A2 |
| ATOM | 975 | OE1 | GLU | 124 | 64.733 | 63.729 | -7.824 | 1.00 86.84 | A2 |
| ATOM | 976 | OE2 | GLU | 124 | 64.006 | 62.075 | -9.024 | 1.00 86.39 | A2 |
| ATOM | 977 | C | GLU | 124 | 65.534 | 65.705 | -12.612 | 1.00 78.01 | A2 |
| ATOM | 978 | O | GLU | 124 | 66.480 | 65.057 | -13.060 | 1.00 78.91 | A2 |
| ATOM | 979 | N | LEU | 125 | 64.460 | 65.943 | -13.363 | 1.00 77.11 | A2 |
| ATOM | 980 | H | LEU | 125 | 63.666 | 66.340 | -12.945 | 1.00 0.00 | A2 |
| ATOM | 981 | CA | LEU | 125 | 64.387 | 65.583 | -14.771 | 1.00 76.23 | A2 |
| ATOM | 982 | CB | LEU | 125 | 63.061 | 64.832 | -14.952 | 1.00 76.88 | A2 |
| ATOM | 983 | CG | LEU | 125 | 62.392 | 64.382 | -16.263 | 1.00 76.63 | A2 |
| ATOM | 984 | CD1 | LEU | 125 | 63.350 | 63.754 | -17.276 | 1.00 76.67 | A2 |
| ATOM | 985 | CD2 | LEU | 125 | 61.309 | 63.402 | -15.839 | 1.00 75.89 | A2 |
| ATOM | 986 | C | LEU | 125 | 64.506 | 66.827 | -15.648 | 1.00 75.84 | A2 |
| ATOM | 987 | O | LEU | 125 | 64.360 | 66.788 | -16.871 | 1.00 75.36 | A2 |
| ATOM | 988 | N | GLY | 126 | 64.759 | 67.968 | -15.027 | 1.00 75.90 | A2 |
| ATOM | 989 | H | GLY | 126 | 64.741 | 67.976 | -14.056 | 1.00 0.00 | A2 |
| ATOM | 990 | CA | GLY | 126 | 64.968 | 69.213 | -15.736 | 1.00 77.58 | A2 |
| ATOM | 991 | C | GLY | 126 | 63.697 | 69.814 | -16.330 | 1.00 78.63 | A2 |
| ATOM | 992 | O | GLY | 126 | 63.735 | 70.736 | -17.146 | 1.00 78.55 | A2 |
| ATOM | 993 | N | MET | 127 | 62.524 | 69.343 | -15.933 | 1.00 80.08 | A2 |
| ATOM | 994 | H | MET | 127 | 62.522 | 68.603 | -15.293 | 1.00 0.00 | A2 |
| ATOM | 995 | CA | MET | 127 | 61.266 | 69.902 | -16.415 | 1.00 81.46 | A2 |
| ATOM | 996 | CB | MET | 127 | 60.191 | 68.802 | -16.361 | 1.00 81.86 | A2 |
| ATOM | 997 | CG | MET | 127 | 60.708 | 67.599 | -17.147 | 1.00 82.66 | A2 |
| ATOM | 998 | SD | MET | 127 | 59.682 | 66.115 | -17.282 | 1.00 83.70 | A2 |
| ATOM | 999 | CE | MET | 127 | 60.236 | 65.620 | -18.900 | 1.00 83.23 | A2 |
| ATOM | 1000 | C | MET | 127 | 60.847 | 71.131 | -15.599 | 1.00 82.18 | A2 |
| ATOM | 1001 | OT1 | MET | 127 | 60.116 | 71.958 | -16.142 | 1.00 83.86 | A2 |
| ATOM | 1002 | OT2 | MET | 127 | 61.267 | 71.285 | -14.446 | 1.00 82.04 | A2 |
| ATOM | 1003 | CB | MET | 138 | 39.323 | 80.595 | -4.492 | 1.00 59.39 | A3 |
| ATOM | 1004 | CG | MET | 138 | 40.123 | 79.298 | -4.421 | 1.00 57.97 | A3 |
| ATOM | 1005 | SD | MET | 138 | 40.561 | 78.973 | -6.145 | 1.00 60.85 | A3 |
| ATOM | 1006 | CE | MET | 138 | 41.129 | 77.310 | -6.351 | 1.00 61.48 | A3 |
| ATOM | 1007 | C | MET | 138 | 37.021 | 81.072 | -5.454 | 1.00 60.26 | A3 |
| ATOM | 1008 | O | MET | 138 | 36.832 | 82.262 | -5.181 | 1.00 62.98 | A3 |
| ATOM | 1009 | HT1 | MET | 138 | 38.497 | 82.600 | -6.075 | 1.00 0.00 | A3 |
| ATOM | 1010 | HT2 | MET | 138 | 38.313 | 81.757 | -7.529 | 1.00 0.00 | A3 |
| ATOM | 1011 | N | MET | 138 | 38.839 | 81.784 | -6.639 | 1.00 60.49 | A3 |
| ATOM | 1012 | HT3 | MET | 138 | 39.865 | 81.816 | -6.768 | 1.00 0.00 | A3 |
| ATOM | 1013 | CA | MET | 138 | 38.445 | 80.672 | -5.787 | 1.00 60.51 | A3 |
| ATOM | 1014 | N | PRO | 139 | 35.995 | 80.242 | -5.612 | 1.00 57.82 | A3 |
| ATOM | 1015 | CD | PRO | 139 | 36.028 | 79.060 | -6.448 | 1.00 58.10 | A3 |
| ATOM | 1016 | CA | PRO | 139 | 34.654 | 80.538 | -5.142 | 1.00 54.67 | A3 |
| ATOM | 1017 | CB | PRO | 139 | 33.870 | 79.323 | -5.525 | 1.00 54.54 | A3 |
| ATOM | 1018 | CG | PRO | 139 | 34.945 | 78.290 | -5.755 | 1.00 58.20 | A3 |
| ATOM | 1019 | C | PRO | 139 | 34.588 | 80.875 | -3.664 | 1.00 52.24 | A3 |
| ATOM | 1020 | O | PRO | 139 | 35.507 | 80.623 | -2.882 | 1.00 51.89 | A3 |
| ATOM | 1021 | N | ALA | 140 | 33.499 | 81.547 | -3.342 | 1.00 49.86 | A3 |
| ATOM | 1022 | H | ALA | 140 | 32.789 | 81.676 | -4.005 | 1.00 0.00 | A3 |
| ATOM | 1023 | CA | ALA | 140 | 33.234 | 81.926 | -1.994 | 1.00 49.39 | A3 |
| ATOM | 1024 | CB | ALA | 140 | 32.966 | 83.413 | -1.895 | 1.00 49.94 | A3 |
| ATOM | 1025 | C | ALA | 140 | 31.978 | 81.153 | -1.590 | 1.00 49.25 | A3 |
| ATOM | 1026 | O | ALA | 140 | 30.889 | 81.162 | -2.205 | 1.00 49.06 | A3 |
| ATOM | 1027 | N | PHE | 141 | 32.293 | 80.442 | -0.506 | 1.00 47.48 | A3 |
| ATOM | 1028 | H | PHE | 141 | 33.190 | 80.550 | -0.122 | 1.00 0.00 | A3 |
| ATOM | 1029 | CA | PHE | 141 | 31.401 | 79.552 | 0.208 | 1.00 45.66 | A3 |
| ATOM | 1030 | CB | PHE | 141 | 32.215 | 78.305 | 0.792 | 1.00 40.28 | A3 |
| ATOM | 1031 | CG | PHE | 141 | 32.684 | 77.404 | -0.349 | 1.00 35.35 | A3 |

FIG. 5M

| ATOM | 1032 | CD1 | PHE | 141 | 31.800 | 76.591 | -1.006 | 1.00 | 34.39 | A3 |
|------|------|-----|-----|-----|--------|--------|--------|------|-------|-----|
| ATOM | 1033 | CD2 | PHE | 141 | 33.966 | 77.497 | -0.830 | 1.00 | 37.69 | A3 |
| ATOM | 1034 | CE1 | PHE | 141 | 32.174 | 75.895 | -2.133 | 1.00 | 34.00 | A3 |
| ATOM | 1035 | CE2 | PHE | 141 | 34.358 | 76.807 | -1.956 | 1.00 | 36.69 | A3 |
| ATOM | 1036 | CZ  | PHE | 141 | 33.449 | 76.001 | -2.614 | 1.00 | 37.29 | A3 |
| ATOM | 1037 | C   | PHE | 141 | 31.003 | 80.580 | 1.242  | 1.00 | 46.54 | A3 |
| ATOM | 1038 | O   | PHE | 141 | 31.584 | 80.664 | 2.317  | 1.00 | 48.26 | A3 |
| ATOM | 1039 | N   | ALA | 142 | 30.067 | 81.452 | 0.843  | 1.00 | 48.28 | A3 |
| ATOM | 1040 | H   | ALA | 142 | 29.624 | 81.295 | -0.020 | 1.00 | 0.00  | A3 |
| ATOM | 1041 | CA  | ALA | 142 | 29.581 | 82.564 | 1.668  | 1.00 | 46.06 | A3 |
| ATOM | 1042 | CB  | ALA | 142 | 28.731 | 83.546 | 0.879  | 1.00 | 45.04 | A3 |
| ATOM | 1043 | C   | ALA | 142 | 28.703 | 82.132 | 2.802  | 1.00 | 45.27 | A3 |
| ATOM | 1044 | O   | ALA | 142 | 28.343 | 83.002 | 3.584  | 1.00 | 47.38 | A3 |
| ATOM | 1045 | N   | SER | 143 | 28.318 | 80.860 | 2.899  | 1.00 | 43.36 | A3 |
| ATOM | 1046 | H   | SER | 143 | 28.724 | 80.201 | 2.303  | 1.00 | 0.00  | A3 |
| ATOM | 1047 | CA  | SER | 143 | 27.377 | 80.392 | 3.897  | 1.00 | 41.94 | A3 |
| ATOM | 1048 | CB  | SER | 143 | 26.036 | 80.129 | 3.181  | 1.00 | 44.17 | A3 |
| ATOM | 1049 | OG  | SER | 143 | 25.323 | 78.918 | 3.536  | 1.00 | 48.18 | A3 |
| ATOM | 1050 | HG  | SER | 143 | 24.455 | 78.974 | 3.098  | 1.00 | 0.00  | A3 |
| ATOM | 1051 | C   | SER | 143 | 27.877 | 79.145 | 4.602  | 1.00 | 39.79 | A3 |
| ATOM | 1052 | O   | SER | 143 | 28.763 | 78.452 | 4.132  | 1.00 | 38.50 | A3 |
| ATOM | 1053 | N   | ALA | 144 | 27.218 | 78.775 | 5.683  | 1.00 | 39.10 | A3 |
| ATOM | 1054 | H   | ALA | 144 | 26.449 | 79.312 | 5.960  | 1.00 | 0.00  | A3 |
| ATOM | 1055 | CA  | ALA | 144 | 27.566 | 77.586 | 6.411  | 1.00 | 39.22 | A3 |
| ATOM | 1056 | CB  | ALA | 144 | 26.982 | 77.598 | 7.802  | 1.00 | 36.97 | A3 |
| ATOM | 1057 | C   | ALA | 144 | 26.964 | 76.420 | 5.627  | 1.00 | 41.58 | A3 |
| ATOM | 1058 | O   | ALA | 144 | 27.706 | 75.448 | 5.444  | 1.00 | 42.07 | A3 |
| ATOM | 1059 | N   | PHE | 145 | 25.719 | 76.407 | 5.076  | 1.00 | 40.77 | A3 |
| ATOM | 1060 | H   | PHE | 145 | 25.149 | 77.203 | 5.110  | 1.00 | 0.00  | A3 |
| ATOM | 1061 | CA  | PHE | 145 | 25.307 | 75.234 | 4.312  | 1.00 | 39.31 | A3 |
| ATOM | 1062 | CB  | PHE | 145 | 23.877 | 75.396 | 3.798  | 1.00 | 36.46 | A3 |
| ATOM | 1063 | CG  | PHE | 145 | 23.477 | 74.452 | 2.641  | 1.00 | 31.91 | A3 |
| ATOM | 1064 | CD1 | PHE | 145 | 23.579 | 74.900 | 1.323  | 1.00 | 29.02 | A3 |
| ATOM | 1065 | CD2 | PHE | 145 | 23.013 | 73.185 | 2.916  | 1.00 | 29.40 | A3 |
| ATOM | 1066 | CE1 | PHE | 145 | 23.225 | 74.100 | 0.277  | 1.00 | 28.34 | A3 |
| ATOM | 1067 | CE2 | PHE | 145 | 22.661 | 72.389 | 1.858  | 1.00 | 28.80 | A3 |
| ATOM | 1068 | CZ  | PHE | 145 | 22.764 | 72.831 | 0.549  | 1.00 | 30.58 | A3 |
| ATOM | 1069 | C   | PHE | 145 | 26.266 | 75.071 | 3.120  | 1.00 | 40.44 | A3 |
| ATOM | 1070 | O   | PHE | 145 | 26.556 | 73.938 | 2.697  | 1.00 | 40.55 | A3 |
| ATOM | 1071 | N   | GLN | 146 | 26.745 | 76.232 | 2.619  | 1.00 | 39.11 | A3 |
| ATOM | 1072 | H   | GLN | 146 | 26.437 | 77.073 | 3.015  | 1.00 | 0.00  | A3 |
| ATOM | 1073 | CA  | GLN | 146 | 27.660 | 76.263 | 1.511  | 1.00 | 38.01 | A3 |
| ATOM | 1074 | CB  | GLN | 146 | 27.907 | 77.644 | 1.054  | 1.00 | 38.92 | A3 |
| ATOM | 1075 | CG  | GLN | 146 | 26.884 | 78.066 | 0.049  | 1.00 | 43.26 | A3 |
| ATOM | 1076 | CD  | GLN | 146 | 27.171 | 79.440 | -0.522 | 1.00 | 45.37 | A3 |
| ATOM | 1077 | OE1 | GLN | 146 | 27.851 | 80.253 | 0.083  | 1.00 | 47.57 | A3 |
| ATOM | 1078 | NE2 | GLN | 146 | 26.689 | 79.793 | -1.692 | 1.00 | 47.50 | A3 |
| ATOM | 1079 | HE21| GLN | 146 | 26.149 | 79.149 | -2.190 | 1.00 | 0.00  | A3 |
| ATOM | 1080 | HE22| GLN | 146 | 26.913 | 80.690 | -2.021 | 1.00 | 0.00  | A3 |
| ATOM | 1081 | C   | GLN | 146 | 29.005 | 75.670 | 1.836  | 1.00 | 37.25 | A3 |
| ATOM | 1082 | O   | GLN | 146 | 29.634 | 75.093 | 0.950  | 1.00 | 38.28 | A3 |
| ATOM | 1083 | N   | ARG | 147 | 29.511 | 75.775 | 3.054  | 1.00 | 36.37 | A3 |
| ATOM | 1084 | H   | ARG | 147 | 29.044 | 76.300 | 3.738  | 1.00 | 0.00  | A3 |
| ATOM | 1085 | CA  | ARG | 147 | 30.798 | 75.180 | 3.357  | 1.00 | 35.68 | A3 |
| ATOM | 1086 | CB  | ARG | 147 | 31.299 | 75.574 | 4.713  | 1.00 | 37.12 | A3 |
| ATOM | 1087 | CG  | ARG | 147 | 31.730 | 77.016 | 4.697  | 1.00 | 42.68 | A3 |
| ATOM | 1088 | CD  | ARG | 147 | 32.034 | 77.494 | 6.093  | 1.00 | 49.54 | A3 |
| ATOM | 1089 | NE  | ARG | 147 | 32.674 | 78.774 | 5.877  | 1.00 | 58.21 | A3 |
| ATOM | 1090 | HE  | ARG | 147 | 32.475 | 79.252 | 5.045  | 1.00 | 0.00  | A3 |
| ATOM | 1091 | CZ  | ARG | 147 | 33.519 | 79.373 | 6.742  | 1.00 | 62.77 | A3 |
| ATOM | 1092 | NH1 | ARG | 147 | 33.905 | 78.868 | 7.936  | 1.00 | 63.96 | A3 |
| ATOM | 1093 | HH11| ARG | 147 | 34.545 | 79.379 | 8.510  | 1.00 | 0.00  | A3 |
| ATOM | 1094 | HH12| ARG | 147 | 33.561 | 77.980 | 8.239  | 1.00 | 0.00  | A3 |
| ATOM | 1095 | NH2 | ARG | 147 | 33.960 | 80.584 | 6.403  | 1.00 | 64.80 | A3 |
| ATOM | 1096 | HH21| ARG | 147 | 34.599 | 81.069 | 6.999  | 1.00 | 0.00  | A3 |
| ATOM | 1097 | HH22| ARG | 147 | 33.665 | 80.996 | 5.541  | 1.00 | 0.00  | A3 |
| ATOM | 1098 | C   | ARG | 147 | 30.570 | 73.702 | 3.337  | 1.00 | 34.91 | A3 |
| ATOM | 1099 | O   | ARG | 147 | 31.233 | 73.050 | 2.539  | 1.00 | 34.56 | A3 |
| ATOM | 1100 | N   | ALA | 148 | 29.544 | 73.194 | 4.040  | 1.00 | 33.44 | A3 |
| ATOM | 1101 | H   | ALA | 148 | 28.926 | 73.818 | 4.482  | 1.00 | 0.00  | A3 |
| ATOM | 1102 | CA  | ALA | 148 | 29.358 | 71.754 | 4.172  | 1.00 | 33.92 | A3 |
| ATOM | 1103 | CB  | ALA | 148 | 28.217 | 71.426 | 5.163  | 1.00 | 32.85 | A3 |
| ATOM | 1104 | C   | ALA | 148 | 29.077 | 71.095 | 2.843  | 1.00 | 33.40 | A3 |
| ATOM | 1105 | O   | ALA | 148 | 29.765 | 70.141 | 2.457  | 1.00 | 34.31 | A3 |
| ATOM | 1106 | N   | ALA | 149 | 28.169 | 71.657 | 2.077  | 1.00 | 32.60 | A3 |
| ATOM | 1107 | H   | ALA | 149 | 27.662 | 72.424 | 2.411  | 1.00 | 0.00  | A3 |
| ATOM | 1108 | CA  | ALA | 149 | 27.890 | 71.134 | 0.757  | 1.00 | 32.70 | A3 |
| ATOM | 1109 | CB  | ALA | 149 | 26.595 | 71.774 | 0.299  | 1.00 | 31.91 | A3 |
| ATOM | 1110 | C   | ALA | 149 | 29.032 | 71.381 | -0.258 | 1.00 | 33.75 | A3 |
| ATOM | 1111 | O   | ALA | 149 | 29.208 | 70.661 | -1.264 | 1.00 | 34.49 | A3 |
| ATOM | 1112 | N   | GLY | 150 | 29.867 | 72.401 | -0.052 | 1.00 | 33.58 | A3 |
| ATOM | 1113 | H   | GLY | 150 | 29.724 | 73.035 | 0.682  | 1.00 | 0.00  | A3 |
| ATOM | 1114 | CA  | GLY | 150 | 31.017 | 72.608 | -0.913 | 1.00 | 31.79 | A3 |
| ATOM | 1115 | C   | GLY | 150 | 32.113 | 71.629 | -0.478 | 1.00 | 31.39 | A3 |
| ATOM | 1116 | O   | GLY | 150 | 32.997 | 71.261 | -1.265 | 1.00 | 31.77 | A3 |
| ATOM | 1117 | N   | GLY | 151 | 32.075 | 71.161 | 0.773  | 1.00 | 29.83 | A3 |

FIG. 5N

| | | | | | | | | | | | | | | | | | | |
|---|---|---|---|---|---|---|---|---|---|---|---|---|---|---|---|---|---|---|
| ATOM | 1118 | H | GLY | 151 | 31.412 | 71.524 | 1.394 | 1.00 | 0.00 | A3 | ATOM | 1161 | N | HIS | 157 | 35.054 | 65.576 | -6.133 | 1.00 33.90 | A3 |
| ATOM | 1119 | CA | GLY | 151 | 33.018 | 70.166 | 1.243 | 1.00 32.16 | A3 | ATOM | 1162 | H | HIS | 157 | 34.771 | 66.349 | -5.605 | 1.00 0.00 | A3 |
| ATOM | 1120 | C | GLY | 151 | 32.764 | 68.909 | 0.409 | 1.00 33.98 | A3 | ATOM | 1163 | CA | HIS | 157 | 35.821 | 65.773 | -7.383 | 1.00 31.19 | A3 |
| ATOM | 1121 | O | GLY | 151 | 33.664 | 68.501 | -0.349 | 1.00 35.66 | A3 | ATOM | 1164 | CB | HIS | 157 | 35.707 | 67.209 | -7.900 | 1.00 32.59 | A3 |
| ATOM | 1122 | N | VAL | 152 | 31.486 | 68.418 | 0.451 | 1.00 31.87 | A3 | ATOM | 1165 | CG | HIS | 157 | 34.369 | 67.449 | -8.566 | 1.00 31.11 | A3 |
| ATOM | 1123 | H | VAL | 152 | 30.867 | 68.906 | 1.040 | 1.00 0.00 | A3 | ATOM | 1166 | CD2 | HIS | 157 | 34.127 | 67.394 | -9.928 | 1.00 30.78 | A3 |
| ATOM | 1124 | CA | VAL | 152 | 30.978 | 67.240 | -0.275 | 1.00 29.61 | A3 | ATOM | 1167 | ND1 | HIS | 157 | 33.223 | 67.666 | -7.942 | 1.00 32.36 | A3 |
| ATOM | 1125 | CB | VAL | 152 | 29.419 | 67.145 | -0.125 | 1.00 27.63 | A3 | ATOM | 1168 | HD1 | HIS | 157 | 33.080 | 67.773 | -6.979 | 1.00 0.00 | A3 |
| ATOM | 1126 | CG1 | VAL | 152 | 28.883 | 66.035 | -0.976 | 1.00 27.37 | A3 | ATOM | 1169 | CE1 | HIS | 157 | 32.293 | 67.732 | -8.875 | 1.00 32.01 | A3 |
| ATOM | 1127 | CG2 | VAL | 152 | 29.002 | 66.786 | 1.279 | 1.00 24.74 | A3 | ATOM | 1170 | NE2 | HIS | 157 | 32.838 | 67.571 | -10.060 | 1.00 29.18 | A3 |
| ATOM | 1128 | C | VAL | 152 | 31.351 | 67.294 | -1.762 | 1.00 29.91 | A3 | ATOM | 1171 | HE2 | HIS | 157 | 32.327 | 67.621 | -10.895 | 1.00 0.00 | A3 |
| ATOM | 1129 | O | VAL | 152 | 31.805 | 66.329 | -2.393 | 1.00 31.75 | A3 | ATOM | 1172 | C | HIS | 157 | 37.291 | 65.476 | -7.269 | 1.00 29.68 | A3 |
| ATOM | 1130 | N | LEU | 153 | 31.236 | 68.452 | -2.361 | 1.00 29.26 | A3 | ATOM | 1173 | O | HIS | 157 | 37.950 | 65.059 | -8.219 | 1.00 29.65 | A3 |
| ATOM | 1131 | H | LEU | 153 | 30.881 | 69.219 | -1.860 | 1.00 0.00 | A3 | ATOM | 1174 | N | LEU | 158 | 37.801 | 65.669 | -6.071 | 1.00 29.24 | A3 |
| ATOM | 1132 | CA | LEU | 153 | 31.559 | 68.607 | -3.756 | 1.00 26.77 | A3 | ATOM | 1175 | H | LEU | 158 | 37.213 | 65.901 | -5.326 | 1.00 0.00 | A3 |
| ATOM | 1133 | CB | LEU | 153 | 30.881 | 69.858 | -4.160 | 1.00 28.22 | A3 | ATOM | 1176 | CA | LEU | 158 | 39.216 | 65.479 | -5.826 | 1.00 31.94 | A3 |
| ATOM | 1134 | CG | LEU | 153 | 29.943 | 69.894 | -5.316 | 1.00 30.67 | A3 | ATOM | 1177 | CB | LEU | 158 | 39.609 | 65.949 | -4.373 | 1.00 28.66 | A3 |
| ATOM | 1135 | CD1 | LEU | 153 | 28.580 | 69.281 | -5.090 | 1.00 26.48 | A3 | ATOM | 1178 | CG | LEU | 158 | 41.008 | 65.751 | -3.859 | 1.00 24.32 | A3 |
| ATOM | 1136 | CD2 | LEU | 153 | 29.741 | 71.365 | -5.496 | 1.00 34.46 | A3 | ATOM | 1179 | CD1 | LEU | 158 | 41.990 | 66.378 | -4.776 | 1.00 20.87 | A3 |
| ATOM | 1137 | C | LEU | 153 | 33.032 | 68.628 | -4.111 | 1.00 26.08 | A3 | ATOM | 1180 | CD2 | LEU | 158 | 41.099 | 66.330 | -2.477 | 1.00 24.86 | A3 |
| ATOM | 1138 | O | LEU | 153 | 33.419 | 68.187 | -5.212 | 1.00 31.46 | A3 | ATOM | 1181 | C | LEU | 158 | 39.468 | 63.994 | -6.027 | 1.00 31.46 | A3 |
| ATOM | 1139 | N | VAL | 154 | 33.902 | 69.180 | -3.269 | 1.00 26.12 | A3 | ATOM | 1182 | O | LEU | 158 | 40.298 | 63.609 | -6.844 | 1.00 30.58 | A3 |
| ATOM | 1140 | H | VAL | 154 | 33.589 | 69.557 | -2.416 | 1.00 0.00 | A3 | ATOM | 1183 | N | GLN | 159 | 38.652 | 63.225 | -5.340 | 1.00 33.54 | A3 |
| ATOM | 1141 | CA | VAL | 154 | 35.330 | 69.259 | -3.611 | 1.00 26.23 | A3 | ATOM | 1184 | H | GLN | 159 | 38.011 | 63.676 | -4.748 | 1.00 0.00 | A3 |
| ATOM | 1142 | CB | VAL | 154 | 36.057 | 70.299 | -2.692 | 1.00 26.51 | A3 | ATOM | 1185 | CA | GLN | 159 | 38.594 | 61.792 | -5.442 | 1.00 35.73 | A3 |
| ATOM | 1143 | CG1 | VAL | 154 | 37.578 | 70.188 | -2.942 | 1.00 25.01 | A3 | ATOM | 1186 | CB | GLN | 159 | 37.308 | 61.492 | -4.813 | 1.00 37.26 | A3 |
| ATOM | 1144 | CG2 | VAL | 154 | 35.528 | 71.728 | -2.945 | 1.00 27.82 | A3 | ATOM | 1187 | CG | GLN | 159 | 37.064 | 60.063 | -4.520 | 1.00 45.01 | A3 |
| ATOM | 1145 | C | VAL | 154 | 35.933 | 67.850 | -3.375 | 1.00 26.80 | A3 | ATOM | 1188 | CD | GLN | 159 | 37.755 | 59.611 | -3.256 | 1.00 46.24 | A3 |
| ATOM | 1146 | O | VAL | 154 | 36.678 | 67.363 | -4.229 | 1.00 26.27 | A3 | ATOM | 1189 | OE1 | GLN | 159 | 38.142 | 58.443 | -3.232 | 1.00 48.29 | A3 |
| ATOM | 1147 | N | ALA | 155 | 35.635 | 67.241 | -2.199 | 1.00 24.76 | A3 | ATOM | 1190 | NE2 | GLN | 159 | 37.936 | 60.456 | -2.224 | 1.00 47.82 | A3 |
| ATOM | 1148 | H | ALA | 155 | 35.084 | 67.758 | -1.570 | 1.00 0.00 | A3 | ATOM | 1191 | HE21 | GLN | 159 | 37.575 | 61.364 | -2.289 | 1.00 0.00 | A3 |
| ATOM | 1149 | CA | ALA | 155 | 36.095 | 65.940 | -1.782 | 1.00 25.21 | A3 | ATOM | 1192 | HE22 | GLN | 159 | 38.412 | 60.101 | -1.447 | 1.00 0.00 | A3 |
| ATOM | 1150 | CB | ALA | 155 | 35.463 | 65.572 | -0.457 | 1.00 25.25 | A3 | ATOM | 1193 | C | GLN | 159 | 38.686 | 61.381 | -6.921 | 1.00 36.24 | A3 |
| ATOM | 1151 | C | ALA | 155 | 35.708 | 64.946 | -2.841 | 1.00 26.94 | A3 | ATOM | 1194 | O | GLN | 159 | 39.632 | 60.690 | -7.324 | 1.00 38.97 | A3 |
| ATOM | 1152 | O | ALA | 155 | 36.594 | 64.288 | -3.398 | 1.00 26.76 | A3 | ATOM | 1195 | N | SER | 160 | 37.824 | 61.896 | -7.796 | 1.00 35.48 | A3 |
| ATOM | 1153 | N | SER | 156 | 34.450 | 64.982 | -3.282 | 1.00 29.96 | A3 | ATOM | 1196 | H | SER | 160 | 37.142 | 62.540 | -7.498 | 1.00 0.00 | A3 |
| ATOM | 1154 | H | SER | 156 | 33.790 | 65.577 | -2.868 | 1.00 0.00 | A3 | ATOM | 1197 | CA | SER | 160 | 37.869 | 61.564 | -9.203 | 1.00 34.96 | A3 |
| ATOM | 1155 | CA | SER | 156 | 34.034 | 64.105 | -4.354 | 1.00 32.17 | A3 | ATOM | 1198 | CB | SER | 160 | 36.645 | 62.100 | -9.863 | 1.00 37.54 | A3 |
| ATOM | 1156 | CB | SER | 156 | 32.531 | 64.319 | -4.544 | 1.00 34.23 | A3 | ATOM | 1199 | OG | SER | 160 | 35.587 | 62.434 | -8.942 | 1.00 44.81 | A3 |
| ATOM | 1157 | OG | SER | 156 | 32.000 | 64.195 | -5.879 | 1.00 39.35 | A3 | ATOM | 1200 | HG | SER | 160 | 35.340 | 61.689 | -8.387 | 1.00 0.00 | A3 |
| ATOM | 1158 | HG | SER | 156 | 31.120 | 63.815 | -5.851 | 1.00 0.00 | A3 | ATOM | 1201 | C | SER | 160 | 39.090 | 62.095 | -9.922 | 1.00 34.65 | A3 |
| ATOM | 1159 | C | SER | 156 | 34.845 | 64.338 | -5.632 | 1.00 33.46 | A3 | ATOM | 1202 | O | SER | 160 | 39.605 | 61.382 | -10.785 | 1.00 35.42 | A3 |
| ATOM | 1160 | O | SER | 156 | 35.411 | 63.380 | -6.174 | 1.00 34.62 | A3 | ATOM | 1203 | N | PHE | 161 | 39.615 | 63.293 | -9.595 | 1.00 33.82 | A3 |

FIG. 50

| | | | | | | | | |
|---|---|---|---|---|---|---|---|---|
| ATOM | 1204 | H | PHE | 161 | 39.203 | 63.796 | -8.864 | 1.00 0.00 | A3 |
| ATOM | 1205 | CA | PHE | 161 | 40.820 | 63.850 | -10.218 | 1.00 31.21 | A3 |
| ATOM | 1206 | CB | PHE | 161 | 41.110 | 65.264 | -9.629 | 1.00 28.28 | A3 |
| ATOM | 1207 | CG | PHE | 161 | 42.455 | 65.881 | -10.062 | 1.00 24.92 | A3 |
| ATOM | 1208 | CD1 | PHE | 161 | 42.696 | 66.228 | -11.389 | 1.00 22.98 | A3 |
| ATOM | 1209 | CD2 | PHE | 161 | 43.464 | 66.021 | -9.135 | 1.00 23.03 | A3 |
| ATOM | 1210 | CE1 | PHE | 161 | 43.941 | 66.695 | -11.767 | 1.00 21.06 | A3 |
| ATOM | 1211 | CE2 | PHE | 161 | 44.701 | 66.495 | -9.528 | 1.00 20.28 | A3 |
| ATOM | 1212 | CZ | PHE | 161 | 44.939 | 66.826 | -10.832 | 1.00 17.03 | A3 |
| ATOM | 1213 | C | PHE | 161 | 42.008 | 62.907 | -9.943 | 1.00 31.77 | A3 |
| ATOM | 1214 | O | PHE | 161 | 42.786 | 62.578 | -10.845 | 1.00 32.63 | A3 |
| ATOM | 1215 | N | LEU | 162 | 42.117 | 62.434 | -8.690 | 1.00 31.67 | A3 |
| ATOM | 1216 | H | LEU | 162 | 41.420 | 62.691 | -8.054 | 1.00 0.00 | A3 |
| ATOM | 1217 | CA | LEU | 162 | 43.186 | 61.574 | -8.232 | 1.00 31.29 | A3 |
| ATOM | 1218 | CB | LEU | 162 | 43.204 | 61.433 | -6.743 | 1.00 25.84 | A3 |
| ATOM | 1219 | CG | LEU | 162 | 43.693 | 62.674 | -6.003 | 1.00 26.02 | A3 |
| ATOM | 1220 | CD1 | LEU | 162 | 43.594 | 62.455 | -4.516 | 1.00 25.24 | A3 |
| ATOM | 1221 | CD2 | LEU | 162 | 45.107 | 62.994 | -6.415 | 1.00 27.04 | A3 |
| ATOM | 1222 | C | LEU | 162 | 43.061 | 60.212 | -8.813 | 1.00 34.23 | A3 |
| ATOM | 1223 | O | LEU | 162 | 44.107 | 59.654 | -9.070 | 1.00 36.51 | A3 |
| ATOM | 1224 | N | GLU | 163 | 41.926 | 59.589 | -9.082 | 1.00 37.24 | A3 |
| ATOM | 1225 | H | GLU | 163 | 41.072 | 60.002 | -8.826 | 1.00 0.00 | A3 |
| ATOM | 1226 | CA | GLU | 163 | 41.975 | 58.327 | -9.771 | 1.00 40.47 | A3 |
| ATOM | 1227 | CB | GLU | 163 | 40.566 | 57.716 | -9.835 | 1.00 45.38 | A3 |
| ATOM | 1228 | CG | GLU | 163 | 40.264 | 56.975 | -8.526 | 1.00 51.84 | A3 |
| ATOM | 1229 | CD | GLU | 163 | 41.291 | 55.889 | -8.126 | 1.00 57.97 | A3 |
| ATOM | 1230 | OE1 | GLU | 163 | 40.897 | 54.722 | -8.092 | 1.00 62.01 | A3 |
| ATOM | 1231 | OE2 | GLU | 163 | 42.466 | 56.180 | -7.832 | 1.00 59.17 | A3 |
| ATOM | 1232 | C | GLU | 163 | 42.586 | 58.430 | -11.142 | 1.00 41.34 | A3 |
| ATOM | 1233 | O | GLU | 163 | 43.456 | 57.633 | -11.486 | 1.00 42.17 | A3 |
| ATOM | 1234 | N | VAL | 164 | 42.257 | 59.436 | -11.920 | 1.00 42.28 | A3 |
| ATOM | 1235 | H | VAL | 164 | 41.589 | 60.091 | -11.615 | 1.00 0.00 | A3 |
| ATOM | 1236 | CA | VAL | 164 | 42.911 | 59.609 | -13.187 | 1.00 44.13 | A3 |
| ATOM | 1237 | CB | VAL | 164 | 42.207 | 60.711 | -13.940 | 1.00 45.52 | A3 |
| ATOM | 1238 | CG1 | VAL | 164 | 42.892 | 60.975 | -15.278 | 1.00 48.79 | A3 |
| ATOM | 1239 | CG2 | VAL | 164 | 40.786 | 60.269 | -14.226 | 1.00 46.09 | A3 |
| ATOM | 1240 | C | VAL | 164 | 44.386 | 59.933 | -12.991 | 1.00 46.13 | A3 |
| ATOM | 1241 | O | VAL | 164 | 45.192 | 59.473 | -13.794 | 1.00 45.99 | A3 |
| ATOM | 1242 | N | SER | 165 | 44.879 | 60.677 | -12.006 | 1.00 49.51 | A3 |
| ATOM | 1243 | H | SER | 165 | 44.287 | 61.173 | -11.396 | 1.00 0.00 | A3 |
| ATOM | 1244 | CA | SER | 165 | 46.325 | 60.845 | -11.895 | 1.00 53.44 | A3 |
| ATOM | 1245 | CB | SER | 165 | 46.715 | 61.796 | -10.775 | 1.00 54.77 | A3 |
| ATOM | 1246 | OG | SER | 165 | 46.049 | 61.618 | -9.530 | 1.00 59.99 | A3 |
| ATOM | 1247 | HG | SER | 165 | 45.997 | 60.694 | -9.261 | 1.00 0.00 | A3 |
| ATOM | 1248 | C | SER | 165 | 46.958 | 59.502 | -11.630 | 1.00 55.15 | A3 |
| ATOM | 1249 | O | SER | 165 | 48.028 | 59.227 | -12.148 | 1.00 55.02 | A3 |
| ATOM | 1250 | N | TYR | 166 | 46.239 | 58.645 | -10.900 | 1.00 58.57 | A3 |
| ATOM | 1251 | H | TYR | 166 | 45.374 | 58.948 | -10.549 | 1.00 0.00 | A3 |
| ATOM | 1252 | CA | TYR | 166 | 46.617 | 57.273 | -10.625 | 1.00 61.42 | A3 |
| ATOM | 1253 | CB | TYR | 166 | 45.543 | 56.653 | -9.680 | 1.00 64.05 | A3 |
| ATOM | 1254 | CG | TYR | 166 | 45.502 | 55.138 | -9.682 | 1.00 69.00 | A3 |
| ATOM | 1255 | CD1 | TYR | 166 | 44.389 | 54.501 | -10.185 | 1.00 71.64 | A3 |
| ATOM | 1256 | CE1 | TYR | 166 | 44.367 | 53.130 | -10.283 | 1.00 73.15 | A3 |
| ATOM | 1257 | CD2 | TYR | 166 | 46.594 | 54.409 | -9.257 | 1.00 71.27 | A3 |
| ATOM | 1258 | CE2 | TYR | 166 | 46.584 | 53.040 | -9.346 | 1.00 72.92 | A3 |
| ATOM | 1259 | CZ | TYR | 166 | 45.468 | 52.417 | -9.862 | 1.00 75.71 | A3 |
| ATOM | 1260 | OH | TYR | 166 | 45.474 | 51.038 | -10.016 | 1.00 80.61 | A3 |
| ATOM | 1261 | HH | TYR | 166 | 44.571 | 50.736 | -10.134 | 1.00 0.00 | A3 |
| ATOM | 1262 | C | TYR | 166 | 46.712 | 56.567 | -11.987 | 1.00 62.34 | A3 |
| ATOM | 1263 | O | TYR | 166 | 47.766 | 55.981 | -12.282 | 1.00 63.25 | A3 |
| ATOM | 1264 | N | ALA | 167 | 45.727 | 56.622 | -12.884 | 1.00 61.27 | A3 |
| ATOM | 1265 | H | ALA | 167 | 44.893 | 57.089 | -12.678 | 1.00 0.00 | A3 |
| ATOM | 1266 | CA | ALA | 167 | 45.933 | 55.982 | -14.159 | 1.00 61.47 | A3 |
| ATOM | 1267 | CB | ALA | 167 | 44.608 | 55.904 | -14.904 | 1.00 60.98 | A3 |
| ATOM | 1268 | C | ALA | 167 | 46.982 | 56.694 | -15.020 | 1.00 62.19 | A3 |
| ATOM | 1269 | O | ALA | 167 | 47.719 | 56.000 | -15.734 | 1.00 62.63 | A3 |
| ATOM | 1270 | N | VAL | 168 | 47.210 | 58.011 | -14.991 | 1.00 63.37 | A3 |
| ATOM | 1271 | H | VAL | 168 | 46.756 | 58.570 | -14.330 | 1.00 0.00 | A3 |
| ATOM | 1272 | CA | VAL | 168 | 48.174 | 58.593 | -15.923 | 1.00 65.62 | A3 |
| ATOM | 1273 | CB | VAL | 168 | 48.061 | 60.121 | -16.131 | 1.00 66.30 | A3 |
| ATOM | 1274 | CG1 | VAL | 168 | 46.687 | 60.431 | -16.706 | 1.00 66.78 | A3 |
| ATOM | 1275 | CG2 | VAL | 168 | 48.278 | 60.879 | -14.840 | 1.00 68.47 | A3 |
| ATOM | 1276 | C | VAL | 168 | 49.579 | 58.339 | -15.469 | 1.00 66.45 | A3 |
| ATOM | 1277 | O | VAL | 168 | 50.458 | 58.183 | -16.302 | 1.00 66.22 | A3 |
| ATOM | 1278 | N | LEU | 169 | 49.823 | 58.241 | -14.177 | 1.00 68.83 | A3 |
| ATOM | 1279 | H | LEU | 169 | 49.102 | 58.404 | -13.536 | 1.00 0.00 | A3 |
| ATOM | 1280 | CA | LEU | 169 | 51.141 | 57.899 | -13.695 | 1.00 71.81 | A3 |
| ATOM | 1281 | CB | LEU | 169 | 51.249 | 58.228 | -12.188 | 1.00 71.53 | A3 |
| ATOM | 1282 | CG | LEU | 169 | 51.137 | 59.732 | -11.813 | 1.00 70.68 | A3 |
| ATOM | 1283 | CD1 | LEU | 169 | 51.187 | 59.826 | -10.298 | 1.00 69.39 | A3 |
| ATOM | 1284 | CD2 | LEU | 169 | 52.223 | 60.580 | -12.491 | 1.00 68.49 | A3 |
| ATOM | 1285 | C | LEU | 169 | 51.333 | 56.414 | -13.979 | 1.00 73.61 | A3 |
| ATOM | 1286 | O | LEU | 169 | 52.408 | 56.013 | -14.429 | 1.00 74.75 | A3 |
| ATOM | 1287 | N | ARG | 170 | 50.309 | 55.583 | -13.819 | 1.00 75.45 | A3 |
| ATOM | 1288 | H | ARG | 170 | 49.488 | 55.923 | -13.399 | 1.00 0.00 | A3 |
| ATOM | 1289 | CA | ARG | 170 | 50.364 | 54.179 | -14.199 | 1.00 78.17 | A3 |

FIG. 5P

| | | | | | | | | | | | | | | | | | | |
|---|---|---|---|---|---|---|---|---|---|---|---|---|---|---|---|---|---|---|
| ATOM | 1290 | CB | ARG | 170 | 48.944 | 53.642 | -14.004 | 1.00 | 78.45 | A3 | ATOM | 1333 | CB | LEU | 210 | 45.234 | 42.591 | 25.453 | 1.00 | 52.47 | B1 |
| ATOM | 1291 | CG | ARG | 170 | 48.394 | 52.506 | -14.871 | 1.00 | 78.17 | A3 | ATOM | 1334 | CG | LEU | 210 | 43.799 | 42.058 | 25.547 | 1.00 | 51.68 | B1 |
| ATOM | 1292 | CD | ARG | 170 | 48.744 | 51.181 | -14.271 | 1.00 | 77.25 | A3 | ATOM | 1335 | CD1 | LEU | 210 | 43.123 | 42.562 | 26.804 | 1.00 | 53.37 | B1 |
| ATOM | 1293 | NE | ARG | 170 | 48.123 | 51.120 | -12.970 | 1.00 | 76.15 | A3 | ATOM | 1336 | CD2 | LEU | 210 | 43.050 | 42.453 | 24.303 | 1.00 | 51.37 | B1 |
| ATOM | 1294 | CZ | ARG | 170 | 47.245 | 51.528 | -12.824 | 1.00 | 0.00 | A3 | ATOM | 1337 | C | LEU | 210 | 46.770 | 44.374 | 24.596 | 1.00 | 50.98 | B1 |
| ATOM | 1295 | CZ | ARG | 170 | 48.758 | 50.547 | -11.970 | 1.00 | 76.14 | A3 | ATOM | 1338 | O | LEU | 210 | 46.475 | 45.267 | 23.790 | 1.00 | 51.76 | B1 |
| ATOM | 1296 | NH1 | ARG | 170 | 49.973 | 50.017 | -12.112 | 1.00 | 76.84 | A3 | ATOM | 1339 | HT1 | LEU | 210 | 44.382 | 44.922 | 24.421 | 1.00 | 0.00 | B1 |
| ATOM | 1297 | HH11 | ARG | 170 | 50.441 | 50.030 | -12.994 | 1.00 | 0.00 | A3 | ATOM | 1340 | HT2 | LEU | 210 | 45.157 | 45.974 | 25.414 | 1.00 | 0.00 | B1 |
| ATOM | 1298 | HH12 | ARG | 170 | 50.406 | 49.570 | -11.329 | 1.00 | 0.00 | A3 | ATOM | 1341 | N | LEU | 210 | 44.705 | 45.041 | 25.406 | 1.00 | 53.59 | B1 |
| ATOM | 1299 | NH2 | ARG | 170 | 48.147 | 50.492 | -10.806 | 1.00 | 77.02 | A3 | ATOM | 1342 | HT3 | LEU | 210 | 43.855 | 45.012 | 25.997 | 1.00 | 0.00 | B1 |
| ATOM | 1300 | HH21 | ARG | 170 | 47.237 | 50.890 | -10.714 | 1.00 | 0.00 | A3 | ATOM | 1343 | CA | LEU | 210 | 45.730 | 44.038 | 25.676 | 1.00 | 52.35 | B1 |
| ATOM | 1301 | HH22 | ARG | 170 | 48.586 | 50.052 | -10.023 | 1.00 | 0.00 | A3 | ATOM | 1344 | N | PRO | 211 | 47.974 | 43.825 | 24.494 | 1.00 | 49.35 | B1 |
| ATOM | 1302 | C | ARG | 170 | 50.870 | 54.052 | -15.647 | 1.00 | 79.84 | A3 | ATOM | 1345 | CD | PRO | 211 | 48.621 | 43.024 | 25.532 | 1.00 | 49.52 | B1 |
| ATOM | 1303 | O | ARG | 170 | 51.924 | 53.470 | -15.908 | 1.00 | 80.07 | A3 | ATOM | 1346 | CA | PRO | 211 | 48.895 | 44.191 | 23.419 | 1.00 | 49.04 | B1 |
| ATOM | 1304 | N | HIS | 171 | 50.193 | 54.663 | -16.611 | 1.00 | 81.38 | A3 | ATOM | 1347 | CB | PRO | 211 | 50.209 | 43.571 | 23.865 | 1.00 | 49.02 | B1 |
| ATOM | 1305 | H | HIS | 171 | 49.433 | 55.234 | -16.359 | 1.00 | 0.00 | A3 | ATOM | 1348 | CG | PRO | 211 | 49.794 | 42.438 | 24.783 | 1.00 | 49.77 | B1 |
| ATOM | 1306 | CA | HIS | 171 | 50.663 | 54.597 | -17.970 | 1.00 | 84.03 | A3 | ATOM | 1349 | C | PRO | 211 | 48.543 | 43.864 | 21.965 | 1.00 | 48.03 | B1 |
| ATOM | 1307 | CB | HIS | 171 | 49.590 | 55.054 | -18.902 | 1.00 | 86.82 | A3 | ATOM | 1350 | O | PRO | 211 | 47.872 | 42.896 | 21.622 | 1.00 | 49.05 | B1 |
| ATOM | 1308 | CG | HIS | 171 | 48.496 | 54.037 | -19.147 | 1.00 | 90.73 | A3 | ATOM | 1351 | N | GLN | 212 | 49.032 | 44.675 | 21.051 | 1.00 | 46.52 | B1 |
| ATOM | 1309 | CD2 | HIS | 171 | 47.467 | 53.765 | -18.272 | 1.00 | 91.35 | A3 | ATOM | 1352 | H | GLN | 212 | 49.506 | 45.478 | 21.349 | 1.00 | 0.00 | B1 |
| ATOM | 1310 | ND1 | HIS | 171 | 48.308 | 53.301 | -20.248 | 1.00 | 92.24 | A3 | ATOM | 1353 | CA | GLN | 212 | 48.839 | 44.461 | 19.641 | 1.00 | 45.47 | B1 |
| ATOM | 1311 | HD1 | HIS | 171 | 48.887 | 53.287 | -21.044 | 1.00 | 0.00 | A3 | ATOM | 1354 | CB | GLN | 212 | 49.533 | 45.522 | 18.849 | 1.00 | 46.81 | B1 |
| ATOM | 1312 | CE1 | HIS | 171 | 47.204 | 52.605 | -20.077 | 1.00 | 92.41 | A3 | ATOM | 1355 | CG | GLN | 212 | 48.482 | 46.139 | 17.999 | 1.00 | 49.55 | B1 |
| ATOM | 1313 | NE2 | HIS | 171 | 46.711 | 52.892 | -18.891 | 1.00 | 92.59 | A3 | ATOM | 1356 | CD | GLN | 212 | 49.024 | 46.703 | 16.709 | 1.00 | 54.21 | B1 |
| ATOM | 1314 | HE2 | HIS | 171 | 45.884 | 52.511 | -18.518 | 1.00 | 0.00 | A3 | ATOM | 1357 | OE1 | GLN | 212 | 48.429 | 47.672 | 16.232 | 1.00 | 57.72 | B1 |
| ATOM | 1315 | C | HIS | 171 | 51.907 | 55.446 | -18.232 | 1.00 | 85.42 | A3 | ATOM | 1358 | NE2 | GLN | 212 | 50.086 | 46.176 | 16.074 | 1.00 | 52.39 | B1 |
| ATOM | 1316 | O | HIS | 171 | 52.440 | 55.352 | -19.344 | 1.00 | 85.98 | A3 | ATOM | 1359 | HE21 | GLN | 212 | 50.530 | 45.383 | 16.430 | 1.00 | 0.00 | B1 |
| ATOM | 1317 | N | LEU | 172 | 52.359 | 56.307 | -17.302 | 1.00 | 86.13 | A3 | ATOM | 1360 | HE22 | GLN | 212 | 50.341 | 46.625 | 15.244 | 1.00 | 0.00 | B1 |
| ATOM | 1318 | H | LEU | 172 | 51.870 | 56.411 | -16.463 | 1.00 | 0.00 | A3 | ATOM | 1361 | C | GLN | 212 | 49.390 | 43.133 | 19.185 | 1.00 | 44.79 | B1 |
| ATOM | 1319 | CA | LEU | 172 | 53.550 | 57.133 | -17.496 | 1.00 | 86.02 | A3 | ATOM | 1362 | O | GLN | 212 | 48.959 | 42.520 | 18.208 | 1.00 | 44.01 | B1 |
| ATOM | 1320 | CB | LEU | 172 | 53.500 | 58.357 | -16.607 | 1.00 | 86.31 | A3 | ATOM | 1363 | N | SER | 213 | 50.401 | 42.671 | 19.893 | 1.00 | 44.72 | B1 |
| ATOM | 1321 | CG | LEU | 172 | 54.022 | 59.658 | -17.203 | 1.00 | 87.48 | A3 | ATOM | 1364 | H | SER | 213 | 50.730 | 43.115 | 20.698 | 1.00 | 0.00 | B1 |
| ATOM | 1322 | CD1 | LEU | 172 | 53.436 | 59.939 | -18.596 | 1.00 | 87.68 | A3 | ATOM | 1365 | CA | SER | 213 | 51.025 | 41.424 | 19.521 | 1.00 | 43.76 | B1 |
| ATOM | 1323 | CD2 | LEU | 172 | 53.645 | 60.778 | -16.251 | 1.00 | 87.95 | A3 | ATOM | 1366 | CB | SER | 213 | 52.220 | 41.124 | 20.354 | 1.00 | 45.29 | B1 |
| ATOM | 1324 | C | LEU | 172 | 54.813 | 56.357 | -17.180 | 1.00 | 85.92 | A3 | ATOM | 1367 | OG | SER | 213 | 51.802 | 41.455 | 21.681 | 1.00 | 52.50 | B1 |
| ATOM | 1325 | O | LEU | 172 | 55.896 | 56.660 | -17.692 | 1.00 | 86.23 | A3 | ATOM | 1368 | HG | SER | 213 | 52.479 | 41.127 | 22.288 | 1.00 | 0.00 | B1 |
| ATOM | 1326 | N | ALA | 173 | 54.733 | 55.383 | -16.282 | 1.00 | 85.49 | A3 | ATOM | 1369 | C | SER | 213 | 50.014 | 40.376 | 19.784 | 1.00 | 40.92 | B1 |
| ATOM | 1327 | H | ALA | 173 | 53.899 | 55.276 | -15.769 | 1.00 | 0.00 | A3 | ATOM | 1370 | O | SER | 213 | 49.964 | 39.492 | 18.947 | 1.00 | 43.32 | B1 |
| ATOM | 1328 | CA | ALA | 173 | 55.856 | 54.497 | -16.087 | 1.00 | 85.65 | A3 | ATOM | 1371 | N | PHE | 214 | 49.242 | 40.571 | 20.876 | 1.00 | 38.86 | B1 |
| ATOM | 1329 | CB | ALA | 173 | 56.602 | 54.859 | -14.809 | 1.00 | 85.01 | A3 | ATOM | 1372 | H | PHE | 214 | 49.414 | 41.370 | 21.410 | 1.00 | 0.00 | B1 |
| ATOM | 1330 | C | ALA | 173 | 55.330 | 53.073 | -16.008 | 1.00 | 86.54 | A3 | ATOM | 1373 | CA | PHE | 214 | 48.210 | 39.664 | 21.336 | 1.00 | 37.40 | B1 |
| ATOM | 1331 | OT1 | ALA | 173 | 55.585 | 52.347 | -16.971 | 1.00 | 87.21 | A3 | ATOM | 1374 | CB | PHE | 214 | 47.568 | 40.064 | 22.634 | 1.00 | 37.45 | B1 |
| ATOM | 1332 | OT2 | ALA | 173 | 54.650 | 52.707 | -15.036 | 1.00 | 87.31 | A3 | ATOM | 1375 | CG | PHE | 214 | 46.494 | 39.080 | 23.035 | 1.00 | 41.01 | B1 |

FIG. 5Q

| | | | | | | | | | |
|---|---|---|---|---|---|---|---|---|---|
| ATOM | 1376 | CD1 | PHE | 214 | 45.176 | 39.459 | 23.044 | 1.00 42.77 | B1 |
| ATOM | 1377 | CD2 | PHE | 214 | 46.818 | 37.794 | 23.400 | 1.00 42.02 | B1 |
| ATOM | 1378 | CE1 | PHE | 214 | 44.197 | 38.554 | 23.423 | 1.00 41.82 | B1 |
| ATOM | 1379 | CE2 | PHE | 214 | 45.834 | 36.898 | 23.776 | 1.00 41.70 | B1 |
| ATOM | 1380 | CZ | PHE | 214 | 44.519 | 37.277 | 23.791 | 1.00 41.05 | B1 |
| ATOM | 1381 | C | PHE | 214 | 47.109 | 39.656 | 20.321 | 1.00 36.54 | B1 |
| ATOM | 1382 | O | PHE | 214 | 46.735 | 38.566 | 19.889 | 1.00 37.99 | B1 |
| ATOM | 1383 | N | LEU | 215 | 46.616 | 40.812 | 19.893 | 1.00 33.27 | B1 |
| ATOM | 1384 | H | LEU | 215 | 47.008 | 41.642 | 20.238 | 1.00 0.00 | B1 |
| ATOM | 1385 | CA | LEU | 215 | 45.504 | 40.864 | 18.966 | 1.00 30.38 | B1 |
| ATOM | 1386 | CB | LEU | 215 | 45.099 | 42.282 | 18.701 | 1.00 33.82 | B1 |
| ATOM | 1387 | CG | LEU | 215 | 43.857 | 42.530 | 17.893 | 1.00 32.78 | B1 |
| ATOM | 1388 | CD1 | LEU | 215 | 42.727 | 41.963 | 18.737 | 1.00 32.95 | B1 |
| ATOM | 1389 | CD2 | LEU | 215 | 43.688 | 44.011 | 17.508 | 1.00 28.93 | B1 |
| ATOM | 1390 | C | LEU | 215 | 45.811 | 40.232 | 17.648 | 1.00 29.57 | B1 |
| ATOM | 1391 | O | LEU | 215 | 44.922 | 39.632 | 17.055 | 1.00 31.28 | B1 |
| ATOM | 1392 | N | LEU | 216 | 47.031 | 40.379 | 17.155 | 1.00 29.44 | B1 |
| ATOM | 1393 | H | LEU | 216 | 47.677 | 40.935 | 17.646 | 1.00 0.00 | B1 |
| ATOM | 1394 | CA | LEU | 216 | 47.465 | 39.790 | 15.893 | 1.00 29.89 | B1 |
| ATOM | 1395 | CB | LEU | 216 | 48.791 | 40.450 | 15.472 | 1.00 28.61 | B1 |
| ATOM | 1396 | CG | LEU | 216 | 48.682 | 41.877 | 14.939 | 1.00 26.83 | B1 |
| ATOM | 1397 | CD1 | LEU | 216 | 49.925 | 42.558 | 15.344 | 1.00 28.57 | B1 |
| ATOM | 1398 | CD2 | LEU | 216 | 48.446 | 41.950 | 13.452 | 1.00 24.09 | B1 |
| ATOM | 1399 | C | LEU | 216 | 47.613 | 38.274 | 16.062 | 1.00 31.23 | B1 |
| ATOM | 1400 | O | LEU | 216 | 47.328 | 37.514 | 15.138 | 1.00 29.20 | B1 |
| ATOM | 1401 | N | LYS | 217 | 47.999 | 37.826 | 17.261 | 1.00 32.50 | B1 |
| ATOM | 1402 | H | LYS | 217 | 48.305 | 38.482 | 17.926 | 1.00 0.00 | B1 |
| ATOM | 1403 | CA | LYS | 217 | 48.067 | 36.439 | 17.599 | 1.00 34.90 | B1 |
| ATOM | 1404 | CB | LYS | 217 | 48.645 | 36.280 | 19.002 | 1.00 38.07 | B1 |
| ATOM | 1405 | CG | LYS | 217 | 49.394 | 34.978 | 19.109 | 1.00 45.25 | B1 |
| ATOM | 1406 | CD | LYS | 217 | 49.714 | 34.491 | 20.521 | 1.00 53.27 | B1 |
| ATOM | 1407 | CE | LYS | 217 | 50.229 | 33.024 | 20.297 | 1.00 59.03 | B1 |
| ATOM | 1408 | NZ | LYS | 217 | 50.213 | 32.135 | 21.467 | 1.00 62.10 | B1 |
| ATOM | 1409 | HZ1 | LYS | 217 | 49.239 | 32.056 | 21.824 | 1.00 0.00 | B1 |
| ATOM | 1410 | HZ2 | LYS | 217 | 50.830 | 32.515 | 22.214 | 1.00 0.00 | B1 |
| ATOM | 1411 | HZ3 | LYS | 217 | 50.554 | 31.195 | 21.179 | 1.00 0.00 | B1 |
| ATOM | 1412 | C | LYS | 217 | 46.617 | 35.950 | 17.546 | 1.00 36.77 | B1 |
| ATOM | 1413 | O | LYS | 217 | 46.311 | 34.933 | 16.886 | 1.00 39.58 | B1 |
| ATOM | 1414 | N | CYS | 218 | 45.664 | 36.638 | 18.177 | 1.00 34.86 | B1 |
| ATOM | 1415 | H | CYS | 218 | 45.907 | 37.388 | 18.751 | 1.00 0.00 | B1 |
| ATOM | 1416 | CA | CYS | 218 | 44.277 | 36.238 | 18.076 | 1.00 33.61 | B1 |
| ATOM | 1417 | CB | CYS | 218 | 43.430 | 37.175 | 18.846 | 1.00 33.21 | B1 |
| ATOM | 1418 | SG | CYS | 218 | 43.856 | 36.710 | 20.515 | 1.00 35.92 | B1 |
| ATOM | 1419 | C | CYS | 218 | 43.766 | 36.189 | 16.652 | 1.00 32.89 | B1 |
| ATOM | 1420 | O | CYS | 218 | 43.155 | 35.169 | 16.323 | 1.00 34.71 | B1 |
| ATOM | 1421 | N | LEU | 219 | 44.035 | 37.169 | 15.777 | 1.00 29.52 | B1 |
| ATOM | 1422 | H | LEU | 219 | 44.512 | 37.960 | 16.104 | 1.00 0.00 | B1 |
| ATOM | 1423 | CA | LEU | 219 | 43.614 | 37.119 | 14.393 | 1.00 27.44 | B1 |
| ATOM | 1424 | CB | LEU | 219 | 44.116 | 38.412 | 13.727 | 1.00 26.24 | B1 |
| ATOM | 1425 | CG | LEU | 219 | 43.884 | 38.768 | 12.241 | 1.00 25.07 | B1 |
| ATOM | 1426 | CD1 | LEU | 219 | 42.402 | 38.975 | 11.996 | 1.00 26.24 | B1 |
| ATOM | 1427 | CD2 | LEU | 219 | 44.563 | 40.051 | 11.882 | 1.00 22.10 | B1 |
| ATOM | 1428 | C | LEU | 219 | 44.121 | 35.867 | 13.634 | 1.00 28.24 | B1 |
| ATOM | 1429 | O | LEU | 219 | 43.373 | 35.204 | 12.889 | 1.00 27.12 | B1 |
| ATOM | 1430 | N | GLU | 220 | 45.399 | 35.499 | 13.795 | 1.00 28.06 | B1 |
| ATOM | 1431 | H | GLU | 220 | 45.957 | 35.974 | 14.448 | 1.00 0.00 | B1 |
| ATOM | 1432 | CA | GLU | 220 | 45.963 | 34.411 | 13.048 | 1.00 28.38 | B1 |
| ATOM | 1433 | CB | GLU | 220 | 47.376 | 34.198 | 13.469 | 1.00 34.25 | B1 |
| ATOM | 1434 | CG | GLU | 220 | 48.049 | 33.079 | 12.666 | 1.00 46.36 | B1 |
| ATOM | 1435 | CD | GLU | 220 | 49.545 | 32.794 | 12.907 | 1.00 55.51 | B1 |
| ATOM | 1436 | OE1 | GLU | 220 | 50.113 | 32.133 | 12.021 | 1.00 58.95 | B1 |
| ATOM | 1437 | OE2 | GLU | 220 | 50.144 | 33.213 | 13.930 | 1.00 60.41 | B1 |
| ATOM | 1438 | C | GLU | 220 | 45.134 | 33.193 | 13.354 | 1.00 27.30 | B1 |
| ATOM | 1439 | O | GLU | 220 | 44.662 | 32.524 | 12.437 | 1.00 27.08 | B1 |
| ATOM | 1440 | N | GLN | 221 | 44.866 | 33.023 | 14.642 | 1.00 25.42 | B1 |
| ATOM | 1441 | H | GLN | 221 | 45.229 | 33.687 | 15.268 | 1.00 0.00 | B1 |
| ATOM | 1442 | CA | GLN | 221 | 44.074 | 31.940 | 15.176 | 1.00 26.28 | B1 |
| ATOM | 1443 | CB | GLN | 221 | 44.143 | 31.927 | 16.691 | 1.00 26.78 | B1 |
| ATOM | 1444 | CG | GLN | 221 | 45.555 | 31.456 | 17.011 | 1.00 29.19 | B1 |
| ATOM | 1445 | CD | GLN | 221 | 45.752 | 31.067 | 18.442 | 1.00 31.98 | B1 |
| ATOM | 1446 | OE1 | GLN | 221 | 46.472 | 30.162 | 18.808 | 1.00 35.98 | B1 |
| ATOM | 1447 | NE2 | GLN | 221 | 45.110 | 31.736 | 19.347 | 1.00 39.31 | B1 |
| ATOM | 1448 | HE21 | GLN | 221 | 45.263 | 31.423 | 20.246 | 1.00 0.00 | B1 |
| ATOM | 1449 | HE22 | GLN | 221 | 44.571 | 32.514 | 19.111 | 1.00 0.00 | B1 |
| ATOM | 1450 | C | GLN | 221 | 42.615 | 31.925 | 14.789 | 1.00 26.21 | B1 |
| ATOM | 1451 | O | GLN | 221 | 42.186 | 30.896 | 14.269 | 1.00 30.69 | B1 |
| ATOM | 1452 | N | VAL | 222 | 41.814 | 32.962 | 14.984 | 1.00 23.63 | B1 |
| ATOM | 1453 | H | VAL | 222 | 42.199 | 33.746 | 15.426 | 1.00 0.00 | B1 |
| ATOM | 1454 | CA | VAL | 222 | 40.429 | 33.034 | 14.537 | 1.00 21.92 | B1 |
| ATOM | 1455 | CB | VAL | 222 | 39.934 | 34.442 | 14.793 | 1.00 21.36 | B1 |
| ATOM | 1456 | CG1 | VAL | 222 | 38.706 | 34.831 | 14.027 | 1.00 17.72 | B1 |
| ATOM | 1457 | CG2 | VAL | 222 | 39.671 | 34.496 | 16.257 | 1.00 20.95 | B1 |
| ATOM | 1458 | C | VAL | 222 | 40.374 | 32.707 | 13.066 | 1.00 22.65 | B1 |
| ATOM | 1459 | O | VAL | 222 | 39.475 | 32.013 | 12.632 | 1.00 23.72 | B1 |
| ATOM | 1460 | N | ARG | 223 | 41.341 | 33.120 | 12.283 | 1.00 23.95 | B1 |
| ATOM | 1461 | H | ARG | 223 | 42.099 | 33.614 | 12.666 | 1.00 0.00 | B1 |

FIG. 5R

| ATOM | 1462 | CA | ARG | 223 | 41.309 | 32.939 | 10.844 | 1.00 | 27.19 | B1 |
|---|---|---|---|---|---|---|---|---|---|---|
| ATOM | 1463 | CB | ARG | 223 | 42.294 | 33.935 | 10.283 | 1.00 | 29.26 | B1 |
| ATOM | 1464 | CG | ARG | 223 | 42.102 | 34.364 | 8.869 | 1.00 | 35.23 | B1 |
| ATOM | 1465 | CD | ARG | 223 | 42.880 | 33.487 | 7.929 | 1.00 | 41.88 | B1 |
| ATOM | 1466 | NE | ARG | 223 | 41.972 | 32.676 | 7.096 | 1.00 | 47.42 | B1 |
| ATOM | 1467 | HE | ARG | 223 | 41.451 | 31.953 | 7.502 | 1.00 | 0.00 | B1 |
| ATOM | 1468 | CZ | ARG | 223 | 41.875 | 32.896 | 5.784 | 1.00 | 46.15 | B1 |
| ATOM | 1469 | NH1 | ARG | 223 | 42.575 | 33.837 | 5.246 | 1.00 | 49.54 | B1 |
| ATOM | 1470 | HH11 | ARG | 223 | 42.522 | 33.989 | 4.259 | 1.00 | 0.00 | B1 |
| ATOM | 1471 | HH12 | ARG | 223 | 43.156 | 34.428 | 5.805 | 1.00 | 0.00 | B1 |
| ATOM | 1472 | NH2 | ARG | 223 | 41.178 | 32.161 | 4.952 | 1.00 | 45.74 | B1 |
| ATOM | 1473 | HH21 | ARG | 223 | 40.697 | 31.353 | 5.290 | 1.00 | 0.00 | B1 |
| ATOM | 1474 | HH22 | ARG | 223 | 41.154 | 32.399 | 3.980 | 1.00 | 0.00 | B1 |
| ATOM | 1475 | C | ARG | 223 | 41.624 | 31.492 | 10.430 | 1.00 | 29.13 | B1 |
| ATOM | 1476 | O | ARG | 223 | 41.181 | 30.987 | 9.376 | 1.00 | 29.32 | B1 |
| ATOM | 1477 | N | LYS | 224 | 42.413 | 30.791 | 11.259 | 1.00 | 29.17 | B1 |
| ATOM | 1478 | H | LYS | 224 | 42.791 | 31.235 | 12.048 | 1.00 | 0.00 | B1 |
| ATOM | 1479 | CA | LYS | 224 | 42.714 | 29.411 | 10.994 | 1.00 | 27.70 | B1 |
| ATOM | 1480 | CB | LYS | 224 | 43.922 | 29.085 | 11.818 | 1.00 | 30.07 | B1 |
| ATOM | 1481 | CG | LYS | 224 | 44.372 | 27.660 | 11.706 | 1.00 | 36.70 | B1 |
| ATOM | 1482 | CD | LYS | 224 | 45.829 | 27.544 | 12.127 | 1.00 | 41.68 | B1 |
| ATOM | 1483 | CE | LYS | 224 | 46.303 | 26.478 | 11.131 | 1.00 | 48.18 | B1 |
| ATOM | 1484 | NZ | LYS | 224 | 47.750 | 26.492 | 10.913 | 1.00 | 53.57 | B1 |
| ATOM | 1485 | HZ1 | LYS | 224 | 48.230 | 26.241 | 11.801 | 1.00 | 0.00 | B1 |
| ATOM | 1486 | HZ2 | LYS | 224 | 48.057 | 27.436 | 10.606 | 1.00 | 0.00 | B1 |
| ATOM | 1487 | HZ3 | LYS | 224 | 47.998 | 25.792 | 10.183 | 1.00 | 0.00 | B1 |
| ATOM | 1488 | C | LYS | 224 | 41.464 | 28.598 | 11.347 | 1.00 | 26.27 | B1 |
| ATOM | 1489 | O | LYS | 224 | 40.970 | 27.810 | 10.510 | 1.00 | 24.82 | B1 |
| ATOM | 1490 | N | ILE | 225 | 40.892 | 28.835 | 12.547 | 1.00 | 24.75 | B1 |
| ATOM | 1491 | H | ILE | 225 | 41.308 | 29.487 | 13.151 | 1.00 | 0.00 | B1 |
| ATOM | 1492 | CA | ILE | 225 | 39.656 | 28.147 | 12.943 | 1.00 | 23.33 | B1 |
| ATOM | 1493 | CB | ILE | 225 | 39.146 | 28.622 | 14.296 | 1.00 | 18.08 | B1 |
| ATOM | 1494 | CG2 | ILE | 225 | 37.874 | 27.872 | 14.577 | 1.00 | 15.43 | B1 |
| ATOM | 1495 | CG1 | ILE | 225 | 40.161 | 28.400 | 15.380 | 1.00 | 13.38 | B1 |
| ATOM | 1496 | CD | ILE | 225 | 39.787 | 28.967 | 16.749 | 1.00 | 13.59 | B1 |
| ATOM | 1497 | C | ILE | 225 | 38.594 | 28.437 | 11.889 | 1.00 | 27.28 | B1 |
| ATOM | 1498 | O | ILE | 225 | 37.978 | 27.492 | 11.400 | 1.00 | 31.49 | B1 |
| ATOM | 1499 | N | GLN | 226 | 38.396 | 29.677 | 11.402 | 1.00 | 29.69 | B1 |
| ATOM | 1500 | H | GLN | 226 | 38.894 | 30.413 | 11.803 | 1.00 | 0.00 | B1 |
| ATOM | 1501 | CA | GLN | 226 | 37.450 | 29.969 | 10.313 | 1.00 | 29.12 | B1 |
| ATOM | 1502 | CB | GLN | 226 | 37.366 | 31.438 | 9.962 | 1.00 | 32.26 | B1 |
| ATOM | 1503 | CG | GLN | 226 | 36.682 | 32.156 | 11.108 | 1.00 | 36.28 | B1 |
| ATOM | 1504 | CD | GLN | 226 | 36.429 | 33.613 | 10.816 | 1.00 | 37.88 | B1 |
| ATOM | 1505 | OE1 | GLN | 226 | 37.158 | 34.281 | 10.076 | 1.00 | 36.34 | B1 |
| ATOM | 1506 | NE2 | GLN | 226 | 35.359 | 34.114 | 11.421 | 1.00 | 39.62 | B1 |
| ATOM | 1507 | HE21 | GLN | 226 | 34.823 | 33.501 | 11.971 | 1.00 | 0.00 | B1 |
| ATOM | 1508 | HE22 | GLN | 226 | 35.153 | 35.057 | 11.287 | 1.00 | 0.00 | B1 |
| ATOM | 1509 | C | GLN | 226 | 37.714 | 29.295 | 9.007 | 1.00 | 26.82 | B1 |
| ATOM | 1510 | O | GLN | 226 | 36.775 | 28.887 | 8.325 | 1.00 | 27.45 | B1 |
| ATOM | 1511 | N | GLY | 227 | 38.940 | 29.186 | 8.570 | 1.00 | 26.55 | B1 |
| ATOM | 1512 | H | GLY | 227 | 39.688 | 29.612 | 9.043 | 1.00 | 0.00 | B1 |
| ATOM | 1513 | CA | GLY | 227 | 39.195 | 28.427 | 7.348 | 1.00 | 27.27 | B1 |
| ATOM | 1514 | C | GLY | 227 | 38.832 | 26.949 | 7.574 | 1.00 | 27.65 | B1 |
| ATOM | 1515 | O | GLY | 227 | 38.287 | 26.291 | 6.656 | 1.00 | 26.79 | B1 |
| ATOM | 1516 | N | ASP | 228 | 39.025 | 26.429 | 8.819 | 1.00 | 27.03 | B1 |
| ATOM | 1517 | H | ASP | 228 | 39.460 | 26.957 | 9.523 | 1.00 | 0.00 | B1 |
| ATOM | 1518 | CA | ASP | 228 | 38.618 | 25.038 | 9.052 | 1.00 | 28.20 | B1 |
| ATOM | 1519 | CB | ASP | 228 | 38.986 | 24.492 | 10.391 | 1.00 | 26.04 | B1 |
| ATOM | 1520 | CG | ASP | 228 | 40.427 | 24.554 | 10.774 | 1.00 | 24.88 | B1 |
| ATOM | 1521 | OD1 | ASP | 228 | 40.627 | 24.521 | 11.977 | 1.00 | 23.37 | B1 |
| ATOM | 1522 | OD2 | ASP | 228 | 41.302 | 24.637 | 9.912 | 1.00 | 23.32 | B1 |
| ATOM | 1523 | C | ASP | 228 | 37.120 | 24.830 | 8.992 | 1.00 | 27.23 | B1 |
| ATOM | 1524 | O | ASP | 228 | 36.662 | 23.900 | 8.336 | 1.00 | 27.07 | B1 |
| ATOM | 1525 | N | GLY | 229 | 36.390 | 25.739 | 9.639 | 1.00 | 26.74 | B1 |
| ATOM | 1526 | H | GLY | 229 | 36.861 | 26.444 | 10.134 | 1.00 | 0.00 | B1 |
| ATOM | 1527 | CA | GLY | 229 | 34.946 | 25.723 | 9.673 | 1.00 | 25.87 | B1 |
| ATOM | 1528 | C | GLY | 229 | 34.393 | 25.825 | 8.274 | 1.00 | 24.95 | B1 |
| ATOM | 1529 | O | GLY | 229 | 33.370 | 25.222 | 7.956 | 1.00 | 25.73 | B1 |
| ATOM | 1530 | N | ALA | 230 | 35.058 | 26.541 | 7.391 | 1.00 | 23.97 | B1 |
| ATOM | 1531 | H | ALA | 230 | 35.871 | 27.026 | 7.654 | 1.00 | 0.00 | B1 |
| ATOM | 1532 | CA | ALA | 230 | 34.530 | 26.688 | 6.061 | 1.00 | 25.94 | B1 |
| ATOM | 1533 | CB | ALA | 230 | 35.193 | 27.852 | 5.312 | 1.00 | 19.76 | B1 |
| ATOM | 1534 | C | ALA | 230 | 34.794 | 25.403 | 5.304 | 1.00 | 29.42 | B1 |
| ATOM | 1535 | O | ALA | 230 | 34.014 | 25.061 | 4.423 | 1.00 | 32.07 | B1 |
| ATOM | 1536 | N | ALA | 231 | 35.878 | 24.671 | 5.572 | 1.00 | 32.16 | B1 |
| ATOM | 1537 | H | ALA | 231 | 36.556 | 25.045 | 6.175 | 1.00 | 0.00 | B1 |
| ATOM | 1538 | CA | ALA | 231 | 36.141 | 23.364 | 4.957 | 1.00 | 31.99 | B1 |
| ATOM | 1539 | CB | ALA | 231 | 37.489 | 22.847 | 5.428 | 1.00 | 32.77 | B1 |
| ATOM | 1540 | C | ALA | 231 | 35.060 | 22.361 | 5.386 | 1.00 | 32.99 | B1 |
| ATOM | 1541 | O | ALA | 231 | 34.599 | 21.575 | 4.576 | 1.00 | 34.12 | B1 |
| ATOM | 1542 | N | LEU | 232 | 34.662 | 22.309 | 6.652 | 1.00 | 33.30 | B1 |
| ATOM | 1543 | H | LEU | 232 | 35.174 | 22.861 | 7.284 | 1.00 | 0.00 | B1 |
| ATOM | 1544 | CA | LEU | 232 | 33.558 | 21.506 | 7.165 | 1.00 | 35.33 | B1 |
| ATOM | 1545 | CB | LEU | 232 | 33.279 | 21.783 | 8.626 | 1.00 | 34.22 | B1 |
| ATOM | 1546 | CG | LEU | 232 | 32.410 | 20.861 | 9.394 | 1.00 | 33.16 | B1 |
| ATOM | 1547 | CD1 | LEU | 232 | 33.191 | 19.545 | 9.451 | 1.00 | 34.59 | B1 |

FIG. 5S

| | | | | | | | | | |
|---|---|---|---|---|---|---|---|---|---|
| ATOM | 1548 | CD2 | LEU | 232 | 32.107 | 21.381 | 10.800 | 1.00 31.32 | B1 |
| ATOM | 1549 | C | LEU | 232 | 32.271 | 21.829 | 6.440 | 1.00 36.65 | B1 |
| ATOM | 1550 | O | LEU | 232 | 31.703 | 20.986 | 5.749 | 1.00 36.42 | B1 |
| ATOM | 1551 | N | GLN | 233 | 31.836 | 23.084 | 6.570 | 1.00 38.89 | B1 |
| ATOM | 1552 | H | GLN | 233 | 32.378 | 23.719 | 7.087 | 1.00 0.00 | B1 |
| ATOM | 1553 | CA | GLN | 233 | 30.637 | 23.579 | 5.933 | 1.00 40.02 | B1 |
| ATOM | 1554 | CB | GLN | 233 | 30.572 | 25.072 | 6.162 | 1.00 42.25 | B1 |
| ATOM | 1555 | CG | GLN | 233 | 30.290 | 25.398 | 7.626 | 1.00 48.22 | B1 |
| ATOM | 1556 | CD | GLN | 233 | 30.021 | 26.879 | 7.983 | 1.00 53.75 | B1 |
| ATOM | 1557 | OE1 | GLN | 233 | 30.799 | 27.810 | 7.718 | 1.00 55.93 | B1 |
| ATOM | 1558 | NE2 | GLN | 233 | 28.909 | 27.215 | 8.634 | 1.00 56.51 | B1 |
| ATOM | 1559 | HE21 | GLN | 233 | 28.810 | 28.144 | 8.902 | 1.00 0.00 | B1 |
| ATOM | 1560 | HE22 | GLN | 233 | 28.205 | 26.533 | 8.710 | 1.00 0.00 | B1 |
| ATOM | 1561 | C | GLN | 233 | 30.635 | 23.243 | 4.441 | 1.00 39.70 | B1 |
| ATOM | 1562 | O | GLN | 233 | 29.651 | 22.777 | 3.898 | 1.00 40.20 | B1 |
| ATOM | 1563 | N | GLU | 234 | 31.744 | 23.377 | 3.736 | 1.00 39.32 | B1 |
| ATOM | 1564 | H | GLU | 234 | 32.544 | 23.750 | 4.163 | 1.00 0.00 | B1 |
| ATOM | 1565 | CA | GLU | 234 | 31.809 | 23.025 | 2.329 | 1.00 39.23 | B1 |
| ATOM | 1566 | CB | GLU | 234 | 33.155 | 23.434 | 1.811 | 1.00 40.25 | B1 |
| ATOM | 1567 | CG | GLU | 234 | 33.292 | 23.028 | 0.383 | 1.00 47.69 | B1 |
| ATOM | 1568 | CD | GLU | 234 | 34.733 | 23.056 | -0.073 | 1.00 53.40 | B1 |
| ATOM | 1569 | OE1 | GLU | 234 | 34.986 | 23.721 | -1.100 | 1.00 53.78 | B1 |
| ATOM | 1570 | OE2 | GLU | 234 | 35.568 | 22.400 | 0.590 | 1.00 57.55 | B1 |
| ATOM | 1571 | C | GLU | 234 | 31.580 | 21.535 | 2.136 | 1.00 37.09 | B1 |
| ATOM | 1572 | O | GLU | 234 | 30.884 | 21.217 | 1.188 | 1.00 36.67 | B1 |
| ATOM | 1573 | N | LYS | 235 | 32.092 | 20.623 | 2.986 | 1.00 37.27 | B1 |
| ATOM | 1574 | H | LYS | 235 | 32.668 | 20.965 | 3.706 | 1.00 0.00 | B1 |
| ATOM | 1575 | CA | LYS | 235 | 31.832 | 19.177 | 2.942 | 1.00 36.27 | B1 |
| ATOM | 1576 | CB | LYS | 235 | 32.516 | 18.365 | 3.997 | 1.00 34.92 | B1 |
| ATOM | 1577 | CG | LYS | 235 | 33.978 | 18.483 | 4.107 | 1.00 38.47 | B1 |
| ATOM | 1578 | CD | LYS | 235 | 34.762 | 17.999 | 2.921 | 1.00 38.07 | B1 |
| ATOM | 1579 | CE | LYS | 235 | 36.192 | 18.051 | 3.460 | 1.00 39.15 | B1 |
| ATOM | 1580 | NZ | LYS | 235 | 37.117 | 17.460 | 2.521 | 1.00 41.34 | B1 |
| ATOM | 1581 | HZ1 | LYS | 235 | 37.080 | 17.978 | 1.622 | 1.00 0.00 | B1 |
| ATOM | 1582 | HZ2 | LYS | 235 | 36.854 | 16.466 | 2.363 | 1.00 0.00 | B1 |
| ATOM | 1583 | HZ3 | LYS | 235 | 38.080 | 17.497 | 2.911 | 1.00 0.00 | B1 |
| ATOM | 1584 | C | LYS | 235 | 30.363 | 18.847 | 3.204 | 1.00 35.20 | B1 |
| ATOM | 1585 | O | LYS | 235 | 29.722 | 18.102 | 2.463 | 1.00 35.60 | B1 |
| ATOM | 1586 | N | LEU | 236 | 29.807 | 19.332 | 4.301 | 1.00 33.53 | B1 |
| ATOM | 1587 | H | LEU | 236 | 30.363 | 19.888 | 4.885 | 1.00 0.00 | B1 |
| ATOM | 1588 | CA | LEU | 236 | 28.417 | 19.116 | 4.641 | 1.00 32.30 | B1 |
| ATOM | 1589 | CB | LEU | 236 | 28.093 | 19.918 | 5.894 | 1.00 28.85 | B1 |
| ATOM | 1590 | CG | LEU | 236 | 28.791 | 19.441 | 7.148 | 1.00 28.23 | B1 |
| ATOM | 1591 | CD1 | LEU | 236 | 28.703 | 20.460 | 8.268 | 1.00 24.14 | B1 |
| ATOM | 1592 | CD2 | LEU | 236 | 28.132 | 18.163 | 7.587 | 1.00 26.66 | B1 |
| ATOM | 1593 | C | LEU | 236 | 27.590 | 19.574 | 3.453 | 1.00 33.69 | B1 |
| ATOM | 1594 | O | LEU | 236 | 26.691 | 18.849 | 3.064 | 1.00 35.13 | B1 |
| ATOM | 1595 | N | CYS | 237 | 27.870 | 20.670 | 2.753 | 1.00 34.49 | B1 |
| ATOM | 1596 | H | CYS | 237 | 28.611 | 21.251 | 3.025 | 1.00 0.00 | B1 |
| ATOM | 1597 | CA | CYS | 237 | 27.064 | 21.016 | 1.606 | 1.00 34.95 | B1 |
| ATOM | 1598 | C | CYS | 237 | 27.324 | 20.090 | 0.451 | 1.00 35.97 | B1 |
| ATOM | 1599 | O | CYS | 237 | 26.360 | 19.573 | -0.089 | 1.00 36.09 | B1 |
| ATOM | 1600 | CB | CYS | 237 | 27.334 | 22.413 | 1.130 | 1.00 35.18 | B1 |
| ATOM | 1601 | SG | CYS | 237 | 26.409 | 22.880 | -0.365 | 1.00 36.40 | B1 |
| ATOM | 1602 | N | ALA | 238 | 28.571 | 19.804 | 0.074 | 1.00 37.29 | B1 |
| ATOM | 1603 | H | ALA | 238 | 29.324 | 20.158 | 0.591 | 1.00 0.00 | B1 |
| ATOM | 1604 | CA | ALA | 238 | 28.841 | 18.973 | -1.090 | 1.00 36.80 | B1 |
| ATOM | 1605 | CB | ALA | 238 | 30.274 | 18.684 | -1.403 | 1.00 37.35 | B1 |
| ATOM | 1606 | C | ALA | 238 | 28.320 | 17.617 | -0.911 | 1.00 36.49 | B1 |
| ATOM | 1607 | O | ALA | 238 | 27.645 | 17.198 | -1.809 | 1.00 36.54 | B1 |
| ATOM | 1608 | N | THR | 239 | 28.628 | 16.969 | 0.193 | 1.00 38.80 | B1 |
| ATOM | 1609 | H | THR | 239 | 29.236 | 17.391 | 0.821 | 1.00 0.00 | B1 |
| ATOM | 1610 | CA | THR | 239 | 28.230 | 15.587 | 0.464 | 1.00 41.33 | B1 |
| ATOM | 1611 | CB | THR | 239 | 29.158 | 15.035 | 1.554 | 1.00 42.38 | B1 |
| ATOM | 1612 | OG1 | THR | 239 | 30.473 | 15.265 | 1.031 | 1.00 45.70 | B1 |
| ATOM | 1613 | HG1 | THR | 239 | 31.019 | 15.668 | 1.709 | 1.00 0.00 | B1 |
| ATOM | 1614 | CG2 | THR | 239 | 28.936 | 13.574 | 1.916 | 1.00 41.85 | B1 |
| ATOM | 1615 | C | THR | 239 | 26.771 | 15.341 | 0.864 | 1.00 41.94 | B1 |
| ATOM | 1616 | O | THR | 239 | 26.260 | 14.284 | 0.460 | 1.00 43.34 | B1 |
| ATOM | 1617 | N | TYR | 240 | 26.095 | 16.207 | 1.669 | 1.00 40.07 | B1 |
| ATOM | 1618 | H | TYR | 240 | 26.538 | 17.034 | 1.953 | 1.00 0.00 | B1 |
| ATOM | 1619 | CA | TYR | 240 | 24.718 | 15.992 | 2.084 | 1.00 38.21 | B1 |
| ATOM | 1620 | CB | TYR | 240 | 24.594 | 15.993 | 3.618 | 1.00 38.08 | B1 |
| ATOM | 1621 | CG | TYR | 240 | 25.524 | 14.926 | 4.193 | 1.00 43.37 | B1 |
| ATOM | 1622 | CD1 | TYR | 240 | 26.475 | 15.243 | 5.149 | 1.00 45.06 | B1 |
| ATOM | 1623 | CE1 | TYR | 240 | 27.420 | 14.283 | 5.529 | 1.00 47.35 | B1 |
| ATOM | 1624 | CD2 | TYR | 240 | 25.518 | 13.643 | 3.641 | 1.00 43.89 | B1 |
| ATOM | 1625 | CE2 | TYR | 240 | 26.442 | 12.690 | 4.003 | 1.00 44.77 | B1 |
| ATOM | 1626 | CZ | TYR | 240 | 27.410 | 13.005 | 4.943 | 1.00 47.96 | B1 |
| ATOM | 1627 | OH | TYR | 240 | 28.390 | 12.047 | 5.244 | 1.00 46.59 | B1 |
| ATOM | 1628 | HH | TYR | 240 | 28.027 | 11.187 | 4.992 | 1.00 0.00 | B1 |
| ATOM | 1629 | C | TYR | 240 | 23.781 | 17.032 | 1.516 | 1.00 39.49 | B1 |
| ATOM | 1630 | O | TYR | 240 | 22.587 | 16.934 | 1.775 | 1.00 42.76 | B1 |
| ATOM | 1631 | N | LYS | 241 | 24.174 | 18.011 | 0.694 | 1.00 37.36 | B1 |
| ATOM | 1632 | H | LYS | 241 | 25.091 | 18.023 | 0.345 | 1.00 0.00 | B1 |
| ATOM | 1633 | CA | LYS | 241 | 23.314 | 19.115 | 0.275 | 1.00 36.37 | B1 |

FIG. 5T

| | | | | | | | | | | |
|---|---|---|---|---|---|---|---|---|---|---|
| ATOM | 1634 | CB | LYS | 241 | 22.173 | 18.648 | -0.595 | 1.00 | 38.38 | B1 |
| ATOM | 1635 | CG | LYS | 241 | 22.645 | 17.940 | -1.838 | 1.00 | 42.94 | B1 |
| ATOM | 1636 | CD | LYS | 241 | 23.468 | 18.809 | -2.737 | 1.00 | 46.97 | B1 |
| ATOM | 1637 | CE | LYS | 241 | 23.657 | 18.070 | -4.051 | 1.00 | 49.20 | B1 |
| ATOM | 1638 | NZ | LYS | 241 | 22.509 | 18.372 | -4.893 | 1.00 | 51.54 | B1 |
| ATOM | 1639 | HZ1 | LYS | 241 | 22.447 | 19.400 | -5.038 | 1.00 | 0.00 | B1 |
| ATOM | 1640 | HZ2 | LYS | 241 | 21.641 | 18.041 | -4.426 | 1.00 | 0.00 | B1 |
| ATOM | 1641 | HZ3 | LYS | 241 | 22.609 | 17.895 | -5.811 | 1.00 | 0.00 | B1 |
| ATOM | 1642 | C | LYS | 241 | 22.720 | 19.904 | 1.429 | 1.00 | 33.37 | B1 |
| ATOM | 1643 | O | LYS | 241 | 21.728 | 20.580 | 1.223 | 1.00 | 33.90 | B1 |
| ATOM | 1644 | N | LEU | 242 | 23.286 | 19.853 | 2.648 | 1.00 | 31.40 | B1 |
| ATOM | 1645 | H | LEU | 242 | 24.055 | 19.260 | 2.756 | 1.00 | 0.00 | B1 |
| ATOM | 1646 | CA | LEU | 242 | 22.904 | 20.682 | 3.758 | 1.00 | 31.09 | B1 |
| ATOM | 1647 | CB | LEU | 242 | 23.253 | 20.059 | 5.096 | 1.00 | 28.55 | B1 |
| ATOM | 1648 | CG | LEU | 242 | 22.571 | 18.798 | 5.641 | 1.00 | 30.36 | B1 |
| ATOM | 1649 | CD1 | LEU | 242 | 22.530 | 18.814 | 7.138 | 1.00 | 29.62 | B1 |
| ATOM | 1650 | CD2 | LEU | 242 | 21.086 | 18.861 | 5.443 | 1.00 | 31.94 | B1 |
| ATOM | 1651 | C | LEU | 242 | 23.778 | 21.933 | 3.550 | 1.00 | 34.03 | B1 |
| ATOM | 1652 | O | LEU | 242 | 24.903 | 22.027 | 4.058 | 1.00 | 35.53 | B1 |
| ATOM | 1653 | N | CYS | 243 | 23.316 | 22.883 | 2.722 | 1.00 | 34.89 | B1 |
| ATOM | 1654 | H | CYS | 243 | 22.491 | 22.665 | 2.238 | 1.00 | 0.00 | B1 |
| ATOM | 1655 | CA | CYS | 243 | 24.051 | 24.083 | 2.377 | 1.00 | 35.42 | B1 |
| ATOM | 1656 | C | CYS | 243 | 23.492 | 25.335 | 2.975 | 1.00 | 36.85 | B1 |
| ATOM | 1657 | O | CYS | 243 | 23.956 | 26.400 | 2.565 | 1.00 | 40.10 | B1 |
| ATOM | 1658 | CB | CYS | 243 | 24.046 | 24.383 | 0.929 | 1.00 | 33.12 | B1 |
| ATOM | 1659 | SG | CYS | 243 | 24.438 | 22.883 | 0.099 | 1.00 | 38.25 | B1 |
| ATOM | 1660 | N | HIS | 244 | 22.496 | 25.393 | 3.848 | 1.00 | 35.37 | B1 |
| ATOM | 1661 | H | HIS | 244 | 22.185 | 24.588 | 4.318 | 1.00 | 0.00 | B1 |
| ATOM | 1662 | CA | HIS | 244 | 21.939 | 26.676 | 4.191 | 1.00 | 33.29 | B1 |
| ATOM | 1663 | CB | HIS | 244 | 20.655 | 26.987 | 3.340 | 1.00 | 33.64 | B1 |
| ATOM | 1664 | CG | HIS | 244 | 20.915 | 27.205 | 1.857 | 1.00 | 33.12 | B1 |
| ATOM | 1665 | CD2 | HIS | 244 | 20.288 | 26.584 | 0.814 | 1.00 | 37.29 | B1 |
| ATOM | 1666 | ND1 | HIS | 244 | 21.874 | 27.902 | 1.298 | 1.00 | 36.85 | B1 |
| ATOM | 1667 | HD1 | HIS | 244 | 22.648 | 28.281 | 1.778 | 1.00 | 0.00 | B1 |
| ATOM | 1668 | CE1 | HIS | 244 | 21.874 | 27.722 | -0.013 | 1.00 | 35.95 | B1 |
| ATOM | 1669 | NE2 | HIS | 244 | 20.910 | 26.920 | -0.301 | 1.00 | 35.54 | B1 |
| ATOM | 1670 | HE2 | HIS | 244 | 20.616 | 26.706 | -1.214 | 1.00 | 0.00 | B1 |
| ATOM | 1671 | C | HIS | 244 | 21.621 | 26.565 | 5.650 | 1.00 | 33.38 | B1 |
| ATOM | 1672 | O | HIS | 244 | 20.546 | 26.105 | 6.029 | 1.00 | 33.23 | B1 |
| ATOM | 1673 | N | PRO | 245 | 22.539 | 27.018 | 6.499 | 1.00 | 33.21 | B1 |
| ATOM | 1674 | CD | PRO | 245 | 23.851 | 27.524 | 6.099 | 1.00 | 31.29 | B1 |
| ATOM | 1675 | CA | PRO | 245 | 22.373 | 26.979 | 7.948 | 1.00 | 34.16 | B1 |
| ATOM | 1676 | CB | PRO | 245 | 23.490 | 27.799 | 8.467 | 1.00 | 32.85 | B1 |
| ATOM | 1677 | CG | PRO | 245 | 24.564 | 27.549 | 7.428 | 1.00 | 31.74 | B1 |
| ATOM | 1678 | C | PRO | 245 | 21.032 | 27.470 | 8.407 | 1.00 | 36.26 | B1 |
| ATOM | 1679 | O | PRO | 245 | 20.478 | 26.878 | 9.315 | 1.00 | 38.13 | B1 |
| ATOM | 1680 | N | GLU | 246 | 20.529 | 28.463 | 7.640 | 1.00 | 39.64 | B1 |
| ATOM | 1681 | H | GLU | 246 | 21.134 | 28.747 | 6.934 | 1.00 | 0.00 | B1 |
| ATOM | 1682 | CA | GLU | 246 | 19.257 | 29.229 | 7.711 | 1.00 | 41.10 | B1 |
| ATOM | 1683 | CB | GLU | 246 | 19.044 | 30.107 | 6.438 | 1.00 | 43.15 | B1 |
| ATOM | 1684 | CG | GLU | 246 | 20.256 | 30.918 | 5.944 | 1.00 | 47.07 | B1 |
| ATOM | 1685 | CD | GLU | 246 | 20.813 | 30.539 | 4.558 | 1.00 | 52.63 | B1 |
| ATOM | 1686 | OE1 | GLU | 246 | 22.054 | 30.545 | 4.374 | 1.00 | 54.22 | B1 |
| ATOM | 1687 | OE2 | GLU | 246 | 20.002 | 30.250 | 3.656 | 1.00 | 53.39 | B1 |
| ATOM | 1688 | C | GLU | 246 | 18.071 | 28.298 | 7.819 | 1.00 | 40.57 | B1 |
| ATOM | 1689 | O | GLU | 246 | 17.308 | 28.338 | 8.791 | 1.00 | 39.90 | B1 |
| ATOM | 1690 | N | GLU | 247 | 18.025 | 27.388 | 6.840 | 1.00 | 40.32 | B1 |
| ATOM | 1691 | H | GLU | 247 | 18.750 | 27.334 | 6.190 | 1.00 | 0.00 | B1 |
| ATOM | 1692 | CA | GLU | 247 | 17.001 | 26.347 | 6.830 | 1.00 | 40.76 | B1 |
| ATOM | 1693 | CB | GLU | 247 | 17.139 | 25.423 | 5.642 | 1.00 | 44.03 | B1 |
| ATOM | 1694 | CG | GLU | 247 | 16.830 | 26.240 | 4.400 | 1.00 | 48.54 | B1 |
| ATOM | 1695 | CD | GLU | 247 | 17.163 | 25.628 | 3.050 | 1.00 | 50.24 | B1 |
| ATOM | 1696 | OE1 | GLU | 247 | 16.849 | 26.299 | 2.056 | 1.00 | 52.92 | B1 |
| ATOM | 1697 | OE2 | GLU | 247 | 17.744 | 24.533 | 2.987 | 1.00 | 50.84 | B1 |
| ATOM | 1698 | C | GLU | 247 | 16.966 | 25.444 | 8.034 | 1.00 | 39.24 | B1 |
| ATOM | 1699 | O | GLU | 247 | 15.915 | 24.888 | 8.329 | 1.00 | 39.40 | B1 |
| ATOM | 1700 | N | LEU | 248 | 18.066 | 25.280 | 8.760 | 1.00 | 37.92 | B1 |
| ATOM | 1701 | H | LEU | 248 | 18.864 | 25.814 | 8.576 | 1.00 | 0.00 | B1 |
| ATOM | 1702 | CA | LEU | 248 | 18.101 | 24.338 | 9.858 | 1.00 | 35.75 | B1 |
| ATOM | 1703 | CB | LEU | 248 | 19.458 | 23.623 | 9.796 | 1.00 | 34.13 | B1 |
| ATOM | 1704 | CG | LEU | 248 | 19.669 | 22.866 | 8.430 | 1.00 | 34.00 | B1 |
| ATOM | 1705 | CD1 | LEU | 248 | 20.997 | 22.149 | 8.306 | 1.00 | 33.97 | B1 |
| ATOM | 1706 | CD2 | LEU | 248 | 18.620 | 21.810 | 8.322 | 1.00 | 32.33 | B1 |
| ATOM | 1707 | C | LEU | 248 | 17.871 | 25.031 | 11.155 | 1.00 | 36.51 | B1 |
| ATOM | 1708 | O | LEU | 248 | 17.736 | 24.370 | 12.186 | 1.00 | 36.31 | B1 |
| ATOM | 1709 | N | VAL | 249 | 17.663 | 26.350 | 11.146 | 1.00 | 38.88 | B1 |
| ATOM | 1710 | H | VAL | 249 | 17.566 | 26.810 | 10.283 | 1.00 | 0.00 | B1 |
| ATOM | 1711 | CA | VAL | 249 | 17.573 | 27.133 | 12.371 | 1.00 | 41.39 | B1 |
| ATOM | 1712 | CB | VAL | 249 | 17.265 | 28.640 | 12.020 | 1.00 | 43.72 | B1 |
| ATOM | 1713 | CG1 | VAL | 249 | 15.804 | 28.985 | 11.776 | 1.00 | 44.70 | B1 |
| ATOM | 1714 | CG2 | VAL | 249 | 17.702 | 29.434 | 13.214 | 1.00 | 45.20 | B1 |
| ATOM | 1715 | C | VAL | 249 | 16.590 | 26.635 | 13.406 | 1.00 | 42.61 | B1 |
| ATOM | 1716 | O | VAL | 249 | 16.912 | 26.716 | 14.594 | 1.00 | 44.77 | B1 |
| ATOM | 1717 | N | LEU | 250 | 15.453 | 26.035 | 13.016 | 1.00 | 43.61 | B1 |
| ATOM | 1718 | H | LEU | 250 | 15.319 | 25.919 | 12.053 | 1.00 | 0.00 | B1 |
| ATOM | 1719 | CA | LEU | 250 | 14.457 | 25.537 | 13.987 | 1.00 | 43.96 | B1 |

FIG. 5U

| | | | | | | | | | |
|---|---|---|---|---|---|---|---|---|---|
| ATOM | 1720 | CB | LEU | 250 | 13.102 | 25.296 | 13.373 | 1.00 43.88 | B1 |
| ATOM | 1721 | CG | LEU | 250 | 12.729 | 26.281 | 12.313 | 1.00 47.04 | B1 |
| ATOM | 1722 | CD1 | LEU | 250 | 13.092 | 25.577 | 11.011 | 1.00 47.30 | B1 |
| ATOM | 1723 | CD2 | LEU | 250 | 11.286 | 26.772 | 12.441 | 1.00 46.18 | B1 |
| ATOM | 1724 | C | LEU | 250 | 14.852 | 24.207 | 14.626 | 1.00 43.96 | B1 |
| ATOM | 1725 | O | LEU | 250 | 14.450 | 23.887 | 15.764 | 1.00 44.07 | B1 |
| ATOM | 1726 | N | LEU | 251 | 15.691 | 23.446 | 13.893 | 1.00 42.41 | B1 |
| ATOM | 1727 | H | LEU | 251 | 16.049 | 23.788 | 13.048 | 1.00 0.00 | B1 |
| ATOM | 1728 | CA | LEU | 251 | 16.155 | 22.159 | 14.362 | 1.00 40.63 | B1 |
| ATOM | 1729 | CB | LEU | 251 | 16.834 | 21.418 | 13.257 | 1.00 36.17 | B1 |
| ATOM | 1730 | CG | LEU | 251 | 15.996 | 20.629 | 12.267 | 1.00 33.16 | B1 |
| ATOM | 1731 | CD1 | LEU | 251 | 14.595 | 21.168 | 11.956 | 1.00 33.36 | B1 |
| ATOM | 1732 | CD2 | LEU | 251 | 16.875 | 20.619 | 11.050 | 1.00 34.71 | B1 |
| ATOM | 1733 | C | LEU | 251 | 17.104 | 22.372 | 15.493 | 1.00 42.78 | B1 |
| ATOM | 1734 | O | LEU | 251 | 17.124 | 21.554 | 16.395 | 1.00 45.44 | B1 |
| ATOM | 1735 | N | GLY | 252 | 17.826 | 23.477 | 15.610 | 1.00 44.86 | B1 |
| ATOM | 1736 | H | GLY | 252 | 17.750 | 24.160 | 14.910 | 1.00 0.00 | B1 |
| ATOM | 1737 | CA | GLY | 252 | 18.734 | 23.711 | 16.719 | 1.00 46.68 | B1 |
| ATOM | 1738 | C | GLY | 252 | 18.071 | 23.596 | 18.067 | 1.00 49.18 | B1 |
| ATOM | 1739 | O | GLY | 252 | 18.709 | 23.318 | 19.077 | 1.00 49.23 | B1 |
| ATOM | 1740 | N | HIS | 253 | 16.756 | 23.787 | 18.046 | 1.00 53.74 | B1 |
| ATOM | 1741 | H | HIS | 253 | 16.358 | 24.055 | 17.190 | 1.00 0.00 | B1 |
| ATOM | 1742 | CA | HIS | 253 | 15.859 | 23.649 | 19.197 | 1.00 57.46 | B1 |
| ATOM | 1743 | CB | HIS | 253 | 14.468 | 24.157 | 18.764 | 1.00 62.93 | B1 |
| ATOM | 1744 | CG | HIS | 253 | 13.212 | 23.813 | 19.577 | 1.00 68.75 | B1 |
| ATOM | 1745 | CD2 | HIS | 253 | 12.031 | 24.529 | 19.414 | 1.00 71.00 | B1 |
| ATOM | 1746 | ND1 | HIS | 253 | 12.980 | 22.854 | 20.479 | 1.00 70.67 | B1 |
| ATOM | 1747 | HD1 | HIS | 253 | 13.627 | 22.193 | 20.830 | 1.00 0.00 | B1 |
| ATOM | 1748 | CE1 | HIS | 253 | 11.723 | 22.966 | 20.845 | 1.00 73.40 | B1 |
| ATOM | 1749 | NE2 | HIS | 253 | 11.156 | 23.973 | 20.204 | 1.00 72.91 | B1 |
| ATOM | 1750 | HE2 | HIS | 253 | 10.218 | 24.260 | 20.311 | 1.00 0.00 | B1 |
| ATOM | 1751 | C | HIS | 253 | 15.771 | 22.209 | 19.691 | 1.00 56.06 | B1 |
| ATOM | 1752 | O | HIS | 253 | 15.880 | 21.827 | 20.857 | 1.00 56.17 | B1 |
| ATOM | 1753 | N | SER | 254 | 15.395 | 21.435 | 18.724 | 1.00 53.46 | B1 |
| ATOM | 1754 | H | SER | 254 | 15.278 | 21.783 | 17.813 | 1.00 0.00 | B1 |
| ATOM | 1755 | CA | SER | 254 | 15.177 | 20.034 | 18.898 | 1.00 52.61 | B1 |
| ATOM | 1756 | CB | SER | 254 | 14.613 | 19.595 | 17.576 | 1.00 53.04 | B1 |
| ATOM | 1757 | OG | SER | 254 | 13.793 | 20.686 | 17.158 | 1.00 56.04 | B1 |
| ATOM | 1758 | HG | SER | 254 | 13.369 | 20.467 | 16.319 | 1.00 0.00 | B1 |
| ATOM | 1759 | C | SER | 254 | 16.512 | 19.386 | 19.275 | 1.00 51.48 | B1 |
| ATOM | 1760 | O | SER | 254 | 16.596 | 18.639 | 20.245 | 1.00 51.90 | B1 |
| ATOM | 1761 | N | LEU | 255 | 17.577 | 19.790 | 18.562 | 1.00 49.31 | B1 |
| ATOM | 1762 | H | LEU | 255 | 17.430 | 20.480 | 17.889 | 1.00 0.00 | B1 |
| ATOM | 1763 | CA | LEU | 255 | 18.913 | 19.272 | 18.723 | 1.00 46.02 | B1 |
| ATOM | 1764 | CB | LEU | 255 | 19.706 | 19.723 | 17.537 | 1.00 44.66 | B1 |
| ATOM | 1765 | CG | LEU | 255 | 19.362 | 18.968 | 16.274 | 1.00 44.51 | B1 |
| ATOM | 1766 | CD1 | LEU | 255 | 19.810 | 19.679 | 15.006 | 1.00 43.16 | B1 |
| ATOM | 1767 | CD2 | LEU | 255 | 19.969 | 17.604 | 16.456 | 1.00 44.67 | B1 |
| ATOM | 1768 | C | LEU | 255 | 19.536 | 19.718 | 20.012 | 1.00 46.56 | B1 |
| ATOM | 1769 | O | LEU | 255 | 20.565 | 19.174 | 20.440 | 1.00 46.82 | B1 |
| ATOM | 1770 | N | GLY | 256 | 18.918 | 20.759 | 20.581 | 1.00 45.93 | B1 |
| ATOM | 1771 | H | GLY | 256 | 18.210 | 21.225 | 20.101 | 1.00 0.00 | B1 |
| ATOM | 1772 | CA | GLY | 256 | 19.277 | 21.273 | 21.890 | 1.00 46.68 | B1 |
| ATOM | 1773 | C | GLY | 256 | 20.669 | 21.866 | 21.970 | 1.00 47.28 | B1 |
| ATOM | 1774 | O | GLY | 256 | 21.273 | 21.844 | 23.056 | 1.00 49.64 | B1 |
| ATOM | 1775 | N | ILE | 257 | 21.143 | 22.441 | 20.849 | 1.00 45.74 | B1 |
| ATOM | 1776 | H | ILE | 257 | 20.497 | 22.589 | 20.128 | 1.00 0.00 | B1 |
| ATOM | 1777 | CA | ILE | 257 | 22.481 | 23.017 | 20.726 | 1.00 43.64 | B1 |
| ATOM | 1778 | CB | ILE | 257 | 22.684 | 23.363 | 19.257 | 1.00 42.54 | B1 |
| ATOM | 1779 | CG2 | ILE | 257 | 23.988 | 24.110 | 19.073 | 1.00 41.05 | B1 |
| ATOM | 1780 | CG1 | ILE | 257 | 22.694 | 22.088 | 18.437 | 1.00 40.55 | B1 |
| ATOM | 1781 | CD | ILE | 257 | 22.452 | 22.468 | 16.970 | 1.00 39.49 | B1 |
| ATOM | 1782 | C | ILE | 257 | 22.559 | 24.246 | 21.616 | 1.00 43.27 | B1 |
| ATOM | 1783 | O | ILE | 257 | 21.706 | 25.110 | 21.450 | 1.00 43.22 | B1 |
| ATOM | 1784 | N | PRO | 258 | 23.441 | 24.392 | 22.608 | 1.00 43.05 | B1 |
| ATOM | 1785 | CD | PRO | 258 | 24.133 | 23.321 | 23.296 | 1.00 43.29 | B1 |
| ATOM | 1786 | CA | PRO | 258 | 23.559 | 25.616 | 23.360 | 1.00 43.82 | B1 |
| ATOM | 1787 | CB | PRO | 258 | 24.295 | 25.236 | 24.612 | 1.00 41.97 | B1 |
| ATOM | 1788 | CG | PRO | 258 | 25.107 | 24.064 | 24.186 | 1.00 43.79 | B1 |
| ATOM | 1789 | C | PRO | 258 | 24.252 | 26.703 | 22.555 | 1.00 46.06 | B1 |
| ATOM | 1790 | O | PRO | 258 | 24.983 | 26.513 | 21.560 | 1.00 46.59 | B1 |
| ATOM | 1791 | N | TRP | 259 | 23.996 | 27.887 | 23.106 | 1.00 46.75 | B1 |
| ATOM | 1792 | H | TRP | 259 | 23.588 | 27.921 | 23.994 | 1.00 0.00 | B1 |
| ATOM | 1793 | CA | TRP | 259 | 24.427 | 29.143 | 22.517 | 1.00 45.77 | B1 |
| ATOM | 1794 | CB | TRP | 259 | 23.213 | 30.071 | 22.397 | 1.00 46.60 | B1 |
| ATOM | 1795 | CG | TRP | 259 | 23.556 | 31.372 | 21.749 | 1.00 47.51 | B1 |
| ATOM | 1796 | CD2 | TRP | 259 | 23.860 | 31.525 | 20.430 | 1.00 47.83 | B1 |
| ATOM | 1797 | CE2 | TRP | 259 | 24.154 | 32.888 | 20.392 | 1.00 48.47 | B1 |
| ATOM | 1798 | CE3 | TRP | 259 | 23.940 | 30.745 | 19.290 | 1.00 47.39 | B1 |
| ATOM | 1799 | CD1 | TRP | 259 | 23.639 | 32.520 | 22.493 | 1.00 48.60 | B1 |
| ATOM | 1800 | NE1 | TRP | 259 | 24.013 | 33.421 | 21.628 | 1.00 48.27 | B1 |
| ATOM | 1801 | HE1 | TRP | 259 | 24.224 | 34.344 | 21.870 | 1.00 0.00 | B1 |
| ATOM | 1802 | CZ2 | TRP | 259 | 24.531 | 33.486 | 19.195 | 1.00 47.40 | B1 |
| ATOM | 1803 | CZ3 | TRP | 259 | 24.317 | 31.344 | 18.097 | 1.00 49.07 | B1 |
| ATOM | 1804 | CH2 | TRP | 259 | 24.613 | 32.706 | 18.050 | 1.00 49.12 | B1 |
| ATOM | 1805 | C | TRP | 259 | 25.459 | 29.727 | 23.440 | 1.00 44.01 | B1 |

FIG. 5V

| ATOM | 1806 | O | TRP | 259 | 25.340 | 29.664 | 24.671 | 1.00 | 43.25 | B1 | ATOM | 1849 | SG | CYS | 265 | 32.322 | 40.638 | 27.504 | 1.00 | 71.40 | B1 |
|---|---|---|---|---|---|---|---|---|---|---|---|---|---|---|---|---|---|---|---|---|---|
| ATOM | 1807 | N | ALA | 260 | 26.469 | 30.247 | 22.777 | 1.00 | 43.01 | B1 | ATOM | 1850 | C | CYS | 265 | 30.667 | 42.860 | 26.515 | 1.00 | 63.12 | B1 |
| ATOM | 1808 | H | ALA | 260 | 26.523 | 30.198 | 21.796 | 1.00 | 0.00 | B1 | ATOM | 1851 | OT1 | CYS | 265 | 31.065 | 43.360 | 25.444 | 1.00 | 63.44 | B1 |
| ATOM | 1809 | CA | ALA | 260 | 27.493 | 30.973 | 23.482 | 1.00 | 43.48 | B1 | ATOM | 1852 | OT2 | CYS | 265 | 30.809 | 43.408 | 27.610 | 1.00 | 61.72 | B1 |
| ATOM | 1810 | CB | ALA | 260 | 28.874 | 30.549 | 22.969 | 1.00 | 43.33 | B1 | ATOM | 1853 | CB | ALA | 272 | 40.020 | 43.327 | 30.788 | 1.00 | 77.44 | B2 |
| ATOM | 1811 | C | ALA | 260 | 27.249 | 32.486 | 23.216 | 1.00 | 43.41 | B1 | ATOM | 1854 | C | ALA | 272 | 38.698 | 41.201 | 30.601 | 1.00 | 76.53 | B2 |
| ATOM | 1812 | O | ALA | 260 | 27.315 | 32.946 | 22.054 | 1.00 | 40.55 | B1 | ATOM | 1855 | O | ALA | 272 | 37.525 | 40.873 | 30.361 | 1.00 | 76.81 | B2 |
| ATOM | 1813 | N | PRO | 261 | 26.853 | 33.267 | 24.253 | 1.00 | 42.61 | B1 | ATOM | 1856 | HT1 | ALA | 272 | 37.486 | 43.550 | 30.261 | 1.00 | 0.00 | B2 |
| ATOM | 1814 | CD | PRO | 261 | 26.527 | 32.807 | 25.606 | 1.00 | 42.33 | B1 | ATOM | 1857 | HT2 | ALA | 272 | 37.357 | 42.450 | 28.996 | 1.00 | 0.00 | B2 |
| ATOM | 1815 | CA | PRO | 261 | 26.720 | 34.701 | 24.199 | 1.00 | 42.37 | B1 | ATOM | 1858 | N | ALA | 272 | 37.973 | 43.169 | 29.427 | 1.00 | 76.81 | B2 |
| ATOM | 1816 | CB | PRO | 261 | 25.778 | 34.987 | 25.335 | 1.00 | 41.46 | B1 | ATOM | 1859 | HT3 | ALA | 272 | 38.195 | 43.924 | 28.752 | 1.00 | 0.00 | B2 |
| ATOM | 1817 | CG | PRO | 261 | 26.251 | 34.060 | 26.411 | 1.00 | 40.00 | B1 | ATOM | 1860 | CA | ALA | 272 | 39.176 | 42.460 | 29.853 | 1.00 | 77.02 | B2 |
| ATOM | 1818 | C | PRO | 261 | 28.087 | 35.369 | 24.311 | 1.00 | 42.22 | B1 | ATOM | 1861 | N | ALA | 273 | 39.485 | 40.547 | 31.487 | 1.00 | 74.93 | B2 |
| ATOM | 1819 | O | PRO | 261 | 28.988 | 34.956 | 25.037 | 1.00 | 38.82 | B1 | ATOM | 1862 | H | ALA | 273 | 40.334 | 40.963 | 31.745 | 1.00 | 0.00 | B2 |
| ATOM | 1820 | N | LEU | 262 | 28.234 | 36.403 | 23.486 | 1.00 | 45.20 | B1 | ATOM | 1863 | CA | ALA | 273 | 39.244 | 39.241 | 32.119 | 1.00 | 72.64 | B2 |
| ATOM | 1821 | H | LEU | 262 | 27.513 | 36.610 | 22.853 | 1.00 | 0.00 | B1 | ATOM | 1864 | CB | ALA | 273 | 39.704 | 39.279 | 33.558 | 1.00 | 71.92 | B2 |
| ATOM | 1822 | CA | LEU | 262 | 29.434 | 37.210 | 23.498 | 1.00 | 46.50 | B1 | ATOM | 1865 | C | ALA | 273 | 37.872 | 38.599 | 32.118 | 1.00 | 71.60 | B2 |
| ATOM | 1823 | CB | LEU | 262 | 30.531 | 36.609 | 22.610 | 1.00 | 45.09 | B1 | ATOM | 1866 | O | ALA | 273 | 37.806 | 37.458 | 31.702 | 1.00 | 71.68 | B2 |
| ATOM | 1824 | CG | LEU | 262 | 31.903 | 37.157 | 22.964 | 1.00 | 42.55 | B1 | ATOM | 1867 | N | GLY | 274 | 36.775 | 39.282 | 32.484 | 1.00 | 70.20 | B2 |
| ATOM | 1825 | CD1 | LEU | 262 | 32.344 | 36.695 | 24.338 | 1.00 | 41.52 | B1 | ATOM | 1868 | H | GLY | 274 | 36.903 | 40.167 | 32.874 | 1.00 | 0.00 | B2 |
| ATOM | 1826 | CD2 | LEU | 262 | 32.850 | 36.730 | 21.900 | 1.00 | 44.21 | B1 | ATOM | 1869 | CA | GLY | 274 | 35.412 | 38.758 | 32.425 | 1.00 | 66.78 | B2 |
| ATOM | 1827 | C | LEU | 262 | 29.154 | 38.628 | 23.035 | 1.00 | 48.56 | B1 | ATOM | 1870 | C | GLY | 274 | 35.050 | 38.437 | 30.990 | 1.00 | 65.05 | B2 |
| ATOM | 1828 | O | LEU | 262 | 29.633 | 39.470 | 23.790 | 1.00 | 48.23 | B1 | ATOM | 1871 | O | GLY | 274 | 34.627 | 37.320 | 30.709 | 1.00 | 66.44 | B2 |
| ATOM | 1829 | N | SER | 263 | 28.388 | 38.956 | 21.960 | 1.00 | 51.33 | B1 | ATOM | 1872 | N | CYS | 275 | 35.301 | 39.364 | 30.048 | 1.00 | 62.77 | B2 |
| ATOM | 1830 | H | SER | 263 | 27.982 | 38.242 | 21.427 | 1.00 | 0.00 | B1 | ATOM | 1873 | H | CYS | 275 | 35.634 | 40.223 | 30.357 | 1.00 | 0.00 | B2 |
| ATOM | 1831 | CA | SER | 263 | 28.127 | 40.339 | 21.494 | 1.00 | 55.19 | B1 | ATOM | 1874 | CA | CYS | 275 | 35.026 | 39.188 | 28.611 | 1.00 | 59.30 | B2 |
| ATOM | 1832 | CB | SER | 263 | 26.871 | 40.511 | 20.612 | 1.00 | 57.17 | B1 | ATOM | 1875 | C | CYS | 275 | 35.875 | 38.063 | 28.054 | 1.00 | 55.89 | B2 |
| ATOM | 1833 | OG | SER | 263 | 26.498 | 39.411 | 19.776 | 1.00 | 64.12 | B1 | ATOM | 1876 | O | CYS | 275 | 35.425 | 37.152 | 27.351 | 1.00 | 54.41 | B2 |
| ATOM | 1834 | HG | SER | 263 | 26.093 | 38.741 | 20.336 | 1.00 | 0.00 | B1 | ATOM | 1877 | CB | CYS | 275 | 35.349 | 40.466 | 27.827 | 1.00 | 61.50 | B2 |
| ATOM | 1835 | C | SER | 263 | 27.909 | 41.354 | 22.600 | 1.00 | 56.15 | B1 | ATOM | 1878 | SG | CYS | 275 | 34.119 | 40.937 | 26.577 | 1.00 | 66.63 | B2 |
| ATOM | 1836 | O | SER | 263 | 28.744 | 42.243 | 22.753 | 1.00 | 57.88 | B1 | ATOM | 1879 | N | LEU | 276 | 37.124 | 38.114 | 28.506 | 1.00 | 52.23 | B2 |
| ATOM | 1837 | N | SER | 264 | 26.899 | 41.231 | 23.452 | 1.00 | 56.52 | B1 | ATOM | 1880 | H | LEU | 276 | 37.350 | 38.722 | 29.233 | 1.00 | 0.00 | B2 |
| ATOM | 1838 | H | SER | 264 | 26.277 | 40.478 | 23.415 | 1.00 | 0.00 | B1 | ATOM | 1881 | CA | LEU | 276 | 38.091 | 37.163 | 28.066 | 1.00 | 48.93 | B2 |
| ATOM | 1839 | CA | SER | 264 | 26.716 | 42.204 | 24.494 | 1.00 | 58.28 | B1 | ATOM | 1882 | CB | LEU | 276 | 39.483 | 37.564 | 28.542 | 1.00 | 45.96 | B2 |
| ATOM | 1840 | CB | SER | 264 | 25.313 | 41.977 | 25.064 | 1.00 | 58.77 | B1 | ATOM | 1883 | CG | LEU | 276 | 40.241 | 38.557 | 27.670 | 1.00 | 43.20 | B2 |
| ATOM | 1841 | OG | SER | 264 | 25.099 | 40.726 | 25.713 | 1.00 | 58.50 | B1 | ATOM | 1884 | CD1 | LEU | 276 | 41.599 | 38.782 | 28.279 | 1.00 | 44.63 | B2 |
| ATOM | 1842 | HG | SER | 264 | 25.385 | 40.832 | 26.632 | 1.00 | 0.00 | B1 | ATOM | 1885 | CD2 | LEU | 276 | 40.429 | 38.033 | 26.271 | 1.00 | 40.55 | B2 |
| ATOM | 1843 | C | SER | 264 | 27.800 | 42.168 | 25.584 | 1.00 | 59.95 | B1 | ATOM | 1886 | C | LEU | 276 | 37.673 | 35.833 | 28.638 | 1.00 | 47.84 | B2 |
| ATOM | 1844 | O | SER | 264 | 27.610 | 42.805 | 26.620 | 1.00 | 60.44 | B1 | ATOM | 1887 | O | LEU | 276 | 37.784 | 34.803 | 27.964 | 1.00 | 48.51 | B2 |
| ATOM | 1845 | N | CYS | 265 | 28.948 | 41.484 | 25.466 | 1.00 | 61.37 | B1 | ATOM | 1888 | N | ALA | 277 | 37.074 | 35.840 | 29.804 | 1.00 | 45.56 | B2 |
| ATOM | 1846 | H | CYS | 265 | 29.192 | 41.114 | 24.596 | 1.00 | 0.00 | B1 | ATOM | 1889 | H | ALA | 277 | 36.898 | 36.662 | 30.289 | 1.00 | 0.00 | B2 |
| ATOM | 1847 | CA | CYS | 265 | 29.958 | 41.502 | 26.509 | 1.00 | 62.57 | B1 | ATOM | 1890 | CA | ALA | 277 | 36.613 | 34.605 | 30.365 | 1.00 | 45.77 | B2 |
| ATOM | 1848 | CB | CYS | 265 | 30.991 | 40.418 | 26.285 | 1.00 | 64.32 | B1 | ATOM | 1891 | CB | ALA | 277 | 36.147 | 34.810 | 31.783 | 1.00 | 47.87 | B2 |

FIG. 5W

| | | | | | | | | | |
|---|---|---|---|---|---|---|---|---|---|
| ATOM | 1892 | C | ALA | 277 | 35.442 | 34.111 | 29.542 | 1.00 45.03 | B2 |
| ATOM | 1893 | O | ALA | 277 | 35.342 | 32.926 | 29.271 | 1.00 44.20 | B2 |
| ATOM | 1894 | N | GLN | 278 | 34.592 | 35.000 | 29.049 | 1.00 45.13 | B2 |
| ATOM | 1895 | H | GLN | 278 | 34.731 | 35.944 | 29.263 | 1.00 0.00 | B2 |
| ATOM | 1896 | CA | GLN | 278 | 33.435 | 34.601 | 28.284 | 1.00 45.27 | B2 |
| ATOM | 1897 | CB | GLN | 278 | 32.550 | 35.825 | 28.083 | 1.00 48.13 | B2 |
| ATOM | 1898 | CG | GLN | 278 | 31.140 | 35.442 | 28.484 | 1.00 56.00 | B2 |
| ATOM | 1899 | CD | GLN | 278 | 30.045 | 36.464 | 28.178 | 1.00 61.94 | B2 |
| ATOM | 1900 | OE1 | GLN | 278 | 29.048 | 36.530 | 28.896 | 1.00 65.95 | B2 |
| ATOM | 1901 | NE2 | GLN | 278 | 30.080 | 37.291 | 27.132 | 1.00 65.55 | B2 |
| ATOM | 1902 | HE21 | GLN | 278 | 30.829 | 37.221 | 26.510 | 1.00 0.00 | B2 |
| ATOM | 1903 | HE22 | GLN | 278 | 29.343 | 37.927 | 27.056 | 1.00 0.00 | B2 |
| ATOM | 1904 | C | GLN | 278 | 33.812 | 33.971 | 26.950 | 1.00 43.16 | B2 |
| ATOM | 1905 | O | GLN | 278 | 33.173 | 33.050 | 26.462 | 1.00 40.58 | B2 |
| ATOM | 1906 | N | LEU | 279 | 34.869 | 34.476 | 26.331 | 1.00 43.32 | B2 |
| ATOM | 1907 | H | LEU | 279 | 35.328 | 35.227 | 26.767 | 1.00 0.00 | B2 |
| ATOM | 1908 | CA | LEU | 279 | 35.398 | 33.966 | 25.069 | 1.00 42.80 | B2 |
| ATOM | 1909 | CB | LEU | 279 | 36.583 | 34.790 | 24.626 | 1.00 41.42 | B2 |
| ATOM | 1910 | CG | LEU | 279 | 36.885 | 35.014 | 23.190 | 1.00 40.76 | B2 |
| ATOM | 1911 | CD1 | LEU | 279 | 38.239 | 35.647 | 23.130 | 1.00 41.76 | B2 |
| ATOM | 1912 | CD2 | LEU | 279 | 36.943 | 33.753 | 22.411 | 1.00 40.01 | B2 |
| ATOM | 1913 | C | LEU | 279 | 35.876 | 32.554 | 25.341 | 1.00 42.92 | B2 |
| ATOM | 1914 | O | LEU | 279 | 35.572 | 31.598 | 24.640 | 1.00 42.57 | B2 |
| ATOM | 1915 | N | HIS | 280 | 36.654 | 32.463 | 26.403 | 1.00 43.93 | B2 |
| ATOM | 1916 | H | HIS | 280 | 36.837 | 33.282 | 26.917 | 1.00 0.00 | B2 |
| ATOM | 1917 | CA | HIS | 280 | 37.215 | 31.223 | 26.850 | 1.00 46.12 | B2 |
| ATOM | 1918 | CB | HIS | 280 | 38.029 | 31.506 | 28.101 | 1.00 48.74 | B2 |
| ATOM | 1919 | CG | HIS | 280 | 38.914 | 30.320 | 28.394 | 1.00 54.16 | B2 |
| ATOM | 1920 | CD2 | HIS | 280 | 40.041 | 30.069 | 27.650 | 1.00 56.02 | B2 |
| ATOM | 1921 | ND1 | HIS | 280 | 38.759 | 29.326 | 29.264 | 1.00 56.01 | B2 |
| ATOM | 1922 | HD1 | HIS | 280 | 38.012 | 29.203 | 29.890 | 1.00 0.00 | B2 |
| ATOM | 1923 | CE1 | HIS | 280 | 39.744 | 28.483 | 29.058 | 1.00 56.64 | B2 |
| ATOM | 1924 | NE2 | HIS | 280 | 40.507 | 28.937 | 28.088 | 1.00 56.64 | B2 |
| ATOM | 1925 | HE2 | HIS | 280 | 41.282 | 28.478 | 27.684 | 1.00 0.00 | B2 |
| ATOM | 1926 | C | HIS | 280 | 36.161 | 30.134 | 27.117 | 1.00 45.65 | B2 |
| ATOM | 1927 | O | HIS | 280 | 36.362 | 28.977 | 26.711 | 1.00 46.23 | B2 |
| ATOM | 1928 | N | SER | 281 | 35.086 | 30.473 | 27.822 | 1.00 43.91 | B2 |
| ATOM | 1929 | H | SER | 281 | 35.009 | 31.367 | 28.219 | 1.00 0.00 | B2 |
| ATOM | 1930 | CA | SER | 281 | 34.008 | 29.574 | 28.105 | 1.00 43.53 | B2 |
| ATOM | 1931 | CB | SER | 281 | 33.026 | 30.291 | 29.002 | 1.00 44.18 | B2 |
| ATOM | 1932 | OG | SER | 281 | 33.761 | 30.812 | 30.113 | 1.00 47.79 | B2 |
| ATOM | 1933 | HG | SER | 281 | 33.288 | 30.648 | 30.931 | 1.00 0.00 | B2 |
| ATOM | 1934 | C | SER | 281 | 33.382 | 29.169 | 26.787 | 1.00 43.35 | B2 |
| ATOM | 1935 | O | SER | 281 | 33.334 | 27.973 | 26.496 | 1.00 44.83 | B2 |
| ATOM | 1936 | N | GLY | 282 | 32.977 | 30.120 | 25.940 | 1.00 42.33 | B2 |
| ATOM | 1937 | H | GLY | 282 | 33.043 | 31.058 | 26.221 | 1.00 0.00 | B2 |
| ATOM | 1938 | CA | GLY | 282 | 32.363 | 29.869 | 24.632 | 1.00 40.65 | B2 |
| ATOM | 1939 | C | GLY | 282 | 33.175 | 28.937 | 23.755 | 1.00 39.06 | B2 |
| ATOM | 1940 | O | GLY | 282 | 32.584 | 28.075 | 23.107 | 1.00 40.10 | B2 |
| ATOM | 1941 | N | LEU | 283 | 34.514 | 29.066 | 23.776 | 1.00 37.39 | B2 |
| ATOM | 1942 | H | LEU | 283 | 34.880 | 29.807 | 24.304 | 1.00 0.00 | B2 |
| ATOM | 1943 | CA | LEU | 283 | 35.465 | 28.213 | 23.037 | 1.00 35.06 | B2 |
| ATOM | 1944 | CB | LEU | 283 | 36.902 | 28.718 | 23.089 | 1.00 30.20 | B2 |
| ATOM | 1945 | CG | LEU | 283 | 37.167 | 30.001 | 22.302 | 1.00 25.73 | B2 |
| ATOM | 1946 | CD1 | LEU | 283 | 38.539 | 30.461 | 22.664 | 1.00 24.38 | B2 |
| ATOM | 1947 | CD2 | LEU | 283 | 37.036 | 29.802 | 20.815 | 1.00 21.94 | B2 |
| ATOM | 1948 | C | LEU | 283 | 35.470 | 26.851 | 23.651 | 1.00 34.81 | B2 |
| ATOM | 1949 | O | LEU | 283 | 35.314 | 25.859 | 22.947 | 1.00 31.09 | B2 |
| ATOM | 1950 | N | PHE | 284 | 35.533 | 26.842 | 24.973 | 1.00 37.62 | B2 |
| ATOM | 1951 | H | PHE | 284 | 35.567 | 27.686 | 25.467 | 1.00 0.00 | B2 |
| ATOM | 1952 | CA | PHE | 284 | 35.485 | 25.596 | 25.710 | 1.00 42.51 | B2 |
| ATOM | 1953 | CB | PHE | 284 | 35.542 | 25.877 | 27.184 | 1.00 49.49 | B2 |
| ATOM | 1954 | CG | PHE | 284 | 36.221 | 24.770 | 27.968 | 1.00 58.39 | B2 |
| ATOM | 1955 | CD1 | PHE | 284 | 37.265 | 25.108 | 28.816 | 1.00 63.05 | B2 |
| ATOM | 1956 | CD2 | PHE | 284 | 35.810 | 23.453 | 27.861 | 1.00 60.84 | B2 |
| ATOM | 1957 | CE1 | PHE | 284 | 37.900 | 24.124 | 29.563 | 1.00 65.86 | B2 |
| ATOM | 1958 | CE2 | PHE | 284 | 36.444 | 22.480 | 28.605 | 1.00 64.49 | B2 |
| ATOM | 1959 | CZ | PHE | 284 | 37.486 | 22.810 | 29.455 | 1.00 66.32 | B2 |
| ATOM | 1960 | C | PHE | 284 | 34.204 | 24.849 | 25.384 | 1.00 41.44 | B2 |
| ATOM | 1961 | O | PHE | 284 | 34.257 | 23.630 | 25.306 | 1.00 41.42 | B2 |
| ATOM | 1962 | N | LEU | 285 | 33.100 | 25.563 | 25.101 | 1.00 41.24 | B2 |
| ATOM | 1963 | H | LEU | 285 | 33.192 | 26.534 | 25.174 | 1.00 0.00 | B2 |
| ATOM | 1964 | CA | LEU | 285 | 31.781 | 25.025 | 24.730 | 1.00 38.92 | B2 |
| ATOM | 1965 | CB | LEU | 285 | 30.727 | 26.139 | 24.807 | 1.00 39.05 | B2 |
| ATOM | 1966 | CG | LEU | 285 | 29.292 | 25.740 | 24.481 | 1.00 41.16 | B2 |
| ATOM | 1967 | CD1 | LEU | 285 | 28.711 | 24.981 | 25.662 | 1.00 41.12 | B2 |
| ATOM | 1968 | CD2 | LEU | 285 | 28.472 | 26.971 | 24.139 | 1.00 39.60 | B2 |
| ATOM | 1969 | C | LEU | 285 | 31.780 | 24.441 | 23.329 | 1.00 37.34 | B2 |
| ATOM | 1970 | O | LEU | 285 | 31.245 | 23.351 | 23.095 | 1.00 36.97 | B2 |
| ATOM | 1971 | N | TYR | 286 | 32.352 | 25.172 | 22.372 | 1.00 35.26 | B2 |
| ATOM | 1972 | H | TYR | 286 | 32.705 | 26.062 | 22.593 | 1.00 0.00 | B2 |
| ATOM | 1973 | CA | TYR | 286 | 32.455 | 24.660 | 21.033 | 1.00 35.04 | B2 |
| ATOM | 1974 | CB | TYR | 286 | 32.891 | 25.790 | 20.122 | 1.00 34.44 | B2 |
| ATOM | 1975 | CG | TYR | 286 | 31.690 | 26.684 | 19.808 | 1.00 34.75 | B2 |
| ATOM | 1976 | CD1 | TYR | 286 | 31.433 | 27.879 | 20.469 | 1.00 35.67 | B2 |
| ATOM | 1977 | CE1 | TYR | 286 | 30.313 | 28.620 | 20.158 | 1.00 36.90 | B2 |

FIG. 5X

| ATOM | 1978 | CD2 | TYR | 286 | 30.823 | 26.255 | 18.839 | 1.00 | 36.19 | B2 |
|---|---|---|---|---|---|---|---|---|---|---|
| ATOM | 1979 | CE2 | TYR | 286 | 29.707 | 26.990 | 18.521 | 1.00 | 37.55 | B2 |
| ATOM | 1980 | CZ | TYR | 286 | 29.449 | 28.164 | 19.178 | 1.00 | 37.73 | B2 |
| ATOM | 1981 | OH | TYR | 286 | 28.285 | 28.826 | 18.823 | 1.00 | 38.04 | B2 |
| ATOM | 1982 | HH | TYR | 286 | 28.289 | 29.707 | 19.243 | 1.00 | 0.00 | B2 |
| ATOM | 1983 | C | TYR | 286 | 33.393 | 23.464 | 20.926 | 1.00 | 34.80 | B2 |
| ATOM | 1984 | O | TYR | 286 | 33.071 | 22.537 | 20.180 | 1.00 | 35.35 | B2 |
| ATOM | 1985 | N | ALA | 287 | 34.527 | 23.339 | 21.636 | 1.00 | 34.66 | B2 |
| ATOM | 1986 | H | ALA | 287 | 34.803 | 24.088 | 22.206 | 1.00 | 0.00 | B2 |
| ATOM | 1987 | CA | ALA | 287 | 35.350 | 22.108 | 21.565 | 1.00 | 34.28 | B2 |
| ATOM | 1988 | CB | ALA | 287 | 36.617 | 22.291 | 22.415 | 1.00 | 33.63 | B2 |
| ATOM | 1989 | C | ALA | 287 | 34.528 | 20.906 | 22.073 | 1.00 | 33.32 | B2 |
| ATOM | 1990 | O | ALA | 287 | 34.535 | 19.827 | 21.478 | 1.00 | 33.07 | B2 |
| ATOM | 1991 | N | GLY | 288 | 33.723 | 21.118 | 23.111 | 1.00 | 33.19 | B2 |
| ATOM | 1992 | H | GLY | 288 | 33.791 | 21.985 | 23.564 | 1.00 | 0.00 | B2 |
| ATOM | 1993 | CA | GLY | 288 | 32.761 | 20.162 | 23.655 | 1.00 | 35.62 | B2 |
| ATOM | 1994 | C | GLY | 288 | 31.744 | 19.606 | 22.636 | 1.00 | 36.89 | B2 |
| ATOM | 1995 | O | GLY | 288 | 31.624 | 18.379 | 22.444 | 1.00 | 34.97 | B2 |
| ATOM | 1996 | N | LEU | 289 | 31.037 | 20.536 | 21.966 | 1.00 | 36.69 | B2 |
| ATOM | 1997 | H | LEU | 289 | 31.200 | 21.476 | 22.201 | 1.00 | 0.00 | B2 |
| ATOM | 1998 | CA | LEU | 289 | 30.018 | 20.249 | 20.954 | 1.00 | 35.05 | B2 |
| ATOM | 1999 | CB | LEU | 289 | 29.351 | 21.576 | 20.502 | 1.00 | 36.32 | B2 |
| ATOM | 2000 | CG | LEU | 289 | 28.552 | 22.450 | 21.464 | 1.00 | 35.76 | B2 |
| ATOM | 2001 | CD1 | LEU | 289 | 28.256 | 23.821 | 20.890 | 1.00 | 32.66 | B2 |
| ATOM | 2002 | CD2 | LEU | 289 | 27.246 | 21.780 | 21.697 | 1.00 | 35.35 | B2 |
| ATOM | 2003 | C | LEU | 289 | 30.536 | 19.519 | 19.714 | 1.00 | 34.21 | B2 |
| ATOM | 2004 | O | LEU | 289 | 29.871 | 18.694 | 19.078 | 1.00 | 33.28 | B2 |
| ATOM | 2005 | N | LEU | 290 | 31.756 | 19.902 | 19.355 | 1.00 | 33.25 | B2 |
| ATOM | 2006 | H | LEU | 290 | 32.183 | 20.634 | 19.850 | 1.00 | 0.00 | B2 |
| ATOM | 2007 | CA | LEU | 290 | 32.448 | 19.345 | 18.230 | 1.00 | 32.44 | B2 |
| ATOM | 2008 | CB | LEU | 290 | 33.729 | 20.159 | 18.000 | 1.00 | 32.62 | B2 |
| ATOM | 2009 | CG | LEU | 290 | 33.560 | 21.509 | 17.315 | 1.00 | 32.05 | B2 |
| ATOM | 2010 | CD1 | LEU | 290 | 34.889 | 22.189 | 17.349 | 1.00 | 32.58 | B2 |
| ATOM | 2011 | CD2 | LEU | 290 | 33.068 | 21.374 | 15.879 | 1.00 | 31.74 | B2 |
| ATOM | 2012 | C | LEU | 290 | 32.737 | 17.908 | 18.558 | 1.00 | 31.94 | B2 |
| ATOM | 2013 | O | LEU | 290 | 32.432 | 17.020 | 17.772 | 1.00 | 30.50 | B2 |
| ATOM | 2014 | N | GLN | 291 | 33.249 | 17.711 | 19.770 | 1.00 | 33.58 | B2 |
| ATOM | 2015 | H | GLN | 291 | 33.512 | 18.494 | 20.298 | 1.00 | 0.00 | B2 |
| ATOM | 2016 | CA | GLN | 291 | 33.499 | 16.372 | 20.311 | 1.00 | 36.39 | B2 |
| ATOM | 2017 | CB | GLN | 291 | 33.988 | 16.490 | 21.702 | 1.00 | 36.86 | B2 |
| ATOM | 2018 | CG | GLN | 291 | 34.926 | 15.367 | 21.950 | 1.00 | 39.48 | B2 |
| ATOM | 2019 | CD | GLN | 291 | 35.658 | 15.503 | 23.252 | 1.00 | 40.79 | B2 |
| ATOM | 2020 | OE1 | GLN | 291 | 36.457 | 14.626 | 23.549 | 1.00 | 44.80 | B2 |
| ATOM | 2021 | NE2 | GLN | 291 | 35.494 | 16.535 | 24.072 | 1.00 | 42.59 | B2 |
| ATOM | 2022 | HE21 | GLN | 291 | 34.928 | 17.287 | 23.817 | 1.00 | 0.00 | B2 |
| ATOM | 2023 | HE22 | GLN | 291 | 35.910 | 16.463 | 24.958 | 1.00 | 0.00 | B2 |
| ATOM | 2024 | C | GLN | 291 | 32.233 | 15.536 | 20.307 | 1.00 | 36.66 | B2 |
| ATOM | 2025 | O | GLN | 291 | 32.220 | 14.478 | 19.707 | 1.00 | 37.46 | B2 |
| ATOM | 2026 | N | ALA | 292 | 31.143 | 16.023 | 20.913 | 1.00 | 38.37 | B2 |
| ATOM | 2027 | H | ALA | 292 | 31.255 | 16.849 | 21.418 | 1.00 | 0.00 | B2 |
| ATOM | 2028 | CA | ALA | 292 | 29.778 | 15.451 | 20.857 | 1.00 | 39.25 | B2 |
| ATOM | 2029 | CB | ALA | 292 | 28.818 | 16.485 | 21.444 | 1.00 | 40.28 | B2 |
| ATOM | 2030 | C | ALA | 292 | 29.215 | 14.999 | 19.484 | 1.00 | 38.65 | B2 |
| ATOM | 2031 | O | ALA | 292 | 28.411 | 14.067 | 19.356 | 1.00 | 37.58 | B2 |
| ATOM | 2032 | N | LEU | 293 | 29.614 | 15.702 | 18.430 | 1.00 | 39.00 | B2 |
| ATOM | 2033 | H | LEU | 293 | 30.149 | 16.513 | 18.574 | 1.00 | 0.00 | B2 |
| ATOM | 2034 | CA | LEU | 293 | 29.265 | 15.335 | 17.077 | 1.00 | 39.74 | B2 |
| ATOM | 2035 | CB | LEU | 293 | 29.662 | 16.418 | 16.106 | 1.00 | 37.53 | B2 |
| ATOM | 2036 | CG | LEU | 293 | 28.969 | 17.701 | 16.138 | 1.00 | 34.34 | B2 |
| ATOM | 2037 | CD1 | LEU | 293 | 29.547 | 18.582 | 15.053 | 1.00 | 33.88 | B2 |
| ATOM | 2038 | CD2 | LEU | 293 | 27.503 | 17.462 | 15.918 | 1.00 | 35.69 | B2 |
| ATOM | 2039 | C | LEU | 293 | 29.933 | 14.060 | 16.596 | 1.00 | 40.86 | B2 |
| ATOM | 2040 | O | LEU | 293 | 29.686 | 13.669 | 15.449 | 1.00 | 40.58 | B2 |
| ATOM | 2041 | N | GLU | 294 | 30.887 | 13.495 | 17.365 | 1.00 | 42.12 | B2 |
| ATOM | 2042 | H | GLU | 294 | 31.131 | 13.963 | 18.190 | 1.00 | 0.00 | B2 |
| ATOM | 2043 | CA | GLU | 294 | 31.598 | 12.253 | 17.076 | 1.00 | 42.89 | B2 |
| ATOM | 2044 | CB | GLU | 294 | 30.806 | 10.984 | 17.485 | 1.00 | 48.38 | B2 |
| ATOM | 2045 | CG | GLU | 294 | 30.715 | 10.614 | 18.972 | 1.00 | 56.26 | B2 |
| ATOM | 2046 | CD | GLU | 294 | 29.271 | 10.408 | 19.486 | 1.00 | 63.70 | B2 |
| ATOM | 2047 | OE1 | GLU | 294 | 29.058 | 10.603 | 20.702 | 1.00 | 67.72 | B2 |
| ATOM | 2048 | OE2 | GLU | 294 | 28.363 | 10.074 | 18.692 | 1.00 | 64.81 | B2 |
| ATOM | 2049 | C | GLU | 294 | 31.972 | 12.068 | 15.632 | 1.00 | 41.53 | B2 |
| ATOM | 2050 | O | GLU | 294 | 31.804 | 11.007 | 15.021 | 1.00 | 40.29 | B2 |
| ATOM | 2051 | N | GLY | 295 | 32.424 | 13.203 | 15.106 | 1.00 | 40.93 | B2 |
| ATOM | 2052 | H | GLY | 295 | 32.357 | 14.033 | 15.621 | 1.00 | 0.00 | B2 |
| ATOM | 2053 | CA | GLY | 295 | 32.998 | 13.236 | 13.783 | 1.00 | 39.95 | B2 |
| ATOM | 2054 | C | GLY | 295 | 32.027 | 13.230 | 12.634 | 1.00 | 40.60 | B2 |
| ATOM | 2055 | O | GLY | 295 | 32.477 | 13.216 | 11.487 | 1.00 | 40.96 | B2 |
| ATOM | 2056 | N | ILE | 296 | 30.728 | 13.296 | 12.898 | 1.00 | 41.18 | B2 |
| ATOM | 2057 | H | ILE | 296 | 30.446 | 13.210 | 13.825 | 1.00 | 0.00 | B2 |
| ATOM | 2058 | CA | ILE | 296 | 29.687 | 13.306 | 11.888 | 1.00 | 44.02 | B2 |
| ATOM | 2059 | CB | ILE | 296 | 29.683 | 14.580 | 11.009 | 1.00 | 43.49 | B2 |
| ATOM | 2060 | CG2 | ILE | 296 | 28.288 | 14.685 | 10.421 | 1.00 | 40.56 | B2 |
| ATOM | 2061 | CG1 | ILE | 296 | 30.047 | 15.831 | 11.793 | 1.00 | 45.11 | B2 |
| ATOM | 2062 | CD | ILE | 296 | 30.039 | 17.189 | 11.062 | 1.00 | 46.06 | B2 |
| ATOM | 2063 | C | ILE | 296 | 29.820 | 12.107 | 10.949 | 1.00 | 46.71 | B2 |

FIG. 5Y

| | | | | | | | | | | |
|---|---|---|---|---|---|---|---|---|---|---|
| ATOM | 2064 | O | ILE | 296 | 28.918 | 11.279 | 11.060 | 1.00 | 50.61 | B2 |
| ATOM | 2065 | N | SER | 297 | 30.767 | 11.875 | 10.019 | 1.00 | 47.21 | B2 |
| ATOM | 2066 | H | SER | 297 | 31.526 | 12.491 | 9.936 | 1.00 | 0.00 | B2 |
| ATOM | 2067 | CA | SER | 297 | 30.810 | 10.646 | 9.234 | 1.00 | 46.73 | B2 |
| ATOM | 2068 | CB | SER | 297 | 30.239 | 10.884 | 7.865 | 1.00 | 45.48 | B2 |
| ATOM | 2069 | OG | SER | 297 | 30.988 | 11.782 | 7.072 | 1.00 | 46.27 | B2 |
| ATOM | 2070 | HG | SER | 297 | 30.321 | 12.200 | 6.503 | 1.00 | 0.00 | B2 |
| ATOM | 2071 | C | SER | 297 | 32.263 | 10.269 | 9.123 | 1.00 | 48.72 | B2 |
| ATOM | 2072 | O | SER | 297 | 33.120 | 11.122 | 9.391 | 1.00 | 50.55 | B2 |
| ATOM | 2073 | N | PRO | 298 | 32.655 | 9.069 | 8.697 | 1.00 | 49.68 | B2 |
| ATOM | 2074 | CD | PRO | 298 | 31.782 | 7.964 | 8.334 | 1.00 | 50.62 | B2 |
| ATOM | 2075 | CA | PRO | 298 | 34.049 | 8.701 | 8.458 | 1.00 | 50.53 | B2 |
| ATOM | 2076 | CB | PRO | 298 | 33.948 | 7.308 | 7.856 | 1.00 | 51.53 | B2 |
| ATOM | 2077 | CG | PRO | 298 | 32.576 | 7.266 | 7.231 | 1.00 | 50.43 | B2 |
| ATOM | 2078 | C | PRO | 298 | 34.795 | 9.692 | 7.579 | 1.00 | 50.08 | B2 |
| ATOM | 2079 | O | PRO | 298 | 35.883 | 10.137 | 7.930 | 1.00 | 50.50 | B2 |
| ATOM | 2080 | N | GLN | 299 | 34.173 | 10.086 | 6.469 | 1.00 | 50.48 | B2 |
| ATOM | 2081 | H | GLN | 299 | 33.279 | 9.729 | 6.296 | 1.00 | 0.00 | B2 |
| ATOM | 2082 | CA | GLN | 299 | 34.749 | 11.050 | 5.550 | 1.00 | 51.74 | B2 |
| ATOM | 2083 | CB | GLN | 299 | 33.898 | 11.236 | 4.301 | 1.00 | 54.33 | B2 |
| ATOM | 2084 | CG | GLN | 299 | 33.095 | 10.067 | 3.725 | 1.00 | 58.11 | B2 |
| ATOM | 2085 | CD | GLN | 299 | 31.658 | 10.086 | 4.259 | 1.00 | 61.49 | B2 |
| ATOM | 2086 | OE1 | GLN | 299 | 31.160 | 9.083 | 4.776 | 1.00 | 61.00 | B2 |
| ATOM | 2087 | NE2 | GLN | 299 | 30.942 | 11.217 | 4.204 | 1.00 | 62.12 | B2 |
| ATOM | 2088 | HE21 | GLN | 299 | 31.345 | 12.012 | 3.800 | 1.00 | 0.00 | B2 |
| ATOM | 2089 | HE22 | GLN | 299 | 30.034 | 11.191 | 4.566 | 1.00 | 0.00 | B2 |
| ATOM | 2090 | C | GLN | 299 | 34.923 | 12.453 | 6.160 | 1.00 | 51.04 | B2 |
| ATOM | 2091 | O | GLN | 299 | 35.796 | 13.186 | 5.718 | 1.00 | 53.38 | B2 |
| ATOM | 2092 | N | LEU | 300 | 34.118 | 12.918 | 7.120 | 1.00 | 48.15 | B2 |
| ATOM | 2093 | H | LEU | 300 | 33.383 | 12.351 | 7.437 | 1.00 | 0.00 | B2 |
| ATOM | 2094 | CA | LEU | 300 | 34.272 | 14.220 | 7.745 | 1.00 | 43.32 | B2 |
| ATOM | 2095 | CB | LEU | 300 | 32.856 | 14.719 | 8.021 | 1.00 | 41.39 | B2 |
| ATOM | 2096 | CG | LEU | 300 | 32.073 | 15.546 | 6.974 | 1.00 | 37.99 | B2 |
| ATOM | 2097 | CD1 | LEU | 300 | 31.872 | 14.824 | 5.688 | 1.00 | 38.34 | B2 |
| ATOM | 2098 | CD2 | LEU | 300 | 30.705 | 15.809 | 7.522 | 1.00 | 37.67 | B2 |
| ATOM | 2099 | C | LEU | 300 | 35.142 | 14.220 | 9.019 | 1.00 | 42.84 | B2 |
| ATOM | 2100 | O | LEU | 300 | 35.558 | 15.278 | 9.541 | 1.00 | 41.56 | B2 |
| ATOM | 2101 | N | GLY | 301 | 35.467 | 13.016 | 9.528 | 1.00 | 40.83 | B2 |
| ATOM | 2102 | H | GLY | 301 | 35.157 | 12.221 | 9.046 | 1.00 | 0.00 | B2 |
| ATOM | 2103 | CA | GLY | 301 | 36.199 | 12.826 | 10.779 | 1.00 | 38.72 | B2 |
| ATOM | 2104 | C | GLY | 301 | 37.500 | 13.607 | 10.887 | 1.00 | 37.69 | B2 |
| ATOM | 2105 | O | GLY | 301 | 37.665 | 14.406 | 11.809 | 1.00 | 37.31 | B2 |
| ATOM | 2106 | N | PRO | 302 | 38.468 | 13.452 | 9.985 | 1.00 | 37.33 | B2 |
| ATOM | 2107 | CD | PRO | 302 | 38.353 | 12.630 | 8.790 | 1.00 | 37.77 | B2 |
| ATOM | 2108 | CA | PRO | 302 | 39.676 | 14.281 | 9.884 | 1.00 | 37.60 | B2 |
| ATOM | 2109 | CB | PRO | 302 | 40.256 | 13.907 | 8.541 | 1.00 | 36.62 | B2 |
| ATOM | 2110 | CG | PRO | 302 | 39.047 | 13.487 | 7.745 | 1.00 | 37.94 | B2 |
| ATOM | 2111 | C | PRO | 302 | 39.486 | 15.782 | 10.033 | 1.00 | 37.45 | B2 |
| ATOM | 2112 | O | PRO | 302 | 40.132 | 16.398 | 10.901 | 1.00 | 38.33 | B2 |
| ATOM | 2113 | N | THR | 303 | 38.547 | 16.311 | 9.204 | 1.00 | 37.05 | B2 |
| ATOM | 2114 | H | THR | 303 | 38.085 | 15.727 | 8.567 | 1.00 | 0.00 | B2 |
| ATOM | 2115 | CA | THR | 303 | 38.119 | 17.705 | 9.128 | 1.00 | 35.81 | B2 |
| ATOM | 2116 | CB | THR | 303 | 36.963 | 17.770 | 8.123 | 1.00 | 37.26 | B2 |
| ATOM | 2117 | OG1 | THR | 303 | 37.416 | 17.161 | 6.909 | 1.00 | 39.64 | B2 |
| ATOM | 2118 | HG1 | THR | 303 | 37.369 | 17.785 | 6.178 | 1.00 | 0.00 | B2 |
| ATOM | 2119 | CG2 | THR | 303 | 36.469 | 19.204 | 7.927 | 1.00 | 38.55 | B2 |
| ATOM | 2120 | C | THR | 303 | 37.687 | 18.223 | 10.506 | 1.00 | 34.93 | B2 |
| ATOM | 2121 | O | THR | 303 | 38.085 | 19.263 | 11.063 | 1.00 | 35.11 | B2 |
| ATOM | 2122 | N | LEU | 304 | 36.928 | 17.366 | 11.150 | 1.00 | 33.76 | B2 |
| ATOM | 2123 | H | LEU | 304 | 36.672 | 16.500 | 10.762 | 1.00 | 0.00 | B2 |
| ATOM | 2124 | CA | LEU | 304 | 36.436 | 17.746 | 12.418 | 1.00 | 31.01 | B2 |
| ATOM | 2125 | CB | LEU | 304 | 35.345 | 16.803 | 12.708 | 1.00 | 30.31 | B2 |
| ATOM | 2126 | CG | LEU | 304 | 34.234 | 17.567 | 13.320 | 1.00 | 31.32 | B2 |
| ATOM | 2127 | CD1 | LEU | 304 | 33.121 | 17.626 | 12.309 | 1.00 | 28.87 | B2 |
| ATOM | 2128 | CD2 | LEU | 304 | 33.921 | 16.970 | 14.692 | 1.00 | 34.23 | B2 |
| ATOM | 2129 | C | LEU | 304 | 37.553 | 17.726 | 13.421 | 1.00 | 31.86 | B2 |
| ATOM | 2130 | O | LEU | 304 | 37.615 | 18.623 | 14.259 | 1.00 | 34.21 | B2 |
| ATOM | 2131 | N | ASP | 305 | 38.510 | 16.811 | 13.326 | 1.00 | 30.56 | B2 |
| ATOM | 2132 | H | ASP | 305 | 38.456 | 16.117 | 12.635 | 1.00 | 0.00 | B2 |
| ATOM | 2133 | CA | ASP | 305 | 39.576 | 16.797 | 14.303 | 1.00 | 30.72 | B2 |
| ATOM | 2134 | CB | ASP | 305 | 40.504 | 15.608 | 14.114 | 1.00 | 36.20 | B2 |
| ATOM | 2135 | CG | ASP | 305 | 39.912 | 14.201 | 14.288 | 1.00 | 40.64 | B2 |
| ATOM | 2136 | OD1 | ASP | 305 | 38.976 | 14.040 | 15.103 | 1.00 | 37.52 | B2 |
| ATOM | 2137 | OD2 | ASP | 305 | 40.426 | 13.304 | 13.581 | 1.00 | 42.39 | B2 |
| ATOM | 2138 | C | ASP | 305 | 40.435 | 18.034 | 14.238 | 1.00 | 27.56 | B2 |
| ATOM | 2139 | O | ASP | 305 | 40.775 | 18.575 | 15.311 | 1.00 | 24.61 | B2 |
| ATOM | 2140 | N | THR | 306 | 40.781 | 18.417 | 12.979 | 1.00 | 24.77 | B2 |
| ATOM | 2141 | H | THR | 306 | 40.469 | 17.875 | 12.230 | 1.00 | 0.00 | B2 |
| ATOM | 2142 | CA | THR | 306 | 41.553 | 19.633 | 12.751 | 1.00 | 24.39 | B2 |
| ATOM | 2143 | CB | THR | 306 | 41.665 | 19.931 | 11.318 | 1.00 | 24.58 | B2 |
| ATOM | 2144 | OG1 | THR | 306 | 42.074 | 18.753 | 10.665 | 1.00 | 25.13 | B2 |
| ATOM | 2145 | HG1 | THR | 306 | 41.447 | 18.029 | 10.768 | 1.00 | 0.00 | B2 |
| ATOM | 2146 | CG2 | THR | 306 | 42.690 | 21.027 | 11.089 | 1.00 | 25.77 | B2 |
| ATOM | 2147 | C | THR | 306 | 40.893 | 20.844 | 13.419 | 1.00 | 25.24 | B2 |
| ATOM | 2148 | O | THR | 306 | 41.488 | 21.472 | 14.296 | 1.00 | 27.24 | B2 |
| ATOM | 2149 | N | LEU | 307 | 39.615 | 21.134 | 13.139 | 1.00 | 25.91 | B2 |

FIG. 5Z

| ATOM | 2150 | H | LEU | 307 | 39.125 | 20.547 | 12.520 | 1.00 | 0.00 | B2 |
|------|------|---|-----|-----|--------|--------|--------|------|------|-----|
| ATOM | 2151 | CA | LEU | 307 | 38.900 | 22.228 | 13.764 | 1.00 | 25.53 | B2 |
| ATOM | 2152 | CB | LEU | 307 | 37.571 | 22.170 | 13.142 | 1.00 | 25.09 | B2 |
| ATOM | 2153 | CG | LEU | 307 | 36.530 | 23.097 | 13.588 | 1.00 | 27.93 | B2 |
| ATOM | 2154 | CD1 | LEU | 307 | 37.008 | 24.515 | 13.484 | 1.00 | 29.87 | B2 |
| ATOM | 2155 | CD2 | LEU | 307 | 35.311 | 22.846 | 12.728 | 1.00 | 28.93 | B2 |
| ATOM | 2156 | C | LEU | 307 | 38.850 | 22.214 | 15.269 | 1.00 | 27.09 | B2 |
| ATOM | 2157 | O | LEU | 307 | 38.854 | 23.253 | 15.925 | 1.00 | 30.03 | B2 |
| ATOM | 2158 | N | GLN | 308 | 38.875 | 21.044 | 15.879 | 1.00 | 29.09 | B2 |
| ATOM | 2159 | H | GLN | 308 | 38.883 | 20.239 | 15.319 | 1.00 | 0.00 | B2 |
| ATOM | 2160 | CA | GLN | 308 | 38.824 | 20.848 | 17.340 | 1.00 | 29.36 | B2 |
| ATOM | 2161 | CB | GLN | 308 | 38.379 | 19.399 | 17.562 | 1.00 | 29.41 | B2 |
| ATOM | 2162 | CG | GLN | 308 | 37.862 | 19.140 | 18.935 | 1.00 | 32.24 | B2 |
| ATOM | 2163 | CD | GLN | 308 | 37.586 | 17.672 | 19.165 | 1.00 | 34.03 | B2 |
| ATOM | 2164 | OE1 | GLN | 308 | 36.973 | 17.023 | 18.311 | 1.00 | 33.48 | B2 |
| ATOM | 2165 | NE2 | GLN | 308 | 38.053 | 17.127 | 20.299 | 1.00 | 31.67 | B2 |
| ATOM | 2166 | HE21 | GLN | 308 | 38.547 | 17.697 | 20.917 | 1.00 | 0.00 | B2 |
| ATOM | 2167 | HE22 | GLN | 308 | 37.875 | 16.174 | 20.436 | 1.00 | 0.00 | B2 |
| ATOM | 2168 | C | GLN | 308 | 40.154 | 21.138 | 18.051 | 1.00 | 28.94 | B2 |
| ATOM | 2169 | O | GLN | 308 | 40.196 | 21.796 | 19.101 | 1.00 | 28.44 | B2 |
| ATOM | 2170 | N | LEU | 309 | 41.269 | 20.671 | 17.460 | 1.00 | 28.78 | B2 |
| ATOM | 2171 | H | LEU | 309 | 41.157 | 20.120 | 16.655 | 1.00 | 0.00 | B2 |
| ATOM | 2172 | CA | LEU | 309 | 42.632 | 20.923 | 17.967 | 1.00 | 28.56 | B2 |
| ATOM | 2173 | CB | LEU | 309 | 43.671 | 20.154 | 17.106 | 1.00 | 26.54 | B2 |
| ATOM | 2174 | CG | LEU | 309 | 43.632 | 18.636 | 17.241 | 1.00 | 24.98 | B2 |
| ATOM | 2175 | CD1 | LEU | 309 | 44.595 | 17.935 | 16.353 | 1.00 | 24.17 | B2 |
| ATOM | 2176 | CD2 | LEU | 309 | 43.992 | 18.310 | 18.621 | 1.00 | 23.45 | B2 |
| ATOM | 2177 | C | LEU | 309 | 42.893 | 22.416 | 17.909 | 1.00 | 28.24 | B2 |
| ATOM | 2178 | O | LEU | 309 | 43.370 | 22.957 | 18.907 | 1.00 | 30.32 | B2 |
| ATOM | 2179 | N | ASP | 310 | 42.548 | 23.027 | 16.749 | 1.00 | 26.58 | B2 |
| ATOM | 2180 | H | ASP | 310 | 42.296 | 22.437 | 16.007 | 1.00 | 0.00 | B2 |
| ATOM | 2181 | CA | ASP | 310 | 42.495 | 24.477 | 16.495 | 1.00 | 27.90 | B2 |
| ATOM | 2182 | CB | ASP | 310 | 42.025 | 24.659 | 15.076 | 1.00 | 28.41 | B2 |
| ATOM | 2183 | CG | ASP | 310 | 43.162 | 24.556 | 14.096 | 1.00 | 31.54 | B2 |
| ATOM | 2184 | OD1 | ASP | 310 | 42.959 | 24.766 | 12.905 | 1.00 | 31.54 | B2 |
| ATOM | 2185 | OD2 | ASP | 310 | 44.297 | 24.314 | 14.514 | 1.00 | 37.32 | B2 |
| ATOM | 2186 | C | ASP | 310 | 41.666 | 25.410 | 17.422 | 1.00 | 27.99 | B2 |
| ATOM | 2187 | O | ASP | 310 | 42.219 | 26.429 | 17.876 | 1.00 | 27.23 | B2 |
| ATOM | 2188 | N | VAL | 311 | 40.374 | 25.086 | 17.725 | 1.00 | 26.29 | B2 |
| ATOM | 2189 | H | VAL | 311 | 39.961 | 24.347 | 17.225 | 1.00 | 0.00 | B2 |
| ATOM | 2190 | CA | VAL | 311 | 39.546 | 25.803 | 18.706 | 1.00 | 24.29 | B2 |
| ATOM | 2191 | CB | VAL | 311 | 38.098 | 25.217 | 18.869 | 1.00 | 21.47 | B2 |
| ATOM | 2192 | CG1 | VAL | 311 | 37.341 | 25.915 | 19.949 | 1.00 | 19.01 | B2 |
| ATOM | 2193 | CG2 | VAL | 311 | 37.261 | 25.488 | 17.667 | 1.00 | 18.56 | B2 |
| ATOM | 2194 | C | VAL | 311 | 40.270 | 25.638 | 20.020 | 1.00 | 27.21 | B2 |
| ATOM | 2195 | O | VAL | 311 | 40.437 | 26.647 | 20.719 | 1.00 | 29.71 | B2 |
| ATOM | 2196 | N | ALA | 312 | 40.762 | 24.428 | 20.357 | 1.00 | 27.97 | B2 |
| ATOM | 2197 | H | ALA | 312 | 40.585 | 23.674 | 19.756 | 1.00 | 0.00 | B2 |
| ATOM | 2198 | CA | ALA | 312 | 41.515 | 24.157 | 21.583 | 1.00 | 29.24 | B2 |
| ATOM | 2199 | CB | ALA | 312 | 41.855 | 22.688 | 21.532 | 1.00 | 30.53 | B2 |
| ATOM | 2200 | C | ALA | 312 | 42.778 | 25.026 | 21.784 | 1.00 | 30.06 | B2 |
| ATOM | 2201 | O | ALA | 312 | 43.057 | 25.508 | 22.886 | 1.00 | 30.04 | B2 |
| ATOM | 2202 | N | ASP | 313 | 43.554 | 25.286 | 20.735 | 1.00 | 31.33 | B2 |
| ATOM | 2203 | H | ASP | 313 | 43.433 | 24.730 | 19.935 | 1.00 | 0.00 | B2 |
| ATOM | 2204 | CA | ASP | 313 | 44.610 | 26.275 | 20.743 | 1.00 | 34.22 | B2 |
| ATOM | 2205 | CB | ASP | 313 | 45.279 | 26.512 | 19.447 | 1.00 | 38.87 | B2 |
| ATOM | 2206 | CG | ASP | 313 | 46.071 | 25.404 | 18.866 | 1.00 | 44.55 | B2 |
| ATOM | 2207 | OD1 | ASP | 313 | 46.225 | 25.439 | 17.636 | 1.00 | 48.67 | B2 |
| ATOM | 2208 | OD2 | ASP | 313 | 46.521 | 24.553 | 19.647 | 1.00 | 49.25 | B2 |
| ATOM | 2209 | C | ASP | 313 | 44.187 | 27.699 | 21.059 | 1.00 | 35.12 | B2 |
| ATOM | 2210 | O | ASP | 313 | 44.807 | 28.390 | 21.894 | 1.00 | 38.60 | B2 |
| ATOM | 2211 | N | PHE | 314 | 43.192 | 28.216 | 20.339 | 1.00 | 33.36 | B2 |
| ATOM | 2212 | H | PHE | 314 | 42.784 | 27.683 | 19.619 | 1.00 | 0.00 | B2 |
| ATOM | 2213 | CA | PHE | 314 | 42.715 | 29.548 | 20.600 | 1.00 | 31.09 | B2 |
| ATOM | 2214 | CB | PHE | 314 | 41.572 | 29.860 | 19.631 | 1.00 | 32.06 | B2 |
| ATOM | 2215 | CG | PHE | 314 | 41.074 | 31.303 | 19.636 | 1.00 | 33.37 | B2 |
| ATOM | 2216 | CD1 | PHE | 314 | 39.780 | 31.568 | 19.247 | 1.00 | 31.81 | B2 |
| ATOM | 2217 | CD2 | PHE | 314 | 41.907 | 32.354 | 20.021 | 1.00 | 35.65 | B2 |
| ATOM | 2218 | CE1 | PHE | 314 | 39.318 | 32.857 | 19.240 | 1.00 | 29.15 | B2 |
| ATOM | 2219 | CE2 | PHE | 314 | 41.455 | 33.648 | 20.017 | 1.00 | 32.48 | B2 |
| ATOM | 2220 | CZ | PHE | 314 | 40.154 | 33.870 | 19.622 | 1.00 | 32.81 | B2 |
| ATOM | 2221 | C | PHE | 314 | 42.282 | 29.601 | 22.057 | 1.00 | 29.90 | B2 |
| ATOM | 2222 | O | PHE | 314 | 42.658 | 30.550 | 22.764 | 1.00 | 26.87 | B2 |
| ATOM | 2223 | N | ALA | 315 | 41.686 | 28.532 | 22.584 | 1.00 | 29.29 | B2 |
| ATOM | 2224 | H | ALA | 315 | 41.448 | 27.764 | 22.022 | 1.00 | 0.00 | B2 |
| ATOM | 2225 | CA | ALA | 315 | 41.300 | 28.583 | 23.961 | 1.00 | 31.61 | B2 |
| ATOM | 2226 | CB | ALA | 315 | 40.632 | 27.358 | 24.451 | 1.00 | 32.23 | B2 |
| ATOM | 2227 | C | ALA | 315 | 42.482 | 28.751 | 24.836 | 1.00 | 34.41 | B2 |
| ATOM | 2228 | O | ALA | 315 | 42.361 | 29.437 | 25.853 | 1.00 | 37.66 | B2 |
| ATOM | 2229 | N | THR | 316 | 43.646 | 28.250 | 24.476 | 1.00 | 36.16 | B2 |
| ATOM | 2230 | H | THR | 316 | 43.745 | 27.778 | 23.625 | 1.00 | 0.00 | B2 |
| ATOM | 2231 | CA | THR | 316 | 44.780 | 28.388 | 25.374 | 1.00 | 37.99 | B2 |
| ATOM | 2232 | CB | THR | 316 | 45.795 | 27.255 | 25.156 | 1.00 | 41.16 | B2 |
| ATOM | 2233 | OG1 | THR | 316 | 45.049 | 26.081 | 25.521 | 1.00 | 45.50 | B2 |
| ATOM | 2234 | HG1 | THR | 316 | 44.316 | 25.900 | 24.913 | 1.00 | 0.00 | B2 |
| ATOM | 2235 | CG2 | THR | 316 | 47.152 | 27.415 | 25.888 | 1.00 | 40.31 | B2 |

FIG. 5AA

| | | | | | | | | | | |
|---|---|---|---|---|---|---|---|---|---|---|
| ATOM | 2236 | C | THR | 316 | 45.458 | 29.710 | 25.177 | 1.00 | 38.47 | B2 |
| ATOM | 2237 | O | THR | 316 | 45.903 | 30.189 | 26.217 | 1.00 | 39.63 | B2 |
| ATOM | 2238 | N | THR | 317 | 45.620 | 30.287 | 23.970 | 1.00 | 36.53 | B2 |
| ATOM | 2239 | H | THR | 317 | 45.351 | 29.800 | 23.164 | 1.00 | 0.00 | B2 |
| ATOM | 2240 | CA | THR | 317 | 46.092 | 31.657 | 23.844 | 1.00 | 37.07 | B2 |
| ATOM | 2241 | CB | THR | 317 | 45.866 | 32.098 | 22.392 | 1.00 | 36.01 | B2 |
| ATOM | 2242 | HG1 | THR | 317 | 46.752 | 31.352 | 21.575 | 1.00 | 35.31 | B2 |
| ATOM | 2243 | OG1 | THR | 317 | 46.489 | 30.441 | 21.389 | 1.00 | 0.00 | B2 |
| ATOM | 2244 | CG2 | THR | 317 | 46.109 | 33.566 | 22.156 | 1.00 | 34.30 | B2 |
| ATOM | 2245 | C | THR | 317 | 45.338 | 32.597 | 24.832 | 1.00 | 39.30 | B2 |
| ATOM | 2246 | O | THR | 317 | 45.941 | 33.378 | 25.583 | 1.00 | 40.17 | B2 |
| ATOM | 2247 | N | ILE | 318 | 44.003 | 32.481 | 24.912 | 1.00 | 40.83 | B2 |
| ATOM | 2248 | H | ILE | 318 | 43.554 | 31.819 | 24.342 | 1.00 | 0.00 | B2 |
| ATOM | 2249 | CA | ILE | 318 | 43.172 | 33.317 | 25.788 | 1.00 | 40.75 | B2 |
| ATOM | 2250 | CB | ILE | 318 | 41.621 | 32.979 | 25.567 | 1.00 | 37.17 | B2 |
| ATOM | 2251 | CG2 | ILE | 318 | 40.742 | 33.706 | 26.545 | 1.00 | 34.29 | B2 |
| ATOM | 2252 | CG1 | ILE | 318 | 41.216 | 33.310 | 24.160 | 1.00 | 31.39 | B2 |
| ATOM | 2253 | CD | ILE | 318 | 41.626 | 34.657 | 23.614 | 1.00 | 29.66 | B2 |
| ATOM | 2254 | C | ILE | 318 | 43.624 | 33.019 | 27.217 | 1.00 | 42.43 | B2 |
| ATOM | 2255 | O | ILE | 318 | 44.064 | 33.963 | 27.856 | 1.00 | 42.54 | B2 |
| ATOM | 2256 | N | TRP | 319 | 43.662 | 31.784 | 27.744 | 1.00 | 44.17 | B2 |
| ATOM | 2257 | H | TRP | 319 | 43.537 | 31.008 | 27.163 | 1.00 | 0.00 | B2 |
| ATOM | 2258 | CA | TRP | 319 | 43.994 | 31.633 | 29.142 | 1.00 | 46.90 | B2 |
| ATOM | 2259 | CB | TRP | 319 | 43.892 | 30.179 | 29.597 | 1.00 | 50.64 | B2 |
| ATOM | 2260 | CG | TRP | 319 | 43.998 | 30.094 | 31.131 | 1.00 | 56.05 | B2 |
| ATOM | 2261 | CD2 | TRP | 319 | 43.005 | 30.397 | 32.038 | 1.00 | 58.61 | B2 |
| ATOM | 2262 | CE2 | TRP | 319 | 43.685 | 30.281 | 33.251 | 1.00 | 60.50 | B2 |
| ATOM | 2263 | CE3 | TRP | 319 | 41.668 | 30.740 | 32.005 | 1.00 | 60.12 | B2 |
| ATOM | 2264 | CD1 | TRP | 319 | 45.188 | 29.788 | 31.760 | 1.00 | 58.07 | B2 |
| ATOM | 2265 | NE1 | TRP | 319 | 44.968 | 29.921 | 33.042 | 1.00 | 60.07 | B2 |
| ATOM | 2266 | HE1 | TRP | 319 | 45.637 | 29.765 | 33.740 | 1.00 | 0.00 | B2 |
| ATOM | 2267 | CZ2 | TRP | 319 | 43.044 | 30.512 | 34.456 | 1.00 | 61.00 | B2 |
| ATOM | 2268 | CZ3 | TRP | 319 | 41.022 | 30.967 | 33.210 | 1.00 | 61.58 | B2 |
| ATOM | 2269 | CH2 | TRP | 319 | 41.704 | 30.854 | 34.417 | 1.00 | 62.04 | B2 |
| ATOM | 2270 | C | TRP | 319 | 45.398 | 32.136 | 29.456 | 1.00 | 47.85 | B2 |
| ATOM | 2271 | O | TRP | 319 | 45.635 | 32.772 | 30.490 | 1.00 | 47.99 | B2 |
| ATOM | 2272 | N | GLN | 320 | 46.339 | 31.915 | 28.550 | 1.00 | 48.63 | B2 |
| ATOM | 2273 | H | GLN | 320 | 46.091 | 31.482 | 27.708 | 1.00 | 0.00 | B2 |
| ATOM | 2274 | CA | GLN | 320 | 47.706 | 32.319 | 28.767 | 1.00 | 49.45 | B2 |
| ATOM | 2275 | CB | GLN | 320 | 48.567 | 31.988 | 27.589 | 1.00 | 51.44 | B2 |
| ATOM | 2276 | CG | GLN | 320 | 48.828 | 30.494 | 27.444 | 1.00 | 55.03 | B2 |
| ATOM | 2277 | CD | GLN | 320 | 49.958 | 30.349 | 26.438 | 1.00 | 60.17 | B2 |
| ATOM | 2278 | OE1 | GLN | 320 | 51.116 | 30.465 | 26.834 | 1.00 | 65.26 | B2 |
| ATOM | 2279 | NE2 | GLN | 320 | 49.771 | 30.145 | 25.131 | 1.00 | 59.32 | B2 |
| ATOM | 2280 | HE21 | GLN | 320 | 48.859 | 30.087 | 24.789 | 1.00 | 0.00 | B2 |
| ATOM | 2281 | HE22 | GLN | 320 | 50.582 | 30.083 | 24.590 | 1.00 | 0.00 | B2 |
| ATOM | 2282 | C | GLN | 320 | 47.717 | 33.790 | 28.983 | 1.00 | 49.62 | B2 |
| ATOM | 2283 | O | GLN | 320 | 48.251 | 34.209 | 29.987 | 1.00 | 49.91 | B2 |
| ATOM | 2284 | N | GLN | 321 | 46.998 | 34.538 | 28.150 | 1.00 | 51.76 | B2 |
| ATOM | 2285 | H | GLN | 321 | 46.535 | 34.102 | 27.403 | 1.00 | 0.00 | B2 |
| ATOM | 2286 | CA | GLN | 321 | 46.837 | 35.988 | 28.278 | 1.00 | 52.08 | B2 |
| ATOM | 2287 | CB | GLN | 321 | 46.015 | 36.571 | 27.151 | 1.00 | 49.72 | B2 |
| ATOM | 2288 | CG | GLN | 321 | 45.873 | 38.058 | 27.166 | 1.00 | 51.19 | B2 |
| ATOM | 2289 | CD | GLN | 321 | 47.211 | 38.781 | 27.201 | 1.00 | 53.13 | B2 |
| ATOM | 2290 | OE1 | GLN | 321 | 48.090 | 38.622 | 26.364 | 1.00 | 55.36 | B2 |
| ATOM | 2291 | NE2 | GLN | 321 | 47.468 | 39.618 | 28.177 | 1.00 | 53.21 | B2 |
| ATOM | 2292 | HE21 | GLN | 321 | 46.800 | 39.713 | 28.889 | 1.00 | 0.00 | B2 |
| ATOM | 2293 | HE22 | GLN | 321 | 48.338 | 40.057 | 28.168 | 1.00 | 0.00 | B2 |
| ATOM | 2294 | C | GLN | 321 | 46.112 | 36.315 | 29.562 | 1.00 | 53.30 | B2 |
| ATOM | 2295 | O | GLN | 321 | 46.293 | 37.422 | 30.058 | 1.00 | 54.39 | B2 |
| ATOM | 2296 | N | MET | 322 | 45.269 | 35.441 | 30.117 | 1.00 | 54.50 | B2 |
| ATOM | 2297 | H | MET | 322 | 45.098 | 34.592 | 29.662 | 1.00 | 0.00 | B2 |
| ATOM | 2298 | CA | MET | 322 | 44.619 | 35.748 | 31.375 | 1.00 | 55.42 | B2 |
| ATOM | 2299 | CB | MET | 322 | 43.595 | 34.690 | 31.713 | 1.00 | 52.93 | B2 |
| ATOM | 2300 | CG | MET | 322 | 42.527 | 34.865 | 30.658 | 1.00 | 51.76 | B2 |
| ATOM | 2301 | SD | MET | 322 | 40.861 | 34.428 | 31.189 | 1.00 | 54.19 | B2 |
| ATOM | 2302 | CE | MET | 322 | 40.293 | 33.192 | 30.069 | 1.00 | 52.53 | B2 |
| ATOM | 2303 | C | MET | 322 | 45.700 | 35.811 | 32.432 | 1.00 | 57.69 | B2 |
| ATOM | 2304 | O | MET | 322 | 45.781 | 36.739 | 33.248 | 1.00 | 57.85 | B2 |
| ATOM | 2305 | N | GLU | 323 | 46.652 | 34.900 | 32.319 | 1.00 | 60.28 | B2 |
| ATOM | 2306 | H | GLU | 323 | 46.637 | 34.296 | 31.544 | 1.00 | 0.00 | B2 |
| ATOM | 2307 | CA | GLU | 323 | 47.741 | 34.875 | 33.273 | 1.00 | 62.99 | B2 |
| ATOM | 2308 | CB | GLU | 323 | 48.558 | 33.635 | 32.957 | 1.00 | 65.81 | B2 |
| ATOM | 2309 | CG | GLU | 323 | 47.640 | 32.423 | 32.918 | 1.00 | 68.36 | B2 |
| ATOM | 2310 | CD | GLU | 323 | 48.303 | 31.125 | 33.310 | 1.00 | 71.21 | B2 |
| ATOM | 2311 | OE1 | GLU | 323 | 47.651 | 30.364 | 34.044 | 1.00 | 71.19 | B2 |
| ATOM | 2312 | OE2 | GLU | 323 | 49.451 | 30.900 | 32.884 | 1.00 | 72.43 | B2 |
| ATOM | 2313 | C | GLU | 323 | 48.648 | 36.124 | 33.418 | 1.00 | 63.96 | B2 |
| ATOM | 2314 | OT1 | GLU | 323 | 48.782 | 36.492 | 34.584 | 1.00 | 64.11 | B2 |
| ATOM | 2315 | OT2 | GLU | 323 | 49.169 | 36.725 | 32.449 | 1.00 | 62.96 | B2 |
| ATOM | 2316 | CB | MET | 338 | 27.559 | 17.690 | 25.056 | 1.00 | 62.56 | B3 |
| ATOM | 2317 | CG | MET | 338 | 28.087 | 18.862 | 24.222 | 1.00 | 63.85 | B3 |
| ATOM | 2318 | SD | MET | 338 | 28.738 | 20.224 | 25.219 | 1.00 | 66.95 | B3 |
| ATOM | 2319 | CE | MET | 338 | 27.328 | 21.252 | 25.515 | 1.00 | 65.50 | B3 |
| ATOM | 2320 | C | MET | 338 | 24.988 | 17.301 | 25.122 | 1.00 | 57.55 | B3 |
| ATOM | 2321 | O | MET | 338 | 24.417 | 16.347 | 25.667 | 1.00 | 56.47 | B3 |

FIG. 5BB

| | | | | | | | | | | |
|---|---|---|---|---|---|---|---|---|---|---|
| ATOM | 2322 | HT1 MET | 338 | 26.255 | 16.010 | 26.594 | 1.00 | 0.00 | B3 |
| ATOM | 2323 | HT2 MET | 338 | 25.375 | 17.061 | 27.500 | 1.00 | 0.00 | B3 |
| ATOM | 2324 | N MET | 338 | 26.286 | 16.971 | 27.009 | 1.00 | 61.55 | B3 |
| ATOM | 2325 | HT3 MET | 338 | 27.108 | 17.107 | 27.620 | 1.00 | 0.00 | B3 |
| ATOM | 2326 | CA MET | 338 | 26.226 | 17.853 | 25.851 | 1.00 | 60.35 | B3 |
| ATOM | 2327 | N PRO | 339 | 24.493 | 17.830 | 23.998 | 1.00 | 55.58 | B3 |
| ATOM | 2328 | CD PRO | 339 | 24.914 | 19.075 | 23.375 | 1.00 | 54.39 | B3 |
| ATOM | 2329 | CA PRO | 339 | 23.453 | 17.226 | 23.164 | 1.00 | 54.62 | B3 |
| ATOM | 2330 | CB PRO | 339 | 23.463 | 18.098 | 21.903 | 1.00 | 53.52 | B3 |
| ATOM | 2331 | CG PRO | 339 | 24.845 | 18.711 | 21.909 | 1.00 | 53.04 | B3 |
| ATOM | 2332 | C PRO | 339 | 23.666 | 15.748 | 22.881 | 1.00 | 53.61 | B3 |
| ATOM | 2333 | O PRO | 339 | 24.730 | 15.222 | 23.169 | 1.00 | 53.35 | B3 |
| ATOM | 2334 | N ALA | 340 | 22.704 | 15.045 | 22.333 | 1.00 | 54.32 | B3 |
| ATOM | 2335 | H ALA | 340 | 21.844 | 15.460 | 22.111 | 1.00 | 0.00 | B3 |
| ATOM | 2336 | CA ALA | 340 | 22.909 | 13.651 | 21.968 | 1.00 | 56.04 | B3 |
| ATOM | 2337 | CB ALA | 340 | 21.867 | 12.713 | 22.625 | 1.00 | 57.60 | B3 |
| ATOM | 2338 | C ALA | 340 | 22.617 | 13.713 | 20.495 | 1.00 | 55.61 | B3 |
| ATOM | 2339 | O ALA | 340 | 21.426 | 13.783 | 20.196 | 1.00 | 58.64 | B3 |
| ATOM | 2340 | N PHE | 341 | 23.516 | 13.734 | 19.514 | 1.00 | 53.34 | B3 |
| ATOM | 2341 | H PHE | 341 | 24.472 | 13.607 | 19.685 | 1.00 | 0.00 | B3 |
| ATOM | 2342 | CA PHE | 341 | 23.016 | 13.900 | 18.158 | 1.00 | 49.92 | B3 |
| ATOM | 2343 | CB PHE | 341 | 24.050 | 14.541 | 17.244 | 1.00 | 48.16 | B3 |
| ATOM | 2344 | CG PHE | 341 | 24.382 | 15.940 | 17.658 | 1.00 | 45.00 | B3 |
| ATOM | 2345 | CD1 PHE | 341 | 23.510 | 16.923 | 17.359 | 1.00 | 43.44 | B3 |
| ATOM | 2346 | CD2 PHE | 341 | 25.527 | 16.175 | 18.388 | 1.00 | 47.03 | B3 |
| ATOM | 2347 | CE1 PHE | 341 | 23.812 | 18.172 | 17.831 | 1.00 | 49.15 | B3 |
| ATOM | 2348 | CE2 PHE | 341 | 25.827 | 17.426 | 18.862 | 1.00 | 47.86 | B3 |
| ATOM | 2349 | CZ PHE | 341 | 24.952 | 18.437 | 18.580 | 1.00 | 48.36 | B3 |
| ATOM | 2350 | C PHE | 341 | 22.684 | 12.510 | 17.672 | 1.00 | 49.56 | B3 |
| ATOM | 2351 | O PHE | 341 | 23.309 | 11.938 | 16.781 | 1.00 | 51.46 | B3 |
| ATOM | 2352 | N ALA | 342 | 21.625 | 11.985 | 18.245 | 1.00 | 47.40 | B3 |
| ATOM | 2353 | H ALA | 342 | 21.026 | 12.585 | 18.741 | 1.00 | 0.00 | B3 |
| ATOM | 2354 | CA ALA | 342 | 21.167 | 10.650 | 17.997 | 1.00 | 46.11 | B3 |
| ATOM | 2355 | CB ALA | 342 | 19.874 | 10.531 | 18.804 | 1.00 | 47.10 | B3 |
| ATOM | 2356 | C ALA | 342 | 20.962 | 10.149 | 16.556 | 1.00 | 44.37 | B3 |
| ATOM | 2357 | O ALA | 342 | 20.138 | 9.247 | 16.418 | 1.00 | 45.65 | B3 |
| ATOM | 2358 | N SER | 343 | 21.537 | 10.573 | 15.423 | 1.00 | 41.37 | B3 |
| ATOM | 2359 | H SER | 343 | 22.191 | 11.301 | 15.428 | 1.00 | 0.00 | B3 |
| ATOM | 2360 | CA SER | 343 | 21.274 | 9.923 | 14.145 | 1.00 | 38.80 | B3 |
| ATOM | 2361 | CB SER | 343 | 19.842 | 10.138 | 13.656 | 1.00 | 38.79 | B3 |
| ATOM | 2362 | OG SER | 343 | 19.205 | 11.300 | 14.182 | 1.00 | 37.75 | B3 |
| ATOM | 2363 | HG SER | 343 | 18.963 | 11.059 | 15.092 | 1.00 | 0.00 | B3 |
| ATOM | 2364 | C SER | 343 | 22.172 | 10.467 | 13.088 | 1.00 | 38.22 | B3 |
| ATOM | 2365 | O SER | 343 | 22.810 | 11.471 | 13.382 | 1.00 | 38.30 | B3 |
| ATOM | 2366 | N ALA | 344 | 22.206 | 9.845 | 11.888 | 1.00 | 36.73 | B3 |
| ATOM | 2367 | H ALA | 344 | 21.762 | 8.978 | 11.805 | 1.00 | 0.00 | B3 |
| ATOM | 2368 | CA ALA | 344 | 22.914 | 10.384 | 10.715 | 1.00 | 38.09 | B3 |
| ATOM | 2369 | CB ALA | 344 | 22.583 | 9.640 | 9.422 | 1.00 | 36.78 | B3 |
| ATOM | 2370 | C ALA | 344 | 22.472 | 11.842 | 10.496 | 1.00 | 37.72 | B3 |
| ATOM | 2371 | O ALA | 344 | 23.271 | 12.765 | 10.676 | 1.00 | 38.42 | B3 |
| ATOM | 2372 | N PHE | 345 | 21.194 | 12.042 | 10.163 | 1.00 | 36.10 | B3 |
| ATOM | 2373 | H PHE | 345 | 20.668 | 11.298 | 9.811 | 1.00 | 0.00 | B3 |
| ATOM | 2374 | CA PHE | 345 | 20.564 | 13.338 | 10.195 | 1.00 | 34.69 | B3 |
| ATOM | 2375 | CB PHE | 345 | 19.040 | 13.254 | 10.128 | 1.00 | 33.24 | B3 |
| ATOM | 2376 | CG PHE | 345 | 18.462 | 14.656 | 9.918 | 1.00 | 31.72 | B3 |
| ATOM | 2377 | CD1 PHE | 345 | 17.715 | 15.223 | 10.905 | 1.00 | 26.64 | B3 |
| ATOM | 2378 | CD2 PHE | 345 | 18.767 | 15.343 | 8.745 | 1.00 | 29.99 | B3 |
| ATOM | 2379 | CE1 PHE | 345 | 17.284 | 16.503 | 10.682 | 1.00 | 33.56 | B3 |
| ATOM | 2380 | CE2 PHE | 345 | 18.333 | 16.619 | 8.537 | 1.00 | 30.81 | B3 |
| ATOM | 2381 | CZ PHE | 345 | 17.581 | 17.201 | 9.520 | 1.00 | 31.44 | B3 |
| ATOM | 2382 | C PHE | 345 | 20.888 | 14.145 | 11.458 | 1.00 | 35.02 | B3 |
| ATOM | 2383 | O PHE | 345 | 21.246 | 15.319 | 11.292 | 1.00 | 37.81 | B3 |
| ATOM | 2384 | N GLN | 346 | 20.814 | 13.688 | 12.691 | 1.00 | 32.53 | B3 |
| ATOM | 2385 | H GLN | 346 | 20.516 | 12.778 | 12.894 | 1.00 | 0.00 | B3 |
| ATOM | 2386 | CA GLN | 346 | 21.156 | 14.586 | 13.758 | 1.00 | 33.46 | B3 |
| ATOM | 2387 | CB GLN | 346 | 20.899 | 13.985 | 15.061 | 1.00 | 33.80 | B3 |
| ATOM | 2388 | CG GLN | 346 | 19.459 | 14.284 | 15.174 | 1.00 | 35.68 | B3 |
| ATOM | 2389 | CD GLN | 346 | 18.788 | 13.658 | 16.344 | 1.00 | 38.48 | B3 |
| ATOM | 2390 | OE1 GLN | 346 | 19.358 | 13.328 | 17.374 | 1.00 | 41.78 | B3 |
| ATOM | 2391 | NE2 GLN | 346 | 17.508 | 13.463 | 16.167 | 1.00 | 41.08 | B3 |
| ATOM | 2392 | HE21 GLN | 346 | 17.088 | 13.724 | 15.323 | 1.00 | 0.00 | B3 |
| ATOM | 2393 | HE22 GLN | 346 | 17.026 | 13.063 | 16.919 | 1.00 | 0.00 | B3 |
| ATOM | 2394 | C GLN | 346 | 22.564 | 15.051 | 13.773 | 1.00 | 35.73 | B3 |
| ATOM | 2395 | O GLN | 346 | 22.766 | 16.231 | 14.051 | 1.00 | 38.18 | B3 |
| ATOM | 2396 | N ARG | 347 | 23.507 | 14.190 | 13.431 | 1.00 | 35.57 | B3 |
| ATOM | 2397 | H ARG | 347 | 23.248 | 13.289 | 13.157 | 1.00 | 0.00 | B3 |
| ATOM | 2398 | CA ARG | 347 | 24.907 | 14.538 | 13.396 | 1.00 | 35.95 | B3 |
| ATOM | 2399 | CB ARG | 347 | 25.760 | 13.236 | 13.222 | 1.00 | 36.20 | B3 |
| ATOM | 2400 | CG ARG | 347 | 26.198 | 12.549 | 14.540 | 1.00 | 37.41 | B3 |
| ATOM | 2401 | CD ARG | 347 | 26.986 | 11.246 | 14.373 | 1.00 | 39.70 | B3 |
| ATOM | 2402 | NE ARG | 347 | 26.072 | 10.167 | 14.028 | 1.00 | 47.18 | B3 |
| ATOM | 2403 | HE ARG | 347 | 25.416 | 9.893 | 14.701 | 1.00 | 0.00 | B3 |
| ATOM | 2404 | CZ ARG | 347 | 26.071 | 9.516 | 12.846 | 1.00 | 48.49 | B3 |
| ATOM | 2405 | NH1 ARG | 347 | 26.938 | 9.802 | 11.882 | 1.00 | 50.22 | B3 |
| ATOM | 2406 | HH11 ARG | 347 | 27.602 | 10.528 | 12.031 | 1.00 | 0.00 | B3 |
| ATOM | 2407 | HH12 ARG | 347 | 26.905 | 9.313 | 11.011 | 1.00 | 0.00 | B3 |

FIG. 5CC

| ATOM | 2408 | NH2 | ARG | 347 | 25.130 | 8.608 | 12.574 | 1.00 | 48.46 | B3 |
|---|---|---|---|---|---|---|---|---|---|---|
| ATOM | 2409 | HH21 | ARG | 347 | 24.423 | 8.408 | 13.252 | 1.00 | 0.00 | B3 |
| ATOM | 2410 | HH22 | ARG | 347 | 25.126 | 8.131 | 11.697 | 1.00 | 0.00 | B3 |
| ATOM | 2411 | C | ARG | 347 | 25.183 | 15.544 | 12.267 | 1.00 | 35.54 | B3 |
| ATOM | 2412 | O | ARG | 347 | 25.877 | 16.549 | 12.445 | 1.00 | 36.73 | B3 |
| ATOM | 2413 | N | ARG | 348 | 24.611 | 15.353 | 11.096 | 1.00 | 34.74 | B3 |
| ATOM | 2414 | H | ARG | 348 | 24.043 | 14.559 | 11.005 | 1.00 | 0.00 | B3 |
| ATOM | 2415 | CA | ARG | 348 | 24.802 | 16.225 | 9.954 | 1.00 | 35.24 | B3 |
| ATOM | 2416 | CB | ARG | 348 | 24.091 | 15.623 | 8.751 | 1.00 | 36.76 | B3 |
| ATOM | 2417 | CG | ARG | 348 | 24.778 | 14.303 | 8.450 | 1.00 | 44.22 | B3 |
| ATOM | 2418 | CD | ARG | 348 | 24.014 | 13.379 | 7.529 | 1.00 | 49.23 | B3 |
| ATOM | 2419 | NE | ARG | 348 | 24.705 | 12.090 | 7.457 | 1.00 | 54.27 | B3 |
| ATOM | 2420 | HE | ARG | 348 | 25.300 | 11.836 | 8.193 | 1.00 | 0.00 | B3 |
| ATOM | 2421 | CZ | ARG | 348 | 24.557 | 11.226 | 6.430 | 1.00 | 53.75 | B3 |
| ATOM | 2422 | NH1 | ARG | 348 | 23.758 | 11.479 | 5.381 | 1.00 | 51.85 | B3 |
| ATOM | 2423 | HH11 | ARG | 348 | 23.234 | 12.329 | 5.339 | 1.00 | 0.00 | B3 |
| ATOM | 2424 | HH12 | ARG | 348 | 23.680 | 10.807 | 4.645 | 1.00 | 0.00 | B3 |
| ATOM | 2425 | NH2 | ARG | 348 | 25.252 | 10.083 | 6.462 | 1.00 | 54.51 | B3 |
| ATOM | 2426 | HH21 | ARG | 348 | 25.169 | 9.424 | 5.714 | 1.00 | 0.00 | B3 |
| ATOM | 2427 | HH22 | ARG | 348 | 25.860 | 9.894 | 7.232 | 1.00 | 0.00 | B3 |
| ATOM | 2428 | C | ARG | 348 | 24.283 | 17.629 | 10.237 | 1.00 | 34.80 | B3 |
| ATOM | 2429 | O | ARG | 348 | 25.078 | 18.564 | 10.219 | 1.00 | 35.16 | B3 |
| ATOM | 2430 | N | ALA | 349 | 23.008 | 17.795 | 10.607 | 1.00 | 33.85 | B3 |
| ATOM | 2431 | H | ALA | 349 | 22.470 | 16.984 | 10.755 | 1.00 | 0.00 | B3 |
| ATOM | 2432 | CA | ALA | 349 | 22.352 | 19.083 | 10.853 | 1.00 | 32.96 | B3 |
| ATOM | 2433 | CB | ALA | 349 | 20.809 | 18.894 | 11.070 | 1.00 | 33.36 | B3 |
| ATOM | 2434 | C | ALA | 349 | 22.945 | 19.746 | 12.083 | 1.00 | 31.84 | B3 |
| ATOM | 2435 | O | ALA | 349 | 22.981 | 20.969 | 12.210 | 1.00 | 30.69 | B3 |
| ATOM | 2436 | N | GLY | 350 | 23.444 | 18.954 | 13.018 | 1.00 | 31.30 | B3 |
| ATOM | 2437 | H | GLY | 350 | 23.308 | 17.984 | 12.976 | 1.00 | 0.00 | B3 |
| ATOM | 2438 | CA | GLY | 350 | 24.117 | 19.505 | 14.181 | 1.00 | 31.08 | B3 |
| ATOM | 2439 | C | GLY | 350 | 25.462 | 20.025 | 13.753 | 1.00 | 30.79 | B3 |
| ATOM | 2440 | O | GLY | 350 | 25.974 | 21.010 | 14.280 | 1.00 | 31.38 | B3 |
| ATOM | 2441 | N | GLY | 351 | 25.991 | 19.374 | 12.731 | 1.00 | 30.03 | B3 |
| ATOM | 2442 | H | GLY | 351 | 25.546 | 18.582 | 12.367 | 1.00 | 0.00 | B3 |
| ATOM | 2443 | CA | GLY | 351 | 27.263 | 19.735 | 12.184 | 1.00 | 29.95 | B3 |
| ATOM | 2444 | C | GLY | 351 | 27.182 | 21.097 | 11.534 | 1.00 | 29.25 | B3 |
| ATOM | 2445 | O | GLY | 351 | 27.937 | 21.974 | 11.919 | 1.00 | 28.73 | B3 |
| ATOM | 2446 | N | VAL | 352 | 26.336 | 21.285 | 10.522 | 1.00 | 28.92 | B3 |
| ATOM | 2447 | H | VAL | 352 | 25.859 | 20.484 | 10.214 | 1.00 | 0.00 | B3 |
| ATOM | 2448 | CA | VAL | 352 | 26.079 | 22.567 | 9.881 | 1.00 | 28.59 | B3 |
| ATOM | 2449 | CB | VAL | 352 | 24.845 | 22.452 | 9.004 | 1.00 | 28.96 | B3 |
| ATOM | 2450 | CG1 | VAL | 352 | 24.627 | 23.785 | 8.346 | 1.00 | 30.86 | B3 |
| ATOM | 2451 | CG2 | VAL | 352 | 25.021 | 21.475 | 7.875 | 1.00 | 26.94 | B3 |
| ATOM | 2452 | C | VAL | 352 | 25.849 | 23.709 | 10.890 | 1.00 | 29.29 | B3 |
| ATOM | 2453 | O | VAL | 352 | 26.520 | 24.747 | 10.853 | 1.00 | 31.02 | B3 |
| ATOM | 2454 | N | LEU | 353 | 24.923 | 23.543 | 11.819 | 1.00 | 27.52 | B3 |
| ATOM | 2455 | H | LEU | 353 | 24.404 | 22.709 | 11.838 | 1.00 | 0.00 | B3 |
| ATOM | 2456 | CA | LEU | 353 | 24.635 | 24.548 | 12.817 | 1.00 | 26.18 | B3 |
| ATOM | 2457 | CB | LEU | 353 | 23.434 | 24.113 | 13.636 | 1.00 | 27.87 | B3 |
| ATOM | 2458 | CG | LEU | 353 | 22.098 | 24.034 | 12.931 | 1.00 | 26.54 | B3 |
| ATOM | 2459 | CD1 | LEU | 353 | 21.064 | 23.617 | 13.924 | 1.00 | 25.49 | B3 |
| ATOM | 2460 | CD2 | LEU | 353 | 21.750 | 25.372 | 12.320 | 1.00 | 28.23 | B3 |
| ATOM | 2461 | C | LEU | 353 | 25.742 | 24.905 | 13.772 | 1.00 | 27.17 | B3 |
| ATOM | 2462 | O | LEU | 353 | 25.838 | 26.093 | 14.088 | 1.00 | 28.00 | B3 |
| ATOM | 2463 | N | VAL | 354 | 26.539 | 23.906 | 14.318 | 1.00 | 27.20 | B3 |
| ATOM | 2464 | H | VAL | 354 | 26.321 | 23.006 | 14.139 | 1.00 | 0.00 | B3 |
| ATOM | 2465 | CA | VAL | 354 | 27.712 | 24.212 | 15.157 | 1.00 | 24.62 | B3 |
| ATOM | 2466 | CB | VAL | 354 | 28.579 | 23.745 | 13.924 | 1.00 | 22.01 | B3 |
| ATOM | 2467 | CG1 | VAL | 354 | 28.236 | 22.910 | 15.745 | 1.00 | 19.82 | B3 |
| ATOM | 2468 | CG2 | VAL | 354 | 29.568 | 23.089 | 16.406 | 1.00 | 23.96 | B3 |
| ATOM | 2469 | C | VAL | 354 | 27.276 | 22.467 | 16.802 | 1.00 | 25.46 | B3 |
| ATOM | 2470 | O | VAL | 354 | 28.812 | 24.893 | 14.332 | 1.00 | 26.23 | B3 |
| ATOM | 2471 | N | ALA | 355 | 29.439 | 25.832 | 14.798 | 1.00 | 26.12 | B3 |
| ATOM | 2472 | H | ALA | 355 | 29.059 | 24.530 | 13.089 | 1.00 | 0.00 | B3 |
| ATOM | 2473 | CA | ALA | 355 | 28.579 | 23.745 | 12.744 | 1.00 | 26.54 | B3 |
| ATOM | 2474 | CB | ALA | 355 | 30.025 | 25.180 | 12.235 | 1.00 | 22.08 | B3 |
| ATOM | 2475 | C | ALA | 355 | 30.034 | 24.591 | 10.869 | 1.00 | 28.51 | B3 |
| ATOM | 2476 | O | ALA | 355 | 29.533 | 26.601 | 12.096 | 1.00 | 31.93 | B3 |
| ATOM | 2477 | N | SER | 356 | 30.315 | 27.498 | 12.344 | 1.00 | 30.30 | B3 |
| ATOM | 2478 | H | SER | 356 | 28.271 | 26.884 | 11.802 | 1.00 | 0.00 | B3 |
| ATOM | 2479 | CA | SER | 356 | 27.654 | 26.134 | 11.665 | 1.00 | 31.10 | B3 |
| ATOM | 2480 | CB | SER | 356 | 27.778 | 28.249 | 11.625 | 1.00 | 35.23 | B3 |
| ATOM | 2481 | OG | SER | 356 | 26.401 | 28.147 | 11.016 | 1.00 | 43.82 | B3 |
| ATOM | 2482 | HG | SER | 356 | 25.679 | 29.380 | 10.905 | 1.00 | 0.00 | B3 |
| ATOM | 2483 | C | SER | 356 | 26.250 | 30.004 | 10.429 | 1.00 | 29.75 | B3 |
| ATOM | 2484 | O | SER | 356 | 27.763 | 29.095 | 12.901 | 1.00 | 28.35 | B3 |
| ATOM | 2485 | N | HIS | 357 | 28.115 | 30.289 | 12.898 | 1.00 | 27.82 | B3 |
| ATOM | 2486 | H | HIS | 357 | 27.465 | 28.464 | 14.025 | 1.00 | 0.00 | B3 |
| ATOM | 2487 | CA | HIS | 357 | 27.301 | 27.498 | 14.019 | 1.00 | 26.58 | B3 |
| ATOM | 2488 | CB | HIS | 357 | 27.434 | 29.194 | 15.259 | 1.00 | 25.77 | B3 |
| ATOM | 2489 | CG | HIS | 357 | 26.735 | 28.365 | 16.305 | 1.00 | 27.67 | B3 |
| ATOM | 2490 | CD2 | HIS | 357 | 25.219 | 28.360 | 16.063 | 1.00 | 28.94 | B3 |
| ATOM | 2491 | ND1 | HIS | 357 | 24.563 | 28.767 | 14.915 | 1.00 | 28.43 | B3 |
| ATOM | 2492 | HD1 | HIS | 357 | 24.277 | 27.963 | 16.915 | 1.00 | 0.00 | B3 |
| ATOM | 2493 | CE1 | HIS | 357 | 24.456 | 27.622 | 17.828 | 1.00 | 28.64 | B3 |
| ATOM |  |  |  |  | 23.112 | 28.103 | 16.337 |  |  | B3 |

FIG. 5DD

| ATOM | 2494 | NE2 | HIS | 357 | 23.298 | 28.589 | 15.130 | 1.00 | 29.48 | B3 |
|---|---|---|---|---|---|---|---|---|---|---|
| ATOM | 2495 | HE2 | HIS | 357 | 22.576 | 28.801 | 14.495 | 1.00 | 0.00 | B3 |
| ATOM | 2496 | C | HIS | 357 | 28.852 | 29.506 | 15.645 | 1.00 | 27.93 | B3 |
| ATOM | 2497 | O | HIS | 357 | 29.119 | 30.606 | 16.115 | 1.00 | 29.15 | B3 |
| ATOM | 2498 | N | LEU | 358 | 29.830 | 28.637 | 15.383 | 1.00 | 28.33 | B3 |
| ATOM | 2499 | H | LEU | 358 | 29.624 | 27.761 | 14.997 | 1.00 | 0.00 | B3 |
| ATOM | 2500 | CA | LEU | 358 | 31.211 | 28.940 | 15.721 | 1.00 | 26.39 | B3 |
| ATOM | 2501 | CB | LEU | 358 | 32.030 | 27.702 | 15.547 | 1.00 | 21.42 | B3 |
| ATOM | 2502 | CG | LEU | 358 | 33.457 | 27.878 | 15.734 | 1.00 | 20.42 | B3 |
| ATOM | 2503 | CD1 | LEU | 358 | 33.805 | 28.078 | 17.165 | 1.00 | 16.79 | B3 |
| ATOM | 2504 | CD2 | LEU | 358 | 34.075 | 26.714 | 15.072 | 1.00 | 22.89 | B3 |
| ATOM | 2505 | C | LEU | 358 | 31.721 | 30.067 | 14.822 | 1.00 | 26.45 | B3 |
| ATOM | 2506 | O | LEU | 358 | 32.372 | 30.939 | 15.378 | 1.00 | 27.12 | B3 |
| ATOM | 2507 | N | GLN | 359 | 31.460 | 30.130 | 13.518 | 1.00 | 26.41 | B3 |
| ATOM | 2508 | H | GLN | 359 | 31.048 | 29.337 | 13.114 | 1.00 | 0.00 | B3 |
| ATOM | 2509 | CA | GLN | 359 | 31.863 | 31.254 | 12.671 | 1.00 | 29.10 | B3 |
| ATOM | 2510 | CB | GLN | 359 | 31.204 | 31.209 | 11.292 | 1.00 | 30.49 | B3 |
| ATOM | 2511 | CG | GLN | 359 | 31.395 | 29.952 | 10.455 | 1.00 | 38.94 | B3 |
| ATOM | 2512 | CD | GLN | 359 | 32.842 | 29.636 | 10.091 | 1.00 | 42.09 | B3 |
| ATOM | 2513 | OE1 | GLN | 359 | 33.774 | 29.979 | 10.821 | 1.00 | 46.15 | B3 |
| ATOM | 2514 | NE2 | GLN | 359 | 33.103 | 28.987 | 8.967 | 1.00 | 41.34 | B3 |
| ATOM | 2515 | HE21 | GLN | 359 | 32.341 | 28.706 | 8.412 | 1.00 | 0.00 | B3 |
| ATOM | 2516 | HE22 | GLN | 359 | 34.039 | 28.838 | 8.740 | 1.00 | 0.00 | B3 |
| ATOM | 2517 | C | GLN | 359 | 31.512 | 32.621 | 13.254 | 1.00 | 29.39 | B3 |
| ATOM | 2518 | O | GLN | 359 | 32.427 | 33.427 | 13.484 | 1.00 | 30.06 | B3 |
| ATOM | 2519 | N | SER | 360 | 30.201 | 32.810 | 13.528 | 1.00 | 28.66 | B3 |
| ATOM | 2520 | H | SER | 360 | 29.595 | 32.061 | 13.343 | 1.00 | 0.00 | B3 |
| ATOM | 2521 | CA | SER | 360 | 29.570 | 34.003 | 14.071 | 1.00 | 27.31 | B3 |
| ATOM | 2522 | CB | SER | 360 | 28.121 | 33.761 | 14.336 | 1.00 | 26.70 | B3 |
| ATOM | 2523 | OG | SER | 360 | 27.493 | 33.539 | 13.078 | 1.00 | 29.72 | B3 |
| ATOM | 2524 | HG | SER | 360 | 26.637 | 33.112 | 13.288 | 1.00 | 0.00 | B3 |
| ATOM | 2525 | C | SER | 360 | 30.202 | 34.387 | 15.353 | 1.00 | 27.15 | B3 |
| ATOM | 2526 | O | SER | 360 | 30.575 | 35.550 | 15.498 | 1.00 | 26.93 | B3 |
| ATOM | 2527 | N | PHE | 361 | 30.383 | 33.403 | 16.246 | 1.00 | 25.38 | B3 |
| ATOM | 2528 | H | PHE | 361 | 30.055 | 32.499 | 16.040 | 1.00 | 0.00 | B3 |
| ATOM | 2529 | CA | PHE | 361 | 31.066 | 33.626 | 17.517 | 1.00 | 25.20 | B3 |
| ATOM | 2530 | CB | PHE | 361 | 31.092 | 32.335 | 18.302 | 1.00 | 23.30 | B3 |
| ATOM | 2531 | CG | PHE | 361 | 31.796 | 32.394 | 19.655 | 1.00 | 23.63 | B3 |
| ATOM | 2532 | CD1 | PHE | 361 | 31.127 | 32.854 | 20.777 | 1.00 | 22.44 | B3 |
| ATOM | 2533 | CD2 | PHE | 361 | 33.098 | 31.931 | 19.770 | 1.00 | 23.35 | B3 |
| ATOM | 2534 | CE1 | PHE | 361 | 31.772 | 32.834 | 22.000 | 1.00 | 22.78 | B3 |
| ATOM | 2535 | CE2 | PHE | 361 | 33.719 | 31.921 | 21.002 | 1.00 | 21.26 | B3 |
| ATOM | 2536 | CZ | PHE | 361 | 33.058 | 32.368 | 22.114 | 1.00 | 19.54 | B3 |
| ATOM | 2537 | C | PHE | 361 | 32.505 | 34.143 | 17.385 | 1.00 | 26.56 | B3 |
| ATOM | 2538 | O | PHE | 361 | 32.914 | 34.979 | 18.183 | 1.00 | 26.76 | B3 |
| ATOM | 2539 | N | LEU | 362 | 33.309 | 33.645 | 16.441 | 1.00 | 28.17 | B3 |
| ATOM | 2540 | H | LEU | 362 | 32.962 | 32.921 | 15.874 | 1.00 | 0.00 | B3 |
| ATOM | 2541 | CA | LEU | 362 | 34.679 | 34.089 | 16.222 | 1.00 | 28.89 | B3 |
| ATOM | 2542 | CB | LEU | 362 | 35.452 | 33.125 | 15.338 | 1.00 | 28.18 | B3 |
| ATOM | 2543 | CG | LEU | 362 | 35.603 | 31.656 | 15.781 | 1.00 | 29.61 | B3 |
| ATOM | 2544 | CD1 | LEU | 362 | 36.306 | 30.996 | 14.633 | 1.00 | 31.63 | B3 |
| ATOM | 2545 | CD2 | LEU | 362 | 36.374 | 31.433 | 17.055 | 1.00 | 26.38 | B3 |
| ATOM | 2546 | C | LEU | 362 | 34.692 | 35.449 | 15.536 | 1.00 | 29.18 | B3 |
| ATOM | 2547 | O | LEU | 362 | 35.649 | 36.202 | 15.748 | 1.00 | 27.43 | B3 |
| ATOM | 2548 | N | GLU | 363 | 33.664 | 35.763 | 14.710 | 1.00 | 29.54 | B3 |
| ATOM | 2549 | H | GLU | 363 | 33.009 | 35.066 | 14.495 | 1.00 | 0.00 | B3 |
| ATOM | 2550 | CA | GLU | 363 | 33.496 | 37.090 | 14.145 | 1.00 | 30.30 | B3 |
| ATOM | 2551 | CB | GLU | 363 | 32.357 | 37.147 | 13.228 | 1.00 | 30.90 | B3 |
| ATOM | 2552 | CG | GLU | 363 | 32.763 | 36.735 | 11.849 | 1.00 | 38.69 | B3 |
| ATOM | 2553 | CD | GLU | 363 | 33.642 | 37.662 | 11.013 | 1.00 | 42.62 | B3 |
| ATOM | 2554 | OE1 | GLU | 363 | 33.896 | 37.282 | 9.860 | 1.00 | 46.58 | B3 |
| ATOM | 2555 | OE2 | GLU | 363 | 34.051 | 38.734 | 11.488 | 1.00 | 46.47 | B3 |
| ATOM | 2556 | C | GLU | 363 | 33.229 | 38.098 | 15.244 | 1.00 | 30.26 | B3 |
| ATOM | 2557 | O | GLU | 363 | 33.837 | 39.167 | 15.239 | 1.00 | 30.04 | B3 |
| ATOM | 2558 | N | VAL | 364 | 32.397 | 37.726 | 16.217 | 1.00 | 0.00 | B3 |
| ATOM | 2559 | H | VAL | 364 | 31.888 | 36.898 | 16.100 | 1.00 | 31.90 | B3 |
| ATOM | 2560 | CA | VAL | 364 | 32.178 | 38.522 | 17.400 | 1.00 | 31.41 | B3 |
| ATOM | 2561 | CB | VAL | 364 | 31.014 | 38.021 | 18.269 | 1.00 | 30.73 | B3 |
| ATOM | 2562 | CG1 | VAL | 364 | 30.860 | 38.811 | 19.562 | 1.00 | 29.96 | B3 |
| ATOM | 2563 | CG2 | VAL | 364 | 29.750 | 38.200 | 17.497 | 1.00 | 35.89 | B3 |
| ATOM | 2564 | C | VAL | 364 | 33.402 | 38.493 | 18.275 | 1.00 | 37.54 | B3 |
| ATOM | 2565 | O | VAL | 364 | 33.683 | 39.535 | 18.855 | 1.00 | 38.25 | B3 |
| ATOM | 2566 | N | SER | 365 | 34.173 | 37.421 | 18.477 | 1.00 | 0.00 | B3 |
| ATOM | 2567 | H | SER | 365 | 33.971 | 36.577 | 18.030 | 1.00 | 39.61 | B3 |
| ATOM | 2568 | CA | SER | 365 | 35.337 | 37.478 | 19.375 | 1.00 | 43.00 | B3 |
| ATOM | 2569 | CB | SER | 365 | 36.041 | 36.113 | 19.555 | 1.00 | 38.00 | B3 |
| ATOM | 2570 | OG | SER | 365 | 35.201 | 34.953 | 19.575 | 1.00 | 46.29 | B3 |
| ATOM | 2571 | HG | SER | 365 | 34.270 | 35.189 | 19.644 | 1.00 | 0.00 | B3 |
| ATOM | 2572 | C | SER | 365 | 36.398 | 38.418 | 18.840 | 1.00 | 38.21 | B3 |
| ATOM | 2573 | O | SER | 365 | 37.103 | 38.989 | 19.662 | 1.00 | 36.91 | B3 |
| ATOM | 2574 | N | TYR | 366 | 36.575 | 38.540 | 17.514 | 1.00 | 38.00 | B3 |
| ATOM | 2575 | H | TYR | 366 | 36.079 | 37.945 | 16.910 | 1.00 | 0.00 | B3 |
| ATOM | 2576 | CA | TYR | 366 | 37.568 | 39.463 | 16.969 | 1.00 | 39.85 | B3 |
| ATOM | 2577 | CB | TYR | 366 | 37.776 | 39.330 | 15.436 | 1.00 | 38.53 | B3 |
| ATOM | 2578 | CG | TYR | 366 | 38.662 | 40.447 | 14.879 | 1.00 | 38.21 | B3 |
| ATOM | 2579 | CD1 | TYR | 366 | 38.104 | 41.464 | 14.129 | 1.00 | 37.18 | B3 |

FIG. 5EE

| | | | | | | | | | | |
|---|---|---|---|---|---|---|---|---|---|---|
| ATOM | 2580 | CE1 | TYR | 366 | 38.918 | 42.495 | 13.678 | 1.00 | 41.77 | B3 |
| ATOM | 2581 | CD2 | TYR | 366 | 40.021 | 40.443 | 15.182 | 1.00 | 40.21 | B3 |
| ATOM | 2582 | CE2 | TYR | 366 | 40.849 | 41.466 | 14.739 | 1.00 | 40.76 | B3 |
| ATOM | 2583 | CZ | TYR | 366 | 40.297 | 42.504 | 13.976 | 1.00 | 42.82 | B3 |
| ATOM | 2584 | OH | TYR | 366 | 41.151 | 43.522 | 13.493 | 1.00 | 41.30 | B3 |
| ATOM | 2585 | HH | TYR | 366 | 40.743 | 43.977 | 12.755 | 1.00 | 0.00 | B3 |
| ATOM | 2586 | C | TYR | 366 | 37.133 | 40.893 | 17.241 | 1.00 | 40.55 | B3 |
| ATOM | 2587 | O | TYR | 366 | 37.917 | 41.647 | 17.798 | 1.00 | 40.92 | B3 |
| ATOM | 2588 | N | ARG | 367 | 35.933 | 41.309 | 16.853 | 1.00 | 41.88 | B3 |
| ATOM | 2589 | H | ARG | 367 | 35.360 | 40.682 | 16.360 | 1.00 | 0.00 | B3 |
| ATOM | 2590 | CA | ARG | 367 | 35.442 | 42.653 | 17.139 | 1.00 | 43.32 | B3 |
| ATOM | 2591 | CB | ARG | 367 | 34.013 | 42.709 | 16.650 | 1.00 | 46.82 | B3 |
| ATOM | 2592 | CG | ARG | 367 | 33.528 | 44.130 | 16.650 | 1.00 | 56.74 | B3 |
| ATOM | 2593 | CD | ARG | 367 | 32.069 | 44.267 | 16.248 | 1.00 | 61.81 | B3 |
| ATOM | 2594 | NE | ARG | 367 | 31.723 | 45.687 | 16.229 | 1.00 | 66.59 | B3 |
| ATOM | 2595 | HE | ARG | 367 | 32.438 | 46.356 | 16.172 | 1.00 | 0.00 | B3 |
| ATOM | 2596 | CZ | ARG | 367 | 30.458 | 46.091 | 16.308 | 1.00 | 69.75 | B3 |
| ATOM | 2597 | NH1 | ARG | 367 | 29.448 | 45.220 | 16.413 | 1.00 | 72.65 | B3 |
| ATOM | 2598 | HH11 | ARG | 367 | 29.631 | 44.236 | 16.410 | 1.00 | 0.00 | B3 |
| ATOM | 2599 | HH12 | ARG | 367 | 28.503 | 45.548 | 16.445 | 1.00 | 0.00 | B3 |
| ATOM | 2600 | NH2 | ARG | 367 | 30.160 | 47.375 | 16.162 | 1.00 | 71.64 | B3 |
| ATOM | 2601 | HH21 | ARG | 367 | 29.204 | 47.665 | 16.222 | 1.00 | 0.00 | B3 |
| ATOM | 2602 | HH22 | ARG | 367 | 30.888 | 48.043 | 16.013 | 1.00 | 0.00 | B3 |
| ATOM | 2603 | C | ARG | 367 | 35.551 | 43.011 | 18.635 | 1.00 | 40.96 | B3 |
| ATOM | 2604 | O | ARG | 367 | 35.994 | 44.090 | 19.012 | 1.00 | 41.10 | B3 |
| ATOM | 2605 | N | VAL | 368 | 35.160 | 42.135 | 19.542 | 1.00 | 39.83 | B3 |
| ATOM | 2606 | H | VAL | 368 | 34.726 | 41.316 | 19.217 | 1.00 | 0.00 | B3 |
| ATOM | 2607 | CA | VAL | 368 | 35.331 | 42.292 | 20.968 | 1.00 | 37.33 | B3 |
| ATOM | 2608 | CB | VAL | 368 | 34.748 | 41.043 | 21.664 | 1.00 | 35.75 | B3 |
| ATOM | 2609 | CG1 | VAL | 368 | 35.087 | 40.867 | 23.140 | 1.00 | 35.10 | B3 |
| ATOM | 2610 | CG2 | VAL | 368 | 33.259 | 41.230 | 21.586 | 1.00 | 33.28 | B3 |
| ATOM | 2611 | C | VAL | 368 | 36.813 | 42.459 | 21.223 | 1.00 | 38.75 | B3 |
| ATOM | 2612 | O | VAL | 368 | 37.144 | 43.498 | 21.772 | 1.00 | 40.11 | B3 |
| ATOM | 2613 | N | LEU | 369 | 37.759 | 41.600 | 20.835 | 1.00 | 39.59 | B3 |
| ATOM | 2614 | H | LEU | 369 | 37.492 | 40.818 | 20.308 | 1.00 | 0.00 | B3 |
| ATOM | 2615 | CA | LEU | 369 | 39.180 | 41.780 | 21.148 | 1.00 | 40.05 | B3 |
| ATOM | 2616 | CB | LEU | 369 | 39.984 | 40.601 | 20.679 | 1.00 | 37.15 | B3 |
| ATOM | 2617 | CG | LEU | 369 | 39.831 | 39.335 | 21.426 | 1.00 | 37.54 | B3 |
| ATOM | 2618 | CD1 | LEU | 369 | 40.349 | 38.238 | 20.528 | 1.00 | 39.70 | B3 |
| ATOM | 2619 | CD2 | LEU | 369 | 40.563 | 39.394 | 22.747 | 1.00 | 36.86 | B3 |
| ATOM | 2620 | C | LEU | 369 | 39.817 | 43.031 | 20.542 | 1.00 | 41.88 | B3 |
| ATOM | 2621 | O | LEU | 369 | 40.711 | 43.654 | 21.144 | 1.00 | 41.30 | B3 |
| ATOM | 2622 | N | ARG | 370 | 39.333 | 43.413 | 19.354 | 1.00 | 42.80 | B3 |
| ATOM | 2623 | H | ARG | 370 | 38.619 | 42.884 | 18.957 | 1.00 | 0.00 | B3 |
| ATOM | 2624 | CA | ARG | 370 | 39.819 | 44.577 | 18.663 | 1.00 | 44.96 | B3 |
| ATOM | 2625 | CB | ARG | 370 | 39.184 | 44.569 | 17.316 | 1.00 | 42.06 | B3 |
| ATOM | 2626 | CG | ARG | 370 | 39.424 | 45.719 | 16.371 | 1.00 | 43.93 | B3 |
| ATOM | 2627 | CD | ARG | 370 | 40.894 | 45.910 | 16.169 | 1.00 | 45.37 | B3 |
| ATOM | 2628 | NE | ARG | 370 | 41.219 | 46.681 | 14.976 | 1.00 | 48.00 | B3 |
| ATOM | 2629 | HE | ARG | 370 | 40.524 | 46.867 | 14.312 | 1.00 | 0.00 | B3 |
| ATOM | 2630 | CZ | ARG | 370 | 42.469 | 47.153 | 14.791 | 1.00 | 48.45 | B3 |
| ATOM | 2631 | NH1 | ARG | 370 | 43.443 | 46.961 | 15.691 | 1.00 | 49.13 | B3 |
| ATOM | 2632 | HH11 | ARG | 370 | 43.262 | 46.456 | 16.534 | 1.00 | 0.00 | B3 |
| ATOM | 2633 | HH12 | ARG | 370 | 44.357 | 47.326 | 15.520 | 1.00 | 0.00 | B3 |
| ATOM | 2634 | NH2 | ARG | 370 | 42.821 | 47.710 | 13.635 | 1.00 | 47.59 | B3 |
| ATOM | 2635 | HH21 | ARG | 370 | 42.163 | 47.785 | 12.889 | 1.00 | 0.00 | B3 |
| ATOM | 2636 | HH22 | ARG | 370 | 43.751 | 48.057 | 13.516 | 1.00 | 0.00 | B3 |
| ATOM | 2637 | C | ARG | 370 | 39.386 | 45.740 | 19.558 | 1.00 | 49.12 | B3 |
| ATOM | 2638 | O | ARG | 370 | 40.216 | 46.615 | 19.826 | 1.00 | 49.67 | B3 |
| ATOM | 2639 | N | HIS | 371 | 38.162 | 45.728 | 20.123 | 1.00 | 52.30 | B3 |
| ATOM | 2640 | H | HIS | 371 | 37.581 | 44.955 | 19.949 | 1.00 | 0.00 | B3 |
| ATOM | 2641 | CA | HIS | 371 | 37.745 | 46.738 | 21.080 | 1.00 | 56.65 | B3 |
| ATOM | 2642 | CB | HIS | 371 | 36.284 | 46.604 | 21.459 | 1.00 | 62.15 | B3 |
| ATOM | 2643 | CG | HIS | 371 | 35.320 | 46.991 | 20.346 | 1.00 | 71.70 | B3 |
| ATOM | 2644 | CD2 | HIS | 371 | 35.596 | 47.877 | 19.313 | 1.00 | 75.03 | B3 |
| ATOM | 2645 | ND1 | HIS | 371 | 34.067 | 46.546 | 20.166 | 1.00 | 75.91 | B3 |
| ATOM | 2646 | HD1 | HIS | 371 | 33.594 | 45.897 | 20.732 | 1.00 | 0.00 | B3 |
| ATOM | 2647 | CE1 | HIS | 371 | 33.580 | 47.116 | 19.077 | 1.00 | 77.30 | B3 |
| ATOM | 2648 | NE2 | HIS | 371 | 34.507 | 47.914 | 18.573 | 1.00 | 77.52 | B3 |
| ATOM | 2649 | HE2 | HIS | 371 | 34.401 | 48.460 | 17.764 | 1.00 | 0.00 | B3 |
| ATOM | 2650 | C | HIS | 371 | 38.533 | 46.669 | 22.382 | 1.00 | 56.97 | B3 |
| ATOM | 2651 | O | HIS | 371 | 38.458 | 47.592 | 23.176 | 1.00 | 58.12 | B3 |
| ATOM | 2652 | N | LEU | 372 | 39.271 | 45.632 | 22.715 | 1.00 | 56.98 | B3 |
| ATOM | 2653 | H | LEU | 372 | 39.302 | 44.855 | 22.122 | 1.00 | 0.00 | B3 |
| ATOM | 2654 | CA | LEU | 372 | 40.048 | 45.597 | 23.939 | 1.00 | 57.77 | B3 |
| ATOM | 2655 | CB | LEU | 372 | 39.725 | 44.272 | 24.633 | 1.00 | 57.29 | B3 |
| ATOM | 2656 | CG | LEU | 372 | 38.566 | 44.144 | 25.611 | 1.00 | 55.87 | B3 |
| ATOM | 2657 | CD1 | LEU | 372 | 37.358 | 44.892 | 25.123 | 1.00 | 55.77 | B3 |
| ATOM | 2658 | CD2 | LEU | 372 | 38.211 | 42.675 | 25.749 | 1.00 | 55.33 | B3 |
| ATOM | 2659 | C | LEU | 372 | 41.554 | 45.755 | 23.647 | 1.00 | 58.81 | B3 |
| ATOM | 2660 | O | LEU | 372 | 42.447 | 45.475 | 24.476 | 1.00 | 59.12 | B3 |
| ATOM | 2661 | N | ALA | 373 | 41.942 | 46.168 | 22.447 | 1.00 | 59.27 | B3 |
| ATOM | 2662 | H | ALA | 373 | 41.271 | 46.255 | 21.731 | 1.00 | 0.00 | B3 |
| ATOM | 2663 | CA | ALA | 373 | 43.336 | 46.425 | 22.147 | 1.00 | 60.03 | B3 |
| ATOM | 2664 | CB | ALA | 373 | 43.755 | 45.485 | 21.021 | 1.00 | 59.87 | B3 |
| ATOM | 2665 | C | ALA | 373 | 43.616 | 47.895 | 21.762 | 1.00 | 61.22 | B3 |

FIG. 5FF

| ATOM | 2666 | OT1 | ALA | 373 | 44.798 | 48.243 | 21.697 | 1.00 | 62.45 | B3 |
|------|------|-----|-----|-----|--------|--------|--------|------|-------|-----|
| ATOM | 2667 | OT2 | ALA | 373 | 42.682 | 48.700 | 21.583 | 1.00 | 61.55 | B3 |
| ATOM | 2668 | CB  | LEU | 410 | 23.866 | 49.243 | 1.118  | 1.00 | 53.10 | C1 |
| ATOM | 2669 | CG  | LEU | 410 | 23.982 | 47.812 | 0.738  | 1.00 | 51.85 | C1 |
| ATOM | 2670 | CD1 | LEU | 410 | 25.074 | 47.596 | -0.330 | 1.00 | 52.64 | C1 |
| ATOM | 2671 | CD2 | LEU | 410 | 24.125 | 47.081 | 2.058  | 1.00 | 49.28 | C1 |
| ATOM | 2672 | C   | LEU | 410 | 22.381 | 51.214 | 1.635  | 1.00 | 52.99 | C1 |
| ATOM | 2673 | O   | LEU | 410 | 22.242 | 52.166 | 0.845  | 1.00 | 53.00 | C1 |
| ATOM | 2674 | HT1 | LEU | 410 | 22.721 | 50.836 | -0.665 | 1.00 | 0.00  | C1 |
| ATOM | 2675 | HT2 | LEU | 410 | 21.194 | 50.178 | -0.557 | 1.00 | 0.00  | C1 |
| ATOM | 2676 | N   | LEU | 410 | 22.198 | 49.968 | -0.415 | 1.00 | 54.31 | C1 |
| ATOM | 2677 | HT3 | LEU | 410 | 22.529 | 49.174 | -0.998 | 1.00 | 0.00  | C1 |
| ATOM | 2678 | CA  | LEU | 410 | 22.478 | 49.815 | 1.004  | 1.00 | 53.64 | C1 |
| ATOM | 2679 | N   | PRO | 411 | 22.450 | 51.433 | 2.965  | 1.00 | 52.95 | C1 |
| ATOM | 2680 | CD  | PRO | 411 | 22.466 | 50.407 | 4.022  | 1.00 | 52.54 | C1 |
| ATOM | 2681 | CA  | PRO | 411 | 22.666 | 52.766 | 3.548  | 1.00 | 53.25 | C1 |
| ATOM | 2682 | CB  | PRO | 411 | 22.688 | 52.541 | 5.068  | 1.00 | 52.85 | C1 |
| ATOM | 2683 | CG  | PRO | 411 | 23.163 | 51.108 | 5.203  | 1.00 | 52.83 | C1 |
| ATOM | 2684 | C   | PRO | 411 | 23.958 | 53.413 | 3.023  | 1.00 | 53.47 | C1 |
| ATOM | 2685 | O   | PRO | 411 | 25.073 | 52.878 | 3.167  | 1.00 | 54.02 | C1 |
| ATOM | 2686 | N   | GLN | 412 | 23.787 | 54.599 | 2.411  | 1.00 | 53.79 | C1 |
| ATOM | 2687 | H   | GLN | 412 | 22.863 | 54.900 | 2.294  | 1.00 | 0.00  | C1 |
| ATOM | 2688 | CA  | GLN | 412 | 24.873 | 55.413 | 1.871  | 1.00 | 50.44 | C1 |
| ATOM | 2689 | CB  | GLN | 412 | 24.387 | 56.762 | 1.413  | 1.00 | 52.47 | C1 |
| ATOM | 2690 | CG  | GLN | 412 | 25.364 | 57.408 | 0.437  | 1.00 | 56.51 | C1 |
| ATOM | 2691 | CD  | GLN | 412 | 25.228 | 56.954 | -1.017 | 1.00 | 59.40 | C1 |
| ATOM | 2692 | OE1 | GLN | 412 | 25.869 | 57.506 | -1.913 | 1.00 | 59.67 | C1 |
| ATOM | 2693 | NE2 | GLN | 412 | 24.336 | 56.022 | -1.389 | 1.00 | 60.12 | C1 |
| ATOM | 2694 | HE21| GLN | 412 | 23.734 | 55.616 | -0.737 | 1.00 | 0.00  | C1 |
| ATOM | 2695 | HE22| GLN | 412 | 24.396 | 55.748 | -2.328 | 1.00 | 0.00  | C1 |
| ATOM | 2696 | C   | GLN | 412 | 25.930 | 55.646 | 2.916  | 1.00 | 48.22 | C1 |
| ATOM | 2697 | O   | GLN | 412 | 27.089 | 55.591 | 2.545  | 1.00 | 46.78 | C1 |
| ATOM | 2698 | N   | SER | 413 | 25.614 | 55.842 | 4.201  | 1.00 | 47.90 | C1 |
| ATOM | 2699 | H   | SER | 413 | 24.693 | 55.976 | 4.492  | 1.00 | 0.00  | C1 |
| ATOM | 2700 | CA  | SER | 413 | 26.696 | 55.984 | 5.144  | 1.00 | 48.75 | C1 |
| ATOM | 2701 | CB  | SER | 413 | 26.261 | 56.344 | 6.548  | 1.00 | 50.61 | C1 |
| ATOM | 2702 | OG  | SER | 413 | 27.378 | 56.872 | 7.301  | 1.00 | 53.05 | C1 |
| ATOM | 2703 | HG  | SER | 413 | 28.178 | 56.355 | 7.145  | 1.00 | 0.00  | C1 |
| ATOM | 2704 | C   | SER | 413 | 27.480 | 54.684 | 5.267  | 1.00 | 48.71 | C1 |
| ATOM | 2705 | O   | SER | 413 | 28.698 | 54.839 | 5.392  | 1.00 | 50.77 | C1 |
| ATOM | 2706 | N   | PHE | 414 | 26.947 | 53.440 | 5.208  | 1.00 | 46.01 | C1 |
| ATOM | 2707 | H   | PHE | 414 | 25.996 | 53.323 | 5.015  | 1.00 | 0.00  | C1 |
| ATOM | 2708 | CA  | PHE | 414 | 27.787 | 52.233 | 5.274  | 1.00 | 42.92 | C1 |
| ATOM | 2709 | CB  | PHE | 414 | 26.959 | 50.915 | 5.232  | 1.00 | 40.76 | C1 |
| ATOM | 2710 | CG  | PHE | 414 | 27.633 | 49.627 | 4.757  | 1.00 | 35.06 | C1 |
| ATOM | 2711 | CD1 | PHE | 414 | 27.583 | 49.256 | 3.425  | 1.00 | 34.71 | C1 |
| ATOM | 2712 | CD2 | PHE | 414 | 28.262 | 48.800 | 5.663  | 1.00 | 34.81 | C1 |
| ATOM | 2713 | CE1 | PHE | 414 | 28.156 | 48.056 | 3.014  | 1.00 | 36.16 | C1 |
| ATOM | 2714 | CE2 | PHE | 414 | 28.832 | 47.602 | 5.247  | 1.00 | 33.40 | C1 |
| ATOM | 2715 | CZ  | PHE | 414 | 28.781 | 47.223 | 3.923  | 1.00 | 34.22 | C1 |
| ATOM | 2716 | C   | PHE | 414 | 28.667 | 52.271 | 4.044  | 1.00 | 41.25 | C1 |
| ATOM | 2717 | O   | PHE | 414 | 29.831 | 51.902 | 4.110  | 1.00 | 41.47 | C1 |
| ATOM | 2718 | N   | LEU | 415 | 28.122 | 52.748 | 2.942  | 1.00 | 39.50 | C1 |
| ATOM | 2719 | H   | LEU | 415 | 27.188 | 53.044 | 2.946  | 1.00 | 0.00  | C1 |
| ATOM | 2720 | CA  | LEU | 415 | 28.865 | 52.769 | 1.721  | 1.00 | 39.91 | C1 |
| ATOM | 2721 | CB  | LEU | 415 | 27.946 | 53.205 | 0.641  | 1.00 | 41.98 | C1 |
| ATOM | 2722 | CG  | LEU | 415 | 27.903 | 52.274 | -0.526 | 1.00 | 44.75 | C1 |
| ATOM | 2723 | CD1 | LEU | 415 | 26.430 | 51.951 | -0.780 | 1.00 | 42.93 | C1 |
| ATOM | 2724 | CD2 | LEU | 415 | 28.793 | 52.853 | -1.648 | 1.00 | 45.91 | C1 |
| ATOM | 2725 | C   | LEU | 415 | 30.081 | 53.669 | 1.755  | 1.00 | 40.03 | C1 |
| ATOM | 2726 | O   | LEU | 415 | 31.142 | 53.348 | 1.183  | 1.00 | 40.28 | C1 |
| ATOM | 2727 | N   | LEU | 416 | 29.901 | 54.779 | 2.487  | 1.00 | 37.46 | C1 |
| ATOM | 2728 | H   | LEU | 416 | 29.028 | 54.948 | 2.899  | 1.00 | 0.00  | C1 |
| ATOM | 2729 | CA  | LEU | 416 | 30.942 | 55.756 | 2.602  | 1.00 | 34.05 | C1 |
| ATOM | 2730 | CB  | LEU | 416 | 30.294 | 57.089 | 2.998  | 1.00 | 34.67 | C1 |
| ATOM | 2731 | CG  | LEU | 416 | 29.438 | 57.704 | 1.851  | 1.00 | 35.24 | C1 |
| ATOM | 2732 | CD1 | LEU | 416 | 28.770 | 58.948 | 2.358  | 1.00 | 31.87 | C1 |
| ATOM | 2733 | CD2 | LEU | 416 | 30.310 | 57.948 | 0.593  | 1.00 | 35.50 | C1 |
| ATOM | 2734 | C   | LEU | 416 | 31.952 | 55.258 | 3.586  | 1.00 | 31.97 | C1 |
| ATOM | 2735 | O   | LEU | 416 | 33.131 | 55.427 | 3.270  | 1.00 | 33.32 | C1 |
| ATOM | 2736 | N   | ALA | 417 | 31.573 | 54.619 | 4.695  | 1.00 | 29.05 | C1 |
| ATOM | 2737 | H   | ALA | 417 | 30.621 | 54.616 | 4.927  | 1.00 | 0.00  | C1 |
| ATOM | 2738 | CA  | ALA | 417 | 32.524 | 53.882 | 5.561  | 1.00 | 29.64 | C1 |
| ATOM | 2739 | CB  | ALA | 417 | 31.853 | 53.087 | 6.680  | 1.00 | 25.16 | C1 |
| ATOM | 2740 | C   | ALA | 417 | 33.319 | 52.827 | 4.777  | 1.00 | 30.68 | C1 |
| ATOM | 2741 | O   | ALA | 417 | 34.536 | 52.721 | 4.877  | 1.00 | 31.52 | C1 |
| ATOM | 2742 | N   | CYS | 418 | 32.726 | 52.041 | 3.905  | 1.00 | 32.19 | C1 |
| ATOM | 2743 | H   | CYS | 418 | 31.748 | 52.017 | 3.860  | 1.00 | 0.00  | C1 |
| ATOM | 2744 | CA  | CYS | 418 | 33.499 | 51.119 | 3.103  | 1.00 | 33.67 | C1 |
| ATOM | 2745 | CB  | CYS | 418 | 32.657 | 50.250 | 2.226  | 1.00 | 33.85 | C1 |
| ATOM | 2746 | SG  | CYS | 418 | 31.623 | 49.208 | 3.246  | 1.00 | 37.80 | C1 |
| ATOM | 2747 | C   | CYS | 418 | 34.446 | 51.818 | 2.170  | 1.00 | 34.80 | C1 |
| ATOM | 2748 | O   | CYS | 418 | 35.626 | 51.441 | 2.173  | 1.00 | 36.47 | C1 |
| ATOM | 2749 | N   | LEU | 419 | 34.009 | 52.820 | 1.377  | 1.00 | 35.00 | C1 |
| ATOM | 2750 | H   | LEU | 419 | 33.082 | 53.131 | 1.460  | 1.00 | 0.00  | C1 |
| ATOM | 2751 | CA  | LEU | 419 | 34.886 | 53.446 | 0.375  | 1.00 | 34.14 | C1 |

FIG. 5GG

| | | | | | | | | | |
|---|---|---|---|---|---|---|---|---|---|
| ATOM | 2752 | CB | LEU | 419 | 34.062 | 54.484 | -0.413 | 1.00 37.09 | C1 |
| ATOM | 2753 | CG | LEU | 419 | 32.866 | 53.853 | -1.244 | 1.00 39.61 | C1 |
| ATOM | 2754 | CD1 | LEU | 419 | 31.866 | 54.918 | -1.609 | 1.00 39.24 | C1 |
| ATOM | 2755 | CD2 | LEU | 419 | 33.349 | 53.207 | -2.553 | 1.00 40.02 | C1 |
| ATOM | 2756 | C | LEU | 419 | 36.102 | 54.041 | 1.047 | 1.00 32.33 | C1 |
| ATOM | 2757 | O | LEU | 419 | 37.198 | 53.973 | 0.549 | 1.00 31.60 | C1 |
| ATOM | 2758 | N | GLU | 420 | 35.974 | 54.483 | 2.273 | 1.00 31.92 | C1 |
| ATOM | 2759 | H | GLU | 420 | 35.068 | 54.528 | 2.648 | 1.00 0.00 | C1 |
| ATOM | 2760 | CA | GLU | 420 | 37.078 | 54.905 | 3.092 | 1.00 31.79 | C1 |
| ATOM | 2761 | CB | GLU | 420 | 36.477 | 55.462 | 4.344 | 1.00 34.29 | C1 |
| ATOM | 2762 | CG | GLU | 420 | 37.430 | 56.240 | 5.185 | 1.00 38.66 | C1 |
| ATOM | 2763 | CD | GLU | 420 | 36.952 | 56.499 | 6.609 | 1.00 45.20 | C1 |
| ATOM | 2764 | OE1 | GLU | 420 | 37.873 | 56.849 | 7.367 | 1.00 45.67 | C1 |
| ATOM | 2765 | OE2 | GLU | 420 | 35.745 | 56.345 | 6.954 | 1.00 44.21 | C1 |
| ATOM | 2766 | C | GLU | 420 | 38.043 | 53.763 | 3.423 | 1.00 31.87 | C1 |
| ATOM | 2767 | O | GLU | 420 | 39.253 | 53.949 | 3.270 | 1.00 32.82 | C1 |
| ATOM | 2768 | N | GLN | 421 | 37.553 | 52.624 | 3.954 | 1.00 30.46 | C1 |
| ATOM | 2769 | H | GLN | 421 | 36.583 | 52.556 | 4.098 | 1.00 0.00 | C1 |
| ATOM | 2770 | CA | GLN | 421 | 38.366 | 51.461 | 4.283 | 1.00 29.34 | C1 |
| ATOM | 2771 | CB | GLN | 421 | 37.545 | 50.389 | 4.984 | 1.00 30.88 | C1 |
| ATOM | 2772 | CG | GLN | 421 | 37.308 | 50.634 | 6.463 | 1.00 33.58 | C1 |
| ATOM | 2773 | CD | GLN | 421 | 36.320 | 49.625 | 7.058 | 1.00 37.89 | C1 |
| ATOM | 2774 | OE1 | GLN | 421 | 35.357 | 49.236 | 6.398 | 1.00 43.18 | C1 |
| ATOM | 2775 | NE2 | GLN | 421 | 36.427 | 49.095 | 8.275 | 1.00 37.13 | C1 |
| ATOM | 2776 | HE21 | GLN | 421 | 35.695 | 48.505 | 8.556 | 1.00 0.00 | C1 |
| ATOM | 2777 | HE22 | GLN | 421 | 37.207 | 49.330 | 8.812 | 1.00 0.00 | C1 |
| ATOM | 2778 | C | GLN | 421 | 38.991 | 50.862 | 3.026 | 1.00 27.36 | C1 |
| ATOM | 2779 | O | GLN | 421 | 40.152 | 50.445 | 3.099 | 1.00 29.09 | C1 |
| ATOM | 2780 | N | VAL | 422 | 38.379 | 50.845 | 1.847 | 1.00 23.57 | C1 |
| ATOM | 2781 | H | VAL | 422 | 37.448 | 51.138 | 1.803 | 1.00 0.00 | C1 |
| ATOM | 2782 | CA | VAL | 422 | 39.077 | 50.420 | 0.651 | 1.00 23.52 | C1 |
| ATOM | 2783 | CB | VAL | 422 | 38.163 | 50.636 | -0.556 | 1.00 22.67 | C1 |
| ATOM | 2784 | CG1 | VAL | 422 | 38.873 | 50.455 | -1.868 | 1.00 21.56 | C1 |
| ATOM | 2785 | CG2 | VAL | 422 | 37.057 | 49.610 | -0.465 | 1.00 26.79 | C1 |
| ATOM | 2786 | C | VAL | 422 | 40.353 | 51.254 | 0.514 | 1.00 26.22 | C1 |
| ATOM | 2787 | O | VAL | 422 | 41.458 | 50.708 | 0.508 | 1.00 28.77 | C1 |
| ATOM | 2788 | N | ARG | 423 | 40.275 | 52.599 | 0.575 | 1.00 27.49 | C1 |
| ATOM | 2789 | H | ARG | 423 | 39.402 | 53.016 | 0.735 | 1.00 0.00 | C1 |
| ATOM | 2790 | CA | ARG | 423 | 41.436 | 53.456 | 0.346 | 1.00 25.91 | C1 |
| ATOM | 2791 | CB | ARG | 423 | 41.098 | 54.943 | 0.312 | 1.00 24.39 | C1 |
| ATOM | 2792 | CG | ARG | 423 | 40.167 | 55.366 | -0.807 | 1.00 22.81 | C1 |
| ATOM | 2793 | CD | ARG | 423 | 40.525 | 54.798 | -2.172 | 1.00 25.55 | C1 |
| ATOM | 2794 | NE | ARG | 423 | 39.707 | 55.387 | -3.216 | 1.00 25.38 | C1 |
| ATOM | 2795 | HE | ARG | 423 | 39.168 | 56.173 | -2.989 | 1.00 0.00 | C1 |
| ATOM | 2796 | CZ | ARG | 423 | 39.629 | 54.928 | -4.466 | 1.00 27.32 | C1 |
| ATOM | 2797 | NH1 | ARG | 423 | 40.264 | 53.857 | -4.949 | 1.00 26.37 | C1 |
| ATOM | 2798 | HH11 | ARG | 423 | 40.884 | 53.341 | -4.365 | 1.00 0.00 | C1 |
| ATOM | 2799 | HH12 | ARG | 423 | 40.150 | 53.595 | -5.907 | 1.00 0.00 | C1 |
| ATOM | 2800 | NH2 | ARG | 423 | 38.960 | 55.682 | -5.325 | 1.00 30.38 | C1 |
| ATOM | 2801 | HH21 | ARG | 423 | 38.559 | 56.537 | -5.023 | 1.00 0.00 | C1 |
| ATOM | 2802 | HH22 | ARG | 423 | 38.865 | 55.385 | -6.275 | 1.00 0.00 | C1 |
| ATOM | 2803 | C | ARG | 423 | 42.429 | 53.241 | 1.432 | 1.00 23.60 | C1 |
| ATOM | 2804 | O | ARG | 423 | 43.594 | 53.147 | 1.127 | 1.00 24.37 | C1 |
| ATOM | 2805 | N | LYS | 424 | 42.065 | 53.050 | 2.668 | 1.00 24.38 | C1 |
| ATOM | 2806 | H | LYS | 424 | 41.109 | 53.051 | 2.890 | 1.00 0.00 | C1 |
| ATOM | 2807 | CA | LYS | 424 | 43.043 | 52.855 | 3.722 | 1.00 25.12 | C1 |
| ATOM | 2808 | CB | LYS | 424 | 42.352 | 52.791 | 5.051 | 1.00 23.89 | C1 |
| ATOM | 2809 | CG | LYS | 424 | 43.312 | 52.936 | 6.190 | 1.00 28.56 | C1 |
| ATOM | 2810 | CD | LYS | 424 | 42.579 | 52.580 | 7.486 | 1.00 35.51 | C1 |
| ATOM | 2811 | CE | LYS | 424 | 41.338 | 53.425 | 7.853 | 1.00 40.33 | C1 |
| ATOM | 2812 | NZ | LYS | 424 | 40.519 | 52.722 | 8.834 | 1.00 42.23 | C1 |
| ATOM | 2813 | HZ1 | LYS | 424 | 41.079 | 52.559 | 9.695 | 1.00 0.00 | C1 |
| ATOM | 2814 | HZ2 | LYS | 424 | 40.208 | 51.814 | 8.435 | 1.00 0.00 | C1 |
| ATOM | 2815 | HZ3 | LYS | 424 | 39.689 | 53.306 | 9.065 | 1.00 0.00 | C1 |
| ATOM | 2816 | C | LYS | 424 | 43.761 | 51.547 | 3.462 | 1.00 27.10 | C1 |
| ATOM | 2817 | O | LYS | 424 | 44.923 | 51.425 | 3.848 | 1.00 30.64 | C1 |
| ATOM | 2818 | N | ILE | 425 | 43.190 | 50.542 | 2.794 | 1.00 26.83 | C1 |
| ATOM | 2819 | H | ILE | 425 | 42.260 | 50.607 | 2.488 | 1.00 0.00 | C1 |
| ATOM | 2820 | CA | ILE | 425 | 43.949 | 49.312 | 2.561 | 1.00 25.46 | C1 |
| ATOM | 2821 | CB | ILE | 425 | 42.965 | 48.093 | 2.336 | 1.00 24.91 | C1 |
| ATOM | 2822 | CG2 | ILE | 425 | 43.654 | 46.786 | 1.995 | 1.00 22.01 | C1 |
| ATOM | 2823 | CG1 | ILE | 425 | 42.229 | 47.909 | 3.633 | 1.00 25.34 | C1 |
| ATOM | 2824 | CD | ILE | 425 | 40.885 | 47.169 | 3.432 | 1.00 25.68 | C1 |
| ATOM | 2825 | C | ILE | 425 | 44.824 | 49.549 | 1.346 | 1.00 23.84 | C1 |
| ATOM | 2826 | O | ILE | 425 | 45.959 | 49.069 | 1.316 | 1.00 24.57 | C1 |
| ATOM | 2827 | N | GLN | 426 | 44.361 | 50.267 | 0.323 | 1.00 23.28 | C1 |
| ATOM | 2828 | H | GLN | 426 | 43.451 | 50.630 | 0.393 | 1.00 0.00 | C1 |
| ATOM | 2829 | CA | GLN | 426 | 45.164 | 50.531 | -0.871 | 1.00 24.13 | C1 |
| ATOM | 2830 | CB | GLN | 426 | 44.421 | 51.344 | -1.896 | 1.00 24.04 | C1 |
| ATOM | 2831 | CG | GLN | 426 | 43.275 | 50.539 | -2.396 | 1.00 23.56 | C1 |
| ATOM | 2832 | CD | GLN | 426 | 42.446 | 51.105 | -3.511 | 1.00 23.92 | C1 |
| ATOM | 2833 | OE1 | GLN | 426 | 41.704 | 52.047 | -3.345 | 1.00 25.34 | C1 |
| ATOM | 2834 | NE2 | GLN | 426 | 42.337 | 50.509 | -4.672 | 1.00 27.55 | C1 |
| ATOM | 2835 | HE21 | GLN | 426 | 41.755 | 50.948 | -5.323 | 1.00 0.00 | C1 |
| ATOM | 2836 | HE22 | GLN | 426 | 42.850 | 49.696 | -4.851 | 1.00 0.00 | C1 |
| ATOM | 2837 | C | GLN | 426 | 46.404 | 51.312 | -0.488 | 1.00 26.69 | C1 |

FIG. 5HH

| | | | | | | | | | |
|---|---|---|---|---|---|---|---|---|---|
| ATOM | 2838 | O | GLN | 426 | 47.486 | 51.109 | -1.046 | 1.00 29.73 | |
| ATOM | 2839 | N | GLY | 427 | 46.300 | 52.204 | 0.499 | 1.00 26.49 | |
| ATOM | 2840 | H | GLY | 427 | 45.410 | 52.414 | 0.854 | 1.00 0.00 | |
| ATOM | 2841 | CA | GLY | 427 | 47.446 | 52.894 | 1.022 | 1.00 24.25 | |
| ATOM | 2842 | C | GLY | 427 | 48.467 | 51.913 | 1.589 | 1.00 23.08 | |
| ATOM | 2843 | O | GLY | 427 | 49.597 | 51.921 | 1.106 | 1.00 22.28 | |
| ATOM | 2844 | N | ASP | 428 | 48.107 | 51.073 | 2.575 | 1.00 22.75 | |
| ATOM | 2845 | H | ASP | 428 | 47.189 | 51.111 | 2.918 | 1.00 0.00 | |
| ATOM | 2846 | CA | ASP | 428 | 49.039 | 50.108 | 3.131 | 1.00 23.87 | |
| ATOM | 2847 | CB | ASP | 428 | 48.415 | 49.199 | 4.117 | 1.00 26.52 | |
| ATOM | 2848 | CG | ASP | 428 | 47.437 | 49.779 | 5.097 | 1.00 28.84 | |
| ATOM | 2849 | OD1 | ASP | 428 | 46.420 | 49.151 | 5.265 | 1.00 31.81 | |
| ATOM | 2850 | OD2 | ASP | 428 | 47.662 | 50.804 | 5.716 | 1.00 30.77 | |
| ATOM | 2851 | C | ASP | 428 | 49.626 | 49.191 | 2.063 | 1.00 24.16 | |
| ATOM | 2852 | O | ASP | 428 | 50.812 | 48.896 | 2.088 | 1.00 26.17 | |
| ATOM | 2853 | N | GLY | 429 | 48.840 | 48.822 | 1.069 | 1.00 23.01 | |
| ATOM | 2854 | H | GLY | 429 | 47.905 | 49.113 | 1.071 | 1.00 0.00 | |
| ATOM | 2855 | CA | GLY | 429 | 49.289 | 47.964 | 0.029 | 1.00 25.44 | |
| ATOM | 2856 | C | GLY | 429 | 50.405 | 48.649 | -0.716 | 1.00 27.39 | |
| ATOM | 2857 | O | GLY | 429 | 51.528 | 48.135 | -0.741 | 1.00 28.51 | |
| ATOM | 2858 | N | ALA | 430 | 50.127 | 49.840 | -1.271 | 1.00 28.26 | |
| ATOM | 2859 | H | ALA | 430 | 49.216 | 50.185 | -1.172 | 1.00 0.00 | |
| ATOM | 2860 | CA | ALA | 430 | 51.094 | 50.643 | -2.015 | 1.00 26.04 | |
| ATOM | 2861 | CB | ALA | 430 | 50.490 | 51.976 | -2.407 | 1.00 27.93 | |
| ATOM | 2862 | C | ALA | 430 | 52.300 | 50.927 | -1.133 | 1.00 25.19 | |
| ATOM | 2863 | O | ALA | 430 | 53.393 | 51.053 | -1.655 | 1.00 25.43 | |
| ATOM | 2864 | N | ALA | 431 | 52.171 | 50.979 | 0.186 | 1.00 24.05 | |
| ATOM | 2865 | H | ALA | 431 | 51.279 | 50.872 | 0.579 | 1.00 0.00 | |
| ATOM | 2866 | CA | ALA | 431 | 53.295 | 51.213 | 1.035 | 1.00 26.29 | |
| ATOM | 2867 | CB | ALA | 431 | 52.874 | 51.522 | 2.458 | 1.00 24.14 | |
| ATOM | 2868 | C | ALA | 431 | 54.139 | 49.972 | 1.073 | 1.00 29.82 | |
| ATOM | 2869 | O | ALA | 431 | 55.360 | 50.085 | 0.959 | 1.00 31.97 | |
| ATOM | 2870 | N | LEU | 432 | 53.562 | 48.777 | 1.203 | 1.00 31.87 | |
| ATOM | 2871 | H | LEU | 432 | 52.585 | 48.726 | 1.279 | 1.00 0.00 | |
| ATOM | 2872 | CA | LEU | 432 | 54.337 | 47.540 | 1.165 | 1.00 33.92 | |
| ATOM | 2873 | CB | LEU | 432 | 53.430 | 46.315 | 1.301 | 1.00 37.42 | |
| ATOM | 2874 | CG | LEU | 432 | 54.063 | 44.952 | 1.574 | 1.00 37.40 | |
| ATOM | 2875 | CD1 | LEU | 432 | 54.751 | 44.949 | 2.950 | 1.00 38.10 | |
| ATOM | 2876 | CD2 | LEU | 432 | 52.966 | 43.901 | 1.492 | 1.00 36.27 | |
| ATOM | 2877 | C | LEU | 432 | 55.096 | 47.404 | -0.146 | 1.00 33.74 | |
| ATOM | 2878 | O | LEU | 432 | 56.306 | 47.179 | -0.138 | 1.00 33.29 | |
| ATOM | 2879 | N | GLN | 433 | 54.402 | 47.564 | -1.276 | 1.00 34.57 | |
| ATOM | 2880 | H | GLN | 433 | 53.439 | 47.733 | -1.186 | 1.00 0.00 | |
| ATOM | 2881 | CA | GLN | 433 | 55.002 | 47.526 | -2.600 | 1.00 35.83 | C1 |
| ATOM | 2882 | CB | GLN | 433 | 53.999 | 47.892 | -3.664 | 1.00 35.52 | C1 |
| ATOM | 2883 | CG | GLN | 433 | 52.996 | 46.823 | -3.832 | 1.00 39.40 | C1 |
| ATOM | 2884 | CD | GLN | 433 | 52.049 | 47.097 | -4.973 | 1.00 42.46 | C1 |
| ATOM | 2885 | OE1 | GLN | 433 | 50.924 | 47.526 | -4.786 | 1.00 48.22 | C1 |
| ATOM | 2886 | NE2 | GLN | 433 | 52.376 | 46.878 | -6.225 | 1.00 44.77 | C1 |
| ATOM | 2887 | HE21 | GLN | 433 | 53.271 | 46.540 | -6.433 | 1.00 0.00 | C1 |
| ATOM | 2888 | HE22 | GLN | 433 | 51.693 | 47.087 | -6.892 | 1.00 0.00 | C1 |
| ATOM | 2889 | C | GLN | 433 | 56.177 | 48.485 | -2.757 | 1.00 36.48 | C1 |
| ATOM | 2890 | O | GLN | 433 | 57.214 | 48.118 | -3.312 | 1.00 38.08 | C1 |
| ATOM | 2891 | N | GLU | 434 | 56.055 | 49.719 | -2.287 | 1.00 36.11 | C1 |
| ATOM | 2892 | H | GLU | 434 | 55.210 | 49.978 | -1.854 | 1.00 0.00 | C1 |
| ATOM | 2893 | CA | GLU | 434 | 57.089 | 50.719 | -2.426 | 1.00 35.93 | C1 |
| ATOM | 2894 | CB | GLU | 434 | 56.408 | 52.030 | -2.068 | 1.00 41.28 | C1 |
| ATOM | 2895 | CG | GLU | 434 | 57.126 | 53.356 | -2.019 | 1.00 43.07 | C1 |
| ATOM | 2896 | CD | GLU | 434 | 57.832 | 53.516 | -0.698 | 1.00 45.70 | C1 |
| ATOM | 2897 | OE1 | GLU | 434 | 57.190 | 53.538 | 0.367 | 1.00 49.33 | C1 |
| ATOM | 2898 | OE2 | GLU | 434 | 59.051 | 53.579 | -0.760 | 1.00 45.45 | C1 |
| ATOM | 2899 | C | GLU | 434 | 58.257 | 50.348 | -1.548 | 1.00 34.00 | C1 |
| ATOM | 2900 | O | GLU | 434 | 59.388 | 50.481 | -1.983 | 1.00 32.93 | C1 |
| ATOM | 2901 | N | LYS | 435 | 58.067 | 49.860 | -0.330 | 1.00 34.34 | C1 |
| ATOM | 2902 | H | LYS | 435 | 57.146 | 49.837 | 0.014 | 1.00 0.00 | C1 |
| ATOM | 2903 | CA | LYS | 435 | 59.151 | 49.358 | 0.511 | 1.00 34.56 | C1 |
| ATOM | 2904 | CB | LYS | 435 | 58.577 | 49.010 | 1.847 | 1.00 33.89 | C1 |
| ATOM | 2905 | CG | LYS | 435 | 58.357 | 50.231 | 2.709 | 1.00 36.71 | C1 |
| ATOM | 2906 | CD | LYS | 435 | 58.244 | 49.748 | 4.137 | 1.00 40.31 | C1 |
| ATOM | 2907 | CE | LYS | 435 | 58.293 | 50.861 | 5.213 | 1.00 45.32 | C1 |
| ATOM | 2908 | NZ | LYS | 435 | 58.494 | 50.325 | 6.575 | 1.00 47.31 | C1 |
| ATOM | 2909 | HZ1 | LYS | 435 | 59.388 | 49.795 | 6.611 | 1.00 0.00 | C1 |
| ATOM | 2910 | HZ2 | LYS | 435 | 57.708 | 49.689 | 6.818 | 1.00 0.00 | C1 |
| ATOM | 2911 | HZ3 | LYS | 435 | 58.534 | 51.109 | 7.257 | 1.00 0.00 | C1 |
| ATOM | 2912 | C | LYS | 435 | 59.906 | 48.135 | -0.065 | 1.00 36.10 | C1 |
| ATOM | 2913 | O | LYS | 435 | 61.139 | 48.036 | -0.012 | 1.00 37.08 | C1 |
| ATOM | 2914 | N | LEU | 436 | 59.215 | 47.168 | -0.665 | 1.00 36.28 | C1 |
| ATOM | 2915 | H | LEU | 436 | 58.235 | 47.245 | -0.651 | 1.00 0.00 | C1 |
| ATOM | 2916 | CA | LEU | 436 | 59.793 | 45.994 | -1.304 | 1.00 34.25 | C1 |
| ATOM | 2917 | CB | LEU | 436 | 58.655 | 45.076 | -1.753 | 1.00 33.41 | C1 |
| ATOM | 2918 | CG | LEU | 436 | 57.920 | 44.327 | -0.610 | 1.00 34.72 | C1 |
| ATOM | 2919 | CD1 | LEU | 436 | 56.764 | 43.538 | -1.181 | 1.00 33.50 | C1 |
| ATOM | 2920 | CD2 | LEU | 436 | 58.880 | 43.375 | 0.117 | 1.00 36.39 | C1 |
| ATOM | 2921 | C | LEU | 436 | 60.669 | 46.383 | -2.467 | 1.00 33.31 | C1 |
| ATOM | 2922 | O | LEU | 436 | 61.756 | 45.825 | -2.647 | 1.00 33.94 | C1 |
| ATOM | 2923 | N | CYS | 437 | 60.220 | 47.374 | -3.222 | 1.00 32.34 | C1 |

FIG. 51I

| | | | | | | | | | |
|---|---|---|---|---|---|---|---|---|---|
| ATOM | 2924 | H | CYS | 437 | 59.290 | 47.661 | -3.097 | 1.00 | 0.00 | C1 |
| ATOM | 2925 | CA | CYS | 437 | 60.978 | 47.949 | -4.301 | 1.00 | 32.01 | C1 |
| ATOM | 2926 | C | CYS | 437 | 62.214 | 48.704 | -3.857 | 1.00 | 34.70 | C1 |
| ATOM | 2927 | O | CYS | 437 | 63.313 | 48.599 | -4.412 | 1.00 | 36.26 | C1 |
| ATOM | 2928 | CB | CYS | 437 | 60.094 | 48.840 | -5.008 | 1.00 | 30.97 | C1 |
| ATOM | 2929 | SG | CYS | 437 | 61.003 | 49.666 | -6.319 | 1.00 | 36.22 | C1 |
| ATOM | 2930 | N | ALA | 438 | 62.016 | 49.463 | -2.785 | 1.00 | 36.35 | C1 |
| ATOM | 2931 | H | ALA | 438 | 61.108 | 49.547 | -2.431 | 1.00 | 0.00 | C1 |
| ATOM | 2932 | CA | ALA | 438 | 63.060 | 50.226 | -2.170 | 1.00 | 35.83 | C1 |
| ATOM | 2933 | CB | ALA | 438 | 62.440 | 51.107 | -1.153 | 1.00 | 36.38 | C1 |
| ATOM | 2934 | C | ALA | 438 | 64.065 | 49.294 | -1.527 | 1.00 | 37.01 | C1 |
| ATOM | 2935 | O | ALA | 438 | 65.132 | 49.168 | -2.092 | 1.00 | 39.39 | C1 |
| ATOM | 2936 | N | THR | 439 | 63.808 | 48.591 | -0.422 | 1.00 | 36.59 | C1 |
| ATOM | 2937 | H | THR | 439 | 62.947 | 48.723 | 0.014 | 1.00 | 0.00 | C1 |
| ATOM | 2938 | CA | THR | 439 | 64.742 | 47.669 | 0.223 | 1.00 | 35.70 | C1 |
| ATOM | 2939 | CB | THR | 439 | 64.073 | 47.042 | 1.400 | 1.00 | 35.34 | C1 |
| ATOM | 2940 | OG1 | THR | 439 | 63.323 | 48.048 | 2.040 | 1.00 | 38.31 | C1 |
| ATOM | 2941 | HG1 | THR | 439 | 62.419 | 47.999 | 1.706 | 1.00 | 0.00 | C1 |
| ATOM | 2942 | CG2 | THR | 439 | 65.039 | 46.479 | 2.369 | 1.00 | 36.50 | C1 |
| ATOM | 2943 | C | THR | 439 | 65.331 | 46.517 | -0.590 | 1.00 | 36.10 | C1 |
| ATOM | 2944 | O | THR | 439 | 66.448 | 46.093 | -0.312 | 1.00 | 36.51 | C1 |
| ATOM | 2945 | N | TYR | 440 | 64.603 | 45.917 | -1.548 | 1.00 | 36.02 | C1 |
| ATOM | 2946 | H | TYR | 440 | 63.751 | 46.319 | -1.822 | 1.00 | 0.00 | C1 |
| ATOM | 2947 | CA | TYR | 440 | 65.057 | 44.691 | -2.198 | 1.00 | 34.28 | C1 |
| ATOM | 2948 | CB | TYR | 440 | 64.175 | 43.480 | -1.878 | 1.00 | 33.99 | C1 |
| ATOM | 2949 | CG | TYR | 440 | 64.016 | 43.240 | -0.397 | 1.00 | 34.14 | C1 |
| ATOM | 2950 | CD1 | TYR | 440 | 62.773 | 43.230 | 0.169 | 1.00 | 35.16 | C1 |
| ATOM | 2951 | CE1 | TYR | 440 | 62.625 | 43.037 | 1.532 | 1.00 | 36.66 | C1 |
| ATOM | 2952 | CD2 | TYR | 440 | 65.126 | 43.064 | 0.385 | 1.00 | 37.83 | C1 |
| ATOM | 2953 | CE2 | TYR | 440 | 64.992 | 42.881 | 1.752 | 1.00 | 39.02 | C1 |
| ATOM | 2954 | CZ | TYR | 440 | 63.741 | 42.864 | 2.317 | 1.00 | 37.34 | C1 |
| ATOM | 2955 | OH | TYR | 440 | 63.637 | 42.649 | 3.678 | 1.00 | 37.56 | C1 |
| ATOM | 2956 | HH | TYR | 440 | 64.498 | 42.343 | 3.988 | 1.00 | 0.00 | C1 |
| ATOM | 2957 | C | TYR | 440 | 65.088 | 44.768 | -3.681 | 1.00 | 34.07 | C1 |
| ATOM | 2958 | O | TYR | 440 | 65.598 | 43.823 | -4.267 | 1.00 | 35.54 | C1 |
| ATOM | 2959 | N | LYS | 441 | 64.627 | 45.833 | -4.330 | 1.00 | 33.18 | C1 |
| ATOM | 2960 | H | LYS | 441 | 64.345 | 46.623 | -3.822 | 1.00 | 0.00 | C1 |
| ATOM | 2961 | CA | LYS | 441 | 64.595 | 45.957 | -5.763 | 1.00 | 30.44 | C1 |
| ATOM | 2962 | CB | LYS | 441 | 65.983 | 45.759 | -6.364 | 1.00 | 33.76 | C1 |
| ATOM | 2963 | CG | LYS | 441 | 66.729 | 47.080 | -6.407 | 1.00 | 39.59 | C1 |
| ATOM | 2964 | CD | LYS | 441 | 67.273 | 47.497 | -5.045 | 1.00 | 47.69 | C1 |
| ATOM | 2965 | CE | LYS | 441 | 67.503 | 49.028 | -4.984 | 1.00 | 53.37 | C1 |
| ATOM | 2966 | NZ | LYS | 441 | 66.267 | 49.780 | -5.240 | 1.00 | 57.64 | C1 |
| ATOM | 2967 | HZ1 | LYS | 441 | 65.568 | 49.549 | -4.506 | 1.00 | 0.00 | C1 |
| ATOM | 2968 | HZ2 | LYS | 441 | 65.885 | 49.525 | -6.173 | 1.00 | 0.00 | C1 |
| ATOM | 2969 | HZ3 | LYS | 441 | 66.468 | 50.801 | -5.219 | 1.00 | 0.00 | C1 |
| ATOM | 2970 | C | LYS | 441 | 63.629 | 45.015 | -6.425 | 1.00 | 28.86 | C1 |
| ATOM | 2971 | O | LYS | 441 | 63.791 | 44.688 | -7.603 | 1.00 | 29.95 | C1 |
| ATOM | 2972 | N | LEU | 442 | 62.556 | 44.601 | -5.749 | 1.00 | 27.58 | C1 |
| ATOM | 2973 | H | LEU | 442 | 62.392 | 44.924 | -4.837 | 1.00 | 0.00 | C1 |
| ATOM | 2974 | CA | LEU | 442 | 61.554 | 43.780 | -6.402 | 1.00 | 28.82 | C1 |
| ATOM | 2975 | CB | LEU | 442 | 60.947 | 42.694 | -5.466 | 1.00 | 26.98 | C1 |
| ATOM | 2976 | CG | LEU | 442 | 61.905 | 41.634 | -4.847 | 1.00 | 27.75 | C1 |
| ATOM | 2977 | CD1 | LEU | 442 | 61.133 | 40.643 | -4.009 | 1.00 | 24.29 | C1 |
| ATOM | 2978 | CD2 | LEU | 442 | 62.667 | 40.932 | -5.963 | 1.00 | 19.72 | C1 |
| ATOM | 2979 | C | LEU | 442 | 60.575 | 44.892 | -6.635 | 1.00 | 30.59 | C1 |
| ATOM | 2980 | O | LEU | 442 | 59.811 | 45.261 | -5.741 | 1.00 | 32.36 | C1 |
| ATOM | 2981 | N | CYS | 443 | 60.700 | 45.506 | -7.804 | 1.00 | 32.15 | C1 |
| ATOM | 2982 | H | CYS | 443 | 61.423 | 45.199 | -8.389 | 1.00 | 0.00 | C1 |
| ATOM | 2983 | CA | CYS | 443 | 59.866 | 46.645 | -8.191 | 1.00 | 32.69 | C1 |
| ATOM | 2984 | C | CYS | 443 | 58.807 | 46.380 | -9.217 | 1.00 | 33.43 | C1 |
| ATOM | 2985 | O | CYS | 443 | 58.051 | 47.288 | -9.465 | 1.00 | 34.10 | C1 |
| ATOM | 2986 | CB | CYS | 443 | 60.715 | 47.800 | -8.743 | 1.00 | 30.74 | C1 |
| ATOM | 2987 | SG | CYS | 443 | 61.938 | 48.345 | -7.519 | 1.00 | 32.96 | C1 |
| ATOM | 2988 | N | HIS | 444 | 58.649 | 45.260 | -9.911 | 1.00 | 35.65 | C1 |
| ATOM | 2989 | H | HIS | 444 | 59.147 | 44.445 | -9.659 | 1.00 | 0.00 | C1 |
| ATOM | 2990 | CA | HIS | 444 | 57.662 | 45.172 | -10.975 | 1.00 | 37.75 | C1 |
| ATOM | 2991 | CB | HIS | 444 | 58.329 | 45.224 | -12.330 | 1.00 | 37.09 | C1 |
| ATOM | 2992 | CG | HIS | 444 | 59.149 | 46.476 | -12.560 | 1.00 | 41.36 | C1 |
| ATOM | 2993 | CD2 | HIS | 444 | 60.434 | 46.664 | -12.075 | 1.00 | 41.40 | C1 |
| ATOM | 2994 | ND1 | HIS | 444 | 58.811 | 47.563 | -13.261 | 1.00 | 41.74 | C1 |
| ATOM | 2995 | HD1 | HIS | 444 | 57.892 | 47.890 | -13.410 | 1.00 | 0.00 | C1 |
| ATOM | 2996 | CE1 | HIS | 444 | 59.850 | 48.372 | -13.217 | 1.00 | 42.00 | C1 |
| ATOM | 2997 | NE2 | HIS | 444 | 60.817 | 47.832 | -12.502 | 1.00 | 41.38 | C1 |
| ATOM | 2998 | HE2 | HIS | 444 | 61.690 | 48.248 | -12.334 | 1.00 | 0.00 | C1 |
| ATOM | 2999 | C | HIS | 444 | 56.889 | 43.871 | -10.878 | 1.00 | 40.10 | C1 |
| ATOM | 3000 | O | HIS | 444 | 57.461 | 42.867 | -11.309 | 1.00 | 40.15 | C1 |
| ATOM | 3001 | N | PRO | 445 | 55.615 | 43.752 | -10.406 | 1.00 | 42.06 | C1 |
| ATOM | 3002 | CD | PRO | 445 | 54.738 | 44.836 | -9.937 | 1.00 | 41.56 | C1 |
| ATOM | 3003 | CA | PRO | 445 | 54.913 | 42.497 | -10.276 | 1.00 | 40.90 | C1 |
| ATOM | 3004 | CB | PRO | 445 | 53.569 | 42.882 | -9.730 | 1.00 | 39.35 | C1 |
| ATOM | 3005 | CG | PRO | 445 | 53.364 | 44.274 | -10.215 | 1.00 | 39.35 | C1 |
| ATOM | 3006 | C | PRO | 445 | 54.868 | 41.782 | -11.600 | 1.00 | 42.18 | C1 |
| ATOM | 3007 | O | PRO | 445 | 54.769 | 40.571 | -11.569 | 1.00 | 45.69 | C1 |
| ATOM | 3008 | N | GLU | 446 | 55.082 | 42.380 | -12.769 | 1.00 | 41.64 | C1 |
| ATOM | 3009 | H | GLU | 446 | 55.320 | 43.320 | -12.761 | 1.00 | 0.00 | C1 |

FIG. 5JJ

| | | | | | | | | | | | | | | |
|---|---|---|---|---|---|---|---|---|---|---|---|---|---|---|
| ATOM | 3010 | CA | GLU | 446 | 55.025 | 41.656 | -14.029 | 1.00 | 42.05 | C | ATOM | 3053 | O | LEU | 450 | 54.297 | 31.406 | -12.266 | 1.00 | 55.62 | C |
| ATOM | 3011 | CB | GLU | 446 | 54.967 | 42.639 | -15.183 | 1.00 | 47.06 | C | ATOM | 3054 | N | LEU | 451 | 55.685 | 33.097 | -11.575 | 1.00 | 55.46 | C |
| ATOM | 3012 | CG | GLU | 446 | 54.109 | 43.925 | -14.992 | 1.00 | 56.71 | C | ATOM | 3055 | H | LEU | 451 | 56.073 | 33.954 | -11.849 | 1.00 | 0.00 | C |
| ATOM | 3013 | CD | GLU | 446 | 54.728 | 45.083 | -14.162 | 1.00 | 62.28 | C | ATOM | 3056 | CA | LEU | 451 | 55.998 | 32.654 | -10.223 | 1.00 | 56.01 | C |
| ATOM | 3014 | OE1 | GLU | 446 | 54.100 | 45.472 | -13.178 | 1.00 | 66.26 | C | ATOM | 3057 | CB | LEU | 451 | 57.137 | 33.542 | -9.731 | 1.00 | 55.80 | C |
| ATOM | 3015 | OE2 | GLU | 446 | 55.818 | 45.604 | -14.473 | 1.00 | 65.55 | C | ATOM | 3058 | CG | LEU | 451 | 57.745 | 33.278 | -8.394 | 1.00 | 56.96 | C |
| ATOM | 3016 | C | GLU | 446 | 56.237 | 40.722 | -14.197 | 1.00 | 40.44 | C | ATOM | 3059 | CD1 | LEU | 451 | 58.833 | 32.284 | -8.653 | 1.00 | 59.12 | C |
| ATOM | 3017 | O | GLU | 446 | 56.186 | 39.708 | -14.904 | 1.00 | 41.66 | C | ATOM | 3060 | CD2 | LEU | 451 | 58.369 | 34.511 | -7.751 | 1.00 | 58.27 | C |
| ATOM | 3018 | N | GLU | 447 | 57.360 | 40.995 | -13.538 | 1.00 | 37.89 | C | ATOM | 3061 | C | LEU | 451 | 54.785 | 32.700 | -9.280 | 1.00 | 55.96 | C |
| ATOM | 3019 | H | GLU | 447 | 57.394 | 41.809 | -12.999 | 1.00 | 0.00 | C | ATOM | 3062 | O | LEU | 451 | 54.717 | 31.935 | -8.319 | 1.00 | 53.74 | C |
| ATOM | 3020 | CA | GLU | 447 | 58.519 | 40.096 | -13.509 | 1.00 | 36.73 | C | ATOM | 3063 | N | GLY | 452 | 53.774 | 33.533 | -9.522 | 1.00 | 57.52 | C |
| ATOM | 3021 | CB | GLU | 447 | 59.750 | 40.810 | -12.976 | 1.00 | 34.60 | C | ATOM | 3064 | H | GLY | 452 | 53.889 | 34.241 | -10.191 | 1.00 | 0.00 | C |
| ATOM | 3022 | CG | GLU | 447 | 60.320 | 41.883 | -13.850 | 1.00 | 35.27 | C | ATOM | 3065 | CA | GLY | 452 | 52.567 | 33.515 | -8.710 | 1.00 | 60.66 | C |
| ATOM | 3023 | CD | GLU | 447 | 61.450 | 42.699 | -13.197 | 1.00 | 36.14 | C | ATOM | 3066 | C | GLY | 452 | 51.942 | 32.137 | -8.772 | 1.00 | 63.64 | C |
| ATOM | 3024 | OE1 | GLU | 447 | 62.240 | 43.286 | -13.939 | 1.00 | 37.31 | C | ATOM | 3067 | O | GLY | 452 | 51.476 | 31.593 | -7.782 | 1.00 | 62.60 | C |
| ATOM | 3025 | OE2 | GLU | 447 | 61.541 | 42.782 | -11.970 | 1.00 | 32.80 | C | ATOM | 3068 | N | HIS | 453 | 52.089 | 31.545 | -9.969 | 1.00 | 68.46 | C |
| ATOM | 3026 | C | GLU | 447 | 58.311 | 38.850 | -12.599 | 1.00 | 36.31 | C | ATOM | 3069 | H | HIS | 453 | 52.628 | 32.040 | -10.618 | 1.00 | 0.00 | C |
| ATOM | 3027 | O | GLU | 447 | 59.113 | 37.911 | -12.592 | 1.00 | 36.33 | C | ATOM | 3070 | CA | HIS | 453 | 51.606 | 30.205 | -10.326 | 1.00 | 72.27 | C |
| ATOM | 3028 | N | LEU | 448 | 57.273 | 38.763 | -11.769 | 1.00 | 33.81 | C | ATOM | 3071 | CB | HIS | 453 | 51.785 | 29.908 | -11.828 | 1.00 | 73.84 | C |
| ATOM | 3029 | H | LEU | 448 | 56.554 | 39.431 | -11.802 | 1.00 | 0.00 | C | ATOM | 3072 | CG | HIS | 453 | 51.421 | 31.061 | -12.777 | 1.00 | 77.81 | C |
| ATOM | 3030 | CA | LEU | 448 | 57.145 | 37.691 | -10.839 | 1.00 | 31.88 | C | ATOM | 3073 | CD2 | HIS | 453 | 50.599 | 32.148 | -12.498 | 1.00 | 79.29 | C |
| ATOM | 3031 | CB | LEU | 448 | 57.080 | 38.299 | -9.484 | 1.00 | 29.29 | C | ATOM | 3074 | ND1 | HIS | 453 | 51.886 | 31.244 | -14.012 | 1.00 | 79.84 | C |
| ATOM | 3032 | CG | LEU | 448 | 58.008 | 39.432 | -9.140 | 1.00 | 29.81 | C | ATOM | 3075 | HD1 | HIS | 453 | 52.617 | 30.739 | -14.425 | 1.00 | 0.00 | C |
| ATOM | 3033 | CD1 | LEU | 448 | 57.907 | 39.863 | -7.684 | 1.00 | 26.02 | C | ATOM | 3076 | CE1 | HIS | 453 | 51.385 | 32.382 | -14.470 | 1.00 | 81.11 | C |
| ATOM | 3034 | CD2 | LEU | 448 | 59.396 | 38.931 | -9.392 | 1.00 | 31.13 | C | ATOM | 3077 | NE2 | HIS | 453 | 50.613 | 32.923 | -13.551 | 1.00 | 79.85 | C |
| ATOM | 3035 | C | LEU | 448 | 55.863 | 36.977 | -11.165 | 1.00 | 33.75 | C | ATOM | 3078 | HE2 | HIS | 453 | 50.230 | 33.825 | -13.586 | 1.00 | 0.00 | C |
| ATOM | 3036 | O | LEU | 448 | 55.436 | 36.145 | -10.382 | 1.00 | 33.96 | C | ATOM | 3079 | C | HIS | 453 | 52.454 | 29.235 | -9.515 | 1.00 | 73.43 | C |
| ATOM | 3037 | N | VAL | 449 | 55.166 | 37.233 | -12.263 | 1.00 | 36.99 | C | ATOM | 3080 | O | HIS | 453 | 51.875 | 28.531 | -8.692 | 1.00 | 73.56 | C |
| ATOM | 3038 | H | VAL | 449 | 55.580 | 37.800 | -12.942 | 1.00 | 0.00 | C | ATOM | 3081 | N | SER | 454 | 53.785 | 29.207 | -9.651 | 1.00 | 74.64 | C |
| ATOM | 3039 | CA | VAL | 449 | 53.819 | 36.701 | -12.472 | 1.00 | 41.46 | C | ATOM | 3082 | H | SER | 454 | 54.214 | 29.739 | -10.351 | 1.00 | 0.00 | C |
| ATOM | 3040 | CB | VAL | 449 | 53.157 | 37.546 | -13.625 | 1.00 | 41.56 | C | ATOM | 3083 | CA | SER | 454 | 54.639 | 28.411 | -8.765 | 1.00 | 77.07 | C |
| ATOM | 3041 | CG1 | VAL | 449 | 54.002 | 37.614 | -14.880 | 1.00 | 42.22 | C | ATOM | 3084 | CB | SER | 454 | 56.123 | 28.762 | -8.980 | 1.00 | 77.34 | C |
| ATOM | 3042 | CG2 | VAL | 449 | 51.921 | 36.858 | -14.112 | 1.00 | 42.01 | C | ATOM | 3085 | OG | SER | 454 | 57.095 | 27.715 | -9.124 | 1.00 | 75.28 | C |
| ATOM | 3043 | C | VAL | 449 | 53.760 | 35.192 | -12.733 | 1.00 | 44.81 | C | ATOM | 3086 | HG | SER | 454 | 57.149 | 27.211 | -8.306 | 1.00 | 0.00 | C |
| ATOM | 3044 | O | VAL | 449 | 52.866 | 34.469 | -12.227 | 1.00 | 44.54 | C | ATOM | 3087 | C | SER | 454 | 54.332 | 28.608 | -7.262 | 1.00 | 78.84 | C |
| ATOM | 3045 | N | LEU | 450 | 54.716 | 34.669 | -13.515 | 1.00 | 47.21 | C | ATOM | 3088 | O | SER | 454 | 54.270 | 27.617 | -6.535 | 1.00 | 80.57 | C |
| ATOM | 3046 | H | LEU | 450 | 55.416 | 35.260 | -13.870 | 1.00 | 0.00 | C | ATOM | 3089 | N | LEU | 455 | 54.070 | 29.789 | -6.693 | 1.00 | 79.72 | C |
| ATOM | 3047 | CA | LEU | 450 | 54.771 | 33.243 | -13.781 | 1.00 | 50.57 | C | ATOM | 3090 | H | LEU | 455 | 53.956 | 30.582 | -7.250 | 1.00 | 0.00 | C |
| ATOM | 3048 | CB | LEU | 450 | 55.942 | 32.894 | -14.628 | 1.00 | 50.75 | C | ATOM | 3091 | CA | LEU | 455 | 53.849 | 29.915 | -5.257 | 1.00 | 80.43 | C |
| ATOM | 3049 | CG | LEU | 450 | 56.148 | 33.488 | -15.994 | 1.00 | 52.39 | C | ATOM | 3092 | CB | LEU | 455 | 54.085 | 31.347 | -4.838 | 1.00 | 80.20 | C |
| ATOM | 3050 | CD1 | LEU | 450 | 57.152 | 32.586 | -16.673 | 1.00 | 53.05 | C | ATOM | 3093 | CG | LEU | 455 | 55.389 | 31.981 | -5.269 | 1.00 | 81.67 | C |
| ATOM | 3051 | CD2 | LEU | 450 | 54.882 | 33.534 | -16.833 | 1.00 | 54.10 | C | ATOM | 3094 | CD1 | LEU | 455 | 55.254 | 33.494 | -5.419 | 1.00 | 81.36 | C |
| ATOM | 3052 | C | LEU | 450 | 54.911 | 32.468 | -12.471 | 1.00 | 53.83 | C | ATOM | 3095 | CD2 | LEU | 455 | 56.431 | 31.579 | -4.264 | 1.00 | 82.26 | C |

FIG. 5KK

| ATOM | 3096 | C | LEU | 455 | 52.438 | 29.510 | -4.848 | 1.00 | 81.56 | C1 |
| --- | --- | --- | --- | --- | --- | --- | --- | --- | --- | --- |
| ATOM | 3097 | O | LEU | 455 | 52.038 | 29.893 | -3.741 | 1.00 | 82.22 | C1 |
| ATOM | 3098 | N | GLY | 456 | 51.653 | 28.816 | -5.708 | 1.00 | 81.89 | C1 |
| ATOM | 3099 | H | GLY | 456 | 52.026 | 28.592 | -6.584 | 1.00 | 0.00 | C1 |
| ATOM | 3100 | CA | GLY | 456 | 50.269 | 28.361 | -5.467 | 1.00 | 82.22 | C1 |
| ATOM | 3101 | C | GLY | 456 | 49.220 | 29.386 | -4.973 | 1.00 | 82.56 | C1 |
| ATOM | 3102 | O | GLY | 456 | 48.268 | 28.989 | -4.276 | 1.00 | 82.38 | C1 |
| ATOM | 3103 | N | ILE | 457 | 49.342 | 30.697 | -5.286 | 1.00 | 82.54 | C1 |
| ATOM | 3104 | H | ILE | 457 | 50.075 | 30.942 | -5.894 | 1.00 | 0.00 | C1 |
| ATOM | 3105 | CA | ILE | 457 | 48.435 | 31.761 | -4.824 | 1.00 | 81.63 | C1 |
| ATOM | 3106 | CB | ILE | 457 | 49.110 | 33.157 | -5.086 | 1.00 | 80.69 | C1 |
| ATOM | 3107 | CG2 | ILE | 457 | 48.218 | 34.305 | -4.662 | 1.00 | 79.76 | C1 |
| ATOM | 3108 | CG1 | ILE | 457 | 50.369 | 33.275 | -4.253 | 1.00 | 79.82 | C1 |
| ATOM | 3109 | CD | ILE | 457 | 51.506 | 33.868 | -5.081 | 1.00 | 77.89 | C1 |
| ATOM | 3110 | C | ILE | 457 | 47.048 | 31.698 | -5.472 | 1.00 | 81.70 | C1 |
| ATOM | 3111 | O | ILE | 457 | 46.903 | 31.761 | -6.700 | 1.00 | 82.57 | C1 |
| ATOM | 3112 | N | PRO | 458 | 45.963 | 31.583 | -4.705 | 1.00 | 81.40 | C1 |
| ATOM | 3113 | CD | PRO | 458 | 45.959 | 31.225 | -3.278 | 1.00 | 81.21 | C1 |
| ATOM | 3114 | CA | PRO | 458 | 44.607 | 31.643 | -5.264 | 1.00 | 80.74 | C1 |
| ATOM | 3115 | CB | PRO | 458 | 43.779 | 30.942 | -4.157 | 1.00 | 81.12 | C1 |
| ATOM | 3116 | CG | PRO | 458 | 44.757 | 30.293 | -3.173 | 1.00 | 80.47 | C1 |
| ATOM | 3117 | C | PRO | 458 | 44.120 | 33.063 | -5.648 | 1.00 | 79.70 | C1 |
| ATOM | 3118 | O | PRO | 458 | 43.674 | 33.736 | -4.718 | 1.00 | 80.10 | C1 |
| ATOM | 3119 | N | TRP | 459 | 44.171 | 33.662 | -6.861 | 1.00 | 78.19 | C1 |
| ATOM | 3120 | H | TRP | 459 | 44.614 | 33.185 | -7.591 | 1.00 | 0.00 | C1 |
| ATOM | 3121 | CA | TRP | 459 | 43.543 | 34.986 | -7.092 | 1.00 | 77.73 | C1 |
| ATOM | 3122 | CB | TRP | 459 | 43.802 | 35.428 | -8.522 | 1.00 | 78.71 | C1 |
| ATOM | 3123 | CG | TRP | 459 | 43.054 | 36.677 | -9.017 | 1.00 | 81.37 | C1 |
| ATOM | 3124 | CD2 | TRP | 459 | 41.802 | 36.771 | -9.618 | 1.00 | 82.89 | C1 |
| ATOM | 3125 | CE2 | TRP | 459 | 41.717 | 38.139 | -9.883 | 1.00 | 84.21 | C1 |
| ATOM | 3126 | CE3 | TRP | 459 | 40.738 | 35.960 | -9.983 | 1.00 | 84.28 | C1 |
| ATOM | 3127 | CD1 | TRP | 459 | 43.661 | 37.899 | -8.925 | 1.00 | 83.89 | C1 |
| ATOM | 3128 | NE1 | TRP | 459 | 42.828 | 38.765 | -9.460 | 1.00 | 85.23 | C1 |
| ATOM | 3129 | HE1 | TRP | 459 | 42.944 | 39.738 | -9.483 | 1.00 | 0.00 | C1 |
| ATOM | 3130 | CZ2 | TRP | 459 | 40.615 | 38.727 | -10.494 | 1.00 | 84.17 | C1 |
| ATOM | 3131 | CZ3 | TRP | 459 | 39.630 | 36.538 | -10.597 | 1.00 | 84.56 | C1 |
| ATOM | 3132 | CH2 | TRP | 459 | 39.562 | 37.904 | -10.852 | 1.00 | 84.83 | C1 |
| ATOM | 3133 | C | TRP | 459 | 42.009 | 35.013 | -6.827 | 1.00 | 77.31 | C1 |
| ATOM | 3134 | O | TRP | 459 | 41.202 | 34.244 | -7.376 | 1.00 | 76.38 | C1 |
| ATOM | 3135 | N | ALA | 460 | 41.557 | 35.969 | -6.020 | 1.00 | 76.81 | C1 |
| ATOM | 3136 | H | ALA | 460 | 42.187 | 36.640 | -5.689 | 1.00 | 0.00 | C1 |
| ATOM | 3137 | CA | ALA | 460 | 40.158 | 36.044 | -5.613 | 1.00 | 76.44 | C1 |
| ATOM | 3138 | CB | ALA | 460 | 40.072 | 36.724 | -4.243 | 1.00 | 75.51 | C1 |
| ATOM | 3139 | C | ALA | 460 | 39.237 | 36.784 | -6.588 | 1.00 | 76.29 | C1 |
| ATOM | 3140 | O | ALA | 460 | 39.449 | 37.976 | -6.833 | 1.00 | 76.98 | C1 |
| ATOM | 3141 | N | PRO | 461 | 38.217 | 36.147 | -7.187 | 1.00 | 76.26 | C1 |
| ATOM | 3142 | CD | PRO | 461 | 38.104 | 34.684 | -7.245 | 1.00 | 75.88 | C1 |
| ATOM | 3143 | CA | PRO | 461 | 37.242 | 36.793 | -8.068 | 1.00 | 75.46 | C1 |
| ATOM | 3144 | CB | PRO | 461 | 36.605 | 35.605 | -8.755 | 1.00 | 75.71 | C1 |
| ATOM | 3145 | CG | PRO | 461 | 36.703 | 34.458 | -7.767 | 1.00 | 75.60 | C1 |
| ATOM | 3146 | C | PRO | 461 | 36.221 | 37.803 | -7.545 | 1.00 | 75.72 | C1 |
| ATOM | 3147 | O | PRO | 461 | 35.677 | 37.734 | -6.440 | 1.00 | 73.66 | C1 |
| ATOM | 3148 | N | LEU | 462 | 35.996 | 38.767 | -8.449 | 1.00 | 77.19 | C1 |
| ATOM | 3149 | H | LEU | 462 | 36.516 | 38.723 | -9.277 | 1.00 | 0.00 | C1 |
| ATOM | 3150 | CA | LEU | 462 | 35.069 | 39.891 | -8.275 | 1.00 | 78.87 | C1 |
| ATOM | 3151 | CB | LEU | 462 | 35.674 | 40.984 | -7.360 | 1.00 | 78.32 | C1 |
| ATOM | 3152 | CG | LEU | 462 | 34.786 | 41.959 | -6.558 | 1.00 | 78.09 | C1 |
| ATOM | 3153 | CD1 | LEU | 462 | 34.051 | 42.987 | -7.406 | 1.00 | 78.32 | C1 |
| ATOM | 3154 | CD2 | LEU | 462 | 33.767 | 41.092 | -5.828 | 1.00 | 78.62 | C1 |
| ATOM | 3155 | C | LEU | 462 | 34.701 | 40.565 | -9.611 | 1.00 | 80.63 | C1 |
| ATOM | 3156 | OT1 | LEU | 462 | 33.507 | 40.842 | -9.808 | 1.00 | 81.74 | C1 |
| ATOM | 3157 | OT2 | LEU | 462 | 35.606 | 40.847 | -10.417 | 1.00 | 81.39 | C1 |
| ATOM | 3158 | CB | LEU | 472 | 22.074 | 42.654 | -1.426 | 1.00 | 62.24 | C2 |
| ATOM | 3159 | CG | LEU | 472 | 22.278 | 44.145 | -1.189 | 1.00 | 59.98 | C2 |
| ATOM | 3160 | CD1 | LEU | 472 | 23.496 | 44.325 | -0.328 | 1.00 | 59.13 | C2 |
| ATOM | 3161 | CD2 | LEU | 472 | 22.501 | 44.883 | -2.486 | 1.00 | 56.85 | C2 |
| ATOM | 3162 | C | LEU | 472 | 23.504 | 40.625 | -1.996 | 1.00 | 63.91 | C2 |
| ATOM | 3163 | O | LEU | 472 | 23.738 | 39.874 | -2.949 | 1.00 | 64.90 | C2 |
| ATOM | 3164 | HT1 | LEU | 472 | 21.563 | 41.441 | -3.595 | 1.00 | 0.00 | C2 |
| ATOM | 3165 | HT2 | LEU | 472 | 23.091 | 41.291 | -4.237 | 1.00 | 0.00 | C2 |
| ATOM | 3166 | N | LEU | 472 | 22.472 | 41.930 | -3.693 | 1.00 | 64.29 | C2 |
| ATOM | 3167 | HT3 | LEU | 472 | 22.358 | 42.849 | -4.160 | 1.00 | 0.00 | C2 |
| ATOM | 3168 | CA | LEU | 472 | 23.092 | 42.037 | -2.386 | 1.00 | 63.85 | C2 |
| ATOM | 3169 | N | ALA | 473 | 23.652 | 40.229 | -0.733 | 1.00 | 63.02 | C2 |
| ATOM | 3170 | H | ALA | 473 | 23.533 | 40.867 | 0.002 | 1.00 | 0.00 | C2 |
| ATOM | 3171 | CA | ALA | 473 | 24.023 | 38.881 | -0.353 | 1.00 | 62.37 | C2 |
| ATOM | 3172 | CB | ALA | 473 | 22.870 | 37.939 | -0.558 | 1.00 | 63.65 | C2 |
| ATOM | 3173 | C | ALA | 473 | 25.196 | 38.354 | -1.126 | 1.00 | 62.01 | C2 |
| ATOM | 3174 | O | ALA | 473 | 26.301 | 38.651 | -0.715 | 1.00 | 63.36 | C2 |
| ATOM | 3175 | N | GLY | 474 | 25.032 | 37.784 | -2.306 | 1.00 | 61.43 | C2 |
| ATOM | 3176 | H | GLY | 474 | 24.148 | 37.818 | -2.722 | 1.00 | 0.00 | C2 |
| ATOM | 3177 | CA | GLY | 474 | 26.101 | 37.137 | -3.047 | 1.00 | 63.80 | C2 |
| ATOM | 3178 | C | GLY | 474 | 27.354 | 37.950 | -3.356 | 1.00 | 65.13 | C2 |
| ATOM | 3179 | O | GLY | 474 | 28.482 | 37.417 | -3.257 | 1.00 | 66.24 | C2 |
| ATOM | 3180 | N | CYS | 475 | 27.175 | 39.237 | -3.757 | 1.00 | 64.88 | C2 |
| ATOM | 3181 | H | CYS | 475 | 26.261 | 39.550 | -3.885 | 1.00 | 0.00 | C2 |

FIG. 5LL

| | | | | | | | | | | | | | | | |
|---|---|---|---|---|---|---|---|---|---|---|---|---|---|---|---|
| ATOM | 3182 | CA | CYS | 475 | 28.308 | 40.127 | -4.068 | 1.00 | 61.84 | C2 | ATOM | 3225 | N | HIS | 480 | 33.609 | 39.766 | 0.950 | 1.00 | 39.56 | C2 |
| ATOM | 3183 | CB | CYS | 475 | 27.925 | 41.413 | -4.806 | 1.00 | 63.74 | C2 | ATOM | 3226 | H | HIS | 480 | 32.658 | 39.935 | 0.763 | 1.00 | 0.00 | C2 |
| ATOM | 3184 | SG | CYS | 475 | 29.494 | 42.075 | -5.437 | 1.00 | 68.86 | C2 | ATOM | 3227 | CA | HIS | 480 | 33.979 | 39.108 | 2.179 | 1.00 | 37.81 | C2 |
| ATOM | 3185 | C | CYS | 475 | 28.995 | 40.567 | -2.795 | 1.00 | 57.30 | C2 | ATOM | 3228 | CB | HIS | 480 | 32.742 | 38.714 | 2.922 | 1.00 | 34.29 | C2 |
| ATOM | 3186 | O | CYS | 475 | 30.214 | 40.449 | -2.724 | 1.00 | 57.14 | C2 | ATOM | 3229 | CG | HIS | 480 | 33.094 | 38.241 | 4.309 | 1.00 | 33.82 | C2 |
| ATOM | 3187 | N | LEU | 476 | 28.230 | 40.983 | -1.779 | 1.00 | 53.29 | C2 | ATOM | 3230 | CD2 | HIS | 480 | 33.123 | 36.932 | 4.709 | 1.00 | 33.44 | C2 |
| ATOM | 3188 | H | LEU | 476 | 27.264 | 41.024 | -1.885 | 1.00 | 0.00 | C2 | ATOM | 3231 | ND1 | HIS | 480 | 33.450 | 38.995 | 5.344 | 1.00 | 34.27 | C2 |
| ATOM | 3189 | CA | LEU | 476 | 28.797 | 41.315 | -0.493 | 1.00 | 50.43 | C2 | ATOM | 3232 | HD1 | HIS | 480 | 33.505 | 39.976 | 5.362 | 1.00 | 0.00 | C2 |
| ATOM | 3190 | CB | LEU | 476 | 27.719 | 41.723 | 0.523 | 1.00 | 45.68 | C2 | ATOM | 3233 | CE1 | HIS | 480 | 33.706 | 38.223 | 6.365 | 1.00 | 33.80 | C2 |
| ATOM | 3191 | CG | LEU | 476 | 27.130 | 43.165 | 0.497 | 1.00 | 42.80 | C2 | ATOM | 3234 | NE2 | HIS | 480 | 33.504 | 36.986 | 5.965 | 1.00 | 37.12 | C2 |
| ATOM | 3192 | CD1 | LEU | 476 | 26.670 | 43.559 | 1.896 | 1.00 | 36.25 | C2 | ATOM | 3235 | HE2 | HIS | 480 | 33.637 | 36.202 | 6.544 | 1.00 | 0.00 | C2 |
| ATOM | 3193 | CD2 | LEU | 476 | 28.180 | 44.180 | 0.057 | 1.00 | 40.22 | C2 | ATOM | 3236 | C | HIS | 480 | 34.836 | 37.860 | 1.961 | 1.00 | 39.08 | C2 |
| ATOM | 3194 | C | LEU | 476 | 29.546 | 40.108 | 0.042 | 1.00 | 50.42 | C2 | ATOM | 3237 | O | HIS | 480 | 35.716 | 37.631 | 2.791 | 1.00 | 40.93 | C2 |
| ATOM | 3195 | O | LEU | 476 | 30.614 | 40.222 | 0.646 | 1.00 | 50.61 | C2 | ATOM | 3238 | N | SER | 481 | 34.615 | 37.029 | 0.935 | 1.00 | 39.24 | C2 |
| ATOM | 3196 | N | SER | 477 | 29.053 | 38.922 | -0.270 | 1.00 | 50.62 | C2 | ATOM | 3239 | H | SER | 481 | 33.900 | 37.241 | 0.305 | 1.00 | 0.00 | C2 |
| ATOM | 3197 | H | SER | 477 | 28.196 | 38.860 | -0.729 | 1.00 | 0.00 | C2 | ATOM | 3240 | CA | SER | 481 | 35.391 | 35.818 | 0.683 | 1.00 | 38.17 | C2 |
| ATOM | 3198 | CA | SER | 477 | 29.721 | 37.697 | 0.125 | 1.00 | 51.41 | C2 | ATOM | 3241 | CB | SER | 481 | 34.813 | 34.943 | -0.420 | 1.00 | 40.42 | C2 |
| ATOM | 3199 | CB | SER | 477 | 28.778 | 36.524 | -0.051 | 1.00 | 53.45 | C2 | ATOM | 3242 | OG | SER | 481 | 33.454 | 34.597 | -0.137 | 1.00 | 47.61 | C2 |
| ATOM | 3200 | OG | SER | 477 | 27.732 | 36.616 | 0.926 | 1.00 | 57.65 | C2 | ATOM | 3243 | HG | SER | 481 | 32.898 | 35.385 | -0.162 | 1.00 | 0.00 | C2 |
| ATOM | 3201 | HG | SER | 477 | 27.280 | 37.462 | 0.828 | 1.00 | 0.00 | C2 | ATOM | 3244 | C | SER | 481 | 36.724 | 36.272 | 0.211 | 1.00 | 36.12 | C2 |
| ATOM | 3202 | C | SER | 477 | 30.978 | 37.525 | -0.681 | 1.00 | 50.75 | C2 | ATOM | 3245 | O | SER | 481 | 37.692 | 35.793 | 0.765 | 1.00 | 36.23 | C2 |
| ATOM | 3203 | O | SER | 477 | 31.980 | 37.143 | -0.068 | 1.00 | 51.41 | C2 | ATOM | 3246 | N | GLY | 482 | 36.786 | 37.206 | -0.744 | 1.00 | 36.21 | C2 |
| ATOM | 3204 | N | GLN | 478 | 31.037 | 37.788 | -1.984 | 1.00 | 50.21 | C2 | ATOM | 3247 | H | GLY | 482 | 35.956 | 37.498 | -1.168 | 1.00 | 0.00 | C2 |
| ATOM | 3205 | H | GLN | 478 | 30.222 | 38.056 | -2.457 | 1.00 | 0.00 | C2 | ATOM | 3248 | CA | GLY | 482 | 38.028 | 37.792 | -1.266 | 1.00 | 36.50 | C2 |
| ATOM | 3206 | CA | GLN | 478 | 32.307 | 37.697 | -2.715 | 1.00 | 51.37 | C2 | ATOM | 3249 | C | GLY | 482 | 38.958 | 38.296 | -0.151 | 1.00 | 36.14 | C2 |
| ATOM | 3207 | CB | GLN | 478 | 32.064 | 37.929 | -4.166 | 1.00 | 53.65 | C2 | ATOM | 3250 | O | GLY | 482 | 40.142 | 37.936 | -0.055 | 1.00 | 36.65 | C2 |
| ATOM | 3208 | CG | GLN | 478 | 31.983 | 36.570 | -4.788 | 1.00 | 57.32 | C2 | ATOM | 3251 | N | LEU | 483 | 38.381 | 39.084 | 0.750 | 1.00 | 34.04 | C2 |
| ATOM | 3209 | CD | GLN | 478 | 31.354 | 36.649 | -6.160 | 1.00 | 60.47 | C2 | ATOM | 3252 | H | LEU | 483 | 37.445 | 39.326 | 0.608 | 1.00 | 0.00 | C2 |
| ATOM | 3210 | OE1 | GLN | 478 | 31.999 | 36.504 | -7.205 | 1.00 | 62.26 | C2 | ATOM | 3253 | CA | LEU | 483 | 39.073 | 39.593 | 1.900 | 1.00 | 32.07 | C2 |
| ATOM | 3211 | NE2 | GLN | 478 | 30.045 | 36.878 | -6.167 | 1.00 | 62.16 | C2 | ATOM | 3254 | CB | LEU | 483 | 38.134 | 40.442 | 2.731 | 1.00 | 31.17 | C2 |
| ATOM | 3212 | HE21 | GLN | 478 | 29.569 | 36.972 | -5.317 | 1.00 | 0.00 | C2 | ATOM | 3255 | CG | LEU | 483 | 37.535 | 41.687 | 2.081 | 1.00 | 31.11 | C2 |
| ATOM | 3213 | HE22 | GLN | 478 | 29.641 | 36.928 | -7.054 | 1.00 | 0.00 | C2 | ATOM | 3256 | CD1 | LEU | 483 | 36.757 | 42.411 | 3.156 | 1.00 | 30.82 | C2 |
| ATOM | 3214 | C | GLN | 478 | 33.398 | 38.670 | -2.249 | 1.00 | 50.56 | C2 | ATOM | 3257 | CD2 | LEU | 483 | 38.599 | 42.593 | 1.480 | 1.00 | 29.50 | C2 |
| ATOM | 3215 | O | GLN | 478 | 34.584 | 38.314 | -2.217 | 1.00 | 50.13 | C2 | ATOM | 3258 | C | LEU | 483 | 39.600 | 38.461 | 2.745 | 1.00 | 32.91 | C2 |
| ATOM | 3216 | N | LEU | 479 | 33.045 | 39.909 | -1.859 | 1.00 | 48.78 | C2 | ATOM | 3259 | O | LEU | 483 | 40.752 | 38.498 | 3.199 | 1.00 | 31.25 | C2 |
| ATOM | 3217 | H | LEU | 479 | 32.131 | 40.223 | -2.039 | 1.00 | 0.00 | C2 | ATOM | 3260 | N | PHE | 484 | 38.767 | 37.422 | 2.925 | 1.00 | 34.08 | C2 |
| ATOM | 3218 | CA | LEU | 479 | 34.015 | 40.800 | -1.235 | 1.00 | 45.87 | C2 | ATOM | 3261 | H | PHE | 484 | 37.900 | 37.408 | 2.471 | 1.00 | 0.00 | C2 |
| ATOM | 3219 | CB | LEU | 479 | 33.434 | 42.141 | -0.827 | 1.00 | 47.03 | C2 | ATOM | 3262 | CA | PHE | 484 | 39.105 | 36.298 | 3.788 | 1.00 | 34.60 | C2 |
| ATOM | 3220 | CG | LEU | 479 | 32.853 | 43.083 | -1.818 | 1.00 | 49.40 | C2 | ATOM | 3263 | CB | PHE | 484 | 37.975 | 35.300 | 3.925 | 1.00 | 37.46 | C2 |
| ATOM | 3221 | CD1 | LEU | 479 | 32.596 | 44.393 | -1.078 | 1.00 | 48.15 | C2 | ATOM | 3264 | CG | PHE | 484 | 38.268 | 34.183 | 4.897 | 1.00 | 40.86 | C2 |
| ATOM | 3222 | CD2 | LEU | 479 | 33.779 | 43.258 | -3.000 | 1.00 | 48.59 | C2 | ATOM | 3265 | CD1 | PHE | 484 | 38.219 | 32.884 | 4.482 | 1.00 | 45.62 | C2 |
| ATOM | 3223 | C | LEU | 479 | 34.505 | 40.146 | 0.056 | 1.00 | 42.13 | C2 | ATOM | 3266 | CD2 | PHE | 484 | 38.528 | 34.445 | 6.210 | 1.00 | 43.62 | C2 |
| ATOM | 3224 | O | LEU | 479 | 35.695 | 39.955 | 0.262 | 1.00 | 40.90 | C2 | ATOM | 3267 | CE1 | PHE | 484 | 38.421 | 31.858 | 5.395 | 1.00 | 47.98 | C2 |

FIG. 5MM

| | | | | | | | | | | |
|---|---|---|---|---|---|---|---|---|---|---|
| ATOM | 3268 | CE2 | PHE | 484 | 38.731 | 33.427 | 7.119 | 1.00 | 46.78 | C2 |
| ATOM | 3269 | CZ | PHE | 484 | 38.677 | 32.119 | 6.720 | 1.00 | 48.06 | C2 |
| ATOM | 3270 | C | PHE | 484 | 40.245 | 35.602 | 3.113 | 1.00 | 33.92 | C2 |
| ATOM | 3271 | O | PHE | 484 | 41.162 | 35.289 | 3.826 | 1.00 | 34.25 | C2 |
| ATOM | 3272 | N | LEU | 485 | 40.326 | 35.413 | 1.799 | 1.00 | 32.75 | C2 |
| ATOM | 3273 | H | LEU | 485 | 39.577 | 35.717 | 1.250 | 1.00 | 0.00 | C2 |
| ATOM | 3274 | CA | LEU | 485 | 41.475 | 34.778 | 1.163 | 1.00 | 33.74 | C2 |
| ATOM | 3275 | CB | LEU | 485 | 41.183 | 34.629 | -0.305 | 1.00 | 35.35 | C2 |
| ATOM | 3276 | CG | LEU | 485 | 42.101 | 33.962 | -1.275 | 1.00 | 37.80 | C2 |
| ATOM | 3277 | CD1 | LEU | 485 | 41.181 | 33.404 | -2.345 | 1.00 | 41.44 | C2 |
| ATOM | 3278 | CD2 | LEU | 485 | 43.125 | 34.903 | -1.899 | 1.00 | 40.07 | C2 |
| ATOM | 3279 | C | LEU | 485 | 42.740 | 35.585 | 1.376 | 1.00 | 33.95 | C2 |
| ATOM | 3280 | O | LEU | 485 | 43.766 | 35.060 | 1.850 | 1.00 | 33.84 | C2 |
| ATOM | 3281 | N | TYR | 486 | 42.609 | 36.885 | 1.034 | 1.00 | 33.67 | C2 |
| ATOM | 3282 | H | TYR | 486 | 41.757 | 37.186 | 0.659 | 1.00 | 0.00 | C2 |
| ATOM | 3283 | CA | TYR | 486 | 43.662 | 37.862 | 1.242 | 1.00 | 31.33 | C2 |
| ATOM | 3284 | CB | TYR | 486 | 43.210 | 39.290 | 0.714 | 1.00 | 35.33 | C2 |
| ATOM | 3285 | CG | TYR | 486 | 43.300 | 39.325 | -0.825 | 1.00 | 33.37 | C2 |
| ATOM | 3286 | CD1 | TYR | 486 | 42.154 | 39.405 | -1.579 | 1.00 | 32.79 | C2 |
| ATOM | 3287 | CE1 | TYR | 486 | 42.228 | 39.290 | -2.944 | 1.00 | 33.73 | C2 |
| ATOM | 3288 | CD2 | TYR | 486 | 44.533 | 39.153 | -1.445 | 1.00 | 34.59 | C2 |
| ATOM | 3289 | CE2 | TYR | 486 | 44.618 | 39.033 | -2.818 | 1.00 | 34.63 | C2 |
| ATOM | 3290 | CZ | TYR | 486 | 43.451 | 39.096 | -3.562 | 1.00 | 35.58 | C2 |
| ATOM | 3291 | OH | TYR | 486 | 43.484 | 38.880 | -4.942 | 1.00 | 38.24 | C2 |
| ATOM | 3292 | HH | TYR | 486 | 42.614 | 39.086 | -5.306 | 1.00 | 0.00 | C2 |
| ATOM | 3293 | C | TYR | 486 | 44.068 | 37.905 | 2.697 | 1.00 | 27.39 | C2 |
| ATOM | 3294 | O | TYR | 486 | 45.258 | 38.007 | 2.942 | 1.00 | 26.06 | C2 |
| ATOM | 3295 | N | GLN | 487 | 43.270 | 37.691 | 3.708 | 1.00 | 26.95 | C2 |
| ATOM | 3296 | H | GLN | 487 | 42.315 | 37.545 | 3.565 | 1.00 | 0.00 | C2 |
| ATOM | 3297 | CA | GLN | 487 | 43.835 | 37.646 | 5.031 | 1.00 | 28.33 | C2 |
| ATOM | 3298 | CB | GLN | 487 | 42.690 | 37.578 | 6.050 | 1.00 | 32.66 | C2 |
| ATOM | 3299 | CG | GLN | 487 | 43.092 | 37.979 | 7.485 | 1.00 | 37.50 | C2 |
| ATOM | 3300 | CD | GLN | 487 | 43.966 | 39.252 | 7.469 | 1.00 | 40.54 | C2 |
| ATOM | 3301 | OE1 | GLN | 487 | 43.441 | 40.346 | 7.292 | 1.00 | 40.45 | C2 |
| ATOM | 3302 | NE2 | GLN | 487 | 43.305 | 39.206 | 7.549 | 1.00 | 38.19 | C2 |
| ATOM | 3303 | HE21 | GLN | 487 | 45.755 | 40.057 | 7.452 | 1.00 | 0.00 | C2 |
| ATOM | 3304 | HE22 | GLN | 487 | 45.736 | 38.340 | 7.702 | 1.00 | 0.00 | C2 |
| ATOM | 3305 | C | GLN | 487 | 44.791 | 36.455 | 5.207 | 1.00 | 28.53 | C2 |
| ATOM | 3306 | O | GLN | 487 | 45.774 | 36.542 | 5.964 | 1.00 | 28.72 | C2 |
| ATOM | 3307 | N | GLY | 488 | 44.550 | 35.363 | 4.454 | 1.00 | 28.32 | C2 |
| ATOM | 3308 | H | GLY | 488 | 43.799 | 35.400 | 3.824 | 1.00 | 0.00 | C2 |
| ATOM | 3309 | CA | GLY | 488 | 45.291 | 34.120 | 4.557 | 1.00 | 26.04 | C2 |
| ATOM | 3310 | C | GLY | 488 | 46.660 | 34.264 | 4.033 | 1.00 | 25.75 | C2 |
| ATOM | 3311 | O | GLY | 488 | 47.660 | 33.946 | 4.712 | 1.00 | 25.86 | C2 |
| ATOM | 3312 | N | LEU | 489 | 46.655 | 34.798 | 2.818 | 1.00 | 25.05 | C2 |
| ATOM | 3313 | H | LEU | 489 | 45.798 | 35.062 | 2.416 | 1.00 | 0.00 | C2 |
| ATOM | 3314 | CA | LEU | 489 | 47.911 | 34.990 | 2.099 | 1.00 | 25.63 | C2 |
| ATOM | 3315 | CB | LEU | 489 | 47.708 | 35.570 | 0.725 | 1.00 | 27.66 | C2 |
| ATOM | 3316 | CG | LEU | 489 | 46.761 | 34.755 | -0.189 | 1.00 | 30.83 | C2 |
| ATOM | 3317 | CD1 | LEU | 489 | 46.373 | 35.506 | -1.471 | 1.00 | 30.43 | C2 |
| ATOM | 3318 | CD2 | LEU | 489 | 47.472 | 33.454 | -0.502 | 1.00 | 32.62 | C2 |
| ATOM | 3319 | C | LEU | 489 | 48.783 | 35.936 | 2.853 | 1.00 | 25.28 | C2 |
| ATOM | 3320 | O | LEU | 489 | 49.973 | 35.705 | 2.914 | 1.00 | 27.37 | C2 |
| ATOM | 3321 | N | LEU | 490 | 48.237 | 36.935 | 3.534 | 1.00 | 25.79 | C2 |
| ATOM | 3322 | H | LEU | 490 | 47.267 | 37.079 | 3.515 | 1.00 | 0.00 | C2 |
| ATOM | 3323 | CA | LEU | 490 | 49.072 | 37.868 | 4.220 | 1.00 | 25.96 | C2 |
| ATOM | 3324 | CB | LEU | 490 | 48.274 | 39.139 | 4.567 | 1.00 | 27.96 | C2 |
| ATOM | 3325 | CG | LEU | 490 | 47.823 | 40.131 | 3.474 | 1.00 | 27.89 | C2 |
| ATOM | 3326 | CD1 | LEU | 490 | 46.772 | 41.019 | 4.123 | 1.00 | 28.03 | C2 |
| ATOM | 3327 | CD2 | LEU | 490 | 48.988 | 40.942 | 2.899 | 1.00 | 28.15 | C2 |
| ATOM | 3328 | C | LEU | 490 | 49.619 | 37.243 | 5.459 | 1.00 | 27.33 | C2 |
| ATOM | 3329 | O | LEU | 490 | 50.740 | 37.528 | 5.865 | 1.00 | 26.73 | C2 |
| ATOM | 3330 | N | GLN | 491 | 48.883 | 36.370 | 6.111 | 1.00 | 29.88 | C2 |
| ATOM | 3331 | H | GLN | 491 | 47.984 | 36.127 | 5.799 | 1.00 | 0.00 | C2 |
| ATOM | 3332 | CA | GLN | 491 | 49.430 | 35.809 | 7.314 | 1.00 | 33.01 | C2 |
| ATOM | 3333 | CB | GLN | 491 | 48.305 | 35.113 | 8.027 | 1.00 | 38.68 | C2 |
| ATOM | 3334 | CG | GLN | 491 | 47.856 | 35.963 | 9.197 | 1.00 | 46.07 | C2 |
| ATOM | 3335 | CD | GLN | 491 | 46.348 | 36.262 | 9.278 | 1.00 | 50.83 | C2 |
| ATOM | 3336 | OE1 | GLN | 491 | 45.965 | 37.436 | 9.402 | 1.00 | 51.92 | C2 |
| ATOM | 3337 | NE2 | GLN | 491 | 45.425 | 35.294 | 9.278 | 1.00 | 51.67 | C2 |
| ATOM | 3338 | HE21 | GLN | 491 | 45.723 | 34.353 | 9.288 | 1.00 | 0.00 | C2 |
| ATOM | 3339 | HE22 | GLN | 491 | 44.489 | 35.560 | 9.286 | 1.00 | 0.00 | C2 |
| ATOM | 3340 | C | GLN | 491 | 50.582 | 34.867 | 6.986 | 1.00 | 33.58 | C2 |
| ATOM | 3341 | O | GLN | 491 | 51.582 | 34.828 | 7.715 | 1.00 | 34.65 | C2 |
| ATOM | 3342 | N | ALA | 492 | 50.482 | 34.191 | 5.824 | 1.00 | 34.15 | C2 |
| ATOM | 3343 | H | ALA | 492 | 49.701 | 34.382 | 5.264 | 1.00 | 0.00 | C2 |
| ATOM | 3344 | CA | ALA | 492 | 51.416 | 33.177 | 5.321 | 1.00 | 33.64 | C2 |
| ATOM | 3345 | CB | ALA | 492 | 50.818 | 32.500 | 4.081 | 1.00 | 31.67 | C2 |
| ATOM | 3346 | C | ALA | 492 | 52.802 | 33.678 | 4.959 | 1.00 | 34.79 | C2 |
| ATOM | 3347 | O | ALA | 492 | 53.789 | 32.943 | 4.879 | 1.00 | 36.03 | C2 |
| ATOM | 3348 | N | LEU | 493 | 52.885 | 34.981 | 4.728 | 1.00 | 35.94 | C2 |
| ATOM | 3349 | H | LEU | 493 | 52.060 | 35.510 | 4.721 | 1.00 | 0.00 | C2 |
| ATOM | 3350 | CA | LEU | 493 | 54.139 | 35.634 | 4.426 | 1.00 | 34.86 | C2 |
| ATOM | 3351 | CB | LEU | 493 | 53.898 | 36.990 | 3.747 | 1.00 | 31.36 | C2 |
| ATOM | 3352 | CG | LEU | 493 | 53.127 | 37.065 | 2.443 | 1.00 | 28.27 | C2 |
| ATOM | 3353 | CD1 | LEU | 493 | 52.715 | 38.495 | 2.214 | 1.00 | 31.74 | C2 |

FIG. 5NN

| ATOM | 3354 | CD2 | LEU | 493 | 53.977 | 36.608 | 1.285 | 1.00 | 28.79 | C2 |
|---|---|---|---|---|---|---|---|---|---|---|
| ATOM | 3355 | C | LEU | 493 | 54.879 | 35.843 | 5.721 | 1.00 | 36.15 | C2 |
| ATOM | 3356 | O | LEU | 493 | 55.985 | 36.374 | 5.694 | 1.00 | 36.70 | C2 |
| ATOM | 3357 | N | GLU | 494 | 54.300 | 35.497 | 6.855 | 1.00 | 38.35 | C2 |
| ATOM | 3358 | H | GLU | 494 | 53.395 | 35.130 | 6.836 | 1.00 | 0.00 | C2 |
| ATOM | 3359 | CA | GLU | 494 | 54.910 | 35.648 | 8.157 | 1.00 | 43.14 | C2 |
| ATOM | 3360 | CB | GLU | 494 | 55.621 | 34.340 | 8.545 | 1.00 | 46.61 | C2 |
| ATOM | 3361 | CG | GLU | 494 | 54.711 | 33.471 | 9.419 | 1.00 | 53.71 | C2 |
| ATOM | 3362 | CD | GLU | 494 | 54.195 | 32.160 | 8.785 | 1.00 | 60.27 | C2 |
| ATOM | 3363 | OE1 | GLU | 494 | 53.146 | 31.653 | 9.230 | 1.00 | 63.52 | C2 |
| ATOM | 3364 | OE2 | GLU | 494 | 54.839 | 31.630 | 7.862 | 1.00 | 62.76 | C2 |
| ATOM | 3365 | C | GLU | 494 | 55.865 | 36.825 | 8.343 | 1.00 | 44.32 | C2 |
| ATOM | 3366 | O | GLU | 494 | 57.055 | 36.678 | 8.610 | 1.00 | 46.91 | C2 |
| ATOM | 3367 | N | GLY | 495 | 55.358 | 38.046 | 8.114 | 1.00 | 44.32 | C2 |
| ATOM | 3368 | H | GLY | 495 | 54.450 | 38.112 | 7.753 | 1.00 | 0.00 | C2 |
| ATOM | 3369 | CA | GLY | 495 | 56.104 | 39.272 | 8.368 | 1.00 | 42.36 | C2 |
| ATOM | 3370 | C | GLY | 495 | 57.015 | 39.695 | 7.238 | 1.00 | 42.33 | C2 |
| ATOM | 3371 | O | GLY | 495 | 57.397 | 40.866 | 7.220 | 1.00 | 42.42 | C2 |
| ATOM | 3372 | N | ILE | 496 | 57.310 | 38.802 | 6.279 | 1.00 | 41.04 | C2 |
| ATOM | 3373 | H | ILE | 496 | 56.927 | 37.906 | 6.374 | 1.00 | 0.00 | C2 |
| ATOM | 3374 | CA | ILE | 496 | 58.259 | 38.993 | 5.192 | 1.00 | 41.15 | C2 |
| ATOM | 3375 | CB | ILE | 496 | 57.929 | 40.216 | 4.253 | 1.00 | 38.60 | C2 |
| ATOM | 3376 | CG2 | ILE | 496 | 59.077 | 40.437 | 3.248 | 1.00 | 37.62 | C2 |
| ATOM | 3377 | CG1 | ILE | 496 | 56.662 | 39.964 | 3.480 | 1.00 | 36.39 | C2 |
| ATOM | 3378 | CD | ILE | 496 | 56.104 | 39.272 | 2.470 | 1.00 | 35.27 | C2 |
| ATOM | 3379 | C | ILE | 496 | 59.672 | 39.203 | 5.749 | 1.00 | 42.91 | C2 |
| ATOM | 3380 | O | ILE | 496 | 60.541 | 38.396 | 5.448 | 1.00 | 44.22 | C2 |
| ATOM | 3381 | N | SER | 497 | 59.998 | 40.228 | 6.533 | 1.00 | 44.31 | C2 |
| ATOM | 3382 | H | SER | 497 | 59.297 | 40.852 | 6.827 | 1.00 | 0.00 | C2 |
| ATOM | 3383 | CA | SER | 497 | 61.346 | 40.501 | 6.992 | 1.00 | 44.86 | C2 |
| ATOM | 3384 | CB | SER | 497 | 62.204 | 41.254 | 5.938 | 1.00 | 44.13 | C2 |
| ATOM | 3385 | OG | SER | 497 | 62.181 | 42.673 | 6.033 | 1.00 | 40.74 | C2 |
| ATOM | 3386 | HG | SER | 497 | 62.531 | 42.964 | 5.170 | 1.00 | 0.00 | C2 |
| ATOM | 3387 | C | SER | 497 | 61.164 | 41.413 | 8.185 | 1.00 | 45.85 | C2 |
| ATOM | 3388 | O | SER | 497 | 60.132 | 42.110 | 8.288 | 1.00 | 47.55 | C2 |
| ATOM | 3389 | N | PRO | 498 | 62.164 | 41.490 | 9.071 | 1.00 | 44.96 | C2 |
| ATOM | 3390 | CD | PRO | 498 | 63.338 | 40.621 | 9.126 | 1.00 | 42.33 | C2 |
| ATOM | 3391 | CA | PRO | 498 | 62.086 | 42.327 | 10.250 | 1.00 | 44.88 | C2 |
| ATOM | 3392 | CB | PRO | 498 | 63.431 | 42.038 | 10.885 | 1.00 | 45.13 | C2 |
| ATOM | 3393 | CG | PRO | 498 | 63.629 | 40.581 | 10.603 | 1.00 | 42.00 | C2 |
| ATOM | 3394 | C | PRO | 498 | 61.760 | 43.799 | 9.983 | 1.00 | 45.22 | C2 |
| ATOM | 3395 | O | PRO | 498 | 61.215 | 44.446 | 10.869 | 1.00 | 45.24 | C2 |
| ATOM | 3396 | N | GLU | 499 | 62.017 | 44.314 | 8.777 | 1.00 | 46.16 | C2 |
| ATOM | 3397 | H | GLU | 499 | 62.362 | 43.716 | 8.081 | 1.00 | 0.00 | C2 |
| ATOM | 3398 | CA | GLU | 499 | 61.731 | 45.699 | 8.391 | 1.00 | 48.06 | C2 |
| ATOM | 3399 | CB | GLU | 499 | 62.498 | 46.193 | 7.155 | 1.00 | 52.19 | C2 |
| ATOM | 3400 | CG | GLU | 499 | 64.001 | 46.187 | 7.100 | 1.00 | 57.51 | C2 |
| ATOM | 3401 | CD | GLU | 499 | 64.544 | 44.777 | 7.076 | 1.00 | 60.61 | C2 |
| ATOM | 3402 | OE1 | GLU | 499 | 64.755 | 44.231 | 8.162 | 1.00 | 62.96 | C2 |
| ATOM | 3403 | OE2 | GLU | 499 | 64.739 | 44.234 | 5.984 | 1.00 | 62.79 | C2 |
| ATOM | 3404 | C | GLU | 499 | 60.269 | 45.896 | 7.981 | 1.00 | 46.94 | C2 |
| ATOM | 3405 | O | GLU | 499 | 59.600 | 46.895 | 8.272 | 1.00 | 48.15 | C2 |
| ATOM | 3406 | N | LEU | 500 | 59.806 | 44.934 | 7.193 | 1.00 | 44.38 | C2 |
| ATOM | 3407 | H | LEU | 500 | 60.351 | 44.137 | 7.027 | 1.00 | 0.00 | C2 |
| ATOM | 3408 | CA | LEU | 500 | 58.491 | 44.997 | 6.651 | 1.00 | 41.08 | C2 |
| ATOM | 3409 | CB | LEU | 500 | 58.519 | 44.197 | 5.445 | 1.00 | 41.37 | C2 |
| ATOM | 3410 | CG | LEU | 500 | 59.303 | 44.862 | 4.351 | 1.00 | 42.70 | C2 |
| ATOM | 3411 | CD1 | LEU | 500 | 59.776 | 43.828 | 3.351 | 1.00 | 43.98 | C2 |
| ATOM | 3412 | CD2 | LEU | 500 | 58.427 | 45.874 | 3.671 | 1.00 | 45.04 | C2 |
| ATOM | 3413 | C | LEU | 500 | 57.455 | 44.521 | 7.628 | 1.00 | 40.59 | C2 |
| ATOM | 3414 | O | LEU | 500 | 56.274 | 44.835 | 7.463 | 1.00 | 40.69 | C2 |
| ATOM | 3415 | N | GLY | 501 | 57.866 | 43.835 | 8.685 | 1.00 | 39.37 | C2 |
| ATOM | 3416 | H | GLY | 501 | 58.808 | 43.579 | 8.730 | 1.00 | 0.00 | C2 |
| ATOM | 3417 | CA | GLY | 501 | 56.974 | 43.386 | 9.734 | 1.00 | 39.59 | C2 |
| ATOM | 3418 | C | GLY | 501 | 55.816 | 44.324 | 10.092 | 1.00 | 39.66 | C2 |
| ATOM | 3419 | O | GLY | 501 | 54.661 | 44.034 | 9.777 | 1.00 | 40.66 | C2 |
| ATOM | 3420 | N | PRO | 502 | 55.986 | 45.462 | 10.742 | 1.00 | 39.90 | C2 |
| ATOM | 3421 | CD | PRO | 502 | 57.227 | 45.908 | 11.335 | 1.00 | 41.18 | C2 |
| ATOM | 3422 | CA | PRO | 502 | 54.912 | 46.387 | 11.045 | 1.00 | 38.67 | C2 |
| ATOM | 3423 | CB | PRO | 502 | 55.594 | 47.494 | 11.791 | 1.00 | 39.23 | C2 |
| ATOM | 3424 | CG | PRO | 502 | 56.989 | 47.405 | 11.221 | 1.00 | 41.36 | C2 |
| ATOM | 3425 | C | PRO | 502 | 54.158 | 46.849 | 9.817 | 1.00 | 37.54 | C2 |
| ATOM | 3426 | O | PRO | 502 | 52.966 | 47.139 | 9.961 | 1.00 | 38.36 | C2 |
| ATOM | 3427 | N | THR | 503 | 54.728 | 46.887 | 8.609 | 1.00 | 35.13 | C2 |
| ATOM | 3428 | H | THR | 503 | 55.663 | 46.638 | 8.449 | 1.00 | 0.00 | C2 |
| ATOM | 3429 | CA | THR | 503 | 53.940 | 47.283 | 7.462 | 1.00 | 35.09 | C2 |
| ATOM | 3430 | CB | THR | 503 | 54.832 | 47.376 | 6.245 | 1.00 | 34.48 | C2 |
| ATOM | 3431 | OG1 | THR | 503 | 56.025 | 48.018 | 6.668 | 1.00 | 38.23 | C2 |
| ATOM | 3432 | HG1 | THR | 503 | 55.857 | 48.946 | 6.845 | 1.00 | 0.00 | C2 |
| ATOM | 3433 | CG2 | THR | 503 | 54.197 | 48.162 | 5.126 | 1.00 | 35.56 | C2 |
| ATOM | 3434 | C | THR | 503 | 52.836 | 46.252 | 7.215 | 1.00 | 35.37 | C2 |
| ATOM | 3435 | O | THR | 503 | 51.671 | 46.552 | 6.915 | 1.00 | 37.11 | C2 |
| ATOM | 3436 | N | LEU | 504 | 53.218 | 44.996 | 7.380 | 1.00 | 34.02 | C2 |
| ATOM | 3437 | H | LEU | 504 | 54.146 | 44.799 | 7.647 | 1.00 | 0.00 | C2 |
| ATOM | 3438 | CA | LEU | 504 | 52.301 | 43.912 | 7.173 | 1.00 | 32.50 | C2 |
| ATOM | 3439 | CB | LEU | 504 | 53.127 | 42.650 | 7.002 | 1.00 | 34.78 | C2 |

FIG. 500

| | | | | | | | | | | | | | | |
|---|---|---|---|---|---|---|---|---|---|---|---|---|---|---|
| ATOM | 3440 | CG | LEU | 504 | 53.464 | 42.256 | 5.601 | 1.00 | 34.07 | C2 | ATOM | 3483 | O | GLN | 508 | 43.978 | 42.650 | 9.014 | 1.00 | 24.06 | C2 |
| ATOM | 3441 | CD1 | LEU | 504 | 54.163 | 40.977 | 5.667 | 1.00 | 37.97 | C2 | ATOM | 3484 | N | LEU | 509 | 45.375 | 44.019 | 10.090 | 1.00 | 26.07 | C2 |
| ATOM | 3442 | CD2 | LEU | 504 | 52.254 | 41.865 | 4.809 | 1.00 | 37.34 | C2 | ATOM | 3485 | H | LEU | 509 | 46.316 | 44.262 | 10.222 | 1.00 | 0.00 | C2 |
| ATOM | 3443 | C | LEU | 504 | 51.324 | 43.821 | 8.328 | 1.00 | 29.54 | C2 | ATOM | 3486 | CA | LEU | 509 | 44.378 | 44.640 | 10.977 | 1.00 | 25.71 | C2 |
| ATOM | 3444 | O | LEU | 504 | 50.141 | 43.562 | 8.078 | 1.00 | 30.40 | C2 | ATOM | 3487 | CB | LEU | 509 | 44.993 | 45.555 | 12.031 | 1.00 | 25.60 | C2 |
| ATOM | 3445 | N | ASP | 505 | 51.736 | 44.106 | 9.551 | 1.00 | 26.09 | C2 | ATOM | 3488 | CG | LEU | 509 | 45.838 | 44.757 | 13.042 | 1.00 | 29.00 | C2 |
| ATOM | 3446 | H | ASP | 505 | 52.689 | 44.269 | 9.699 | 1.00 | 0.00 | C2 | ATOM | 3489 | CD1 | LEU | 509 | 46.658 | 45.705 | 13.886 | 1.00 | 28.93 | C2 |
| ATOM | 3447 | CA | ASP | 505 | 50.798 | 44.084 | 10.643 | 1.00 | 27.88 | C2 | ATOM | 3490 | CD2 | LEU | 509 | 44.950 | 43.919 | 13.937 | 1.00 | 27.94 | C2 |
| ATOM | 3448 | CB | ASP | 505 | 51.446 | 44.345 | 11.926 | 1.00 | 29.86 | C2 | ATOM | 3491 | C | LEU | 509 | 43.465 | 45.471 | 10.130 | 1.00 | 25.17 | C2 |
| ATOM | 3449 | CG | ASP | 505 | 52.500 | 43.312 | 12.239 | 1.00 | 34.64 | C2 | ATOM | 3492 | O | LEU | 509 | 42.274 | 45.411 | 10.408 | 1.00 | 27.22 | C2 |
| ATOM | 3450 | OD1 | ASP | 505 | 52.663 | 42.298 | 11.534 | 1.00 | 41.04 | C2 | ATOM | 3493 | N | ASP | 510 | 43.899 | 46.208 | 9.101 | 1.00 | 23.77 | C2 |
| ATOM | 3451 | OD2 | ASP | 505 | 53.179 | 43.542 | 13.224 | 1.00 | 37.40 | C2 | ATOM | 3494 | H | ASP | 510 | 44.865 | 46.277 | 8.930 | 1.00 | 0.00 | C2 |
| ATOM | 3452 | C | ASP | 505 | 49.661 | 45.060 | 10.568 | 1.00 | 28.61 | C2 | ATOM | 3495 | CA | ASP | 510 | 42.955 | 46.898 | 8.240 | 1.00 | 22.66 | C2 |
| ATOM | 3453 | O | ASP | 505 | 48.566 | 44.739 | 11.039 | 1.00 | 30.30 | C2 | ATOM | 3496 | CB | ASP | 510 | 43.652 | 47.829 | 7.306 | 1.00 | 25.21 | C2 |
| ATOM | 3454 | N | THR | 506 | 49.894 | 46.242 | 10.002 | 1.00 | 28.29 | C2 | ATOM | 3497 | CG | ASP | 510 | 44.316 | 48.966 | 8.068 | 1.00 | 33.01 | C2 |
| ATOM | 3455 | H | THR | 506 | 50.823 | 46.493 | 9.804 | 1.00 | 0.00 | C2 | ATOM | 3498 | OD1 | ASP | 510 | 45.178 | 49.621 | 7.477 | 1.00 | 34.28 | C2 |
| ATOM | 3456 | CA | THR | 506 | 48.860 | 47.225 | 9.731 | 1.00 | 25.74 | C2 | ATOM | 3499 | OD2 | ASP | 510 | 43.988 | 49.209 | 9.250 | 1.00 | 34.44 | C2 |
| ATOM | 3457 | CB | THR | 506 | 49.497 | 48.556 | 9.336 | 1.00 | 26.14 | C2 | ATOM | 3500 | C | ASP | 510 | 42.104 | 45.980 | 7.398 | 1.00 | 23.72 | C2 |
| ATOM | 3458 | OG1 | THR | 506 | 49.944 | 49.099 | 10.588 | 1.00 | 31.63 | C2 | ATOM | 3501 | O | ASP | 510 | 40.897 | 46.220 | 7.387 | 1.00 | 24.80 | C2 |
| ATOM | 3459 | HG1 | THR | 506 | 49.243 | 49.072 | 11.246 | 1.00 | 0.00 | C2 | ATOM | 3502 | N | VAL | 511 | 42.632 | 44.984 | 6.659 | 1.00 | 22.38 | C2 |
| ATOM | 3460 | CG2 | THR | 506 | 48.594 | 49.517 | 8.619 | 1.00 | 24.46 | C2 | ATOM | 3503 | H | VAL | 511 | 43.611 | 44.900 | 6.620 | 1.00 | 0.00 | C2 |
| ATOM | 3461 | C | THR | 506 | 48.022 | 46.735 | 8.615 | 1.00 | 24.00 | C2 | ATOM | 3504 | CA | VAL | 511 | 41.823 | 44.010 | 5.961 | 1.00 | 21.89 | C2 |
| ATOM | 3462 | O | THR | 506 | 46.817 | 46.864 | 8.719 | 1.00 | 25.85 | C2 | ATOM | 3505 | CB | VAL | 511 | 42.752 | 42.924 | 5.366 | 1.00 | 22.71 | C2 |
| ATOM | 3463 | N | LEU | 507 | 48.554 | 46.196 | 7.525 | 1.00 | 23.51 | C2 | ATOM | 3506 | CG1 | VAL | 511 | 41.954 | 41.756 | 4.792 | 1.00 | 20.43 | C2 |
| ATOM | 3464 | H | LEU | 507 | 49.527 | 46.073 | 7.453 | 1.00 | 0.00 | C2 | ATOM | 3507 | CG2 | VAL | 511 | 43.529 | 43.524 | 4.210 | 1.00 | 16.19 | C2 |
| ATOM | 3465 | CA | LEU | 507 | 47.682 | 45.770 | 6.434 | 1.00 | 23.85 | C2 | ATOM | 3508 | C | VAL | 511 | 40.827 | 43.403 | 6.960 | 1.00 | 21.92 | C2 |
| ATOM | 3466 | CB | LEU | 507 | 48.574 | 45.408 | 5.196 | 1.00 | 23.33 | C2 | ATOM | 3509 | O | VAL | 511 | 39.625 | 43.447 | 6.719 | 1.00 | 23.46 | C2 |
| ATOM | 3467 | CG | LEU | 507 | 48.010 | 44.919 | 3.858 | 1.00 | 20.85 | C2 | ATOM | 3510 | N | ALA | 512 | 41.258 | 43.017 | 8.163 | 1.00 | 20.49 | C2 |
| ATOM | 3468 | CD1 | LEU | 507 | 46.771 | 45.650 | 3.455 | 1.00 | 24.13 | C2 | ATOM | 3511 | H | ALA | 512 | 42.216 | 43.063 | 8.361 | 1.00 | 0.00 | C2 |
| ATOM | 3469 | CD2 | LEU | 507 | 49.074 | 45.055 | 2.842 | 1.00 | 20.13 | C2 | ATOM | 3512 | CA | ALA | 512 | 40.388 | 42.357 | 9.108 | 1.00 | 20.83 | C2 |
| ATOM | 3470 | C | LEU | 507 | 46.766 | 44.640 | 6.880 | 1.00 | 24.09 | C2 | ATOM | 3513 | CB | ALA | 512 | 41.103 | 41.974 | 10.344 | 1.00 | 17.89 | C2 |
| ATOM | 3471 | O | LEU | 507 | 45.600 | 44.764 | 6.541 | 1.00 | 25.80 | C2 | ATOM | 3514 | C | ALA | 512 | 39.250 | 43.205 | 9.550 | 1.00 | 23.89 | C2 |
| ATOM | 3472 | N | GLN | 508 | 47.152 | 43.618 | 7.661 | 1.00 | 24.01 | C2 | ATOM | 3515 | O | ALA | 512 | 38.201 | 42.668 | 9.874 | 1.00 | 24.61 | C2 |
| ATOM | 3473 | H | GLN | 508 | 48.112 | 43.555 | 7.866 | 1.00 | 0.00 | C2 | ATOM | 3516 | N | ASP | 513 | 39.417 | 44.539 | 9.544 | 1.00 | 25.96 | C2 |
| ATOM | 3474 | CA | GLN | 508 | 46.228 | 42.625 | 8.214 | 1.00 | 23.71 | C2 | ATOM | 3517 | H | ASP | 513 | 40.300 | 44.888 | 9.291 | 1.00 | 0.00 | C2 |
| ATOM | 3475 | CB | GLN | 508 | 46.961 | 41.627 | 9.036 | 1.00 | 23.83 | C2 | ATOM | 3518 | CA | ASP | 513 | 38.374 | 45.471 | 9.947 | 1.00 | 25.37 | C2 |
| ATOM | 3476 | CG | GLN | 508 | 47.937 | 40.899 | 8.173 | 1.00 | 31.64 | C2 | ATOM | 3519 | CB | ASP | 513 | 38.958 | 46.787 | 10.373 | 1.00 | 26.88 | C2 |
| ATOM | 3477 | CD | GLN | 508 | 48.842 | 40.080 | 9.054 | 1.00 | 34.00 | C2 | ATOM | 3520 | CG | ASP | 513 | 39.682 | 46.679 | 11.712 | 1.00 | 32.35 | C2 |
| ATOM | 3478 | OE1 | GLN | 508 | 50.031 | 40.346 | 9.161 | 1.00 | 38.32 | C2 | ATOM | 3521 | OD1 | ASP | 513 | 40.371 | 47.644 | 12.058 | 1.00 | 35.06 | C2 |
| ATOM | 3479 | NE2 | GLN | 508 | 48.321 | 39.090 | 9.748 | 1.00 | 36.30 | C2 | ATOM | 3522 | OD2 | ASP | 513 | 39.580 | 45.646 | 12.390 | 1.00 | 34.10 | C2 |
| ATOM | 3480 | HE21 | GLN | 508 | 47.373 | 38.880 | 9.639 | 1.00 | 0.00 | C2 | ATOM | 3523 | C | ASP | 513 | 37.392 | 45.730 | 8.846 | 1.00 | 24.95 | C2 |
| ATOM | 3481 | HE22 | GLN | 508 | 48.891 | 38.636 | 10.406 | 1.00 | 0.00 | C2 | ATOM | 3524 | O | ASP | 513 | 36.185 | 45.868 | 9.090 | 1.00 | 26.92 | C2 |
| ATOM | 3482 | C | GLN | 508 | 45.105 | 43.123 | 9.111 | 1.00 | 24.24 | C2 | ATOM | 3525 | N | PHE | 514 | 37.867 | 45.739 | 7.634 | 1.00 | 22.88 | C2 |

FIG. 5PP

| | | | | | | | |
|---|---|---|---|---|---|---|---|
| ATOM | 3526 | H | PHE | 514 | 38.829 45.614 7.475 | 1.00 0.00 | C2 |
| ATOM | 3527 | CA | PHE | 514 | 36.974 45.922 6.530 | 1.00 24.09 | C2 |
| ATOM | 3528 | CB | PHE | 514 | 37.812 46.061 5.266 | 1.00 18.11 | C2 |
| ATOM | 3529 | CG | PHE | 514 | 36.956 46.470 4.072 | 1.00 17.86 | C2 |
| ATOM | 3530 | CD1 | PHE | 514 | 35.715 47.089 4.245 | 1.00 15.18 | C2 |
| ATOM | 3531 | CD2 | PHE | 514 | 37.440 46.197 2.804 | 1.00 13.77 | C2 |
| ATOM | 3532 | CE1 | PHE | 514 | 34.983 47.419 3.130 | 1.00 14.53 | C2 |
| ATOM | 3533 | CE2 | PHE | 514 | 36.693 46.539 1.705 | 1.00 12.10 | C2 |
| ATOM | 3534 | CZ | PHE | 514 | 35.468 47.146 1.868 | 1.00 10.68 | C2 |
| ATOM | 3535 | C | PHE | 514 | 36.026 44.703 6.450 | 1.00 29.23 | C2 |
| ATOM | 3536 | O | PHE | 514 | 34.788 44.828 6.350 | 1.00 29.80 | C2 |
| ATOM | 3537 | N | ALA | 515 | 36.604 43.490 6.531 | 1.00 31.15 | C2 |
| ATOM | 3538 | H | ALA | 515 | 37.581 43.450 6.639 | 1.00 0.00 | C2 |
| ATOM | 3539 | CA | ALA | 515 | 35.839 42.260 6.416 | 1.00 32.36 | C2 |
| ATOM | 3540 | CB | ALA | 515 | 36.851 41.126 6.402 | 1.00 32.35 | C2 |
| ATOM | 3541 | C | ALA | 515 | 34.801 42.089 7.535 | 1.00 32.39 | C2 |
| ATOM | 3542 | O | ALA | 515 | 33.676 41.609 7.331 | 1.00 32.63 | C2 |
| ATOM | 3543 | N | THR | 516 | 35.164 42.457 8.735 | 1.00 33.01 | C2 |
| ATOM | 3544 | H | THR | 516 | 36.117 42.578 8.935 | 1.00 0.00 | C2 |
| ATOM | 3545 | CA | THR | 516 | 34.231 42.566 9.821 | 1.00 35.18 | C2 |
| ATOM | 3546 | CB | THR | 516 | 35.016 43.018 10.988 | 1.00 35.40 | C2 |
| ATOM | 3547 | OG1 | THR | 516 | 35.685 41.818 11.336 | 1.00 42.65 | C2 |
| ATOM | 3548 | HG1 | THR | 516 | 36.505 41.713 10.816 | 1.00 0.00 | C2 |
| ATOM | 3549 | CG2 | THR | 516 | 34.262 43.672 12.097 | 1.00 35.56 | C2 |
| ATOM | 3550 | C | THR | 516 | 33.140 43.554 9.482 | 1.00 37.62 | C2 |
| ATOM | 3551 | O | THR | 516 | 32.005 43.315 9.857 | 1.00 40.37 | C2 |
| ATOM | 3552 | N | THR | 517 | 33.387 44.666 8.802 | 1.00 38.61 | C2 |
| ATOM | 3553 | H | THR | 517 | 34.291 44.850 8.469 | 1.00 0.00 | C2 |
| ATOM | 3554 | CA | THR | 517 | 32.359 45.641 8.512 | 1.00 38.92 | C2 |
| ATOM | 3555 | CB | THR | 517 | 33.123 46.903 7.962 | 1.00 40.46 | C2 |
| ATOM | 3556 | OG1 | THR | 517 | 33.832 47.429 9.103 | 1.00 43.22 | C2 |
| ATOM | 3557 | HG1 | THR | 517 | 34.536 46.815 9.335 | 1.00 0.00 | C2 |
| ATOM | 3558 | CG2 | THR | 517 | 32.232 47.926 7.253 | 1.00 39.90 | C2 |
| ATOM | 3559 | C | THR | 517 | 31.343 45.012 7.551 | 1.00 38.69 | C2 |
| ATOM | 3560 | O | THR | 517 | 30.137 45.125 7.811 | 1.00 38.69 | C2 |
| ATOM | 3561 | N | ILE | 518 | 31.790 44.344 6.466 | 1.00 37.54 | C2 |
| ATOM | 3562 | H | ILE | 518 | 32.756 44.386 6.297 | 1.00 0.00 | C2 |
| ATOM | 3563 | CA | ILE | 518 | 30.923 43.646 5.510 | 1.00 36.10 | C2 |
| ATOM | 3564 | CB | ILE | 518 | 31.699 42.912 4.439 | 1.00 33.81 | C2 |
| ATOM | 3565 | CG2 | ILE | 518 | 30.703 42.202 3.555 | 1.00 33.46 | C2 |
| ATOM | 3566 | CG1 | ILE | 518 | 32.623 43.842 3.699 | 1.00 32.91 | C2 |
| ATOM | 3567 | CD | ILE | 518 | 32.019 44.700 2.596 | 1.00 34.89 | C2 |
| ATOM | 3568 | C | ILE | 518 | 30.172 42.591 6.317 | 1.00 38.63 | C2 |
| ATOM | 3569 | O | ILE | 518 | 28.938 42.545 6.205 | 1.00 39.93 | C2 |
| ATOM | 3570 | N | TRP | 519 | 30.842 41.785 7.179 | 1.00 38.64 | C2 |
| ATOM | 3571 | H | TRP | 519 | 31.785 41.959 7.361 | 1.00 0.00 | C2 |
| ATOM | 3572 | CA | TRP | 519 | 30.144 40.784 7.945 | 1.00 38.15 | C2 |
| ATOM | 3573 | CB | TRP | 519 | 31.124 40.083 8.780 | 1.00 38.52 | C2 |
| ATOM | 3574 | CG | TRP | 519 | 30.493 38.793 9.255 | 1.00 42.26 | C2 |
| ATOM | 3575 | CD2 | TRP | 519 | 29.880 38.578 10.473 | 1.00 41.70 | C2 |
| ATOM | 3576 | CE2 | TRP | 519 | 29.437 37.278 10.335 | 1.00 41.69 | C2 |
| ATOM | 3577 | CE3 | TRP | 519 | 29.648 39.282 11.629 | 1.00 42.26 | C2 |
| ATOM | 3578 | CD1 | TRP | 519 | 30.448 37.695 8.419 | 1.00 42.92 | C2 |
| ATOM | 3579 | NE1 | TRP | 519 | 29.788 36.793 9.115 | 1.00 44.19 | C2 |
| ATOM | 3580 | HE1 | TRP | 519 | 29.485 35.935 8.741 | 1.00 0.00 | C2 |
| ATOM | 3581 | CZ2 | TRP | 519 | 28.753 36.671 11.360 | 1.00 41.91 | C2 |
| ATOM | 3582 | CZ3 | TRP | 519 | 28.964 38.666 12.652 | 1.00 41.77 | C2 |
| ATOM | 3583 | CH2 | TRP | 519 | 28.522 37.375 12.515 | 1.00 41.05 | C2 |
| ATOM | 3584 | C | TRP | 519 | 29.027 41.368 8.815 | 1.00 39.33 | C2 |
| ATOM | 3585 | O | TRP | 519 | 27.888 40.919 8.726 | 1.00 38.28 | C2 |
| ATOM | 3586 | N | GLN | 520 | 29.264 42.375 9.650 | 1.00 41.86 | C2 |
| ATOM | 3587 | H | GLN | 520 | 30.180 42.717 9.700 | 1.00 0.00 | C2 |
| ATOM | 3588 | CA | GLN | 520 | 28.240 43.016 10.464 | 1.00 44.63 | C2 |
| ATOM | 3589 | CB | GLN | 520 | 28.691 44.198 11.239 | 1.00 47.03 | C2 |
| ATOM | 3590 | CG | GLN | 520 | 29.602 43.808 12.360 | 1.00 54.78 | C2 |
| ATOM | 3591 | CD | GLN | 520 | 29.910 45.009 13.243 | 1.00 60.14 | C2 |
| ATOM | 3592 | OE1 | GLN | 520 | 28.998 45.566 13.854 | 1.00 61.62 | C2 |
| ATOM | 3593 | NE2 | GLN | 520 | 31.172 45.456 13.371 | 1.00 60.46 | C2 |
| ATOM | 3594 | HE21 | GLN | 520 | 31.289 46.260 13.910 | 1.00 0.00 | C2 |
| ATOM | 3595 | HE22 | GLN | 520 | 31.895 44.966 12.932 | 1.00 0.00 | C2 |
| ATOM | 3596 | C | GLN | 520 | 27.141 43.577 9.621 | 1.00 46.28 | C2 |
| ATOM | 3597 | O | GLN | 520 | 26.001 43.474 10.059 | 1.00 48.62 | C2 |
| ATOM | 3598 | N | GLN | 521 | 27.362 44.145 8.442 | 1.00 46.99 | C2 |
| ATOM | 3599 | H | GLN | 521 | 28.272 44.257 8.092 | 1.00 0.00 | C2 |
| ATOM | 3600 | CA | GLN | 521 | 26.226 44.638 7.716 | 1.00 49.02 | C2 |
| ATOM | 3601 | CB | GLN | 521 | 26.632 45.553 6.566 | 1.00 50.06 | C2 |
| ATOM | 3602 | CG | GLN | 521 | 25.456 46.226 5.790 | 1.00 50.87 | C2 |
| ATOM | 3603 | CD | GLN | 521 | 24.616 47.278 6.534 | 1.00 51.82 | C2 |
| ATOM | 3604 | OE1 | GLN | 521 | 24.864 47.694 7.671 | 1.00 52.47 | C2 |
| ATOM | 3605 | NE2 | GLN | 521 | 23.577 47.776 5.888 | 1.00 50.36 | C2 |
| ATOM | 3606 | HE21 | GLN | 521 | 23.392 47.455 4.987 | 1.00 0.00 | C2 |
| ATOM | 3607 | HE22 | GLN | 521 | 23.044 48.424 6.390 | 1.00 0.00 | C2 |
| ATOM | 3608 | C | GLN | 521 | 25.454 43.446 7.155 | 1.00 50.15 | C2 |
| ATOM | 3609 | O | GLN | 521 | 24.214 43.514 7.177 | 1.00 51.82 | C2 |
| ATOM | 3610 | N | MET | 522 | 26.057 42.348 6.668 | 1.00 49.18 | C2 |
| ATOM | 3611 | H | MET | 522 | 27.038 42.291 6.688 | 1.00 0.00 | C2 |

FIG. 5QQ

| ATOM | 3612 | CA | MET | 522 | 25.280 | 41.227 | 6.171 | 1.00 | 48.22 | C2 | ATOM | 3655 | OT2 | MET | 527 | 23.949 | 37.104 | 6.500 | 1.00 | 82.90 | C2 |
|------|------|----|-----|-----|--------|--------|-------|------|-------|-----|------|------|-----|-----|-----|--------|--------|-------|------|-------|-----|
| ATOM | 3613 | CB | MET | 522 | 26.185 | 40.167 | 5.607 | 1.00 | 46.36 | C2 | ATOM | 3656 | CB | MET | 538 | 47.224 | 28.531 | 2.401 | 1.00 | 77.43 | C3 |
| ATOM | 3614 | CG | MET | 522 | 26.942 | 40.661 | 4.412 | 1.00 | 44.32 | C2 | ATOM | 3657 | CG | MET | 538 | 47.397 | 30.041 | 2.427 | 1.00 | 77.15 | C3 |
| ATOM | 3615 | SD | MET | 522 | 27.855 | 39.435 | 3.426 | 1.00 | 48.35 | C2 | ATOM | 3658 | SD | MET | 538 | 46.205 | 30.708 | 3.604 | 1.00 | 79.03 | C3 |
| ATOM | 3616 | CE | MET | 522 | 28.795 | 38.447 | 4.565 | 1.00 | 42.80 | C2 | ATOM | 3659 | CE | MET | 538 | 44.850 | 31.067 | 2.515 | 1.00 | 77.20 | C3 |
| ATOM | 3617 | C | MET | 522 | 24.453 | 40.642 | 7.316 | 1.00 | 50.14 | C2 | ATOM | 3660 | C | MET | 538 | 48.549 | 27.839 | 0.386 | 1.00 | 75.32 | C3 |
| ATOM | 3618 | O | MET | 522 | 23.380 | 40.124 | 7.038 | 1.00 | 50.60 | C2 | ATOM | 3661 | O | MET | 538 | 49.130 | 26.745 | 0.405 | 1.00 | 77.11 | C3 |
| ATOM | 3619 | N | GLU | 523 | 24.848 | 40.722 | 8.596 | 1.00 | 51.91 | C2 | ATOM | 3662 | HT1 | MET | 538 | 47.563 | 26.068 | 1.449 | 1.00 | 0.00 | C3 |
| ATOM | 3620 | H | GLU | 523 | 25.766 | 41.031 | 8.769 | 1.00 | 0.00 | C2 | ATOM | 3663 | HT2 | MET | 538 | 46.658 | 26.204 | 0.075 | 1.00 | 0.00 | C3 |
| ATOM | 3621 | CA | GLU | 523 | 24.027 | 40.313 | 9.718 | 1.00 | 54.53 | C2 | ATOM | 3664 | N | MET | 538 | 46.724 | 26.552 | 1.050 | 1.00 | 77.52 | C3 |
| ATOM | 3622 | CB | GLU | 523 | 24.654 | 40.486 | 11.081 | 1.00 | 54.60 | C2 | ATOM | 3665 | HT3 | MET | 538 | 45.873 | 26.401 | 1.617 | 1.00 | 0.00 | C3 |
| ATOM | 3623 | CG | GLU | 523 | 25.732 | 39.525 | 11.398 | 1.00 | 57.05 | C2 | ATOM | 3666 | CA | MET | 538 | 47.153 | 27.940 | 0.995 | 1.00 | 76.57 | C3 |
| ATOM | 3624 | CD | GLU | 523 | 25.386 | 38.150 | 10.888 | 1.00 | 61.72 | C2 | ATOM | 3667 | N | PRO | 539 | 49.089 | 28.870 | -0.224 | 1.00 | 72.65 | C3 |
| ATOM | 3625 | OE1 | GLU | 523 | 24.515 | 37.487 | 11.477 | 1.00 | 64.60 | C2 | ATOM | 3668 | CD | PRO | 539 | 48.346 | 29.821 | -1.046 | 1.00 | 72.26 | C3 |
| ATOM | 3626 | OE2 | GLU | 523 | 25.979 | 37.773 | 9.872 | 1.00 | 63.19 | C2 | ATOM | 3669 | CA | PRO | 539 | 50.526 | 29.020 | -0.349 | 1.00 | 70.34 | C3 |
| ATOM | 3627 | C | GLU | 523 | 22.773 | 41.116 | 9.836 | 1.00 | 58.29 | C2 | ATOM | 3670 | CB | PRO | 539 | 50.677 | 30.365 | -1.006 | 1.00 | 71.39 | C3 |
| ATOM | 3628 | O | GLU | 523 | 21.688 | 40.538 | 9.850 | 1.00 | 59.32 | C2 | ATOM | 3671 | CG | PRO | 539 | 49.437 | 30.503 | -1.837 | 1.00 | 71.52 | C3 |
| ATOM | 3629 | N | ALA | 524 | 22.920 | 42.432 | 9.992 | 1.00 | 61.41 | C2 | ATOM | 3672 | C | PRO | 539 | 51.250 | 28.931 | 0.991 | 1.00 | 67.83 | C3 |
| ATOM | 3630 | H | ALA | 524 | 23.834 | 42.798 | 10.024 | 1.00 | 0.00 | C2 | ATOM | 3673 | O | PRO | 539 | 50.666 | 29.294 | 2.029 | 1.00 | 68.05 | C3 |
| ATOM | 3631 | CA | ALA | 524 | 21.815 | 43.360 | 10.076 | 1.00 | 63.58 | C2 | ATOM | 3674 | N | ALA | 540 | 52.484 | 28.417 | 0.961 | 1.00 | 64.48 | C3 |
| ATOM | 3632 | CB | ALA | 524 | 22.382 | 44.768 | 9.992 | 1.00 | 64.11 | C2 | ATOM | 3675 | H | ALA | 540 | 52.858 | 28.098 | 0.111 | 1.00 | 0.00 | C3 |
| ATOM | 3633 | C | ALA | 524 | 20.818 | 43.109 | 8.946 | 1.00 | 64.79 | C2 | ATOM | 3676 | CA | ALA | 540 | 53.389 | 28.498 | 2.112 | 1.00 | 61.83 | C3 |
| ATOM | 3634 | O | ALA | 524 | 19.655 | 42.824 | 9.206 | 1.00 | 65.69 | C2 | ATOM | 3677 | CB | ALA | 540 | 54.004 | 27.200 | 2.619 | 1.00 | 63.57 | C3 |
| ATOM | 3635 | N | ALA | 525 | 21.251 | 43.083 | 7.693 | 1.00 | 66.44 | C2 | ATOM | 3678 | C | ALA | 540 | 54.559 | 29.212 | 1.496 | 1.00 | 58.74 | C3 |
| ATOM | 3636 | H | ALA | 525 | 22.196 | 43.283 | 7.516 | 1.00 | 0.00 | C2 | ATOM | 3679 | O | ALA | 540 | 54.835 | 29.036 | 0.301 | 1.00 | 58.30 | C3 |
| ATOM | 3637 | CA | ALA | 525 | 20.371 | 42.789 | 6.574 | 1.00 | 68.58 | C2 | ATOM | 3680 | N | PHE | 541 | 55.256 | 30.008 | 2.292 | 1.00 | 55.25 | C3 |
| ATOM | 3638 | CB | ALA | 525 | 21.117 | 43.044 | 5.288 | 1.00 | 67.42 | C2 | ATOM | 3681 | H | PHE | 541 | 55.093 | 30.068 | 3.257 | 1.00 | 0.00 | C3 |
| ATOM | 3639 | C | ALA | 525 | 19.841 | 41.356 | 6.558 | 1.00 | 71.11 | C2 | ATOM | 3682 | CA | PHE | 541 | 56.299 | 30.814 | 1.702 | 1.00 | 51.38 | C3 |
| ATOM | 3640 | O | ALA | 525 | 19.116 | 40.946 | 5.651 | 1.00 | 71.65 | C2 | ATOM | 3683 | CB | PHE | 541 | 55.964 | 32.306 | 1.942 | 1.00 | 48.80 | C3 |
| ATOM | 3641 | N | GLY | 526 | 20.257 | 40.510 | 7.498 | 1.00 | 74.20 | C2 | ATOM | 3684 | CG | PHE | 541 | 54.789 | 32.703 | 1.058 | 1.00 | 45.77 | C3 |
| ATOM | 3642 | H | GLY | 526 | 21.019 | 40.780 | 8.043 | 1.00 | 0.00 | C2 | ATOM | 3685 | CD1 | PHE | 541 | 54.992 | 32.939 | -0.279 | 1.00 | 44.20 | C3 |
| ATOM | 3643 | CA | GLY | 526 | 19.728 | 39.157 | 7.653 | 1.00 | 76.30 | C2 | ATOM | 3686 | CD2 | PHE | 541 | 53.507 | 32.747 | 1.582 | 1.00 | 44.76 | C3 |
| ATOM | 3644 | C | GLY | 526 | 20.430 | 38.085 | 6.842 | 1.00 | 78.19 | C2 | ATOM | 3687 | CE1 | PHE | 541 | 53.901 | 33.207 | -1.074 | 1.00 | 43.98 | C3 |
| ATOM | 3645 | O | GLY | 526 | 20.174 | 36.910 | 7.094 | 1.00 | 79.05 | C2 | ATOM | 3688 | CE2 | PHE | 541 | 52.428 | 33.018 | 0.769 | 1.00 | 42.86 | C3 |
| ATOM | 3646 | N | MET | 527 | 21.388 | 38.433 | 5.970 | 1.00 | 80.23 | C2 | ATOM | 3689 | CZ | PHE | 541 | 52.625 | 33.247 | -0.563 | 1.00 | 42.52 | C3 |
| ATOM | 3647 | H | MET | 527 | 21.759 | 39.337 | 6.075 | 1.00 | 0.00 | C2 | ATOM | 3690 | C | PHE | 541 | 57.586 | 30.364 | 2.333 | 1.00 | 49.80 | C3 |
| ATOM | 3648 | CA | MET | 527 | 22.055 | 37.489 | 5.063 | 1.00 | 81.73 | C2 | ATOM | 3691 | O | PHE | 541 | 58.002 | 30.807 | 3.395 | 1.00 | 49.55 | C3 |
| ATOM | 3649 | CB | MET | 527 | 22.771 | 38.256 | 3.928 | 1.00 | 81.72 | C2 | ATOM | 3692 | N | ALA | 542 | 58.172 | 29.442 | 1.562 | 1.00 | 48.21 | C3 |
| ATOM | 3650 | CG | MET | 527 | 22.385 | 39.719 | 3.720 | 1.00 | 83.52 | C2 | ATOM | 3693 | H | ALA | 542 | 57.825 | 29.298 | 0.656 | 1.00 | 0.00 | C3 |
| ATOM | 3651 | SD | MET | 527 | 23.364 | 40.523 | 2.436 | 1.00 | 87.64 | C2 | ATOM | 3694 | CA | ALA | 542 | 59.326 | 28.711 | 1.968 | 1.00 | 45.37 | C3 |
| ATOM | 3652 | CE | MET | 527 | 22.600 | 42.117 | 2.409 | 1.00 | 82.69 | C2 | ATOM | 3695 | CB | ALA | 542 | 59.700 | 27.749 | 0.898 | 1.00 | 45.21 | C3 |
| ATOM | 3653 | C | MET | 527 | 23.078 | 36.584 | 5.780 | 1.00 | 82.64 | C2 | ATOM | 3696 | C | ALA | 542 | 60.510 | 29.567 | 2.266 | 1.00 | 44.87 | C3 |
| ATOM | 3654 | OT1 | MET | 527 | 22.974 | 35.357 | 5.624 | 1.00 | 83.38 | C2 | ATOM | 3697 | O | ALA | 542 | 61.001 | 29.504 | 3.374 | 1.00 | 46.49 | C3 |

FIG. 5RR

| ATOM | 3698 | N | SER | 543 | 61.013 | 30.408 | 1.395 | 1.00 | 42.63 | C3 |
|------|------|------|------|-----|--------|--------|--------|------|-------|-----|
| ATOM | 3699 | H | SER | 543 | 60.477 | 30.685 | 0.630 | 1.00 | 0.00 | C3 |
| ATOM | 3700 | CA | SER | 543 | 62.253 | 31.108 | 1.708 | 1.00 | 40.31 | C3 |
| ATOM | 3701 | CB | SER | 543 | 63.170 | 30.861 | 0.587 | 1.00 | 37.74 | C3 |
| ATOM | 3702 | OG | SER | 543 | 62.391 | 31.181 | -0.554 | 1.00 | 35.74 | C3 |
| ATOM | 3703 | HG | SER | 543 | 61.824 | 30.423 | -0.751 | 1.00 | 0.00 | C3 |
| ATOM | 3704 | C | SER | 543 | 62.087 | 32.613 | 1.896 | 1.00 | 40.88 | C3 |
| ATOM | 3705 | O | SER | 543 | 61.016 | 33.115 | 1.536 | 1.00 | 42.63 | C3 |
| ATOM | 3706 | N | ALA | 544 | 63.120 | 33.383 | 2.310 | 1.00 | 38.84 | C3 |
| ATOM | 3707 | H | ALA | 544 | 63.929 | 32.951 | 2.650 | 1.00 | 0.00 | C3 |
| ATOM | 3708 | CA | ALA | 544 | 63.035 | 34.836 | 2.345 | 1.00 | 37.31 | C3 |
| ATOM | 3709 | CB | ALA | 544 | 64.340 | 35.450 | 2.808 | 1.00 | 35.74 | C3 |
| ATOM | 3710 | C | ALA | 544 | 62.723 | 35.372 | 0.947 | 1.00 | 37.06 | C3 |
| ATOM | 3711 | O | ALA | 544 | 61.829 | 36.220 | 0.820 | 1.00 | 38.23 | C3 |
| ATOM | 3712 | N | PHE | 545 | 63.357 | 34.881 | -0.130 | 1.00 | 35.72 | C3 |
| ATOM | 3713 | H | PHE | 545 | 64.131 | 34.298 | -0.010 | 1.00 | 0.00 | C3 |
| ATOM | 3714 | CA | PHE | 545 | 62.992 | 35.268 | -1.484 | 1.00 | 33.66 | C3 |
| ATOM | 3715 | CB | PHE | 545 | 63.738 | 34.534 | -2.593 | 1.00 | 29.71 | C3 |
| ATOM | 3716 | CG | PHE | 545 | 63.140 | 34.742 | -3.990 | 1.00 | 29.62 | C3 |
| ATOM | 3717 | CD1 | PHE | 545 | 62.317 | 33.788 | -4.557 | 1.00 | 29.80 | C3 |
| ATOM | 3718 | CD2 | PHE | 545 | 63.371 | 35.915 | -4.689 | 1.00 | 31.90 | C3 |
| ATOM | 3719 | CE1 | PHE | 545 | 61.723 | 33.984 | -5.795 | 1.00 | 28.61 | C3 |
| ATOM | 3720 | CE2 | PHE | 545 | 62.777 | 36.113 | -5.928 | 1.00 | 31.00 | C3 |
| ATOM | 3721 | CZ | PHE | 545 | 61.955 | 35.150 | -6.480 | 1.00 | 31.01 | C3 |
| ATOM | 3722 | C | PHE | 545 | 61.543 | 34.900 | -1.667 | 1.00 | 34.81 | C3 |
| ATOM | 3723 | O | PHE | 545 | 60.901 | 35.660 | -2.389 | 1.00 | 38.88 | C3 |
| ATOM | 3724 | N | GLN | 546 | 60.912 | 33.847 | -1.135 | 1.00 | 34.77 | C3 |
| ATOM | 3725 | H | GLN | 546 | 61.396 | 33.223 | -0.558 | 1.00 | 0.00 | C3 |
| ATOM | 3726 | CA | GLN | 546 | 59.490 | 33.637 | -1.433 | 1.00 | 33.72 | C3 |
| ATOM | 3727 | CB | GLN | 546 | 59.145 | 32.232 | -1.140 | 1.00 | 34.85 | C3 |
| ATOM | 3728 | CG | GLN | 546 | 59.582 | 31.585 | -2.444 | 1.00 | 42.45 | C3 |
| ATOM | 3729 | CD | GLN | 546 | 59.374 | 30.085 | -2.473 | 1.00 | 46.05 | C3 |
| ATOM | 3730 | OE1 | GLN | 546 | 59.287 | 29.472 | -1.399 | 1.00 | 48.90 | C3 |
| ATOM | 3731 | NE2 | GLN | 546 | 59.339 | 29.442 | -3.644 | 1.00 | 47.20 | C3 |
| ATOM | 3732 | HE21 | GLN | 546 | 59.476 | 29.948 | -4.472 | 1.00 | 0.00 | C3 |
| ATOM | 3733 | HE22 | GLN | 546 | 59.154 | 28.481 | -3.609 | 1.00 | 0.00 | C3 |
| ATOM | 3734 | C | GLN | 546 | 58.504 | 34.541 | -0.729 | 1.00 | 31.62 | C3 |
| ATOM | 3735 | O | GLN | 546 | 57.429 | 34.850 | -1.233 | 1.00 | 29.88 | C3 |
| ATOM | 3736 | N | ARG | 547 | 58.907 | 34.929 | 0.465 | 1.00 | 31.09 | C3 |
| ATOM | 3737 | H | ARG | 547 | 59.750 | 34.566 | 0.811 | 1.00 | 0.00 | C3 |
| ATOM | 3738 | CA | ARG | 547 | 58.160 | 35.830 | 1.282 | 1.00 | 31.43 | C3 |
| ATOM | 3739 | CB | ARG | 547 | 58.813 | 35.874 | 2.601 | 1.00 | 31.74 | C3 |
| ATOM | 3740 | CG | ARG | 547 | 57.906 | 35.224 | 3.623 | 1.00 | 37.02 | C3 |
| ATOM | 3741 | CD | ARG | 547 | 58.344 | 33.858 | 4.076 | 1.00 | 40.56 | C3 |
| ATOM | 3742 | NE | ARG | 547 | 59.743 | 34.058 | 4.345 | 1.00 | 47.90 | C3 |
| ATOM | 3743 | HE | ARG | 547 | 60.389 | 33.924 | 3.620 | 1.00 | 0.00 | C3 |
| ATOM | 3744 | CZ | ARG | 547 | 60.190 | 34.394 | 5.543 | 1.00 | 49.48 | C3 |
| ATOM | 3745 | NH1 | ARG | 547 | 59.361 | 34.522 | 6.593 | 1.00 | 51.97 | C3 |
| ATOM | 3746 | HH11 | ARG | 547 | 58.380 | 34.356 | 6.488 | 1.00 | 0.00 | C3 |
| ATOM | 3747 | HH12 | ARG | 547 | 59.731 | 34.763 | 7.491 | 1.00 | 0.00 | C3 |
| ATOM | 3748 | NH2 | ARG | 547 | 61.464 | 34.775 | 5.616 | 1.00 | 48.55 | C3 |
| ATOM | 3749 | HH21 | ARG | 547 | 62.025 | 34.803 | 4.788 | 1.00 | 0.00 | C3 |
| ATOM | 3750 | HH22 | ARG | 547 | 61.854 | 35.034 | 6.501 | 1.00 | 0.00 | C3 |
| ATOM | 3751 | C | ARG | 547 | 58.167 | 37.181 | 0.590 | 1.00 | 32.26 | C3 |
| ATOM | 3752 | O | ARG | 547 | 57.084 | 37.694 | 0.317 | 1.00 | 34.25 | C3 |
| ATOM | 3753 | N | ARG | 548 | 59.348 | 37.717 | 0.205 | 1.00 | 31.44 | C3 |
| ATOM | 3754 | H | ARG | 548 | 60.148 | 37.203 | 0.444 | 1.00 | 0.00 | C3 |
| ATOM | 3755 | CA | ARG | 548 | 59.529 | 38.980 | -0.555 | 1.00 | 30.01 | C3 |
| ATOM | 3756 | CB | ARG | 548 | 60.995 | 39.213 | -0.949 | 1.00 | 25.42 | C3 |
| ATOM | 3757 | CG | ARG | 548 | 61.820 | 39.361 | 0.294 | 1.00 | 26.11 | C3 |
| ATOM | 3758 | CD | ARG | 548 | 63.280 | 39.158 | -0.054 | 1.00 | 29.34 | C3 |
| ATOM | 3759 | NE | ARG | 548 | 64.044 | 39.162 | 1.189 | 1.00 | 32.30 | C3 |
| ATOM | 3760 | HE | ARG | 548 | 63.572 | 38.883 | 1.995 | 1.00 | 0.00 | C3 |
| ATOM | 3761 | CZ | ARG | 548 | 65.344 | 39.518 | 1.325 | 1.00 | 32.66 | C3 |
| ATOM | 3762 | NH1 | ARG | 548 | 66.159 | 39.923 | 0.335 | 1.00 | 34.98 | C3 |
| ATOM | 3763 | HH11 | ARG | 548 | 67.107 | 40.170 | 0.533 | 1.00 | 0.00 | C3 |
| ATOM | 3764 | HH12 | ARG | 548 | 65.812 | 39.981 | -0.600 | 1.00 | 0.00 | C3 |
| ATOM | 3765 | NH2 | ARG | 548 | 65.837 | 39.518 | 2.549 | 1.00 | 32.03 | C3 |
| ATOM | 3766 | HH21 | ARG | 548 | 66.788 | 39.783 | 2.708 | 1.00 | 0.00 | C3 |
| ATOM | 3767 | HH22 | ARG | 548 | 65.250 | 39.275 | 3.321 | 1.00 | 0.00 | C3 |
| ATOM | 3768 | C | ARG | 548 | 58.713 | 38.997 | -1.832 | 1.00 | 29.81 | C3 |
| ATOM | 3769 | O | ARG | 548 | 57.778 | 39.790 | -1.968 | 1.00 | 33.03 | C3 |
| ATOM | 3770 | N | ALA | 549 | 58.979 | 38.102 | -2.761 | 1.00 | 27.87 | C3 |
| ATOM | 3771 | H | ALA | 549 | 59.684 | 37.436 | -2.601 | 1.00 | 0.00 | C3 |
| ATOM | 3772 | CA | ALA | 549 | 58.227 | 38.045 | -3.984 | 1.00 | 27.18 | C3 |
| ATOM | 3773 | CB | ALA | 549 | 58.797 | 36.934 | -4.857 | 1.00 | 28.72 | C3 |
| ATOM | 3774 | C | ALA | 549 | 56.748 | 37.810 | -3.770 | 1.00 | 25.91 | C3 |
| ATOM | 3775 | O | ALA | 549 | 55.896 | 38.337 | -4.468 | 1.00 | 26.03 | C3 |
| ATOM | 3776 | N | GLY | 550 | 56.421 | 37.074 | -2.748 | 1.00 | 26.53 | C3 |
| ATOM | 3777 | H | GLY | 550 | 57.103 | 36.657 | -2.185 | 1.00 | 0.00 | C3 |
| ATOM | 3778 | CA | GLY | 550 | 55.055 | 36.805 | -2.457 | 1.00 | 26.08 | C3 |
| ATOM | 3779 | C | GLY | 550 | 54.410 | 38.098 | -2.075 | 1.00 | 26.94 | C3 |
| ATOM | 3780 | O | GLY | 550 | 53.339 | 38.380 | -2.608 | 1.00 | 26.59 | C3 |
| ATOM | 3781 | N | GLY | 551 | 55.073 | 38.917 | -1.234 | 1.00 | 27.78 | C3 |
| ATOM | 3782 | H | GLY | 551 | 55.958 | 38.642 | -0.925 | 1.00 | 0.00 | C3 |
| ATOM | 3783 | CA | GLY | 551 | 54.540 | 40.212 | -0.779 | 1.00 | 26.51 | C3 |

FIG. 5SS

| | | | | | | | | | |
|---|---|---|---|---|---|---|---|---|---|
| ATOM | 3784 | C | GLY | 551 | 54.302 | 41.113 | -1.994 | 1.00 26.82 | C3 |
| ATOM | 3785 | O | GLY | 551 | 53.313 | 41.852 | -2.065 | 1.00 27.82 | C3 |
| ATOM | 3786 | N | VAL | 552 | 55.154 | 41.013 | -3.012 | 1.00 25.81 | C3 |
| ATOM | 3787 | H | VAL | 552 | 55.916 | 40.396 | -2.954 | 1.00 0.00 | C3 |
| ATOM | 3788 | CA | VAL | 552 | 54.952 | 41.843 | -4.176 | 1.00 28.39 | C3 |
| ATOM | 3789 | CB | VAL | 552 | 56.178 | 41.743 | -5.190 | 1.00 26.20 | C3 |
| ATOM | 3790 | CG1 | VAL | 552 | 55.917 | 42.391 | -6.541 | 1.00 26.53 | C3 |
| ATOM | 3791 | CG2 | VAL | 552 | 57.327 | 42.546 | -4.594 | 1.00 26.44 | C3 |
| ATOM | 3792 | C | VAL | 552 | 53.650 | 41.406 | -4.820 | 1.00 29.05 | C3 |
| ATOM | 3793 | O | VAL | 552 | 52.744 | 42.251 | -4.888 | 1.00 31.68 | C3 |
| ATOM | 3794 | N | LEU | 553 | 53.455 | 40.120 | -5.176 | 1.00 27.20 | C3 |
| ATOM | 3795 | H | LEU | 553 | 54.122 | 39.447 | -4.908 | 1.00 0.00 | C3 |
| ATOM | 3796 | CA | LEU | 553 | 52.266 | 39.705 | -5.915 | 1.00 23.80 | C3 |
| ATOM | 3797 | CB | LEU | 553 | 52.357 | 38.262 | -6.363 | 1.00 24.86 | C3 |
| ATOM | 3798 | CG | LEU | 553 | 53.432 | 37.955 | -7.357 | 1.00 23.06 | C3 |
| ATOM | 3799 | CD1 | LEU | 553 | 54.073 | 36.623 | -7.092 | 1.00 24.31 | C3 |
| ATOM | 3800 | CD2 | LEU | 553 | 52.794 | 38.061 | -8.703 | 1.00 21.87 | C3 |
| ATOM | 3801 | C | LEU | 553 | 51.012 | 39.825 | -5.114 | 1.00 23.72 | C3 |
| ATOM | 3802 | O | LEU | 553 | 49.982 | 40.138 | -5.712 | 1.00 24.63 | C3 |
| ATOM | 3803 | N | VAL | 554 | 50.962 | 39.580 | -3.803 | 1.00 24.37 | C3 |
| ATOM | 3804 | H | VAL | 554 | 51.774 | 39.350 | -3.295 | 1.00 0.00 | C3 |
| ATOM | 3805 | CA | VAL | 554 | 49.660 | 39.691 | -3.180 | 1.00 26.36 | C3 |
| ATOM | 3806 | CB | VAL | 554 | 49.472 | 38.751 | -1.802 | 1.00 26.55 | C3 |
| ATOM | 3807 | CG1 | VAL | 554 | 50.696 | 37.933 | -1.418 | 1.00 23.95 | C3 |
| ATOM | 3808 | CG2 | VAL | 554 | 48.953 | 39.614 | -0.682 | 1.00 25.58 | C3 |
| ATOM | 3809 | C | VAL | 554 | 49.322 | 41.175 | -2.960 | 1.00 27.53 | C3 |
| ATOM | 3810 | O | VAL | 554 | 48.142 | 41.502 | -3.192 | 1.00 28.04 | C3 |
| ATOM | 3811 | N | ALA | 555 | 50.277 | 42.106 | -2.716 | 1.00 28.04 | C3 |
| ATOM | 3812 | H | ALA | 555 | 51.221 | 41.831 | -2.658 | 1.00 0.00 | C3 |
| ATOM | 3813 | CA | ALA | 555 | 49.956 | 43.539 | -2.509 | 1.00 28.57 | C3 |
| ATOM | 3814 | CB | ALA | 555 | 51.161 | 44.427 | -2.217 | 1.00 28.07 | C3 |
| ATOM | 3815 | C | ALA | 555 | 49.402 | 44.055 | -3.803 | 1.00 28.12 | C3 |
| ATOM | 3816 | O | ALA | 555 | 48.425 | 44.803 | -3.847 | 1.00 30.12 | C3 |
| ATOM | 3817 | N | SER | 556 | 49.985 | 43.521 | -4.839 | 1.00 0.00 | C3 |
| ATOM | 3818 | H | SER | 556 | 50.781 | 42.956 | -4.710 | 1.00 0.00 | C3 |
| ATOM | 3819 | CA | SER | 556 | 49.548 | 43.810 | -6.152 | 1.00 30.09 | C3 |
| ATOM | 3820 | CB | SER | 556 | 50.684 | 43.277 | -6.965 | 1.00 31.42 | C3 |
| ATOM | 3821 | OG | SER | 556 | 50.442 | 43.338 | -8.344 | 1.00 37.88 | C3 |
| ATOM | 3822 | HG | SER | 556 | 49.966 | 44.144 | -8.576 | 1.00 0.00 | C3 |
| ATOM | 3823 | C | SER | 556 | 48.143 | 43.243 | -6.454 | 1.00 32.78 | C3 |
| ATOM | 3824 | O | SER | 556 | 47.287 | 43.961 | -7.003 | 1.00 34.56 | C3 |
| ATOM | 3825 | N | HIS | 557 | 47.750 | 42.019 | -6.088 | 1.00 32.78 | C3 |
| ATOM | 3826 | H | HIS | 557 | 48.350 | 41.453 | -5.560 | 1.00 0.00 | C3 |
| ATOM | 3827 | CA | HIS | 557 | 46.396 | 41.605 | -6.401 | 1.00 33.64 | C3 |
| ATOM | 3828 | CB | HIS | 557 | 46.203 | 40.142 | -6.242 | 1.00 37.88 | C3 |
| ATOM | 3829 | CG | HIS | 557 | 46.986 | 39.518 | -7.348 | 1.00 42.44 | C3 |
| ATOM | 3830 | CD2 | HIS | 557 | 46.694 | 39.665 | -8.675 | 1.00 43.63 | C3 |
| ATOM | 3831 | ND1 | HIS | 557 | 48.108 | 38.837 | -7.209 | 1.00 45.23 | C3 |
| ATOM | 3832 | HD1 | HIS | 557 | 48.641 | 38.764 | -6.385 | 1.00 0.00 | C3 |
| ATOM | 3833 | CE1 | HIS | 557 | 48.524 | 38.569 | -8.414 | 1.00 46.56 | C3 |
| ATOM | 3834 | NE2 | HIS | 557 | 47.676 | 39.066 | -9.283 | 1.00 45.62 | C3 |
| ATOM | 3835 | HE2 | HIS | 557 | 47.793 | 39.018 | -10.257 | 1.00 0.00 | C3 |
| ATOM | 3836 | C | HIS | 557 | 45.383 | 42.249 | -5.520 | 1.00 32.94 | C3 |
| ATOM | 3837 | O | HIS | 557 | 44.256 | 42.444 | -5.934 | 1.00 33.08 | C3 |
| ATOM | 3838 | N | LEU | 558 | 45.744 | 42.534 | -4.280 | 1.00 33.05 | C3 |
| ATOM | 3839 | H | LEU | 558 | 46.657 | 42.356 | -3.986 | 1.00 0.00 | C3 |
| ATOM | 3840 | CA | LEU | 558 | 44.817 | 43.125 | -3.348 | 1.00 31.91 | C3 |
| ATOM | 3841 | CB | LEU | 558 | 45.420 | 43.107 | -1.965 | 1.00 29.25 | C3 |
| ATOM | 3842 | CG | LEU | 558 | 44.605 | 43.615 | -0.818 | 1.00 26.02 | C3 |
| ATOM | 3843 | CD1 | LEU | 558 | 43.279 | 42.883 | -0.742 | 1.00 25.00 | C3 |
| ATOM | 3844 | CD2 | LEU | 558 | 45.496 | 43.571 | 0.408 | 1.00 22.86 | C3 |
| ATOM | 3845 | C | LEU | 558 | 44.527 | 44.521 | -3.783 | 1.00 32.47 | C3 |
| ATOM | 3846 | O | LEU | 558 | 43.402 | 44.944 | -3.596 | 1.00 33.97 | C3 |
| ATOM | 3847 | N | GLN | 559 | 45.482 | 45.231 | -4.370 | 1.00 34.36 | C3 |
| ATOM | 3848 | H | GLN | 559 | 46.386 | 44.855 | -4.406 | 1.00 0.00 | C3 |
| ATOM | 3849 | CA | GLN | 559 | 45.255 | 46.569 | -4.912 | 1.00 36.75 | C3 |
| ATOM | 3850 | CB | GLN | 559 | 46.598 | 47.067 | -5.470 | 1.00 39.63 | C3 |
| ATOM | 3851 | CG | GLN | 559 | 46.707 | 48.543 | -5.875 | 1.00 42.07 | C3 |
| ATOM | 3852 | CD | GLN | 559 | 46.530 | 49.618 | -4.793 | 1.00 41.53 | C3 |
| ATOM | 3853 | OE1 | GLN | 559 | 45.961 | 50.687 | -5.057 | 1.00 41.25 | C3 |
| ATOM | 3854 | NE2 | GLN | 559 | 46.951 | 49.416 | -3.561 | 1.00 37.96 | C3 |
| ATOM | 3855 | HE21 | GLN | 559 | 47.271 | 48.528 | -3.311 | 1.00 0.00 | C3 |
| ATOM | 3856 | HE22 | GLN | 559 | 47.001 | 50.190 | -2.967 | 1.00 0.00 | C3 |
| ATOM | 3857 | C | GLN | 559 | 44.142 | 46.635 | -5.976 | 1.00 35.22 | C3 |
| ATOM | 3858 | O | GLN | 559 | 43.165 | 47.404 | -5.839 | 1.00 34.99 | C3 |
| ATOM | 3859 | N | SER | 560 | 44.260 | 45.817 | -7.025 | 1.00 33.46 | C3 |
| ATOM | 3860 | H | SER | 560 | 45.083 | 45.292 | -7.154 | 1.00 0.00 | C3 |
| ATOM | 3861 | CA | SER | 560 | 43.222 | 45.683 | -8.049 | 1.00 32.88 | C3 |
| ATOM | 3862 | CB | SER | 560 | 43.693 | 44.776 | -9.088 | 1.00 34.05 | C3 |
| ATOM | 3863 | OG | SER | 560 | 45.021 | 45.174 | -9.281 | 1.00 42.40 | C3 |
| ATOM | 3864 | HG | SER | 560 | 45.042 | 45.996 | -9.783 | 1.00 0.00 | C3 |
| ATOM | 3865 | C | SER | 560 | 41.885 | 45.133 | -7.559 | 1.00 32.01 | C3 |
| ATOM | 3866 | O | SER | 560 | 40.791 | 45.582 | -7.920 | 1.00 32.23 | C3 |
| ATOM | 3867 | N | PHE | 561 | 41.969 | 44.123 | -6.710 | 1.00 29.50 | C3 |
| ATOM | 3868 | H | PHE | 561 | 42.850 | 43.767 | -6.464 | 1.00 0.00 | C3 |
| ATOM | 3869 | CA | PHE | 561 | 40.803 | 43.529 | -6.118 | 1.00 28.17 | C3 |

FIG. 5TT

| | | | | | | | | | |
|---|---|---|---|---|---|---|---|---|---|
| ATOM | 3870 | CB | PHE | 561 | 41.237 | 42.541 | -5.040 | 1.00 26.27 | C3 |
| ATOM | 3871 | CG | PHE | 561 | 40.069 | 41.966 | -4.268 | 1.00 25.68 | C3 |
| ATOM | 3872 | CD1 | PHE | 561 | 39.282 | 40.999 | -4.846 | 1.00 25.44 | C3 |
| ATOM | 3873 | CD2 | PHE | 561 | 39.761 | 42.482 | -3.051 | 1.00 25.45 | C3 |
| ATOM | 3874 | CE1 | PHE | 561 | 38.166 | 40.551 | -4.215 | 1.00 21.49 | C3 |
| ATOM | 3875 | CE2 | PHE | 561 | 38.635 | 42.027 | -2.421 | 1.00 26.89 | C3 |
| ATOM | 3876 | CZ | PHE | 561 | 37.853 | 41.074 | -3.008 | 1.00 24.29 | C3 |
| ATOM | 3877 | C | PHE | 561 | 39.987 | 44.645 | -5.505 | 1.00 28.81 | C3 |
| ATOM | 3878 | O | PHE | 561 | 38.789 | 44.697 | -5.731 | 1.00 29.31 | C3 |
| ATOM | 3879 | N | LEU | 562 | 40.672 | 45.565 | -4.797 | 1.00 28.39 | C3 |
| ATOM | 3880 | H | LEU | 562 | 41.643 | 45.462 | -4.707 | 1.00 0.00 | C3 |
| ATOM | 3881 | CA | LEU | 562 | 40.033 | 46.617 | -4.057 | 1.00 26.51 | C3 |
| ATOM | 3882 | CB | LEU | 562 | 40.964 | 47.203 | -3.074 | 1.00 23.80 | C3 |
| ATOM | 3883 | CG | LEU | 562 | 41.047 | 46.411 | -1.816 | 1.00 24.85 | C3 |
| ATOM | 3884 | CD1 | LEU | 562 | 42.207 | 46.868 | -1.049 | 1.00 24.07 | C3 |
| ATOM | 3885 | CD2 | LEU | 562 | 39.794 | 46.551 | -1.008 | 1.00 25.13 | C3 |
| ATOM | 3886 | C | LEU | 562 | 39.586 | 47.669 | -4.988 | 1.00 29.27 | C3 |
| ATOM | 3887 | O | LEU | 562 | 38.580 | 48.304 | -4.681 | 1.00 29.83 | C3 |
| ATOM | 3888 | N | GLU | 563 | 40.239 | 47.871 | -6.115 | 1.00 30.88 | C3 |
| ATOM | 3889 | H | GLU | 563 | 41.052 | 47.368 | -6.325 | 1.00 0.00 | C3 |
| ATOM | 3890 | CA | GLU | 563 | 39.738 | 48.908 | -6.966 | 1.00 36.88 | C3 |
| ATOM | 3891 | CB | GLU | 563 | 40.660 | 49.142 | -8.137 | 1.00 40.80 | C3 |
| ATOM | 3892 | CG | GLU | 563 | 41.999 | 49.628 | -7.682 | 1.00 48.55 | C3 |
| ATOM | 3893 | CD | GLU | 563 | 43.148 | 49.277 | -8.619 | 1.00 55.42 | C3 |
| ATOM | 3894 | OE1 | GLU | 563 | 44.301 | 49.283 | -8.135 | 1.00 57.39 | C3 |
| ATOM | 3895 | OE2 | GLU | 563 | 42.886 | 48.986 | -9.808 | 1.00 56.44 | C3 |
| ATOM | 3896 | C | GLU | 563 | 38.375 | 48.469 | -7.466 | 1.00 39.02 | C3 |
| ATOM | 3897 | O | GLU | 563 | 37.388 | 49.170 | -7.270 | 1.00 39.09 | C3 |
| ATOM | 3898 | N | VAL | 564 | 38.289 | 47.255 | -8.030 | 1.00 42.30 | C3 |
| ATOM | 3899 | H | VAL | 564 | 39.107 | 46.714 | -8.074 | 1.00 0.00 | C3 |
| ATOM | 3900 | CA | VAL | 564 | 37.052 | 46.683 | -8.558 | 1.00 41.84 | C3 |
| ATOM | 3901 | CB | VAL | 564 | 37.333 | 45.255 | -9.041 | 1.00 42.27 | C3 |
| ATOM | 3902 | CG1 | VAL | 564 | 36.055 | 44.538 | -9.435 | 1.00 41.17 | C3 |
| ATOM | 3903 | CG2 | VAL | 564 | 38.283 | 45.348 | -10.241 | 1.00 42.11 | C3 |
| ATOM | 3904 | C | VAL | 564 | 36.030 | 46.709 | -7.442 | 1.00 41.68 | C3 |
| ATOM | 3905 | O | VAL | 564 | 34.892 | 47.015 | -7.697 | 1.00 42.34 | C3 |
| ATOM | 3906 | N | SER | 565 | 36.419 | 46.501 | -6.206 | 1.00 42.75 | C3 |
| ATOM | 3907 | H | SER | 565 | 37.333 | 46.173 | -6.061 | 1.00 0.00 | C3 |
| ATOM | 3908 | CA | SER | 565 | 35.562 | 46.602 | -5.064 | 1.00 44.85 | C3 |
| ATOM | 3909 | CB | SER | 565 | 36.344 | 46.013 | -3.894 | 1.00 46.54 | C3 |
| ATOM | 3910 | OG | SER | 565 | 35.590 | 45.714 | -2.731 | 1.00 51.75 | C3 |
| ATOM | 3911 | HG | SER | 565 | 35.060 | 46.481 | -2.491 | 1.00 0.00 | C3 |
| ATOM | 3912 | C | SER | 565 | 35.167 | 48.063 | -4.871 | 1.00 45.70 | C3 |
| ATOM | 3913 | O | SER | 565 | 34.038 | 48.287 | -4.446 | 1.00 46.87 | C3 |
| ATOM | 3914 | N | TYR | 566 | 35.965 | 49.093 | -5.146 | 1.00 47.59 | C3 |
| ATOM | 3915 | H | TYR | 566 | 36.893 | 48.908 | -5.386 | 1.00 0.00 | C3 |
| ATOM | 3916 | CA | TYR | 566 | 35.518 | 50.474 | -5.086 | 1.00 49.68 | C3 |
| ATOM | 3917 | CB | TYR | 566 | 36.765 | 51.362 | -5.164 | 1.00 56.17 | C3 |
| ATOM | 3918 | CG | TYR | 566 | 36.715 | 52.622 | -6.007 | 1.00 64.64 | C3 |
| ATOM | 3919 | CD1 | TYR | 566 | 37.264 | 52.538 | -7.278 | 1.00 69.53 | C3 |
| ATOM | 3920 | CE1 | TYR | 566 | 37.212 | 53.613 | -8.151 | 1.00 73.71 | C3 |
| ATOM | 3921 | CD2 | TYR | 566 | 36.109 | 53.797 | -5.569 | 1.00 67.98 | C3 |
| ATOM | 3922 | CE2 | TYR | 566 | 36.048 | 54.888 | -6.441 | 1.00 72.92 | C3 |
| ATOM | 3923 | CZ | TYR | 566 | 36.599 | 54.787 | -7.735 | 1.00 75.29 | C3 |
| ATOM | 3924 | OH | TYR | 566 | 36.538 | 55.838 | -8.652 | 1.00 77.42 | C3 |
| ATOM | 3925 | HH | TYR | 566 | 36.905 | 55.565 | -9.494 | 1.00 0.00 | C3 |
| ATOM | 3926 | C | TYR | 566 | 34.524 | 50.696 | -6.217 | 1.00 48.48 | C3 |
| ATOM | 3927 | O | TYR | 566 | 33.545 | 51.376 | -5.950 | 1.00 46.35 | C3 |
| ATOM | 3928 | N | ALA | 567 | 34.679 | 50.115 | -7.417 | 1.00 49.14 | C3 |
| ATOM | 3929 | H | ALA | 567 | 35.512 | 49.625 | -7.572 | 1.00 0.00 | C3 |
| ATOM | 3930 | CA | ALA | 567 | 33.670 | 50.165 | -8.490 | 1.00 52.09 | C3 |
| ATOM | 3931 | CB | ALA | 567 | 34.210 | 49.574 | -9.788 | 1.00 48.37 | C3 |
| ATOM | 3932 | C | ALA | 567 | 32.315 | 49.449 | -8.238 | 1.00 55.31 | C3 |
| ATOM | 3933 | O | ALA | 567 | 31.226 | 50.008 | -8.501 | 1.00 56.87 | C3 |
| ATOM | 3934 | N | VAL | 568 | 32.247 | 48.211 | -7.736 | 1.00 57.66 | C3 |
| ATOM | 3935 | H | VAL | 568 | 33.083 | 47.729 | -7.564 | 1.00 0.00 | C3 |
| ATOM | 3936 | CA | VAL | 568 | 30.980 | 47.573 | -7.490 | 1.00 59.61 | C3 |
| ATOM | 3937 | CB | VAL | 568 | 31.119 | 46.031 | -7.339 | 1.00 58.96 | C3 |
| ATOM | 3938 | CG1 | VAL | 568 | 31.239 | 45.508 | -5.911 | 1.00 60.27 | C3 |
| ATOM | 3939 | CG2 | VAL | 568 | 29.851 | 45.471 | -7.922 | 1.00 60.44 | C3 |
| ATOM | 3940 | C | VAL | 568 | 30.393 | 48.177 | -6.245 | 1.00 62.66 | C3 |
| ATOM | 3941 | O | VAL | 568 | 29.174 | 48.154 | -6.180 | 1.00 64.78 | C3 |
| ATOM | 3942 | N | LEU | 569 | 31.075 | 48.737 | -5.248 | 1.00 66.15 | C3 |
| ATOM | 3943 | H | LEU | 569 | 32.058 | 48.719 | -5.243 | 1.00 0.00 | C3 |
| ATOM | 3944 | CA | LEU | 569 | 30.359 | 49.334 | -4.123 | 1.00 69.85 | C3 |
| ATOM | 3945 | CB | LEU | 569 | 31.285 | 49.858 | -3.023 | 1.00 69.91 | C3 |
| ATOM | 3946 | CG | LEU | 569 | 32.007 | 48.887 | -2.095 | 1.00 70.17 | C3 |
| ATOM | 3947 | CD1 | LEU | 569 | 32.847 | 49.687 | -1.140 | 1.00 70.19 | C3 |
| ATOM | 3948 | CD2 | LEU | 569 | 31.039 | 48.054 | -1.286 | 1.00 70.56 | C3 |
| ATOM | 3949 | C | LEU | 569 | 29.567 | 50.509 | -4.667 | 1.00 72.69 | C3 |
| ATOM | 3950 | O | LEU | 569 | 28.365 | 50.553 | -4.425 | 1.00 73.80 | C3 |
| ATOM | 3951 | N | ARG | 570 | 30.180 | 51.391 | -5.479 | 1.00 75.95 | C3 |
| ATOM | 3952 | H | ARG | 570 | 31.153 | 51.299 | -5.580 | 1.00 0.00 | C3 |
| ATOM | 3953 | CA | ARG | 570 | 29.510 | 52.498 | -6.173 | 1.00 78.78 | C3 |
| ATOM | 3954 | CB | ARG | 570 | 30.399 | 53.068 | -7.308 | 1.00 80.07 | C3 |
| ATOM | 3955 | CG | ARG | 570 | 29.658 | 54.222 | -7.997 | 1.00 84.16 | C3 |

FIG. 5UU

| | | | | | | | | | | | | | | | | |
|---|---|---|---|---|---|---|---|---|---|---|---|---|---|---|---|---|
| ATOM | 3956 | CD | ARG | 570 | 29.976 | 54.744 | -9.417 | 1.00 | 85.66 | C3 | ATOM | 3999 | H2 | H2O | 603 | 26.288 23.435 4.992 1.00 0.00 W |
| ATOM | 3957 | NE | ARG | 570 | 28.892 | 55.690 | -9.737 | 1.00 | 85.67 | C3 | ATOM | 4000 | OH2 | H2O | 605 | 47.880 37.960 12.073 1.00 56.30 W |
| ATOM | 3958 | HE | ARG | 570 | 27.971 | 55.354 | -9.727 | 1.00 | 0.00 | C3 | ATOM | 4001 | H1 | H2O | 605 | 47.789 37.874 13.031 1.00 0.00 W |
| ATOM | 3959 | CZ | ARG | 570 | 29.051 | 56.991 | -10.026 | 1.00 | 85.06 | C3 | ATOM | 4002 | H2 | H2O | 605 | 46.980 37.858 11.753 1.00 0.00 W |
| ATOM | 3960 | NH1 | ARG | 570 | 30.240 | 57.590 | -10.082 | 1.00 | 84.43 | C3 | ATOM | 4003 | OH2 | H2O | 607 | 40.001 49.224 7.214 1.00 40.04 W |
| ATOM | 3961 | HH11 | ARG | 570 | 31.069 | 57.056 | -9.908 | 1.00 | 0.00 | C3 | ATOM | 4004 | H1 | H2O | 607 | 40.471 48.761 7.909 1.00 0.00 W |
| ATOM | 3962 | HH12 | ARG | 570 | 30.295 | 58.561 | -10.314 | 1.00 | 0.00 | C3 | ATOM | 4005 | H2 | H2O | 607 | 40.123 48.642 6.457 1.00 0.00 W |
| ATOM | 3963 | NH2 | ARG | 570 | 27.958 | 57.736 | -10.154 | 1.00 | 84.57 | C3 | ATOM | 4006 | OH2 | H2O | 610 | 59.883 42.530 -9.698 1.00 38.90 W |
| ATOM | 3964 | HH21 | ARG | 570 | 27.059 | 57.316 | -10.030 | 1.00 | 0.00 | C3 | ATOM | 4007 | H1 | H2O | 610 | 60.512 41.833 -9.477 1.00 0.00 W |
| ATOM | 3965 | HH22 | ARG | 570 | 28.042 | 58.708 | -10.375 | 1.00 | 0.00 | C3 | ATOM | 4008 | H2 | H2O | 610 | 59.189 42.046 -10.160 1.00 0.00 W |
| ATOM | 3966 | C | ARG | 570 | 28.201 | 52.009 | -6.812 | 1.00 | 79.92 | C3 | ATOM | 4009 | OH2 | H2O | 611 | 57.178 35.940 -14.220 1.00 34.63 W |
| ATOM | 3967 | O | ARG | 570 | 27.107 | 52.565 | -6.709 | 1.00 | 79.61 | C3 | ATOM | 4010 | H1 | H2O | 611 | 57.174 36.545 -14.974 1.00 0.00 W |
| ATOM | 3968 | N | HIS | 571 | 28.362 | 50.900 | -7.511 | 1.00 | 81.35 | C3 | ATOM | 4011 | H2 | H2O | 611 | 57.989 36.211 -13.757 1.00 0.00 W |
| ATOM | 3969 | H | HIS | 571 | 29.214 | 50.417 | -7.440 | 1.00 | 0.00 | C3 | ATOM | 4012 | OH2 | H2O | 612 | 25.793 27.337 19.130 1.00 29.21 W |
| ATOM | 3970 | CA | HIS | 571 | 27.247 | 50.306 | -8.197 | 1.00 | 82.75 | C3 | ATOM | 4013 | H1 | H2O | 612 | 26.709 27.661 19.145 1.00 0.00 W |
| ATOM | 3971 | CB | HIS | 571 | 27.882 | 49.274 | -9.167 | 1.00 | 83.42 | C3 | ATOM | 4014 | H2 | H2O | 612 | 25.762 26.792 19.929 1.00 0.00 W |
| ATOM | 3972 | CG | HIS | 571 | 28.633 | 50.029 | -10.280 | 1.00 | 85.08 | C3 | ATOM | 4015 | OH2 | H2O | 615 | 29.766 34.284 9.444 1.00 45.03 W |
| ATOM | 3973 | CD2 | HIS | 571 | 28.921 | 49.529 | -11.532 | 1.00 | 85.81 | C3 | ATOM | 4016 | H1 | H2O | 615 | 30.017 34.618 10.308 1.00 0.00 W |
| ATOM | 3974 | ND1 | HIS | 571 | 29.074 | 51.303 | -10.268 | 1.00 | 86.25 | C3 | ATOM | 4017 | H2 | H2O | 615 | 29.113 33.592 9.660 1.00 0.00 W |
| ATOM | 3975 | HD1 | HIS | 571 | 29.080 | 51.900 | -9.489 | 1.00 | 0.00 | C3 | ATOM | 4018 | OH2 | H2O | 617 | 37.316 40.012 10.872 1.00 35.21 W |
| ATOM | 3976 | CE1 | HIS | 571 | 29.595 | 51.595 | -11.439 | 1.00 | 86.01 | C3 | ATOM | 4019 | H1 | H2O | 617 | 36.600 40.017 11.519 1.00 0.00 W |
| ATOM | 3977 | NE2 | HIS | 571 | 29.494 | 50.518 | -12.187 | 1.00 | 86.28 | C3 | ATOM | 4020 | H2 | H2O | 617 | 37.944 39.376 11.259 1.00 0.00 W |
| ATOM | 3978 | HE2 | HIS | 571 | 29.801 | 50.468 | -13.119 | 1.00 | 0.00 | C3 | ATOM | 4021 | OH2 | H2O | 619 | 40.370 52.041 -7.387 1.00 29.62 W |
| ATOM | 3979 | C | HIS | 571 | 26.225 | 49.759 | -7.195 | 1.00 | 83.31 | C3 | ATOM | 4022 | H1 | H2O | 619 | 40.672 52.724 -6.779 1.00 0.00 W |
| ATOM | 3980 | O | HIS | 571 | 25.075 | 50.194 | -7.301 | 1.00 | 84.06 | C3 | ATOM | 4023 | H2 | H2O | 619 | 39.505 51.810 -7.052 1.00 0.00 W |
| ATOM | 3981 | N | LEU | 572 | 26.340 | 48.963 | -6.158 | 1.00 | 83.11 | C3 | ATOM | 4024 | OH2 | H2O | 621 | 27.903 32.440 10.664 1.00 39.99 W |
| ATOM | 3982 | H | LEU | 572 | 27.474 | 48.824 | -5.915 | 1.00 | 0.00 | C3 | ATOM | 4025 | H1 | H2O | 621 | 27.553 33.207 11.141 1.00 0.00 W |
| ATOM | 3983 | CA | LEU | 572 | 25.527 | 48.457 | -5.241 | 1.00 | 83.71 | C3 | ATOM | 4026 | H2 | H2O | 621 | 27.929 31.808 11.398 1.00 0.00 W |
| ATOM | 3984 | CB | LEU | 572 | 26.085 | 47.267 | -4.454 | 1.00 | 83.57 | C3 | ATOM | 4027 | OH2 | H2O | 622 | 25.057 31.972 13.675 1.00 32.70 W |
| ATOM | 3985 | CG | LEU | 572 | 25.439 | 45.884 | -4.721 | 1.00 | 83.79 | C3 | ATOM | 4028 | H1 | H2O | 622 | 24.393 32.417 14.215 1.00 0.00 W |
| ATOM | 3986 | CD1 | LEU | 572 | 25.783 | 45.386 | -6.127 | 1.00 | 84.16 | C3 | ATOM | 4029 | H2 | H2O | 622 | 24.469 31.428 13.112 1.00 0.00 W |
| ATOM | 3987 | CD2 | LEU | 572 | 25.958 | 44.866 | -3.714 | 1.00 | 84.08 | C3 | ATOM | 4030 | OH2 | H2O | 623 | 20.791 28.583 14.218 1.00 50.17 W |
| ATOM | 3988 | C | LEU | 572 | 24.997 | 49.511 | -4.261 | 1.00 | 84.78 | C3 | ATOM | 4031 | H1 | H2O | 623 | 20.499 28.803 13.325 1.00 0.00 W |
| ATOM | 3989 | O | LEU | 572 | 24.265 | 49.192 | -3.295 | 1.00 | 84.85 | C3 | ATOM | 4032 | H2 | H2O | 623 | 19.939 28.549 14.688 1.00 0.00 W |
| ATOM | 3990 | N | ALA | 573 | 25.349 | 50.796 | -4.483 | 1.00 | 85.56 | C3 | ATOM | 4033 | OH2 | H2O | 625 | 22.680 78.881 2.761 1.00 40.48 W |
| ATOM | 3991 | H | ALA | 573 | 26.020 | 50.980 | -5.174 | 1.00 | 0.00 | C3 | ATOM | 4034 | H1 | H2O | 625 | 21.938 78.856 3.375 1.00 0.00 W |
| ATOM | 3992 | CA | ALA | 573 | 24.822 | 51.925 | -3.721 | 1.00 | 85.90 | C3 | ATOM | 4035 | H2 | H2O | 625 | 22.266 79.246 1.970 1.00 0.00 W |
| ATOM | 3993 | CB | ALA | 573 | 25.600 | 53.207 | -3.970 | 1.00 | 85.79 | C3 | ATOM | 4036 | OH2 | H2O | 626 | 39.689 36.486 9.730 1.00 23.36 W |
| ATOM | 3994 | C | ALA | 573 | 23.373 | 52.245 | -4.057 | 1.00 | 87.21 | C3 | ATOM | 4037 | H1 | H2O | 626 | 39.090 35.724 9.672 1.00 0.00 W |
| ATOM | 3995 | OT1 | ALA | 573 | 22.610 | 52.413 | -3.099 | 1.00 | 88.33 | C3 | ATOM | 4038 | H2 | H2O | 626 | 39.627 36.872 8.853 1.00 0.00 W |
| ATOM | 3996 | OT2 | ALA | 573 | 23.022 | 52.309 | -5.248 | 1.00 | 88.34 | C3 | ATOM | 4039 | OH2 | H2O | 627 | 42.035 78.320 5.697 1.00 46.19 W |
| ATOM | 3997 | OH2 | H2O | 603 | 26.735 | 24.280 | 5.161 | 1.00 | 27.42 | W | ATOM | 4040 | H1 | H2O | 627 | 42.416 77.450 5.832 1.00 0.00 W |
| ATOM | 3998 | H1 | H2O | 603 | 27.332 | 24.335 | 4.407 | 1.00 | 0.00 | W | ATOM | 4041 | H2 | H2O | 627 | 41.243 78.146 5.181 1.00 0.00 W |

FIG. 5VV

| | | | | | | | | | |
|---|---|---|---|---|---|---|---|---|---|
| ATOM | 4042 | OH2 | H2O | 631 | 47.227 | 31.440 | 6.299 | 1.00 34.17 | W |
| ATOM | 4043 | H1 | H2O | 631 | 47.533 | 32.209 | 5.809 | 1.00 0.00 | W |
| ATOM | 4044 | H2 | H2O | 631 | 47.442 | 30.713 | 5.714 | 1.00 0.00 | W |
| ATOM | 4045 | OH2 | H2O | 636 | 24.043 | 65.423 | -0.336 | 1.00 73.38 | W |
| ATOM | 4046 | H1 | H2O | 636 | 24.179 | 65.781 | -1.228 | 1.00 0.00 | W |
| ATOM | 4047 | H2 | H2O | 636 | 23.469 | 66.096 | 0.054 | 1.00 0.00 | W |
| ATOM | 4048 | OH2 | H2O | 638 | 38.984 | 67.955 | -11.226 | 1.00 29.97 | W |
| ATOM | 4049 | H1 | H2O | 638 | 38.283 | 67.402 | -11.580 | 1.00 0.00 | W |
| ATOM | 4050 | H2 | H2O | 638 | 39.568 | 68.046 | -11.998 | 1.00 0.00 | W |
| ATOM | 4051 | OH2 | H2O | 639 | 27.930 | 66.675 | -7.733 | 1.00 43.40 | W |
| ATOM | 4052 | H1 | H2O | 639 | 28.192 | 67.028 | -6.876 | 1.00 0.00 | W |
| ATOM | 4053 | H2 | H2O | 639 | 26.975 | 66.791 | -7.705 | 1.00 0.00 | W |
| ATOM | 4054 | OH2 | H2O | 643 | 50.619 | 62.802 | 0.813 | 1.00 36.55 | W |
| ATOM | 4055 | H1 | H2O | 643 | 51.575 | 62.904 | 0.824 | 1.00 0.00 | W |
| ATOM | 4056 | H2 | H2O | 643 | 50.301 | 63.665 | 0.525 | 1.00 0.00 | W |
| ATOM | 4057 | OH2 | H2O | 646 | 62.897 | 38.367 | 3.759 | 1.00 73.55 | W |
| ATOM | 4058 | H1 | H2O | 646 | 62.414 | 38.098 | 2.978 | 1.00 0.00 | W |
| ATOM | 4059 | H2 | H2O | 646 | 62.244 | 38.247 | 4.461 | 1.00 0.00 | W |
| ATOM | 4060 | OH2 | H2O | 650 | 29.587 | 68.480 | -9.555 | 1.00 65.67 | W |
| ATOM | 4061 | H1 | H2O | 650 | 28.846 | 68.630 | -10.148 | 1.00 0.00 | W |
| ATOM | 4062 | H2 | H2O | 650 | 29.180 | 67.844 | -8.936 | 1.00 0.00 | W |
| ATOM | 4063 | OH2 | H2O | 652 | 51.408 | 56.331 | 4.056 | 1.00 62.90 | W |
| ATOM | 4064 | H1 | H2O | 652 | 50.718 | 56.353 | 3.365 | 1.00 0.00 | W |
| ATOM | 4065 | H2 | H2O | 652 | 51.052 | 55.671 | 4.648 | 1.00 0.00 | W |
| ATOM | 4066 | OH2 | H2O | 653 | 49.404 | 56.022 | 2.161 | 1.00 51.28 | W |
| ATOM | 4067 | H1 | H2O | 653 | 49.442 | 55.351 | 1.474 | 1.00 0.00 | W |
| ATOM | 4068 | H2 | H2O | 653 | 49.323 | 56.829 | 1.630 | 1.00 0.00 | W |
| ATOM | 4069 | OH2 | H2O | 654 | 68.215 | 42.294 | -2.563 | 1.00 40.77 | W |
| ATOM | 4070 | H1 | H2O | 654 | 68.347 | 41.745 | -1.777 | 1.00 0.00 | W |
| ATOM | 4071 | H2 | H2O | 654 | 68.189 | 43.181 | -2.190 | 1.00 0.00 | W |
| ATOM | 4072 | OH2 | H2O | 655 | 66.374 | 40.425 | -2.489 | 1.00 42.31 | W |
| ATOM | 4073 | H1 | H2O | 655 | 66.936 | 41.162 | -2.766 | 1.00 0.00 | W |
| ATOM | 4074 | H2 | H2O | 655 | 66.452 | 39.841 | -3.252 | 1.00 0.00 | W |
| ATOM | 4075 | OH2 | H2O | 656 | 66.927 | 41.428 | -5.011 | 1.00 44.08 | W |
| ATOM | 4076 | H1 | H2O | 656 | 66.207 | 42.071 | -4.989 | 1.00 0.00 | W |
| ATOM | 4077 | H2 | H2O | 656 | 67.542 | 41.824 | -4.374 | 1.00 0.00 | W |
| ATOM | 4078 | OH2 | H2O | 657 | 40.371 | 57.111 | 5.730 | 1.00 66.56 | W |
| ATOM | 4079 | H1 | H2O | 657 | 39.958 | 56.259 | 5.613 | 1.00 0.00 | W |
| ATOM | 4080 | H2 | H2O | 657 | 40.021 | 57.651 | 5.014 | 1.00 0.00 | W |
| ATOM | 4081 | OH2 | H2O | 658 | 48.780 | 47.580 | -3.122 | 1.00 52.09 | W |
| ATOM | 4082 | H1 | H2O | 658 | 48.811 | 46.671 | -3.438 | 1.00 0.00 | W |
| ATOM | 4083 | H2 | H2O | 658 | 49.568 | 47.955 | -3.542 | 1.00 0.00 | W |
| ATOM | 4084 | OH2 | H2O | 663 | 29.095 | 62.889 | 1.825 | 1.00 39.23 | W |
| ATOM | 4085 | H1 | H2O | 663 | 29.380 | 62.827 | 2.739 | 1.00 0.00 | W |
| ATOM | 4086 | H2 | H2O | 663 | 28.377 | 63.526 | 1.887 | 1.00 0.00 | W |
| ATOM | 4087 | OH2 | H2O | 664 | 27.132 | 25.640 | 7.430 | 1.00 50.65 | W |
| ATOM | 4088 | H1 | H2O | 664 | 26.870 | 24.838 | 7.876 | 1.00 0.00 | W |
| ATOM | 4089 | H2 | H2O | 664 | 27.001 | 25.362 | 6.496 | 1.00 0.00 | W |
| ATOM | 4090 | OH2 | H2O | 665 | 23.367 | 30.554 | 12.167 | 1.00 49.69 | W |
| ATOM | 4091 | H1 | H2O | 665 | 24.026 | 30.006 | 11.707 | 1.00 0.00 | W |
| ATOM | 4092 | H2 | H2O | 665 | 22.941 | 31.016 | 11.438 | 1.00 0.00 | W |
| ATOM | 4093 | OH2 | H2O | 666 | 46.015 | 32.192 | 10.179 | 1.00 66.86 | W |
| ATOM | 4094 | H1 | H2O | 666 | 46.060 | 31.519 | 9.497 | 1.00 0.00 | W |
| ATOM | 4095 | H2 | H2O | 666 | 45.411 | 31.827 | 10.833 | 1.00 0.00 | W |
| ATOM | 4096 | OH2 | H2O | 667 | 38.943 | 37.883 | 11.978 | 1.00 47.87 | W |
| ATOM | 4097 | H1 | H2O | 667 | 39.367 | 37.487 | 11.188 | 1.00 0.00 | W |
| ATOM | 4098 | H2 | H2O | 667 | 38.521 | 37.114 | 12.362 | 1.00 0.00 | W |
| ATOM | 4099 | OH2 | H2O | 671 | 33.437 | 58.101 | 2.269 | 1.00 46.65 | W |
| ATOM | 4100 | H1 | H2O | 671 | 33.555 | 57.162 | 2.433 | 1.00 0.00 | W |
| ATOM | 4101 | H2 | H2O | 671 | 33.962 | 58.514 | 2.961 | 1.00 0.00 | W |
| ATOM | 4102 | OH2 | H2O | 672 | 27.551 | 31.314 | 20.022 | 1.00 30.15 | W |
| ATOM | 4103 | H1 | H2O | 672 | 27.929 | 32.042 | 20.533 | 1.00 0.00 | W |
| ATOM | 4104 | H2 | H2O | 672 | 26.845 | 31.764 | 19.552 | 1.00 0.00 | W |
| ATOM | 4105 | OH2 | H2O | 673 | 25.714 | 36.908 | 21.385 | 1.00 36.95 | W |
| ATOM | 4106 | H1 | H2O | 673 | 24.806 | 37.123 | 21.637 | 1.00 0.00 | W |
| ATOM | 4107 | H2 | H2O | 673 | 25.599 | 36.284 | 20.654 | 1.00 0.00 | W |
| ATOM | 4108 | OH2 | H2O | 674 | 38.244 | 66.897 | 12.076 | 1.00 57.36 | W |
| ATOM | 4109 | H1 | H2O | 674 | 37.773 | 67.536 | 12.626 | 1.00 0.00 | W |
| ATOM | 4110 | H2 | H2O | 674 | 38.153 | 66.104 | 12.618 | 1.00 0.00 | W |
| ATOM | 4111 | OH2 | H2O | 675 | 35.762 | 36.553 | -3.986 | 1.00 58.40 | W |
| ATOM | 4112 | H1 | H2O | 675 | 35.600 | 37.449 | -3.677 | 1.00 0.00 | W |
| ATOM | 4113 | H2 | H2O | 675 | 35.549 | 36.642 | -4.923 | 1.00 0.00 | W |
| ATOM | 4114 | OH2 | H2O | 676 | 30.689 | 32.814 | 25.675 | 1.00 59.30 | W |
| ATOM | 4115 | H1 | H2O | 676 | 30.093 | 33.571 | 25.680 | 1.00 0.00 | W |
| ATOM | 4116 | H2 | H2O | 676 | 31.550 | 33.214 | 25.540 | 1.00 0.00 | W |
| END | | | | | | | | | |

SEQUENCE LISTING (1) GENERAL INFORMATION:

(iii) NUMBER OF SEQUENCES: 110

(2) INFORMATION FOR SEQ ID NO: 1:

(i) SEQUENCE CHARACTERISTICS:
        (A) LENGTH: 565 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 30..554

(xi) SEQUENCE DESCRIPTION: SEQ ID NO: 1:

```
TCTAGAAAAA ACCAAGGAGG TAATAAATA ATG ACT CCA TTA GGT CCT GCT TCT        53
                               Met Thr Pro Leu Gly Pro Ala Ser
                                 1               5

TCT CTG CCG CAA AGC TTT CTG CTG AAA TGT CTG GAA CAG GTT CGT AAA       101
Ser Leu Pro Gln Ser Phe Leu Leu Lys Cys Leu Glu Gln Val Arg Lys
     10              15                  20

ATC CAG GGT GAC GGT GCT GCA CTG CAA GAA AAA CTG TGC GCT ACT TAC       149
Ile Gln Gly Asp Gly Ala Ala Leu Gln Glu Lys Leu Cys Ala Thr Tyr
 25              30                  35                  40

AAA CTG TGC CAT CCG GAA GAA CTG GTA CTG CTG GGT CAT TCT CTT GGG       197
Lys Leu Cys His Pro Glu Glu Leu Val Leu Leu Gly His Ser Leu Gly
                 45                  50                  55

ATC CCG TGG GCT CCG CTG TCT TCT TGC CCA TCT CAA GCT CTT CAG CTG       245
Ile Pro Trp Ala Pro Leu Ser Ser Cys Pro Ser Gln Ala Leu Gln Leu
                 60                  65                  70

GCT GGT TGT CTG TCT CAA CTG CAT TCT GGT CTG TTC CTG TAT CAG GGT       293
Ala Gly Cys Leu Ser Gln Leu His Ser Gly Leu Phe Leu Tyr Gln Gly
             75                  80                  85

CTT CTG CAA GCT CTG GAA GGT ATC TCT CCG GAA CTG GGT CCG ACT CTG       341
Leu Leu Gln Ala Leu Glu Gly Ile Ser Pro Glu Leu Gly Pro Thr Leu
         90                  95                 100

GAC ACT CTG CAG CTA GAT GTA GCT GAC TTT GCT ACT ACT ATT TGG CAA       389
Asp Thr Leu Gln Leu Asp Val Ala Asp Phe Ala Thr Thr Ile Trp Gln
105                 110                 115                 120

CAG ATG GAA GAG CTC GGT ATG GCA CCA GCT CTG CAA CCG ACT CAA GGT       437
Gln Met Glu Glu Leu Gly Met Ala Pro Ala Leu Gln Pro Thr Gln Gly
                125                 130                 135

GCT ATG CCG GCA TTC GCT TCT GCA TTC CAG CGT CGT GCA GGA GGT GTA       485
Ala Met Pro Ala Phe Ala Ser Ala Phe Gln Arg Arg Ala Gly Gly Val
            140                 145                 150

CTG GTT GCT TCT CAT CTG CAA TCT TTC CTG GAA GTA TCT TAC CGT GTT       533
Leu Val Ala Ser His Leu Gln Ser Phe Leu Glu Val Ser Tyr Arg Val
            155                 160                 165

CTG CGT CAT CTG GCT CAG CCG TAATAGAATT C                              565
Leu Arg His Leu Ala Gln Pro
170                 175
```

(2) INFORMATION FOR SEQ ID NO: 2:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Thr Pro Leu Gly Pro Ala Ser Ser Leu Pro Gln Ser Phe Leu Leu
  1               5                  10                  15
```

```
Lys Cys Leu Glu Gln Val Arg Lys Ile Gln Gly Asp Gly Ala Ala Leu
             20                   25                  30

Gln Glu Lys Leu Cys Ala Thr Tyr Lys Leu Cys His Pro Glu Glu Leu
         35                  40                  45

Val Leu Leu Gly His Ser Leu Gly Ile Pro Trp Ala Pro Leu Ser Ser
     50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

CTTTCTGCTG CGTTGTCTGG AACA                                  24

(2) INFORMATION FOR SEQ ID NO: 4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

ACAGGTTCGT CGTATCCAGG GTG                                   23

(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

CACTGCAAGA ACGTCTGTGC GTC                                   23

(2) INFORMATION FOR SEQ ID NO: 6:

(i) SEQUENCE CHARACTERISTICS:

```
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

CGCTACTTAC CGTCTGTGCC ATC                                               23

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

CTTTCTGCTG CGTTGTCTGG AACA                                              24

(2) INFORMATION FOR SEQ ID NO: 8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

ACAGGTTCGT CGTATCCAGG GTG                                               23

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

CACTGCAAGA ACGTCTGTGC GCT                                               23

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

CTTTCTGCTG CGTTGTCTGG AACA                                              24

(2) INFORMATION FOR SEQ ID NO: 11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO: 11:

ACAGGTTCGT CGTATCCAGG GTG                                              23

(2) INFORMATION FOR SEQ ID NO: 12:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 12:

CGCTACTTAC CGTCTGTCCC ATC                                              23

(2) INFORMATION FOR SEQ ID NO: 13:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 13:

CTTTCTGCTG CGTTGTCTGG AACA                                             24

(2) INFORMATION FOR SEQ ID NO: 14:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 14:

CACTGCAAGA ACGTCTGTGC GCT                                              23

(2) INFORMATION FOR SEQ ID NO: 15:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 15:

CGCTACTTAC CGTCTGTGCC ATC                                              23

(2) INFORMATION FOR SEQ ID NO: 16:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 16:

ACAGGTTCGT CGTATCCAGG GTG                                             23

(2) INFORMATION FOR SEQ ID NO: 17:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 17:

CACTGCAAGA ACGTCTGTGC GCT                                             23

(2) INFORMATION FOR SEQ ID NO: 18:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 18:

CGCTACTTAC CGTCTGTGCC ATC                                             23

(2) INFORMATION FOR SEQ ID NO: 19:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 19:

CTTTCTGCTG CGTTGTCTGG AACA                                            24

(2) INFORMATION FOR SEQ ID NO: 20:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 20:

ACAGGTTCGT CGTATCCAGG GTG                                             23

(2) INFORMATION FOR SEQ ID NO: 21:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 21:

CACTGCAAGA ACGTCTGTGC GCT                                             23

```
(2) INFORMATION FOR SEQ ID NO: 22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

CGCTACTTAC CGTCTGTGCC ATC                                              23

(2) INFORMATION FOR SEQ ID NO: 23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

TCTGCTGAAA GCTCTGGAAC AGG                                              23

(2) INFORMATION FOR SEQ ID NO: 24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

CTTGTCCATC TGAAGCTCTT CAG                                              23

(2) INFORMATION FOR SEQ ID NO: 25:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

GAAAAACTGT CCGCTACTTA CAAACTGTCC CATCCGG                               37

(2) INFORMATION FOR SEQ ID NO: 26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

TTCGTAAAAT CGCGGGTGAC GG                                               22

(2) INFORMATION FOR SEQ ID NO: 27:

(i) SEQUENCE CHARACTERISTICS:
        (A) LENGTH: 22 base pairs
```

(B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 27:

TCATCTGGCT GCGCCGTAAT AG                                              22

(2) INFORMATION FOR SEQ ID NO: 28:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 28:

CCGTGTTCTG GCTCATCTGG CT                                              22

(2) INFORMATION FOR SEQ ID NO: 29:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 29:

GAAGTATCTT ACGCTGTTCT GCGT                                            24

(2) INFORMATION FOR SEQ ID NO: 30:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 30:

GAAGTATCTT ACTAAGTTCT GCGTC                                           25

(2) INFORMATION FOR SEQ ID NO: 31:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 31:

CGCTACTTAC GCACTGTGCC AT                                              22

(2) INFORMATION FOR SEQ ID NO: 32:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 32:

CAAACTGTGC AAGCCGGAAG AG                                    22

(2) INFORMATION FOR SEQ ID NO: 33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

CATCCGGAAG CACTGGTACT GC                                    22

(2) INFORMATION FOR SEQ ID NO: 34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:

GGAACAGGTT GCTAAAATCC AGG                                   23

(2) INFORMATION FOR SEQ ID NO: 35:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 35:

GAACAGGTTC GTGCGATCCA GGGTG                                 25

(2) INFORMATION FOR SEQ ID NO: 36:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 36:

GAAATGTCTG GCACAGGTTC GT                                    22

(2) INFORMATION FOR SEQ ID NO: 37:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 37:

```
TCCAGGGTGC CGGTGCTGC                                                          19
```

(2) INFORMATION FOR SEQ ID NO: 38:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 38:

```
AAGAGCTCGG TGAGGCACCA GCT                                                     23
```

(2) INFORMATION FOR SEQ ID NO: 39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 39:

```
CTCAAGGTGC TGAGCCGGCA TTC                                                     23
```

(2) INFORMATION FOR SEQ ID NO: 40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 40:

```
GAGCTCGGTC TGGCACCAGC                                                         20
```

(2) INFORMATION FOR SEQ ID NO: 41:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 41:

```
TCAAGGTGCT CTGCCGGCAT T                                                       21
```

(2) INFORMATION FOR SEQ ID NO: 42:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 42:

```
TCTGCCGCAA GCCTTTCTGC TGA                                                     23
```

(2) INFORMATION FOR SEQ ID NO: 43:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 43:

CTTTCTGCTG GCATGTCTGG AACA                                                  24

(2) INFORMATION FOR SEQ ID NO: 44:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 44:

CTATTTGGCA AGCGATGGAA GAGC                                                  24

(2) INFORMATION FOR SEQ ID NO: 45:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 45:

CAGATGGAAG CGCTCGGTAT G                                                     21

(2) INFORMATION FOR SEQ ID NO: 46:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 46:

GAGCTCGGTC TGGCACCAGC                                                       20

(2) INFORMATION FOR SEQ ID NO: 47:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 47:

TCAAGGTGCT CTGCCGGCAT T                                                     21

(2) INFORMATION FOR SEQ ID NO: 48:

(i) SEQUENCE CHARACTERISTICS:
            (A) LENGTH: 22 base pairs
            (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO: 48:

GAAATGTCTG GCACAGGTTC GT                                            22

(2) INFORMATION FOR SEQ ID NO: 49:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 49:

TTCCGGAGCG CACAGTTTG                                                19

(2) INFORMATION FOR SEQ ID NO: 50:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 50:

CGAGAAGGCC TCGGGTGTCA AAC                                           23

(2) INFORMATION FOR SEQ ID NO: 51:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 51:

ATGCCAAATT GCAGTAGCAA AG                                            22

(2) INFORMATION FOR SEQ ID NO: 52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 52:

ACAACGGTTT AACGTCATCG TTTC                                          24

(2) INFORMATION FOR SEQ ID NO: 53:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 53:

ATCAGCTACT GCTAGCTGCA GA                                          22

(2) INFORMATION FOR SEQ ID NO: 54:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 54:

TCAGTCGATG ACGATCGACG TCT                                         23

(2) INFORMATION FOR SEQ ID NO: 55:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 55:

TTACGAACCG CTTCCAGACA TT                                          22

(2) INFORMATION FOR SEQ ID NO: 56:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 56:

TAAAATGCTT GGCGAAGGTC TGTAA                                       25

(2) INFORMATION FOR SEQ ID NO: 57:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 57:

GTAGCAAATG CAGCTACATC TA                                          22

(2) INFORMATION FOR SEQ ID NO: 58:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 58:

CATCATCGTT TACGTCGATG TAGAT                                       25

(2) INFORMATION FOR SEQ ID NO: 59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 59:

CCAAGAGAAG CACCCAGCAG                                         20

(2) INFORMATION FOR SEQ ID NO: 60:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 60:

AGGGTTCTCT TCGTGGGTCG TC                                      22

(2) INFORMATION FOR SEQ ID NO: 61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 61:

CACTGGCGGT GATAATGAGC                                         20

(2) INFORMATION FOR SEQ ID NO: 62:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 62:

CTAGGCCAGG CATTACTGG                                           19

(2) INFORMATION FOR SEQ ID NO: 63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 63:

CCACTGGCGG TGATACTGAG C                                        21

(2) INFORMATION FOR SEQ ID NO: 64:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 64:

AGCAGAAAGC TTTCCGGCAG AGAAGAAGCA GGA                                     33

(2) INFORMATION FOR SEQ ID NO: 65:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 65:

GCCGCAAAGC TTTCTGCTGA AATGTCTGGA AGAGGTTCGT AAAATCCAGG GTGA              54

(2) INFORMATION FOR SEQ ID NO: 66:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 66:

CTGGAATGCA GAAGCAAATG CCGGCATAGC ACCTTCAGTC GGTTGCAGAG CTGGTGCCA         59

(2) INFORMATION FOR SEQ ID NO: 67:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 67:

Met Thr Pro Leu Gly Pro Ala Ser Ser Leu Pro Gln Ser Phe Leu Leu
  1               5                  10                  15

Arg Cys Leu Glu Gln Val Arg Lys Ile Gln Gly Asp Gly Ala Ala Leu
                 20                  25                  30

Gln Glu Lys Leu Cys Ala Thr Tyr Lys Leu Cys His Pro Glu Glu Leu
             35                  40                  45

Val Leu Leu Gly His Ser Leu Gly Ile Pro Trp Ala Pro Leu Ser Ser
 50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala

```
              130                 135                 140
Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 68:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 68:

Met Thr Pro Leu Gly Pro Ala Ser Ser Leu Pro Gln Ser Phe Leu Leu
 1               5                  10                  15

Lys Cys Leu Glu Gln Val Arg Arg Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
       50                   55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 69:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 69:

Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Arg Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
       50                   55                  60

Cys Pro Ser Gln Ala Leu Gln Leu Ala Gly Cys Leu Ser Gln Leu His
65                  70                  75                  80
```

```
Ser Gly Leu Phe Leu Tyr Gln Gly Leu Leu Gln Ala Leu Glu Gly Ile
            85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135             140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
            165                 170                 175
```

(2) INFORMATION FOR SEQ ID NO: 70:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 70:

```
Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Arg Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
            85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135             140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
            165                 170                 175
```

(2) INFORMATION FOR SEQ ID NO: 71:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 71:

```
Met Thr Pro Leu Gly Pro Ala Ser Ser Leu Pro Gln Ser Phe Leu Leu
1               5                   10                  15
```

```
Arg Cys Leu Glu Gln Val Arg Arg Ile Gln Gly Asp Gly Ala Ala Leu
             20                  25                  30

Gln Glu Arg Leu Cys Ala Thr Tyr Lys Leu Cys His Pro Glu Glu Leu
         35                  40                  45

Val Leu Leu Gly His Ser Leu Gly Ile Pro Trp Ala Pro Leu Ser Ser
 50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 72:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 72:

Met Thr Pro Leu Gly Pro Ala Ser Ser Leu Pro Gln Ser Phe Leu Leu
  1               5                  10                  15

Arg Cys Leu Glu Gln Val Arg Lys Ile Gln Gly Asp Gly Ala Ala Leu
             20                  25                  30

Gln Glu Arg Leu Cys Ala Thr Tyr Arg Leu Cys His Pro Glu Glu Leu
         35                  40                  45

Val Leu Leu Gly His Ser Leu Gly Ile Pro Trp Ala Pro Leu Ser Ser
 50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 73:

(i) SEQUENCE CHARACTERISTICS:
```

(A) LENGTH: 175 amino acids
(B) TYPE: amino acid
(D) TOPOLOGY: linear (ii) MOLECULE TYPE: protein (xi) SEQUENCE DESCRIPTION: SEQ ID NO: 73:

```
Met Thr Pro Leu Gly Pro Ala Ser Ser Leu Pro Gln Ser Phe Leu Leu
 1               5                  10                  15

Lys Cys Leu Glu Gln Val Arg Arg Ile Gln Gly Asp Gly Ala Ala Leu
                20                  25                  30

Gln Glu Arg Leu Cys Ala Thr Tyr Arg Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
               100                 105                 110

Asp Phe Ala Thr Thr Ile Trp Gln Gln Met Glu Glu Leu Gly Met Ala
           115                 120                 125

Pro Ala Leu Gln Pro Thr Gln Gly Ala Met Pro Ala Phe Ala Ser Ala
       130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
               165                 170                 175
```

(2) INFORMATION FOR SEQ ID NO: 74:

(i) SEQUENCE CHARACTERISTICS:
(A) LENGTH: 175 amino acids
(B) TYPE: amino acid
(D) TOPOLOGY: linear (ii) MOLECULE TYPE: protein (xi) SEQUENCE DESCRIPTION: SEQ ID NO: 74:

```
Met Thr Pro Leu Gly Pro Ala Ser Ser Leu Pro Gln Ser Phe Leu Leu
 1               5                  10                  15

Arg Cys Leu Glu Gln Val Arg Arg Ile Gln Gly Asp Gly Ala Ala Leu
                20                  25                  30

Gln Glu Arg Leu Cys Ala Thr Tyr Arg Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
               100                 105                 110

Asp Phe Ala Thr Thr Ile Trp Gln Gln Met Glu Glu Leu Gly Met Ala
           115                 120                 125

Pro Ala Leu Gln Pro Thr Gln Gly Ala Met Pro Ala Phe Ala Ser Ala
       130                 135                 140
```

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
            165                 170                 175

(2) INFORMATION FOR SEQ ID NO: 75:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 75:

Met Thr Pro Leu Gly Pro Ala Ser Ser Leu Pro Gln Ser Phe Leu Leu
1               5                   10                  15

Arg Cys Leu Glu Gln Val Arg Arg Ile Gln Gly Asp Gly Ala Ala Leu
                20                  25                  30

Gln Glu Lys Leu Cys Ala Thr Tyr Arg Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
            165                 170                 175

(2) INFORMATION FOR SEQ ID NO: 76:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 76:

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Glu Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
            85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
            165                 170                 175

(2) INFORMATION FOR SEQ ID NO: 77:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 77:

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Ser Ala Thr Tyr Lys Leu Ser His Pro Glu Glu Leu
            35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
            85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
            165                 170                 175

(2) INFORMATION FOR SEQ ID NO: 78:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 78:

Met Thr Pro Leu Gly Pro Ala Ser Ser Leu Pro Gln Ser Phe Leu Leu
1               5                   10                  15

Lys Cys Leu Glu Gln Val Arg Lys Ile Ala Gly Asp Gly Ala Ala Leu

```
                20                  25                  30
Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
               100                 105                 110

Asp Phe Ala Thr Thr Ile Trp Gln Gln Met Glu Glu Leu Gly Met Ala
               115                 120                 125

Pro Ala Leu Gln Pro Thr Gln Gly Ala Met Pro Ala Phe Ala Ser Ala
               130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 79:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 79:

Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
               100                 105                 110

Asp Phe Ala Thr Thr Ile Trp Gln Gln Met Glu Glu Leu Gly Met Ala
               115                 120                 125

Pro Ala Leu Gln Pro Thr Gln Gly Ala Met Pro Ala Phe Ala Ser Ala
               130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Ala Pro
                165                 170                 175

(2) INFORMATION FOR SEQ ID NO: 80:

(i) SEQUENCE CHARACTERISTICS:
        (A) LENGTH: 175 amino acids
```

(B) TYPE: amino acid
         (D) TOPOLOGY: linear (ii) MOLECULE TYPE: protein (xi) SEQUENCE DESCRIPTION: SEQ ID NO: 80:

Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
               100                 105                 110

Asp Phe Ala Thr Thr Ile Trp Gln Gln Met Glu Glu Leu Gly Met Ala
           115                 120                 125

Pro Ala Leu Gln Pro Thr Gln Gly Ala Met Pro Ala Phe Ala Ser Ala
       130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Ala His Leu Ala Gln Pro
                165                 170                 175

(2) INFORMATION FOR SEQ ID NO: 81:

(i) SEQUENCE CHARACTERISTICS:
         (A) LENGTH: 175 amino acids
         (B) TYPE: amino acid
         (D) TOPOLOGY: linear (ii) MOLECULE TYPE: protein (xi) SEQUENCE DESCRIPTION: SEQ ID NO: 81:

Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
               100                 105                 110

Asp Phe Ala Thr Thr Ile Trp Gln Gln Met Glu Glu Leu Gly Met Ala
           115                 120                 125

Pro Ala Leu Gln Pro Thr Gln Gly Ala Met Pro Ala Phe Ala Ser Ala
       130                 135                 140

```
Phe Gln Arg Arg Ala Gly Gly Val Leu Val Ala Ser His Leu Gln Ser
145                 150                 155                 160

Phe Leu Glu Val Ser Tyr Ala Val Leu Arg His Leu Ala Gln Pro
                165                 170                 175

(2) INFORMATION FOR SEQ ID NO: 82:

(i) SEQUENCE CHARACTERISTICS:
        (A) LENGTH: 174 amino acids
        (B) TYPE: amino acid
        (D) TOPOLOGY: linear (ii) MOLECULE TYPE: protein (xi) SEQUENCE DESCRIPTION: SEQ ID NO: 82:

Met Thr Pro Leu Gly Pro Ala Ser Ser Leu Pro Gln Ser Phe Leu Leu
1                   5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
                35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Val Leu Arg His Leu Ala Gln Pro
                165                 170                 174

(2) INFORMATION FOR SEQ ID NO: 83:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 83:

Met Thr Pro Leu Gly Pro Ala Ser Ser Leu Pro Gln Ser Phe Leu Leu
1                   5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Ala Leu Cys His Pro Glu Glu Leu
                35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
```

```
                    85                  90                  95
Ser Pro Glu Leu Gly Pro Thr Leu Asp Thr Leu Gln Leu Asp Val Ala
                100                 105                 110
Asp Phe Ala Thr Thr Ile Trp Gln Gln Met Glu Glu Leu Gly Met Ala
                115                 120                 125
Pro Ala Leu Gln Pro Thr Gln Gly Ala Met Pro Ala Phe Ala Ser Ala
        130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro
                165                 170                 175

(2) INFORMATION FOR SEQ ID NO: 84:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 84:

Met Thr Pro Leu Gly Pro Ala Ser Ser Leu Pro Gln Ser Phe Leu Leu
1               5                   10                  15
Lys Cys Leu Glu Gln Val Arg Lys Ile Gln Gly Asp Gly Ala Ala Leu
                20                  25                  30
Gln Glu Lys Leu Cys Ala Thr Tyr Lys Leu Cys Lys Pro Glu Glu Leu
            35                  40                  45
Val Leu Leu Gly His Ser Leu Gly Ile Pro Trp Ala Pro Leu Ser Ser
        50                  55                  60
Cys Pro Ser Gln Ala Leu Gln Leu Ala Gly Cys Leu Ser Gln Leu His
65                  70                  75                  80
Ser Gly Leu Phe Leu Tyr Gln Gly Leu Leu Gln Ala Leu Glu Gly Ile
                85                  90                  95
Ser Pro Glu Leu Gly Pro Thr Leu Asp Thr Leu Gln Leu Asp Val Ala
                100                 105                 110
Asp Phe Ala Thr Thr Ile Trp Gln Gln Met Glu Glu Leu Gly Met Ala
                115                 120                 125
Pro Ala Leu Gln Pro Thr Gln Gly Ala Met Pro Ala Phe Ala Ser Ala
        130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro
                165                 170                 175

(2) INFORMATION FOR SEQ ID NO: 85:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 85:

Met Thr Pro Leu Gly Pro Ala Ser Ser Leu Pro Gln Ser Phe Leu Leu
1               5                   10                  15
Lys Cys Leu Glu Gln Val Arg Lys Ile Gln Gly Asp Gly Ala Ala Leu
                20                  25                  30
```

```
Gln Glu Lys Leu Cys Ala Thr Tyr Lys Leu Cys His Pro Glu Ala Leu
         35                  40                  45

Val Leu Leu Gly His Ser Leu Gly Ile Pro Trp Ala Pro Leu Ser Ser
 50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
             100                 105                 110

Asp Phe Ala Thr Thr Ile Trp Gln Gln Met Glu Glu Leu Gly Met Ala
             115                 120                 125

Pro Ala Leu Gln Pro Thr Gln Gly Ala Met Pro Ala Phe Ala Ser Ala
             130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                 165                 170                 175

(2) INFORMATION FOR SEQ ID NO: 86:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 86:

Met Thr Pro Leu Gly Pro Ala Ser Ser Leu Pro Gln Ser Phe Leu Leu
 1               5                  10                  15

Lys Cys Leu Glu Gln Val Ala Lys Ile Gln Gly Asp Gly Ala Ala Leu
                 20                  25                  30

Gln Glu Lys Leu Cys Ala Thr Tyr Lys Leu Cys His Pro Glu Glu Leu
         35                  40                  45

Val Leu Leu Gly His Ser Leu Gly Ile Pro Trp Ala Pro Leu Ser Ser
 50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
             100                 105                 110

Asp Phe Ala Thr Thr Ile Trp Gln Gln Met Glu Glu Leu Gly Met Ala
             115                 120                 125

Pro Ala Leu Gln Pro Thr Gln Gly Ala Met Pro Ala Phe Ala Ser Ala
             130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                 165                 170                 175

(2) INFORMATION FOR SEQ ID NO: 87:

(i) SEQUENCE CHARACTERISTICS:
        (A) LENGTH: 175 amino acids
        (B) TYPE: amino acid
```

(D) TOPOLOGY: linear (ii) MOLECULE TYPE: protein (xi) SEQUENCE DESCRIPTION: SEQ ID NO: 87:

```
Met Thr Pro Leu Gly Pro Ala Ser Ser Leu Pro Gln Ser Phe Leu Leu
 1               5                  10                  15

Lys Cys Leu Glu Gln Val Arg Ala Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

(2) INFORMATION FOR SEQ ID NO: 88:

(i) SEQUENCE CHARACTERISTICS:
       (A) LENGTH: 175 amino acids
       (B) TYPE: amino acid
       (D) TOPOLOGY: linear (ii) MOLECULE TYPE: protein (xi) SEQUENCE DESCRIPTION: SEQ ID NO: 88:

```
Met Thr Pro Leu Gly Pro Ala Ser Ser Leu Pro Gln Ser Phe Leu Leu
 1               5                  10                  15

Lys Cys Leu Ala Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
```

```
                    145                 150                 155                 160
Phe Leu Glu Val Ser Tyr Arg Val Leu Arg His Leu Ala Gln Pro
                165                 170                 175
```

(2) INFORMATION FOR SEQ ID NO: 89:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 89:

```
Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Ala Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

(2) INFORMATION FOR SEQ ID NO: 90:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 90:

```
Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95
```

```
Ser Pro Glu Leu Gly Pro Thr Leu Asp Thr Leu Gln Leu Asp Val Ala
            100                 105                 110
Asp Phe Ala Thr Thr Ile Trp Gln Gln Met Glu Glu Leu Gly Glu Ala
            115                 120                 125
Pro Ala Leu Gln Pro Thr Gln Gly Ala Met Pro Ala Phe Ala Ser Ala
            130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro
                165                 170                 175

(2) INFORMATION FOR SEQ ID NO: 91:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 91:

Met Thr Pro Leu Gly Pro Ala Ser Ser Leu Pro Gln Ser Phe Leu Leu
  1                 5                  10                  15
Lys Cys Leu Glu Gln Val Arg Lys Ile Gln Gly Asp Gly Ala Ala Leu
            20                  25                  30
Gln Glu Lys Leu Cys Ala Thr Tyr Lys Leu Cys His Pro Glu Glu Leu
            35                  40                  45
Val Leu Leu Gly His Ser Leu Gly Ile Pro Trp Ala Pro Leu Ser Ser
     50                  55                  60
Cys Pro Ser Gln Ala Leu Gln Leu Ala Gly Cys Leu Ser Gln Leu His
 65                  70                  75                  80
Ser Gly Leu Phe Leu Tyr Gln Gly Leu Leu Gln Ala Leu Glu Gly Ile
                85                  90                  95
Ser Pro Glu Leu Gly Pro Thr Leu Asp Thr Leu Gln Leu Asp Val Ala
            100                 105                 110
Asp Phe Ala Thr Thr Ile Trp Gln Gln Met Glu Glu Leu Gly Met Ala
            115                 120                 125
Pro Ala Leu Gln Pro Thr Gln Gly Ala Glu Pro Ala Phe Ala Ser Ala
            130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro
                165                 170                 175

(2) INFORMATION FOR SEQ ID NO: 92:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 92:

Met Thr Pro Leu Gly Pro Ala Ser Ser Leu Pro Gln Ser Phe Leu Leu
  1                 5                  10                  15
Lys Cys Leu Glu Gln Val Arg Lys Ile Gln Gly Asp Gly Ala Ala Leu
            20                  25                  30
```

```
Gln Glu Lys Leu Cys Ala Thr Tyr Lys Leu Cys His Pro Glu Glu Leu
             35                  40                  45

Val Leu Leu Gly His Ser Leu Gly Ile Pro Trp Ala Pro Leu Ser Ser
         50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Leu Ala
                115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 93:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 93:

Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
             20                  25                  30

Gln Glu Lys Leu Cys Ala Thr Tyr Lys Leu Cys His Pro Glu Glu Leu
             35                  40                  45

Val Leu Leu Gly His Ser Leu Gly Ile Pro Trp Ala Pro Leu Ser Ser
         50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Leu Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 94:

(i) SEQUENCE CHARACTERISTICS:
        (A) LENGTH: 175 amino acids
        (B) TYPE: amino acid
        (D) TOPOLOGY: linear
```

(ii) MOLECULE TYPE: protein (xi) SEQUENCE DESCRIPTION: SEQ ID NO: 94:

```
Met Thr Pro Leu Gly Pro Ala Ser Ser Leu Pro Gln Ser Phe Leu Leu
 1               5                  10                  15

Lys Ala Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
               100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

(2) INFORMATION FOR SEQ ID NO: 95:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 95:

```
Met Thr Pro Leu Gly Pro Ala Ser Ser Leu Pro Glu Ser Phe Leu Leu
 1               5                  10                  15

Lys Cys Leu Glu Glu Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
               100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160
```

Phe Leu Glu Val Ser Tyr Arg Val Leu Arg His Leu Ala Gln Pro
                165                 170                 175

(2) INFORMATION FOR SEQ ID NO: 96:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 96:

Met Thr Pro Leu Gly Pro Ala Ser Ser Leu Pro Glu Ser Phe Leu Leu
 1               5                  10                  15

Lys Cys Leu Glu Glu Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
                35                  40                  45

Val Leu Leu Gly His Ser Leu Gly Ile Pro Trp Ala Pro Leu Ser Ser
        50                  55                  60

Cys Pro Ser Glu Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 97:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 97:

Met Thr Pro Leu Gly Pro Ala Ser Ser Leu Pro Gln Gly Phe Leu Leu
 1               5                  10                  15

Lys Cys Leu Ala Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
                35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

-continued

```
Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 98:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 98:

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Leu Ala
            115                 120                 125

Pro Ala Leu Gln Pro Thr Gln Gly Ala Leu Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 99:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 99:

Met Thr Pro Leu Gly Pro Ala Ser Ser Leu Pro Gln Ala Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
```

-continued

```
            35                  40                  45
Val Leu Leu Gly His Ser Leu Gly Ile Pro Trp Ala Pro Leu Ser Ser
    50                  55                  60
Cys Pro Ser Gln Ala Leu Gln Leu Ala Gly Cys Leu Ser Gln Leu His
 65                  70                  75                  80
Ser Gly Leu Phe Leu Tyr Gln Gly Leu Leu Gln Ala Leu Glu Gly Ile
                 85                  90                  95
Ser Pro Glu Leu Gly Pro Thr Leu Asp Thr Leu Gln Leu Asp Val Ala
                100                 105                 110
Asp Phe Ala Thr Thr Ile Trp Gln Gln Met Glu Glu Leu Gly Met Ala
                115                 120                 125
Pro Ala Leu Gln Pro Thr Gln Gly Ala Met Pro Ala Phe Ala Ser Ala
                130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro
                165                 170                 175
```

(2) INFORMATION FOR SEQ ID NO: 100:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 100:

```
Met Thr Pro Leu Gly Pro Ala Ser Ser Leu Pro Gln Ser Phe Leu Leu
  1                   5                  10                  15
Ala Cys Leu Glu Gln Val Arg Lys Ile Gln Gly Asp Gly Ala Ala Leu
                 20                  25                  30
Gln Glu Lys Leu Cys Ala Thr Tyr Lys Leu Cys His Pro Glu Glu Leu
                 35                  40                  45
Val Leu Leu Gly His Ser Leu Gly Ile Pro Trp Ala Pro Leu Ser Ser
    50                  55                  60
Cys Pro Ser Gln Ala Leu Gln Leu Ala Gly Cys Leu Ser Gln Leu His
 65                  70                  75                  80
Ser Gly Leu Phe Leu Tyr Gln Gly Leu Leu Gln Ala Leu Glu Gly Ile
                 85                  90                  95
Ser Pro Glu Leu Gly Pro Thr Leu Asp Thr Leu Gln Leu Asp Val Ala
                100                 105                 110
Asp Phe Ala Thr Thr Ile Trp Gln Gln Met Glu Glu Leu Gly Met Ala
                115                 120                 125
Pro Ala Leu Gln Pro Thr Gln Gly Ala Met Pro Ala Phe Ala Ser Ala
                130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro
                165                 170                 175
```

(2) INFORMATION FOR SEQ ID NO: 101:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 101:

```
Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Ala Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

(2) INFORMATION FOR SEQ ID NO: 102:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 102:

```
Met Thr Pro Leu Gly Pro Ala Ser Ser Leu Pro Gln Ser Phe Leu Leu
 1               5                  10                  15

Lys Cys Leu Glu Ala Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160
```

```
Phe Leu Glu Val Ser Tyr Arg Val Leu Arg His Leu Ala Gln Pro
                165                 170                 175

(2) INFORMATION FOR SEQ ID NO: 103:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 103:

Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys Ala Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 104:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 104:

Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly Ala Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
```

-continued

```
                100                 105                 110
Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

(2) INFORMATION FOR SEQ ID NO: 105:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 105:

```
Met Thr Pro Leu Gly Pro Ala Ser Ser Leu Pro Gln Ser Phe Leu Leu
1                   5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Ala Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

(2) INFORMATION FOR SEQ ID NO: 106:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 106:

```
Met Thr Pro Leu Gly Pro Ala Ser Ser Leu Pro Gln Ser Phe Leu Leu
1                   5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45
```

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Ala Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 107:

(i) SEQUENCE CHARACTERISTICS:
       (A) LENGTH: 175 amino acids
       (B) TYPE: amino acid
       (D) TOPOLOGY: linear (ii) MOLECULE TYPE: protein (xi) SEQUENCE DESCRIPTION: SEQ ID NO: 107:

Met Thr Pro Leu Gly Pro Ala Ser Ser Leu Pro Gln Ser Phe Leu Leu
1                   5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
                35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Ala Ile Trp Gln Gln Met Glu Glu Leu Gly Met Ala
                115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

(2) INFORMATION FOR SEQ ID NO: 108:

(i) SEQUENCE CHARACTERISTICS:
       (A) LENGTH: 175 amino acids
       (B) TYPE: amino acid
       (D) TOPOLOGY: linear (ii) MOLECULE TYPE: protein (xi) SEQUENCE DESCRIPTION: SEQ ID NO: 108:

```
Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Ala Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Ala Val Ala
               100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

(2) INFORMATION FOR SEQ ID NO: 109:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 109:

```
Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
               100                 105                 110

Asp Phe Ala Thr Thr Ile Trp Gln Gln Met Glu Ala Leu Gly Met Ala
            115                 120                 125

Pro Ala Leu Gln Pro Thr Gln Gly Ala Met Pro Ala Phe Ala Ser Ala
130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
```

-continued (2) INFORMATION FOR SEQ ID NO: 110:

(i) SEQUENCE CHARACTERISTICS:
      (A) LENGTH: 175 amino acids
      (B) TYPE: amino acid
      (D) TOPOLOGY: linear (ii) MOLECULE TYPE: protein (xi) SEQUENCE DESCRIPTION: SEQ ID NO: 110:

```
Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
            85                  90                  95

Ser Pro Glu Leu Gly Pro Thr Leu Asp Thr Leu Gln Leu Asp Val Ala
            100                 105                 110

Asp Val Ala Thr Ala Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
            165                 170                 175
```

G-CSF HYBRID MOLECULES AND PHARMACEUTICAL COMPOSITIONS

CROSS REFERENCE TO RELATED APPLICATIONS

The present application is a continuation of U.S. patent application Ser. No. 09/027,508, filed Feb. 20, 1998, now abandoned, which is a continuation of U.S. patent application Ser. No. 08/956,812, filed Oct. 23, 1997, now abandoned, which is a divisional of U.S. patent application Ser. No. 08/448,716, filed May 24, 1995, now U.S. Pat. No. 5,790,421, which is a divisional of U.S. patent application Ser. No. 08/010,099, filed Jan. 28, 1993, now U.S. Pat. No. 5,581,476.

BACKGROUND OF THE INVENTION

1. Field of the Invention

This invention relates to granulocyte colony stimulating factor ("G-CSF") analogs, compositions containing such analogs, and related compositions. In another aspect, the present invention relates to nucleic acids encoding the present analogs or related nucleic acids, related host cells and vectors. In another aspect, the invention relates to computer programs and apparatuses for expressing the three dimensional structure of G-CSF and analogs thereof. In another aspect, the invention relates to methods for rationally designing G-CSF analogs and related compositions. In yet another aspect, the present invention relates to methods for treatment using the present G-CSF analogs.

2. Description of the Related Art

Hematopoiesis is controlled by two systems: the cells within the bone marrow microenvironment and growth factors. The growth factors, also called colony stimulating factors, stimulate committed progenitor cells to proliferate and to form colonies of differentiating blood cells. One of these factors is granulocyte colony stimulating factor, herein called G-CSF, which preferentially stimulates the growth and development of neutrophils, indicating a potential use in neutropenic states. Welte et al. *PNAS-USA* 82: 1526–1530 (1985); Souza et al. *Science* 232: 61–65 (1986) and Gabrilove, *J. Seminars in Hematology* 26:2 1–14 (1989).

In humans, endogenous G-CSF is detectable in blood plasma. Jones et al. *Bailliere's Clinical Hematology* 2:1 83–111 (1989). G-CSF is produced by fibroblasts, macrophages, T cells trophoblasts, endothelial cells and epithelial cells and is the expression product of a single copy gene comprised of four exons and five introns located on chromosome seventeen. Transcription of this locus produces a mRNA species which is differentially processed, resulting in two forms of G-CSF mRNA, one version coding for a protein of 177 amino acids, the other coding for a protein of 174 amino acids, Nagata et al. *EMBO J* 5: 575–581 (1986), and the form comprised of 174 amino acids has been found to have the greatest specific in vivo biological activity. G-CSF is species cross-reactive, such that when human G-CSF is administered to another mammal such as a mouse, canine or monkey, sustained neutrophil leukocytosis is elicited. Moore et al. *PNAS-USA* 84: 7134–7138 (1987).

Human G-CSF can be obtained and purified from a number of sources. Natural human G-CSF (nhG-CSF) can be isolated from the supernatants of cultured human tumor cell lines. The development of recombinant DNA technology, see, for instance, U.S. Pat. No. 4,810,643 (Souza) incorporated herein by reference, has enabled the production of commercial scale quantities of G-CSF in glycosylated form as a product of eukaryotic host cell expression, and of G-CSF in non-glycosylated form as a product of prokaryotic host cell expression.

G-CSF has been found to be useful in the treatment of indications where an increase in neutrophils will provide benefits. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture, for example, for bone marrow transplants.

Signal transduction, the way in which G-CSF effects cellular metabolism, is not currently thoroughly understood. G-CSF binds to a cell-surface receptor which apparently initiates the changes within particular progenitor cells, leading to cell differentiation.

Various altered G-CSF's have been reported. Generally, for design of drugs, certain changes are known to have certain structural effects. For example, deleting one cysteine could result in the unfolding of a molecule which is, in its unaltered state, is normally folded via a disulfide bridge. There are other known methods for adding, deleting or substituting amino acids in order to change the function of a protein.

Recombinant human G-CSF mutants have been prepared, but the method of preparation does not include overall structure/function relationship information. For example, the mutation and biochemical modification of $Cys^{18}$ has been reported. Kuga et al. *Biochem. Biophy. Res. Comm* 159: 103–111 (1989); Lu et al. *Arch. Biochem. Biophys.* 268: 81–92 (1989).

In U.S. Pat. No. 4,810,643, entitled, "Production of Pluripotent Granulocyte Colony-Stimulating Factor" (as cited above), polypeptide analogs and peptide fragments of G-CSF are disclosed generally. Specific G-CSF analogs disclosed include those with the cysteins at positions 17, 36, 42, 64, and 74 (of the 174 amino acid species or of those having 175 amino acids, the additional amino acid being an N-terminal methionine) substituted with another amino acid, (such as serine), and G-CSF with an alanine in the first (N-terminal) position.

EP 0 335 423 entitled "Modified human G-CSF" reportedly discloses the modification of at least one amino group in a polypeptide having hG-CSF activity.

EP 0 272 703 entitled "Novel Polypeptide" reportedly discloses G-CSF derivatives having an amino acid substituted or deleted at or "in the neighborhood" of the N-terminus.

EP 0 459 630, entitled "Polypeptides" reportedly discloses derivatives of naturally occurring G-CSF having at least one of the biological properties of naturally occurring G-CSF and a solution stability of at least 35% at 5 mg/ml in which the derivative has at least $Cys^{17}$ of the native sequence replaced by a $Ser^{17}$ residue and $Asp^{27}$ of the native sequence replaced by a $Ser^{27}$ residue.

EP 0 256 843 entitled "Expression of G-CSF and Muteins Thereof and Their Uses" reportedly discloses a modified DNA sequence encoding G-CSF wherein the N-terminus is modified for enhanced expression of protein in recombinant host cells, without changing the amino acid sequence of the protein.

EP 0 243 153 entitled "Human G-CSF Protein Expression" reportedly discloses G-CSF to be modified by inactivating at least one yeast KEX2 protease processing site for increased yield in recombinant production using yeast.

Shaw,.U.S. Pat. No. 4,904,584, entitled "Site-Specific Homogeneous Modification of Polypeptides," reportedly discloses lysine altered proteins.

WO/9012874 reportedly discloses cysteine altered variants of proteins.

Australian patent application Document No. AU-A-10948/92, entitled, "Improved Activation of Recombinant Proteins" reportedly discloses the addition of amino acids to either terminus of a G-CSF molecule for the purpose of aiding in the folding of the molecule after prokaryotic expression.

Australian patent application Document No. AU-A-76380/91, entitled, "Muteins of the Granulocyte Colony Stimulating Factor (G-CSF)" reportedly discloses muteins of the granulocyte stimulating factor G-CSF in the sequence Leu-Gly-His-Ser-Leu-Gly-Ile at position 50–56 of G-CSF with 174 amino acids, and position 53 to 59 of the G-CSF with 177 amino acids, or/and at least one of the four histadine residues at positions 43, 79, 156 and 170 of the mature G-CSF with 174 amino acids or at positions 46, 82, 159, or 173 of the mature G-CSF with 177 amino acids.

GB 2 213 821, entitled "Synthetic Human Granulocyte Colony Stimulating Factor Gene" reportedly discloses a synthetic G-CSF-encoding nucleic acid sequence incorporating restriction sites to facilitate the cassette mutagenesis of selected regions, and flanking restriction sites to facilitate the incorporation of the gene into a desired expression system.

G-CSF has reportedly been crystallized to some extent, i.e., EP 344 796, and the overall structure of G-CSF has been surmised, but only on a gross level. Bazan, *Immunology Today* 11: 350–354 (1990); Parry et al. *J.Molecular Recognition* 8: 107–110 (1988). To date, there have been no reports of the overall structure of G-CSF, and no systematic studies of the relationship of the overall structure and function of the molecule, studies which are essential to the systematic design of G-CSF analogs. Accordingly, there exists a need for a method of this systematic design of G-CSF analogs, and the resultant compositions.

SUMMARY OF THE INVENTION

The three dimensional structure of G-CSF has now been determined to the atomic level. From this three-dimensional structure, one can now forecast with substantial certainty how changes in the composition of a G-CSF molecule may result in structural changes. These structural characteristics may be correlated with biological activity to design and produce G-CSF analogs.

Although others had speculated regarding the three dimensional structure of G-CSF, Bazan, *Immunology Today* 11: 350–354 (1990); Parry et al. *J. Molecular Recognition* 8: 107–110 (1988), these speculations were of no help to those wishing to prepare G-CSF analogs either because the surmised structure was incorrect (Parry et al., supra) and/or because the surmised structure provided no detail correlating the constituent moieties with structure. The present determination of the three-dimensional structure to the atomic level is by far the most complete analysis to date, and provides important information to those wishing to design and prepare G-CSF analogs. For example, from the present three dimensional structural analysis, precise areas of hydrophobicity and hydrophilicity have been determined.

Relative hydrophobicity is important because it directly relates to the stability of the molecule. Generally, biological molecules, found in aqueous environments, are externally hydrophilic and internally hydrophobic; in accordance with the second law of thermodynamics provides, this is the lowest energy state and provides for stability. Although one could have speculated that G-CSF's internal core would be hydrophobic, and the outer areas would be hydrophilic, one would have had no way of knowing specific hydrophobic or hydrophilic areas. With the presently provided knowledge of areas of hydrophobicity/philicity, one may forecast with substantial certainty which changes to the G-CSF molecule will affect the overall structure of the molecule.

As a general rule, one may use knowledge of the geography of the hydrophobic and hydrophilic regions to design analogs in which the overall G-CSF structure is not changed, but change does affect biological activity ("biological activity" being used here in its broadest sense to denote function). One may correlate biological activity to structure. If the structure is not changed, and the mutation has no effect on biological activity, then the mutation has no biological function. If, however, the structure is not changed and the mutation does affect biological activity, then the residue (or atom) is essential to at least one biological function. Some of the present working examples were designed to provide no change in overall structure, yet have a change in biological function.

Based on the correlation of structure to biological activity, one aspect of the present invention relates to G-CSF analogs. These analogs are molecules which have more, fewer, different or modified amino acid residues from the G-CSF amino acid sequence. The modifications may be by addition, substitution, or deletion of one or more amino acid residues. The modification may include the addition or substitution of analogs of the amino acids themselves, such as peptidomimetics or amino acids with altered moieties such as altered side groups. The G-CSF used as a basis for comparison may be of human, animal or recombinant nucleic acid-technology origin (although the working examples disclosed herein are based on the recombinant production of the 174 amino acid species of human G-CSF, having an extra N-terminus methionyl residue). The analogs may possess functions different from natural human G-CSF molecule, or may exhibit the same functions, or varying degrees of the same functions. For example, the analogs may be designed to have a higher or lower biological activity, have a longer shelf-life or a decrease in stability, be easier to formulate, or more difficult to combine with other ingredients. The analogs may have no hematopoietic activity, and may therefore be useful as an antagonist against G-CSF effect (as, for example, in the overproduction of G-CSF). From time to time herein the present analogs are referred to as proteins or peptides for convenience, but contemplated herein are other types of molecules, such as peptidomimetics or chemically modified peptides.

In another aspect, the present invention relates to related compositions containing a G-CSF analog as an active ingredient. The term, "related composition," as used herein, is meant to denote a composition which may be obtained once the identity of the G-CSF analog is ascertained (such as a G-CSF analog labeled with a detectable label, related receptor or pharmaceutical composition). Also considered a related composition are chemically modified versions of the G-CSF analog, such as those having attached at least one polyethylene glycol molecule.

For example, one may prepare a G-CSF analog to which a detectable label is attached, such as a fluorescent, chemiluminescent or radioactive molecule.

Another example is a pharmaceutical composition which may be formulated by known techniques using known materials, see, *Remington's Pharmaceutical Sciences,* 18th Ed. (1990, Mack Publishing Co., Easton, Pa. 18042) pp. 1435–1712, which are herein incorporated by reference. Generally, the formulation will depend on a variety of factors such as administration, stability, production concerns and other factors. The G-CSF analog may be administered by injection or by pulmonary administration via inhalation. Enteric dosage forms may also be available for the present G-CSF analog compositions, and therefore oral administration may be effective. G-CSF analogs may be inserted into liposomes or other microcarriers for delivery, and may be formulated in gels or other compositions for sustained release. Although preferred compositions will vary depending on the use to which the composition will be put, generally, for G-CSF analogs having at least one of the biological activities of natural G-CSF, preferred pharmaceutical compositions are those prepared for subcutaneous injection or for pulmonary administration via inhalation, although the particular formulations for each type of administration will depend on the characteristics of the analog.

Another example of related composition is a receptor for the present analog. As used herein, the term "receptor" indicates a moiety which selectively binds to the present analog molecule. For example, antibodies, or fragments thereof, or "recombinant antibodies" (see Huse et al. *Science* 246: 1275 (1989)) may be used as receptors. Selective binding does not mean only specific binding (although binding-specific receptors are encompassed herein), but rather that the binding is not a random event. Receptors may be on the cell surface or intra- or extra-cellular, and may act to effectuate, inhibit or localize the biological activity of the present analogs. Receptor binding may also be a triggering mechanism for a cascade of activity indirectly related to the analog itself. Also contemplated herein are nucleic acids, vectors containing such nucleic acids and host cells containing such nucleic acids which encode such receptors.

Another example of a related composition is a G-CSF analog with a chemical moiety attached. Generally, chemical modification may alter biological activity or antigenicity of a protein, or may alter other characteristics, and these factors will be taken into account by a skilled practitioner. As noted above, one example of such chemical moiety is polyethylene glycol. Modification may include the addition of one or more hydrophilic or hydrophobic polymer molecules, fatty acid molecules, or polysaccharide molecules. Examples of chemical modifiers include polyethylene glycol, alklpolyethylene glycols, DI-poly(amino acids), polyvinylpyrrolidone, polyvinyl alcohol, pyran copolymer, acetic acid/acylation, proprionic acid, palmitic acid, stearic acid, dextran, carboxymethyl cellulose, pullulan, or agarose. See, Francis, *Focus on Growth Factors* 3: 4–10 (May 1992)(published by Mediscript, Mountview Court, Friern Barnet Lane, London N20 OLD, UK). Also, chemical modification may include an additional protein or portion thereof, use of a cytotoxic agent, or an antibody. The chemical modification may also include lecithin.

In another aspect, the present invention relates to nucleic acids encoding such analogs. The nucleic acids may be DNAs or RNAs or derivatives thereof, and will typically be cloned and expressed on a vector, such as a phage or plasmid containing appropriate regulatory sequences. The nucleic acids may be labeled (such as using a radioactive, chemiluminescent, or fluorescent label) for diagnostic or prognostic purposes, for example. The nucleic acid sequence may be optimized for expression, such as including codons preferred for bacterial expression. The nucleic acid and its complementary strand, and modifications thereof which do not prevent encoding of the desired analog are here contemplated.

In another aspect, the present invention relates to host cells containing the above nucleic acids encoding the present analogs. Host cells may be eukaryotic or prokaryotic, and expression systems may include extra steps relating to the attachment (or prevention) of sugar groups (glycosylation), proper folding of the molecule, the addition or deletion of leader sequences or other factors incident to recombinant expression.

In another aspect the present invention relates to antisense nucleic acids which act to prevent or modify the type or amount of expression of such nucleic acid sequences. These may be prepared by known methods.

In another aspect of the present invention, the nucleic acids encoding a present analog may be used for gene therapy purposes, for example, by placing a vector containing the analog-encoding sequence into a recipient so the nucleic acid itself is expressed inside the recipient who is in need of the analog composition. The vector may first be placed in a carrier, such as a cell, and then the carrier placed into the recipient. Such expression may be localized or systemic. Other carriers include non-naturally occurring carriers, such as liposomes or other microcarriers or particles, which may act to mediate gene transfer into a recipient.

The present invention also provides for computer programs for the expression (such as visual display) of the G-CSF or analog three dimensional structure, and further, a computer program which expresses the identity of each constituent of a G-CSF molecule and the precise location within the overall structure of that constituent, down to the atomic level. Set forth below is one example of such program. There are many currently available computer programs for the expression of the three dimensional structure of a molecule. Generally, these programs provide for inputting of the coordinates for the three dimensional structure of a molecule (i.e., for example, a numerical assignment for each atom of a G-CSF molecule along an x, y, and z axis), means to express (such as visually display) such coordinates, means to alter such coordinates and means to express an image of a molecule having such altered coordinates. One may program crystallographic information, i.e., the coordinates of the location of the atoms of a G-CSF molecule in three dimension space, wherein such coordinates have been obtained from crystallographic analysis of said G-CSF molecule, into such programs to generate a computer program for the expression (such as visual display) of the G-CSF three dimensional structure. Also provided, therefore, is a computer program for the expression of G-CSF analog three dimensional structure. Preferred is the computer program Insight II, version 4, available from Biosym, San Diego, Calif., with the coordinates as set forth in FIG. 5 input. Preferred expression means is on a Silicon Graphics 320 VGX computer, with Crystal Eyes glasses (also available from Silicon Graphics), which allows one to view the G-CSF molecule or its analog stereoscopically. Alternatively, the present G-CSF crystallographic coordinates and diffraction data are also deposited in the Protein Data Bank, Chemistry Department, Brookhaven National Laboratory, Upton, N.Y. 19723, USA. One may use these data in preparing a different computer program for expression of the three dimensional structure of a G-CSF molecule or analog thereof. Therefore, another aspect of the present invention is a computer program for the expression of the three dimensional structure of a G-CSF molecule. Also provided is said computer program for visual display of the three dimensional structure of a G-CSF molecule; and further, said program having means for altering such visual display. Apparatus useful for expression of such computer program, particularly for the visual display of the computer image of said three dimensional structure of a G-CSF molecule or analog thereof is also therefore here provided, as well as means for preparing said computer program and apparatus.

The computer program is useful for preparation of G-CSF analogs because one may select specific sites on the G-CSF molecule for alteration and readily ascertain the effect the alteration will have on the overall structure of the G-CSF molecule. Selection of said site for alteration will depend on the desired biological characteristic of the G-CSF analog. If one were to randomly change said G-CSF molecule (r-met-hu-G-CSF) there would be $175^{20}$ possible substitutions, and even more analogs having multiple changes, additions or deletions. By viewing the three dimensional structure wherein said structure is correlated with the composition of the molecule, the selection for sites of alteration is no longer a random event, but sites for alteration may be determined rationally.

As set forth above, identity of the three dimensional structure of G-CSF, including the placement of each constituent down to the atomic level has now yielded information regarding which moieties are necessary to maintain the overall structure of the G-CSF molecule. One may therefore select whether to maintain the overall structure of the G-CSF molecule when preparing a G-CSF analog of the present invention, or whether (and how) to change the overall structure of the G-CSF molecule when preparing a G-CSF analog of the present invention. Optionally, once one has prepared such analog, one may test such analog for a desired characteristic.

One may, for example, seek to maintain the overall structure possessed by a non-altered natural or recombinant G-CSF molecule. The overall structure is presented in FIGS. 2, 3, and 4, and is described in more detail below. Maintenance of the overall structure may ensure receptor binding, a necessary characteristic for an analog possessing the hematopoietic capabilities of natural G-CSF (if no receptor binding, signal transduction does not result from the presence of the analog). It is contemplated that one class of G-CSF analogs will possess the three dimensional core structure of a natural or recombinant (non-altered) G-CSF molecule, yet possess different characteristics, such as an increased ability to selectively stimulate neutrophils. Another class of G-CSF analogs are those with a different overall structure which diminishes the ability of a G-CSF analog molecule to bind to a G-CSF receptor, and possesses a diminished ability to selectively stimulate neutrophils as compared to non-altered natural or recombinant G-CSF.

For example, it is now known which moieties within the internal regions of the G-CSF molecule are hydrophobic, and, correspondingly, which moieties on the external portion of the G-CSF molecule are hydrophilic. Without knowledge of the overall three dimensional structure, preferably to the atomic level as provided herein, one could not forecast which alterations within this hydrophobic internal area would result in a change in the overall structural conformation of the molecule. An overall structural change could result in a functional change, such as lack of receptor binding, for example, and therefore, diminishment of biological activity as found in non-altered G-CSF. Another class of G-CSF analogs is therefore G-CSF analogs which possess the same hydrophobicity as (non-altered) natural or recombinant G-CSF. More particularly, another class of G-CSF analogs possesses the same hydrophobic moieties within the four helical bundle of its internal core as those hydrophobic moieties possessed by (non-altered) natural or recombinant G-CSF yet have a composition different from said non-altered natural or recombinant G-CSF.

Another example relates to external loops which are structures which connect the internal core (helices) of the G-CSF molecule. From the three dimensional structure—including information regarding the spatial location of the amino acid residues—one may forecast that certain changes in certain loops will not result in overall conformational changes. Therefore, another class of G-CSF analogs provided herein is that having an altered external loop but possessing the same overall structure as (non-altered) natural or recombinant G-CSF. More particularly, another class of G-CSF analogs provided herein are those having an altered external loop, said loop being selected from the loop present between helices A and B; between helices B and C; between helices C and D; between helices D and A, as those loops and helices are identified herein. More particularly, said loops, preferably the AB loop and/or the CD loop are altered to increase the half life of the molecule by stabilizing said loops. Such stabilization may be by connecting all or a portion of said loop(s) to a portion of an alpha helical bundle found in the core of a G-CSF (or analog) molecule. Such connection may be via beta sheet, salt bridge, disulfide bonds, hydrophobic interaction or other connecting means available to those skilled in the art, wherein such connecting means serves to stabilize said external loop or loops. For example, one may stabilize the AB or CD loops by connecting the AB loop to one of the helices within the internal region of the molecule.

The N-terminus also may be altered without change in the overall structure of a G-CSF molecule, because the N-terminus does not effect structural stability of the internal helices, and, although the external loops are preferred for modification, the same general statements apply to the N-terminus.

Additionally, such external loops may be the site(s) for chemical modification because in (non-altered) natural or recombinant G-CSF such loops are relatively flexible and tend not to interfere with receptor binding. Thus, there would be additional room for a chemical moiety to be directly attached (or indirectly attached via another chemical moiety which serves as a chemical connecting means). The chemical moiety may be selected from a variety of moieties available for modification of one or more function of a G-CSF molecule. For example, an external loop may provide sites for the addition of one or more polymer which serves to increase serum half-life, such as a polyethylene glycol molecule. Such polyethylene glycol molecule(s) may be added wherein said loop is altered to include additional lysines which have reactive side groups to which polyethylene glycol moieties are capable of attaching. Other classes of chemical moieties may also be attached to one or more external loops, including but not limited to other biologically active molecules, such as receptors, other therapeutic proteins (such as other hematopoietic factors which would engender a hybrid molecule), or cytotoxic agents (such as diphtheria toxin). This list is of course not complete; one skilled in the art possessed of the desired chemical moiety will have the means to effect attachment of said desired moiety to the desired external loop. Therefore, another class of the present G-CSF analogs includes those with at least one alteration in an external loop wherein said alteration provides for the addition of a chemical moiety such as at least one polyethylene glycol molecule.

Deletions, such as deletions of sites recognized by proteins for degradation of the molecule, may also be effectual in the external loops. This provides alternative means for increasing half-life of a molecule otherwise having the G-CSF receptor binding and signal transduction capabilities (i.e., the ability to selectively stimulate the maturation of neutrophils). Therefore, another class of the present G-CSF analogs includes those with at least one alteration in an external loop wherein said alteration decreases the turnover of said analog by proteases. Preferred loops for such alterations are the AB loop and the CD loop. One may prepare an abbreviated G-CSF molecule by deleting a portion of the amino acid residues found in the external loops (identified in more detail below), said abbreviated G-CSF molecule may have additional advantages in preparation or in biological function.

Another example relates to the relative charges between amino acid residues which are in proximity to each other. As noted above, the G-CSF molecule contains a relatively tightly packed four helical bundle. Some of the faces on the helices face other helices. At the point (such as a residue) where a helix faces another helix, the two amino acid moieties which face each other may have the same charge, and thus tend to repel each other, which lends instability to the overall molecule. This may be eliminated by changing the charge (to an opposite charge or a neutral charge) of one or both of the amino acid moieties so that there is no repelling. Therefore, another class of G-CSF analogs includes those G-CSF analogs having been altered to modify instability due to surface interactions, such as electron charge location.

In another aspect, the present invention relates to methods for designing G-CSF analogs and related compositions and the products of those methods. The end products of the methods may be the G-CSF analogs as defined above or related compositions. For instance, the examples disclosed herein demonstrate (a) the effects of changes in the constituents (i.e., chemical moieties) of the G-CSF molecule on the G-CSF structure, and (b) the effects of changes in structure on biological function. Essentially, therefore, another aspect of the present invention is a method for preparing a G-CSF analog comprising the steps of:

(a) viewing information conveying the three dimensional structure of a G-CSF molecule wherein the chemical moieties, such as each amino acid residue or each atom of each amino acid residue, of the G-CSF molecule are correlated with said structure, (b) selecting from said information a site on a G-CSF molecule for alteration;

(c) preparing a G-CSF analog molecule having such alteration; and (d) optionally, testing such G-CSF analog molecule for a desired characteristic.

One may use the here provided computer programs for a computer-based method for preparing a G-CSF analog. Another aspect of the present invention is therefore a computer based method for preparing a G-CSF analog comprising the steps of:

(a) providing computer expression of the three dimensional structure of a G-CSF molecule wherein the chemical moieties, such as each amino acid residue or each atom of each amino acid residue, of the G-CSF molecule are correlated with said structure;

(b) selecting from said computer expression a site on a G-CSF molecule for alteration;

(c) preparing a G-CSF molecule having such alteration; and, (d) optionally, testing such G-CSF molecule for a desired characteristic.

More specifically, the present invention provides a method for preparing a G-CSF analog comprising the steps of:

(a) viewing the three dimensional structure of a G-CSF molecule via a computer, said computer programmed (i) to express the coordinates of a G-CSF molecule in three dimensional space, and (ii) to allow for entry of information for alteration of said G-CSF expression and viewing thereof;

(b) selecting a site on said visual image of said G-CSF molecule for alteration;

(c) entering information for said alteration on said computer;

(d) viewing a three dimensional structure of said altered G-CSF molecule via said computer;

(e) optionally repeating steps (a)–(e);

(f) preparing a G-CSF analog with said alteration; and (g) optionally testing said G-CSF analog for a desired characteristic.

In another aspect, the present invention relates to methods of using the present G-CSF analogs and related compositions and methods for the treatment or protection of mammals, either alone or in combination with other hematopoietic factors or drugs in the treatment of hematopoietic disorders. It is contemplated that one aspect of designing G-CSF analogs will be the goal of enhancing or modifying the characteristics non-modified G-CSF is known to have. For example, the present analogs may possess enhanced or modified activities, so, where G-CSF is useful in the treatment of (for example) neutropenia, the present compositions and methods may also be of such use.

Another example is the modification of G-CSF for the purpose of interacting more effectively when used in combination with other factors particularly in the treatment of hematopoietic disorders. One example of such combination use is to use an early-acting hematopoietic factor (i.e., a factor which acts earlier in the hematopoiesis cascade on relatively undifferentiated cells) and either simultaneously or in seriatim use of a later-acting hematopoietic factor, such as G-CSF or analog thereof (as G-CSF acts on the CFU-GM lineage in the selective stimulation of neutrophils). The present methods and compositions may be useful in therapy involving such combinations or "cocktails" of hematopoietic factors.

The present compositions and methods may also be useful in the treatment of leukopenia, mylogenous leukemia, severe chronic neutropenia, aplastic anemia, glycogen storage disease, mucosistitis, and other bone marrow failure states. The present compositions and methods may also be useful in the treatment of hematopoietic deficits arising from chemotherapy or from radiation therapy. The success of bone marrow transplantation, or the use of peripheral blood progenitor cells for transplantation, for example, may be enhanced by application of the present compositions (proteins or nucleic acids for gene therapy) and methods. The present compositions and methods may also be useful in the treatment of infectious diseases, such in the context of wound healing, burn treatment, bacteremia, septicemia, fungal infections, endocarditis, osteopyelitis, infection related to abdominal trauma, infections not responding to antibiotics, pneumonia and the treatment of bacterial inflammation may also benefit from the application of the present compositions and methods. In addition, the present compositions and methods may be useful in the treatment of leukemia based upon a reported ability to differentiate leukemic cells. Welte et al. *PNAS-USA* 82: 1526–1530

(1985). Other applications include the treatment of individuals with tumors, using the present compositions and methods, optionally in the presence of receptors (such as antibodies) which bind to the tumor cells. For review articles on therapeutic applications, see Lieshhke et al. *N.Engl. J.Med.* 327: 28–34, 99–106 (1992) both of which are herein incorporated by reference.

The present compositions and methods may also be useful to act as intermediaries in the production of other moieties; for example, G-CSF has been reported to influence the production of other hematopoietic factors and this function (if ascertained) may be enhanced or modified via the present compositions and/or methods.

The compositions related to the present G-CSF analogs, such as receptors, may be useful to act as an antagonist which prevents the activity of G-CSF or an analog. One may obtain a composition with some or all of the activity of non-altered G-CSF or a G-CSF analog, and add one or more chemical moieties to alter one or more properties of such G-CSF or analog. With knowledge of the three dimensional conformation, one may forecast the best geographic location for such chemical modification to achieve the desired effect.

General objectives in chemical modification may include improved half-life (such as reduced renal, immunological or cellular clearance), altered bioactivity (such as altered enzymatic properties, dissociated bioactivities or activity in organic solvents), reduced toxicity (such as concealing toxic epitopes, compartmentalization, and selective biodistribution), altered immunoreactivity (reduced immunogenicity, reduced antigenicity or adjuvant action), or altered physical properties (such as increased solubility, improved thermal stability, improved mechanical stability, or conformational stabilization). See Francis, *Focus on Growth Factors* 3: 4–10 (May 1992)(published by Mediscript, Mountview Court, Friern Barnet Lane, London N20 OLD, UK).

The examples below are illustrative of the present invention and are not intended as a limitation. It is understood that variations and modifications will occur to those skilled in the art, and it is intended that the appended claims cover all such equivalent variations which come within the scope of the invention as claimed.

BRIEF DESCRIPTION OF THE DRAWINGS

FIG. 1 is an illustration of the amino acid sequence of the 174 amino acid species of G-CSF with an additional N-terminal methionine (Seq. ID. No. 2).

FIG. 4 is a "barrel diagram" of the three dimensional structure of G-CSF. Shown in various shades of gray are the overall cylinders and their orientations for the three dimensional structure of G-CSF. The numbers indicate amino acid residue position according to FIG. 1 (Seq. ID. No. 2) above.

FIGS. 5 (A–VV) is a list of the coordinates used to generate a computer-aided visual image of the three dimensional structure of G-CSF. The coordinates are set forth below. The columns correspond to separate field:

(i) Field 1 (from the left hand side) is the atom, (ii) Field 2 is the assigned atom number, (iii) Field 3 is the atom name (according to the periodic table standard nomenclature, with CB being carbon atom Beta, CG is Carbon atom Gamma, etc.);

(iv) Field 4 is the residue type (according to three letter nomenclature for amino acids as found in , i.e., Stryer, *Biochemistry*, 3d Ed., W. H. Freeman & Co., New York 1988, inside back cover);

(v) Fields 5–7 are the x-axis, y-axis and z-axis positions of the atom;

(vi) Field 8 (often a "1.00") designates occupancy at that position;

(vii) Field 9 designates the B-factor;

(viii) Field 10 designates the molecule designation three molecules (designated a, b, and c) of G-CSF crystallized together as a unit. The designation a, b, or c indicates which coordinates are from which molecule. The number after the letter (1, 2, or 3) indicates the assigned amino acid residue position, with molecule A having assigned positions 10–175, molecule B having assigned positions 210–375, and molecule C having assigned positions 410–575. These positions were so designated so that there would be no overlap among the three molecules which crystallized together. (The "W" designation indicates water).

Figure 6A:
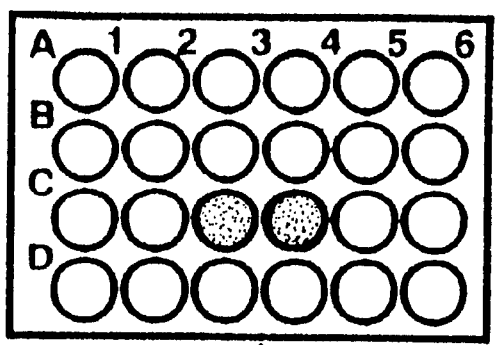
Figure 6B:
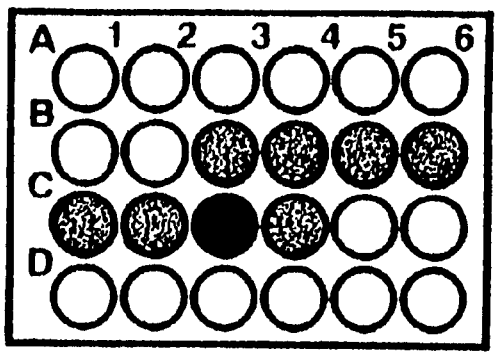
Figure 6C:
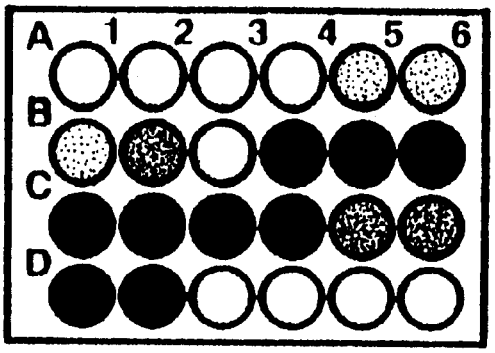

FIGS. 6A–6C are schematic representations of the strategy involved in refining the crystallization matrix for parameters involved in crystallization. The crystallization matrix corresponds to the final concentration of the components (salts, buffers and precipitants) of the crystallization solutions in the wells of a 24 well tissue culture plate. These concentrations are produced by pipetting the appropriate volume of stock solutions into the wells of the microtiter plate. To design the matrix, the crystallographer decides on an upper and lower concentration of the component. These upper and lower concentrations can be pipetted along either the rows (i.e., A1–A6, B1–B6, C1–C6 or D1–D6) or along the entire tray (A1–D6). The former method is useful for checking reproducibility of crystal growth of a single component along a limited number of wells, whereas the later method is more useful in initial screening. The results of several stages of refinement of the crystallization matrix are illustrated by a representation of three plates. The increase in shading in the wells indicates a positive crystallization result which, in the final stages, would be X-ray quality crystals but in the initial stages could be oil droplets, granular precipitates or small crystals approximately less than 0.05 mm in size. Part A represents an initial screen of one parameter in which the range of concentration between the first well (A1) and last well (D6) is large and the concentration increase between wells is calculated as ((concentration A1)–(concentration D6))/23). Part B represents that in later stages of the crystallization matrix refinement of the concentration spread between A1 and D6 would be reduced which would result in more crystals formed per plate. Part C indicates a final stage of matrix refinement in which quality crystals are found in most wells of the plate.

DETAILED DESCRIPTION OF THE INVENTION

The present invention grows out of the discovery of the three dimensional structure of G-CSF. This three dimensional structure has been expressed via computer program for stereoscopic viewing. By viewing this stereoscopically, structure-function relationships identified and G-CSF analogs have been designed and made.

The Overall Three Dimensional Structure of G-CSF

The G-CSF used to ascertain the structure was a non-glycosylated 174 amino acid species having an extra N-terminal methionine residue incident to bacterial expression. The DNA (Seq. ID. No. 1) and amino acid sequence (Seq. ID. No. 2) of this G-CSF are illustrated in FIG. 1.

Overall, the three dimensional structure of G-CSF is predominantly helical, with 103 of the 175 residues forming a 4-alpha-helical bundle. The only other secondary structure is found in the loop between the first two long helices where a 4 residue $3^{10}$ helix is immediately followed by a 6 residue alpha helix. As shown in FIG. 2, the overall structure has been compared with the structure reported for other proteins: growth hormone (Abdel-Meguid et al. *PNAS-USA* 84: 6434 (1987) and Vos et al. *Science* 255: 305–312 (1992)), granulocyte macrophage colony stimulating factor (Diederichs et al. *Science* 254: 1779–1782 (1991)), interferon-β (Senda et al. *EMBO J.* 11: 3193–3201 (1992)), interleukin-2 (McKay *Science* 257: 1673–1677 (1992)) and interleukin-4 (Powers et al. *Science* 256: 1673–1677 (1992), and Smith et al. *J. Mol. Biol.* 224: 899–904 (1992)). Structural similarity among these growth factors occurs despite the absence of similarity in their amino acid sequences.

Presently, the structural information was correlation of G-CSF biochemistry, and this can be summarized as follows (with sequence position 1 being at the N-terminus):

TABLE 1

| Sequence Position | Description of Structure | Analysis |
| --- | --- | --- |
| 1–10 | Extended chain | Deletion causes no loss of biological activity |
| $Cys^{18}$ | Partially buried | Reactive with DTNB and Thimersososl but not with iodo-acetate |
| 34 | Alternative splice site | Insertion reduces biological activity |
| 20–47 (inclusive) | Helix A, first disulfide and portion of AB helix | Predicted receptor binding region based on neutralizing antibody data |
| 20, 23, 24 | Helix A | Single alanine mutation of residue(s) reduces biological activity. Predicted receptor binding (Site B). |
| 165–175 (inclusive) | Carboxy terminus | Deletion reduces biological activity |

This biochemical information, having been gleaned from antibody binding studies, see Layton et al. *Biochemistry* 266: 23815–23823 (1991), was superimposed on the three-dimensional structure in order to design G-CSF analogs. The design, preparation, and testing of these G-CSF analogs is described in Example 1 below.

EXAMPLE 1

This Example describes the preparation of crystalline G-CSF, the visualization of the three dimensional structure of recombinant human G-CSF via computer-generated image, the preparation of analogs, using site-directed mutagenesis or nucleic acid amplification methods, the biological assays and HPLC analysis used to analyze the G-CSF analogs, and the resulting determination of overall structure/function relationships. All cited publications are herein incorporated by reference.

A. Use of Automated Crystallization

The need for a three-dimensional structure of recombinant human granulocyte colony stimulating factor (r-hu-G-CSF), and the availability of large quantities of the purified protein, led to methods of crystal growth by incomplete factorial sampling and seeding. Starting with the implementation of incomplete factorial crystallization described by Jancarik et al. *J. Appl. Crystallogr.* 24: 409 (1991) solution conditions that yielded oil droplets and birefringence aggregates were ascertained. Also, software and hardware of an automated pipetting system were modified to produce some 400 different crystallization conditions per day. Weber *J. Appl. Crystallogr.* 20: 366–373 (1987). This procedure led to a crystallization solution which produced r-hu-G-CSF crystals.

The size, reproducibility and quality of the crystals was improved by a seeding method in which the number of "nucleation initiating units" was estimated by serial dilution of a seeding solution. These methods yielded reproducible growth of 2.0 mm r-hu-G-CSF crystals. The space group of these crystals is $P2_12_12_1$ with cell dimensions of a=90 Å, b=110 Å and c=49 Å, and they diffract to a resolution of 2.0 Å.

1. Overall Methodology

To search for the crystallizing conditions of new protein, Carter et al. *J. Biol. Chem.* 254: 122219–12223 (1979) proposed the incomplete factorial method. They suggested that a sampling of a large number of randomly selected, but generally probable, crystallizing conditions may lead to a successful combination of reagents that produce protein crystallization. This idea was implemented by Jancarik et al. *J. Appl. Crystallogr.* 24: 409 (1991), who described 32 solutions for the initial crystallization trials which cover a range of pH, salts and precipitants. Here we describe an extension of their implementation to an expanded set of 70 solutions. To minimize the human effort and error of solution preparation, the method has been programmed for an automatic pipetting machine.

Following Weber's method of successive automated grid searching (SAGS), *J.Cryst. Growth* 90: 318–324 (1988), the robotic system was used to generate a series of solutions which continually refined the crystallization conditions of temperature, pH, salts and precipitant. Once a solution that could reproducibly grow crystals was determined, a seeding technique which greatly improved the quality of the crystals was developed. When these methods were combined, hundreds of diffraction quality crystals (crystals diffracting to at least about 2.5 Angstroms, preferably having at least portions diffracting to below 2 Angstroms, and more preferably, approximately 1 Angstrom) were produced in a few days.

Generally, the method for crystallization, which may be used with any protein one desires to crystallize, comprises the steps of:

(a) combining aqueous aliquots of the desired protein with either (i) aliquots of a salt solution, each aliquot having a different concentration of salt; or (ii) aliquots of a precipitant solution, each aliquot having a different concentration of precipitant, optionally wherein each combined aliquot is combined in the presence of a range of pH;

(b) observing said combined aliquots for precrystalline formations, and selecting said salt or precipitant combination and said pH which is efficacious in producing precrystalline forms, or, if no precrystalline forms are so produced, increasing the protein starting concentration of said aqueous aliquots of protein;

(c) after said salt or said precipitant concentration is selected, repeating step (a) with said previously unselected solution in the presence of said selected concentration; and (d) repeating step (b) and step (a) until a crystal of desired quality is obtained.

The above method may optionally be automated, which provides vast savings in time and labor. Preferred protein starting concentrations are between 10 mg/ml and 20 mg/ml, however this starting concentration will vary with the protein (the G-CSF below was analyzed using 33 mg/ml). A preferred range of salt solution to begin analysis with is (NaCl) of 0–2.5M. A preferred precipitant is polyethylene glycol 8000, however, other precipitants include organic solvents (such as ethanol,), polyethylene glycol molecules having a molecular weight in the range of 500–20,000, and other precipitants known to those skilled in the art. The preferred pH range is pH 4.5, 5.0, 5.5, 6.0, 6.5, 7.0, 7.5, 8.0, 8.5, and 9.0. Precrystallization forms include oils, birefringement precipitants, small crystals (<approximately 0.05 mm), medium crystals (approximately 0.5 to 0.5 mm) and large crystals (>approximately 0.5 mm). The preferred time for waiting to see a crystalline structure is 48 hours, although weekly observation is also preferred, and generally, after about one month, a different protein concentration is utilized (generally the protein concentration is increased). Automation is preferred, using the Accuflex system as modified. The preferred automation parameters are described below.

Generally, protein with a concentration between 10 mg/ml and 20 mg/ml was combined with a range of NaCl solutions from 0–2.5M, and each such combination was performed (separately) in the presence of the above range of concentrations. Once a precrystallization structure is observed, that salt concentration and pH range are optimized in a separate experiment, until the desired crystal quality is achieved. Next, the precipitant concentration, in the presence of varying levels of pH is also optimized. When both are optimized, the optimal conditions are performed at once to achieve the desired result (this is diagrammed in FIG. 6).

a. Implementation of an Automated Pipetting System

Drops and reservoir solutions were prepared by an Accuflex pipetting system (ICN Pharmaceuticals, Costa Mesa, Calif.) which is controlled by a personal computer that sends ASCII codes through a standard serial interface. The pipetter samples six different solutions by means of a rotating valve and pipettes these solutions onto a plate whose translation in a x-y coordinate system can be controlled. The vertical component of the system manipulates a syringe that is capable both of dispensing and retrieving liquid.

The software provided with the Accuflex was based on the SAGS method as proposed by Cox et al. *J. Appl. Crystallogr.* 20: 366–373 (1987). This method involves the systematic variation of two major crystallization parameters, pH and precipitant concentration, with provision to vary two others. While building on these concepts, the software used here provided greater flexibility in the design and implementation of the crystallization solutions used in the automated grid searching strategy. As a result of this flexibility the present software also created a larger number of different solutions. This is essential for the implementation of the incomplete factorial method as described in that section below.

To improve the speed and design of the automated grid searching strategy, the Accuflex pipetting system required software and hardware modifications. The hardware changes allowed the use of two different micro-titer trays, one used for handing drop and one used for sitting drop experiments, and a Plexiglas tray which held 24 additional buffer, salt and precipitant solutions. These additional solutions expanded the grid of crystallizing conditions that could be surveyed.

To utilize the hardware modifications, the pipetting software was written in two subroutines; one subroutine allows the crystallographer to design a matrix of crystallization solutions based on the concentrations of their components and the second subroutine to translate these concentrations into the computer code which pipettes the proper volumes of the solutions into the crystallization trays. The concentration matrices can be generated by either of two programs. The first program (MRF, available from Amgen Inc., Thousand Oaks, Calif.) refers to a list of stock solution concentrations supplied by the crystallographer and calculates the required volume to be pipette to achieve the designated concentration. The second method, which is preferred, incorporates a spread sheet program (Lotus™) which can be used to make more sophisticated gradients of precipitants or pH. The concentration matrix created by either program is interpreted by the control program (SUX, a modification of the program found in the Accuflex pipetter originally and available from Amgen Inc., Thousand Oaks, Calif.) and the wells are filled accordingly.

b. Implementation of the Incomplete Factorial Method

The convenience of the modified pipetting system for preparing diverse solutions improved the implementation of an expanded incomplete factorial method. The development of a new set of crystallization solutions having "random" components was generated using the program INFAC, Carter et al. *J.Cryst. Growth* 90: 60–73(1988) which produced a list containing 96 random combinations of one factor from three variables. Combinations of calcium and phosphate which immediately precipitated were eliminated, leaving 70 distinct combinations of precipitants, salts and buffers. These combinations were prepared using the automated pipetter and incubated for one week. The mixtures were inspected and solutions which formed precipitants were prepared again with lower concentrations of their components. This was repeated until all wells were clear of precipitant.

c. Crystallization of r-hu-G-CSF

Several different crystallization strategies were used to find a solution which produced x-ray quality crystals. These strategies included the use of the incomplete factorial method, refinement of the crystallization conditions using successive automated grid searches (SAGS), implementation of a seeding technique and development of a crystal production procedure which yielded hundreds of quality crystals overnight. Unless otherwise noted the screening and production of r-hu-G-CSF crystals utilized the hanging drop vapor diffusion method. Afinsen et al. "Physical Principles Of Protein Crystallization." In: Eisenberg (ed.), *Advances in Protein Chemistry* 41: 1–33 (1991).

The initial screening for crystallization conditions of r-hu-G-CSF used the Jancarik et al. *J.Appl.Crystallogr.* 24:

409 (1991) incomplete factorial method which resulted in several solutions that produced "precrystallization" results-These results included birefringent precipitants, oils and very small crystals (<0.05 mm). These precrystallizations solutions then served as the starting points for systematic screening.

The screening process required the development of crystallization matrices. These matrices corresponded to the concentration of the components in the crystallization solutions and were created using the IBM-PC based spread sheet Lotus™ and implemented with the modified Accuflex pipetting system. The strategy in designing the matrices was to vary one crystallization condition (such as salt concentration) while holding the other conditions such as pH, and precipitant concentration constant. At the start of screening, the concentration range of the varied condition was large but the concentration was successively refined until all wells in the micro-titer tray produced the same crystallization result. These results were scored as follows: crystals, birefringement precipitate, granular precipitate, oil droplets and amorphous mass. If the concentration of a crystallization parameter did not produce at least a precipitant, the concentration of that parameter was increased until a precipitant formed. After each tray was produced, it was left undisturbed for at least two days and then inspected for crystal growth. After this initial screening, the trays were then inspected on a weekly basis.

From this screening process, two independent solutions with the same pH and precipitant but differing in salts (MgCl, LiSO$_4$) were identified which produced small (0.1× 0.05×0.05 mm) crystals. Based on these results, a new series of concentration matrices were produced which varied MgCl with respect to LiSO$_4$ while keeping the other crystallization parameters constant. This series of experiments resulted in identification of a solution which produced diffraction quality crystals (>approximately 0.5 mm) in about three weeks. To find this crystallization growth solution (100 mM Mes pH 5.8, 380 mM MgCl$_2$, 220 mM LiSO$_4$ and 8% PEG 8 k) approximately 8,000 conditions had been screened which consumed about 300 mg of protein.

The size of the crystals depended on the number of crystals forming per drop. Typically 3 to 5 crystals would be formed with average size of (1.0×0.7×0.7mm). Two morphologies which had an identical space group (P2$_1$2$_1$2$_1$) and unit cell dimensions a=90.2, b=110.2, c=49.5 were obtained depending on whether or not seeding (see below) was implemented. Without seeding, the r-hu-G-CSF crystals had one long flat surface and rounded edges.

When seeding was employed, crystals with sharp faces were observed in the drop within 4 to 6 hours (0.05 by 0.05 by 0.05 mm). Within 24 hours, crystals had grown to (0.7 by 0.7 by 0.7 mm) and continued to grow beyond 2 mm depending on the number of crystals forming in the drop.

d. Seeding and Determination of Nucleation Initiation Sites

The presently provided method for seeding crystals establishes the number of nucleation initiation units in each individual well used (here, after the optimum conditions for growing crystals had been determined). The method here is advantageous in that the number of "seeds" affects the quality of the crystals, and this in turn affects the degree of resolution. The present seeding here also provides advantages in that with seeding, G-CSF crystal grows in a period of about three days, whereas without seeding, the growth takes approximately three weeks.

In one series of production growth (see methods), showers of small but well defined crystals were produced overnight (<0.01×0.01×0.01 mm). Crystallization conditions were followed as described above except that a pipette tip employed in previously had been reused. Presumably, the crystal showering effect was caused by small nucleation units which had formed in the used tip and which provided sites of nucleation for the crystals. Addition of a small amount (0.5 $\mu$l) of the drops containing the crystal showers to a new drop under standard production growth conditions resulted in a shower of crystals overnight. This method was used to produce several trays of drops containing crystal showers which we termed "seed stock".

The number of nucleation initiation units (NIU) contained within the "seed stock" drops was estimated to attempt to improve the reproducibility and quality of the r-hu-GCSF crystals. To determine the number of NIU in the "seed stock", an aliquot of the drop was serially diluted along a 96 well microtiter plate. The microtiter plate was prepared by adding 50 $\mu$l of a solution containing equal volumes of r-hu-G-CSF (33 mg/ml) and the crystal growth solution (described above) in each well. An aliquot (3 $\mu$l) of one of the "seed stock" drops was transferred to the first well of the microtiter plate. The solution in the well was mixed and 3 $\mu$l was then transferred to the next well along the row of the microtiter plate. Each row of the microtiter plate was similarly prepared and the tray was sealed with plastic tape. Overnight, small crystals formed in the bottom of the wells of the microtiter plate and the number of crystals in the wells were correlated to the dilution of the original "seed stock". To produce large single crystals, the "seed stock" drop was appropriately diluted into fresh CGS and then an aliquot of this solution containing the NIU was transferred to a drop Once crystallization conditions had been optimized, crystals were grown in a production method in which 3 ml each of CGS and r-hu-G-CSF (33 mg/ml) were mixed to create five trays (each having 24 wells). This method included the production of the refined crystallization solution in liter quantities, mixing this solution with protein and placing the protein/crystallization solution in either hanging drop or sitting drop trays. This process typically yielded 100 to 300 quality crystals (>0.5 mm) in about five days.

e. Experimental Methods Materials

Crystallographic information was obtained starting with r-hu-met-G-CSF with the amino acid sequence as provided in FIG. 1 (Seq. ID. No. 2) with a specific activity of 1.0+/−0.6×10$^8$U/mg (as measured by cell mitogenesis assay in a 10 mM acetate buffer at pH 4.0 (in Water for Injection) at a concentration of approximately 3 mg/ml solution was concentrated with an Amicon concentrator at 75 psi using a YM10 filter. The solution was typically concentrated 10 fold at 4° C. and stored for several months.

Initial Screening

Crystals suitable for X-ray analysis were obtained by vapor-diffusion equilibrium using hanging drops. For preliminary screening, 7 $\mu$l of the protein solution at 33 mg/ml (as prepared above) was mixed with an equal volume of the well solution, placed on siliconized glass plates and suspended over the well solution utilizing Linbro tissue culture plates (Flow Laboratories, McLean, Va.). All of the pipetting was performed with the Accuflex pipetter, however, trays were removed from the automated pipetter after the well solutions had been created and thoroughly mixed for at least ten minutes with a table top shaker. The Linbro trays were then returned to the pipetter which added the well and protein solutions to the siliconized cover slips. The cover slips were then inverted and sealed over 1 ml of the well solutions with silicon grease.

The components of the automated crystallization system are as follows. A PC-DOS computer system was used to design a matrix of crystallization solutions based on the concentration of their components. These matrices were produced with either MRF of the Lotus™ spread sheet (described above). The final product of these programs is a data file. This file contains the information required by the SUX program to pipette the appropriate volume of the stock solutions to obtain the concentrations described in the matrices. The SUX program information was passed through a serial I/O port and used to dictate to the Accuflex pipetting system the position of the valve relative to the stock solutions, the amount of solution to be retrieved, and then pipetted into the wells of the microtiter plates and the X-Y position of each well (the column/row of each well). Additional information was transmitted to the pipetter which included the Z position (height) of the syringe during filling as well as the position of a drain where the system pauses to purge the syringe between fillings of different solutions. The 24 well microtiter plate (either Linbro or Cryschem) and cover slip holder was placed on a plate which was moved in the X-Y plane. Movement of the plate allowed the pipetter to position the syringe to pipette into the wells. It also positioned the coverslips and vials and extract solutions from these sources. Prior the pipetting, the Linbro microtiter plates had a thin film of grease applied around the edges of the wells. After the crystallization solutions were prepared in the wells and before they were transferred to the cover slips, the microtiter plate was removed from the pipetting system, and solutions were allowed to mix on a table top shaker for ten minutes. After mixing, the well solution was either transferred to the cover slips (in the case of the hanging drop protocol) or transferred to the middle post in the well (in the case of the sitting drop protocol). Protein was extracted from a vial and added to the coverslip drop containing the well solution (or to the post). Plastic tape was applied to the top of the Cryschem plate to seal the wells.

Production Growth

Once conditions for crystallization had been optimized, crystal growth was performed utilizing a "production" method. The crystallization solution which contained 10 mM Mes pH 5.8, 380 mM MgCl2, 220 mM LiSO4, and 8% PEG 8K was made in one liter quantities. Utilizing an Eppindorf syringe pipetter, 1 ml aliquots of this solution were pipetted into each of the wells of the Linbro plate. A solution containing 50% of this solution and 50% G-CSF (33 mg/ml) was mixed and pipetted onto the siliconized cover slips. Typical volumes of these drops were between 50 and 100 μl and because of the large size of these drops, great care was taken in flipping the coverslips and suspending the drops over the wells.

Data Collection

The structure has been refined with X-PLOR (Bruniger, X-PLOR version 3.0, A system for crystallography and NMR, Yale University, New Haven, Conn.) against 2.2 Å data collected on an R-AXIS (Molecular Structure, Corp. Houston, Tex.) imaging plate detector.

f. Observations

As an effective recombinant human therapeutic, r-hu-G-CSF has been produced in large quantities and gram levels have been made available for structural analysis. The crystallization methods provided herein are likely to find other applications as other proteins of interest become available. This method can be applied to any crystallographic project which has large quantities of protein (approximately >200 mg). As one skilled in the art will recognize, the present materials and methods may be modified and equivalent materials and methods may be available for crystallization of other proteins.

B. Computer Program for Visualizing the Three Dimensional Structure of G-CSF

Although diagrams, such as those in the Figures herein, are useful for visualizing the three dimensional structure of G-CSF, a computer program which allows for stereoscopic viewing of the molecule is contemplated as preferred. This stereoscopic viewing, or "virtual reality" as those in the art sometimes refer to it, allows one to visualize the structure in its three dimensional form from every angle in a wide range of resolution, from macromolecular structure down to the atomic level. The computer programs contemplated herein also allow one to change perspective of the viewing angle of the molecule, for example by rotating the molecule. The contemplated programs also respond to changes so that one may, for example, delete, add, or substitute one or more images of atoms, including entire amino acid residues, or add chemical moieties to existing or substituted groups, and visualize the change in structure.

Other computer based systems may be used; the elements being: (a) a means for entering information such as orthogonal coordinates or other numerically assigned coordinates of the three dimensional structure of G-CSF; (b) a means for expressing such coordinates, such as visual means so that one may view the three dimensional structure and correlate such three dimensional structure with the composition of the G-CSF molecule, such as the amino acid composition; and (c) optionally, means for entering information which alters the composition of the G-CSF molecule expressed, so that the image of such three dimensional structure displays the altered composition.

The coordinates for the preferred computer program used are presented in FIG. 5. The preferred computer program is Insight II, version 4, available from Biosym in San Diego, Calif. For the raw crystall-ographic structure, the observed intensities of the diffraction data ("F-obs") and the orthogonal coordinates are also deposited in the Protein Data Bank, Chemistry Department, Brookhaven National Laboratory, Upton, N.Y. 19723, USA and these are herein incorporated by reference.

Once the coordinates are entered into the Insight II program, one can easily display the three dimensional G-CSF molecule representation on a computer screen. The preferred computer system for display is Silicon Graphics 320 VGX (San Diego, Calif.). For stereoscopic viewing, one may wear eyewear (Crystal Eyes, Silicon Graphics) which allows one to visualize the G-CSF molecule in three dimensions stereoscopically, so one may turn the molecule and envision molecular design.

Thus, the present invention provides a method of designing or preparing a G-CSF analog with the aid of a computer comprising:

(a) providing said computer with the means for displaying the three dimensional structure of a G-CSF molecule including displaying the composition of moieties of said G-CSF molecule, preferably displaying the three dimensional location of each amino acid, and more preferably displaying the three dimensional location of each atom of a G-CSF molecule;

(b) viewing said display;

(c) selecting a site on said display for alteration in the composition of said molecule or the location of a moiety; and (d) preparing a G-CSF analog with such alteration.

The alteration may be selected based on the desired structural characteristics of the end-product G-CSF analog, and considerations for such design are described in more detail below. Such considerations include the location and compositions of hydrophobic amino acid residues, particularly residues internal to the helical structures of a G-CSF molecule which residues, when altered, alter the overall structure of the internal core of the molecule and may prevent receptor binding; the location and compositions of external loop structures, alteration of which may not affect the overall structure of the G-CSF molecule.

Figure 2A:
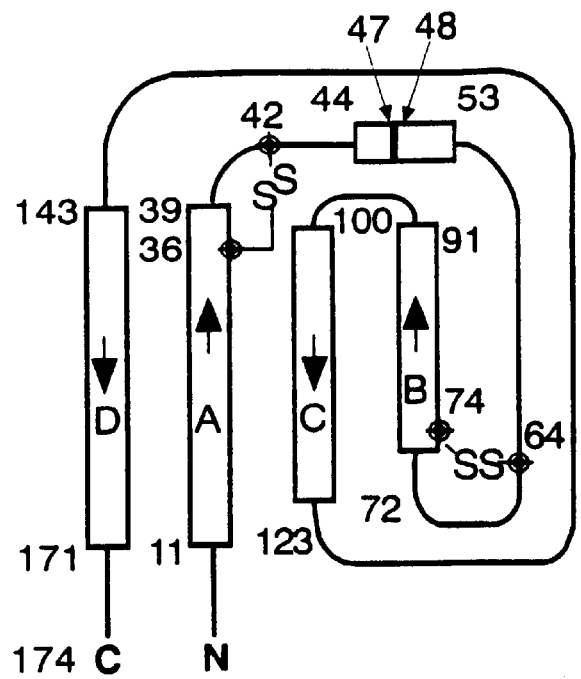
FIGS. 2A–2G are a topology diagrams of the crystalline structure of G-CSF, as well as hGH, pGH, GM-CSF, INF-β, IL-2, and IL-4. These illustrations are based on inspection of cited references. The length of secondary structural elements are drawn in proportion to the number of residues. A, B, C, and D helices are labeled according to the scheme used herein for G-CSF. For INF-β, the original labeling of helices is indicated in parentheses.
Figure 2B:
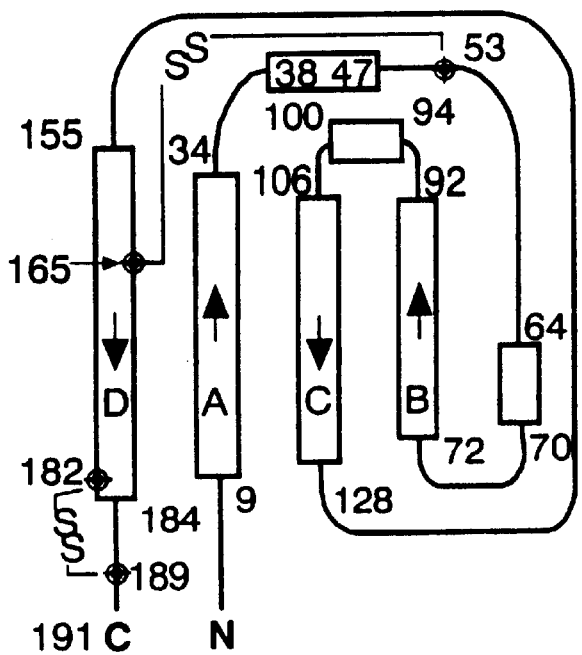
Figure 2C:
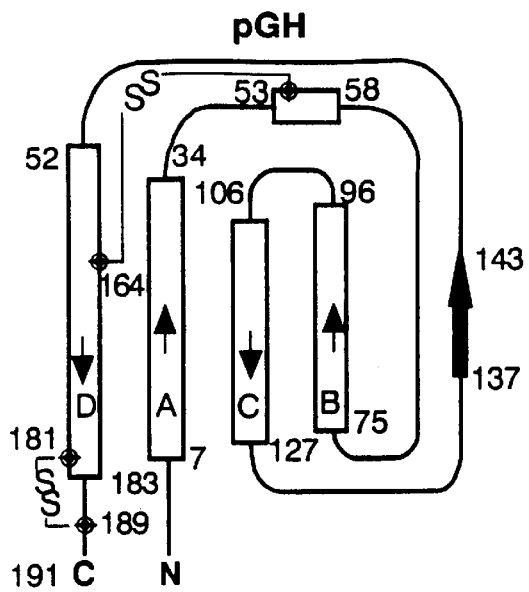
Figure 2D:
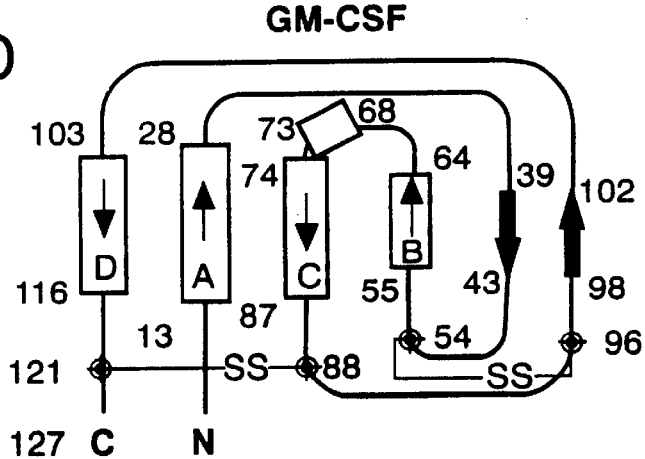
Figure 2E:
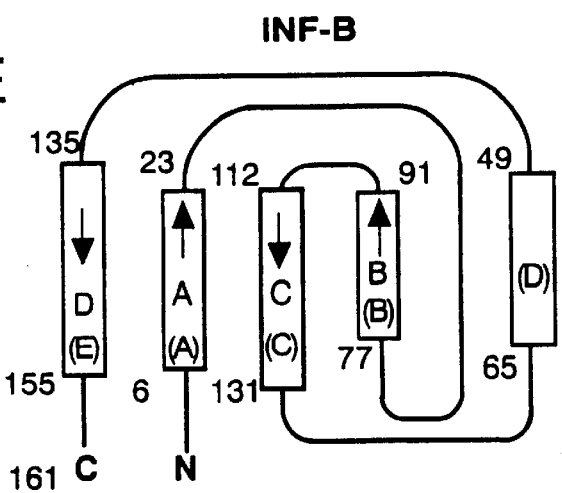
Figure 2F:
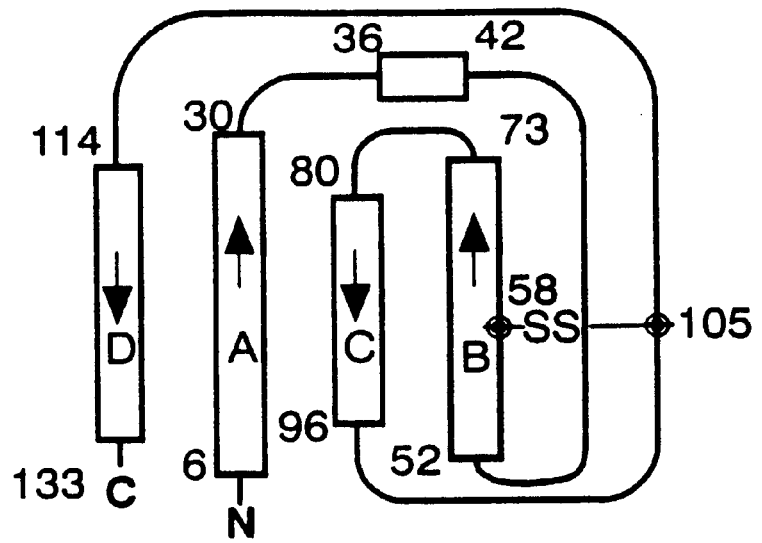
Figure 2G:
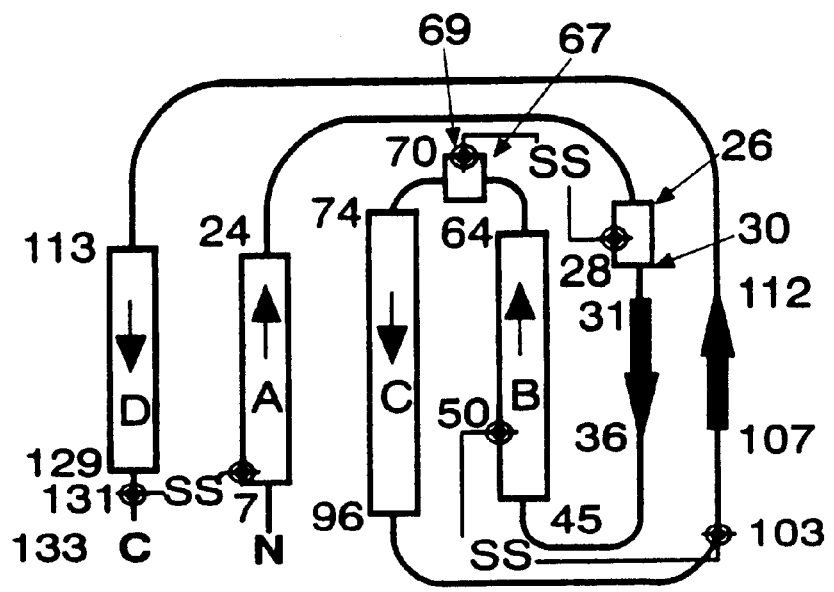
Figures 3A, 3B, 3C, 3D:
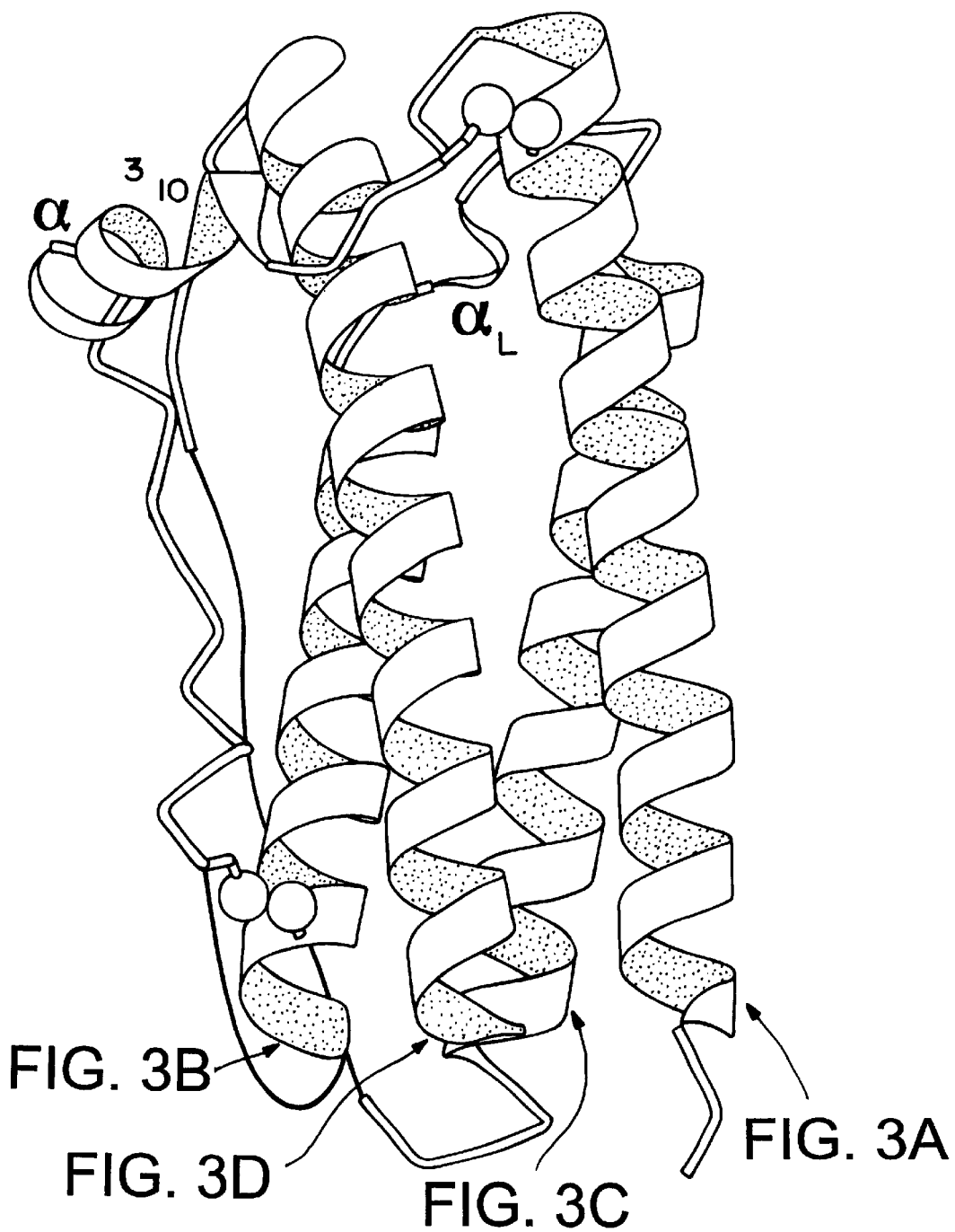
FIG. 3 is an "ribbon diagram" of the three dimensional structure of G-CSF. Helix A is amino acid residues 11–39 (numbered according to FIG. 1, above Seq. ID. No. 2), helix B is amino acid residues 72–91, helix C is amino acid residues 100–123, and helix D is amino acid residues 143–173. The relatively short $3^{10}$ helix is at amino acid residues 45–48, and the alpha helix is at amino acid residues 48–53. Residues 93–95 form almost one turn of a left handed helix.

FIGS. 2–4 illustrate the overall three dimensional conformation in different ways. The topological diagram, the ribbon diagram, and the barrel diagram all illustrate aspects of the conformation of G-CSF.

FIG. 2 illustrates a comparison between G-CSF and other molecules. There is a similarity of architecture, although these growth factors differ in the local conformations of their loops and bundle geometries. The up-up-down-down topology with two long crossover connections is conserved, however, among all six of these molecules, despite the dissimilarity in amino acid sequence.

FIG. 3 illustrates in more detail the secondary structure of recombinant human G-CSF. This ribbon diagram illustrates the handedness of the helices and their positions relative to each other.

FIG. 4 illustrates in a different way the conformation of recombinant human G-CSF. This "barrel" diagram illustrates the overall architecture of recombinant human G-CSF.

C. Preparation of Analogs Using M13 Mutagenesis

This example relates to the preparation of G-CSF analogs using site directed mutagenesis techniques involving the single stranded bacteriophage M13, according to methods published in PCT Application No. WO 85/00817 (Souza et al., published Feb. 28, 1985, herein incorporated by reference). This method essentially involves using a single-stranded nucleic acid template of the non-mutagenized sequence, and binding to it a smaller oligonucleotide containing the desired change in the sequence. Hybridization conditions allow for non-identical sequences to hybridize and the remaining sequence is filled in to be identical to the original template. What results is a double stranded molecule, with one of the two strands containing the desired change. This mutagenized single strand is separated, and used itself as a template for its complementary strand. This creates a double stranded molecule with the desired change.

The original G-CSF nucleic acid sequence used is presented in FIG. 1 (Seq. ID. No. 1), and the oligonucleotides containing the mutagenized nucleic acid(s) are presented in Table 2. Abbreviations used herein for amino acid residues and nucleotides are conventional, see Stryer, *Biochemistry*, 3d Ed., W. H. Freeman and Company, New York, N.Y. 1988, inside back cover.

The original G-CSF nucleic acid sequence was first placed into vector M13mp21. The DNA from single stranded phage M13mp21 containing the original G-CSF sequence was then isolated, and resuspended in water. For each reaction, 200 ng of this DNA was mixed with a 1.5 pmole of phosphorylated oligonucleotide (Table 2) and suspended in 0.1M Tris, 0.01M $MgCl_2$, 0.005M DTT, 0.1 mM ATP, pH 8.0. The DNAs were annealed by heating to 65° C. and slowly cooling to room temperature.

Once cooled, 0.5 mM of each ATP, dATP, dCTP, dGTP, TTP, one unit of T4 DNA ligase and one unit of Klenow fragment of *E. coli polymerase* 1 were added to the one unit of annealed DNA in 0.1M Tris, 0.025M NaCl, 0.01M $MgCl_2$, 0.01M DTT, pH 7.5.

The now double stranded, closed circular DNA was used to transfect *E. coli* without further purification. Plaques were screened by lifting the plaques with nitrocellulose filters, and then hybridizing the filters with single stranded DNA end-labeled with $p^{32}$ for one hour at 55–60°. After hybridization, the filters were washed at 0–3° C. below the melt temperature of the oligo (2° C. for A–T, 4° C. for G–C) which selectively left autoradiography signals corresponding to plaques with phage containing the mutated sequence. Positive clones were confirmed by sequencing.

Set forth below are the oligonucleotides used for each G-CSF analog prepared via the M13 mutagenesis method. The nomenclature indicates the residue and the position of the original amino acid (i.e., lysine at position 17), and the residue and position of the substituted amino acid (i.e., arginine 17). A substitution involving more than one residue is indicated via superscript notation, with commas between the noted positions or a semicolon indicating different residues. Deletions with no substitutions are so noted. The oligonucleotide sequences used for M13-based mutagenesis are next indicated; these oligonucleotides were manufactured synthetically, although the method of preparation is not critical, any nucleic acid synthesis method and/or equipment may be used. The length of the oligo is also indicated. As indicated above, these oligos were allowed to contact the single stranded phage vector, and then single nucleotides were added to complete the G-CSF analog nucleic acid sequence.

TABLE 2

| G-CSF ANALOGS | SEQUENCES(5'→3') | Length (nucleotide) | Seq.ID. Nos. |
|---|---|---|---|
| $Lys^{17}{\rightarrow}Arg^{17}$ | CTT TCT GCT GCG TTG TCT GGA ACA | 24 | Seq.ID. No.3 |
| $Lys^{24}{\rightarrow}Arg^{24}$ | ACA GGT TCG TCG TAT CCA GGG TG | 23 | Seq.ID. No.4 |
| $Lys^{35}{\rightarrow}Arg^{35}$ | CAC TGC AAG AAC GTC TGT GCG CT | 23 | Seq.ID. No.5 |
| $Lys^{41}{\rightarrow}Arg^{41}$ | CGC TAC TTA CCG TCT GTG CCA TC | 23 | Seq.ID. No.6 |
| $Lys^{17,24,35}{\rightarrow}$ | CTT TCT GCT GCG TTG TCT GGA ACA | 24 | Seq.ID. No.7 |

TABLE 2-continued

| G-CSF ANALOGS | SEQUENCES(5'→3') | Length (nucleotide) | Seq.ID. Nos. |
|---|---|---|---|
| Arg$^{17,24,35}$ | ACA GGT TCG TCG TAT CCA GGG TG | 23 | Seq.ID. No.8 |
|  | CAC TGC AAG AAC GTC TGT GCG CT | 23 | Seq.ID. No.9 |
| Lys$^{17,24,41}$→ | CTT TCT GCT GCG TTG TCT GGA ACA | 24 | Seq.ID. No.10 |
| Arg$^{17,24,41}$ | ACA GGT TCG TCG TAT CCA GGG TG | 23 | Seq.ID. No.11 |
|  | CGC TAC TTA CCG TCT GTC CCA TC | 23 | Seq.ID. No.12 |
| Lys$^{17,35,41}$→ | CTT TCT GCT GCG TTG TCT GGA ACA | 24 | Seq.ID. No.13 |
| Arg$^{17,35,41}$ | CAC TGC AAG AAC GTC TGT GCG CT | 23 | Seq.ID. No.14 |
|  | CGC TAC TTA CCG TCT GTG CCA TC | 23 | Seq.ID. No.15 |
| Lys$^{24,35,41}$→ | ACA GGT TCG TCG TAT CCA GGG TG | 23 | Seq.ID. No.16 |
| Arg$^{24,35,41}$ | CAC TGC AAG AAC GTC TGT GCG CT | 23 | Seq.ID. No.17 |
|  | CGC TAC TTA CCG TCT GTG CCA TC | 23 | Seq.ID. No.18 |
| Lys$^{17,24,35,41}$→ | CTT TCT GCT GCG TTG TCT GGA ACA | 24 | Seq.ID. No.19 |
| Arg$^{17,24,35,41}$ | ACA GGT TCG TCG TAT CCA GGG TG | 23 | Seq.ID. No.20 |
|  | CAC TGC AAG AAC GTC TGT GCG CT | 23 | Seq.ID. No.21 |
|  | CGC TAC TTA CCG TCT GTG CCA TC | 23 | Seq.ID. No.22 |
| Cys$^{18}$→Ala$^{18}$ | TCT GCT GAA AGC TCT GGA ACA GG | 23 | Seq.ID. No.23 |
| Gln$^{68}$→Glu$^{68}$ | CTT GTC CAT CTG AAG CTC TTC AG | 23 | Seq.ID. No.24 |
| Cys$^{37,43}$→ | GAA AAA CTG TCC GCT ACT TAC AAA | 37 | Seq.ID. No.25 |
| Ser$^{37,43}$ | CTG TCC CAT CCG G |  |  |
| Gln$^{26}$→Ala$^{26}$ | TTC GTA AAA TCG CGG GTG ACG G | 22 | Seq.ID. No.26 |
| Gln$^{174}$→Ala$^{174}$ | TCA TCT GGC TGC GCC GTA ATA G | 22 | Seq.ID. No.27 |
| Arg$^{170}$→Ala$^{170}$ | CCG TGT TCT GGC TCA TCT GGC T | 22 | Seq.ID. No.28 |
| Arg$^{167}$→Ala$^{167}$ | GAA GTA TCT TAC GCT GTT CTG CGT | 24 | Seq.ID. No.29 |
| Deletion 167 | GAA GTA TCT TAC TAA GTT CTG CGT C | 25 | Seq.ID. No.30 |
| Lys$^{41}$→Ala$^{41}$ | CGC TAC TTA CGC ACT GTG CCA T | 22 | Seq.ID. No.31 |
| His$^{44}$→Lys$^{44}$ | CAA ACT GTG CAA GCC GGA AGA G | 22 | Seq.ID. No.32 |
| Glu$^{47}$→Ala$^{47}$ | CAT CCG GAA GCA CTG GTA CTG C | 22 | Seq.ID. No.33 |
| Arg$^{23}$→Ala$^{23}$ | GGA ACA GGT TGC TAA AAT CCA GG | 23 | Seq.ID. No.34 |
| Lys$^{24}$→Ala$^{24}$ | GAA CAG GTT CGT GCG ATC CAG GGT G | 25 | Seq.ID. No.35 |
| Glu$^{20}$→Ala$^{20}$ | GAA ATG TCT GGC ACA GGT TCG T | 22 | Seq.ID. No.36 |
| Asp$^{28}$→Ala$^{28}$ | TCC AGG GTG CCG GTG CTG C | 19 | Seq.ID. No.37 |
| Met$^{127}$→Glu$^{127}$ | AAG AGC TCG GTG AGG CAC CAG CT | 23 | Seq.ID. No.38 |
| Met$^{138}$→Glu$^{138}$ | CTC AAG GTG CTG AGC CGG CAT TC | 23 | Seq.ID. No.39 |
| Met$^{127}$→Leu$^{127}$ | GAG CTC GGT CTG GCA CCA GC | 20 | Seq.ID. No.40 |
| Met$^{138}$→Leu$^{138}$ | TCA AGG TGC TCT GCC GGC ATT | 21 | Seq.ID. No.41 |
| Ser$^{13}$→Ala$^{13}$ | TCT GCC GCA AGC CTT TCT GCT GA | 23 | Seq.ID. No.42 |
| Lys$^{17}$→Ala$^{17}$ | CTT TCT GCT GGC ATG TCT GGA ACA | 24 | Seq.ID. No.43 |
| Gln$^{121}$→Ala$^{121}$ | CTA TTT GGC AAG CGA TGG AAG AGC | 24 | Seq.ID. No.44 |
| Glu$^{124}$→Ala$^{124}$ | CAG ATG GAA GCG CTC GGT ATG | 21 | Seq.ID. No.45 |
| Met$^{127,138}$→ | GAG CTC GGT CTG GCA CCA GC | 20 | Seq.ID. No.46 |
| Leu$^{127,138}$ | TCA AGG TGC TCT GCC GGC ATT | 21 | Seq.ID. No.47 |
| **Glu$^{20}$→Ala$^{20}$; | GAA ATG TCT GGC ACA GGT TCG T | 22 | Seq.ID. No.48 |
| Ser$^{13}$→Gly$^{13}$ |  |  |  |

**This analog came about during the preparation of G-CSF analog Glu$^{20}$→Ala$^{20}$; As several clones were being sequenced to identify the Glu$^{20}$→Ala$^{20}$ analog, the Glu$^{20}$→Ala$^{20}$; Ser$^{13}$Gly$^{13}$ analog was identified. This double mutant was the result of an <u>invitro</u> Klenow DNA polymerase reaction mistake.

D. Preparation of G-CSF Analogs Using DNA Amplification

This example relates to methods for producing G-CSF analogs using a DNA amplification technique. Essentially, DNA encoding each analog was amplified in two separate pieces, combined, and then the total sequence itself amplified. Depending upon where the desired change in the original G-CSF DNA was to be made, internal primers were used to incorporate the change, and generate the two separate amplified pieces. For example, for amplification of the 5' end of the desired analog DNA, a 5' flanking primer (complementary to a sequence of the plasmid upstream from the G-CSF original DNA) was used at one end of the region to be amplified, and an internal primer, capable of hybridizing to the original DNA but incorporating the desired change, was used for priming the other end. The resulting amplified region stretched from the 5' flanking primer through the internal primer. The same was done for the 3' terminus, using a 3' flanking primer (complementary to a sequence of the plasmid downstream from the G-CSF original DNA) and an internal primer complementary to the region of the intended mutation. Once the two "halves" (which may or may not be equal in size, depending on the location of the internal primer) were amplified, the two "halves" were allowed to connect. Once connected, the 5' flanking primer and the 3' flanking primer were used to amplify the entire sequence containing the desired change.

If more than one change is desired, the above process may be modified to incorporate the change into the internal primer, or the process may be repeated using a different internal primer. Alternatively, the gene amplification process may be used with other methods for creating changes in nucleic acid sequence, such as the phage based mutagenesis technique as described above. Examples of process for preparing analogs with more than one change are described below.

To create the G-CSF analogs described below, the template DNA used was the sequence as in FIG. 1 plus certain flanking regions (from a plasmid containing the G-CSF coding region). These flanking regions were used as the 5' and 3' flanking primers and are set forth below. The amplification reactions were performed in 40 µl volumes containing 10 mM Tris-HCl, 1.5 mM $MgCl_2$, 50 mM KCl, 0.1 mg/ml gelatin, pH 8.3 at 20° C. The 40 µl reactions also contained 0.1 mM of each DNTP, 10 pmoles of each primer, and 1 ng of template DNA. Each amplification was repeated for 15 cycles. Each cycle consisted of 0.5 minutes at 94° C., 0.5 minutes at 50° C., and 0.75 minutes at 72° C. Flanking primers were 20 nucleotides in length and internal primers were 20 to 25 nucleotides in length. This resulted in multiple copies of double stranded DNA encoding either the front portion or the back portion of the desired G-CSF analog.

For combining the two "halves", 1/40 of each of the two reactions was combined in a third DNA amplification reaction. The two portions were allowed to anneal at the internal primer location, as their ends bearing the mutation were complementary, and following a cycle of polymerization, give rise to a full length DNA sequence. Once so annealed, the whole analog was amplified using the 5' and 3' flanking primers. This amplification process was repeated for 15 cycles as described above.

The completed, amplified analog DNA sequence was cleaved with XbaI and XhoI restriction endonuclease to produce cohesive ends for insertion into a vector. The cleaved DNA was placed into a plasmid vector, and that vector was used to transform E. coli. Transformants were challenged with kanamycin at 50 ug/ml and incubated at 30° C. Production of G-CSF analog protein was confirmed by polyacrylamide gel electrophoresis of a whole cell lysate. The presence of the desired mutation was confirmed by DNA sequence analysis of plasmid purified from the production isolate. Cultures were then grown, and cells were harvested, and the G-CSF analogs were purified as set forth below.

Set forth below in Table 3 are the specific primers used for each analog made using gene amplification.

TABLE 3

| Analog | Internal Primer (5'→3') | SEQ.ID.NO. |
|---|---|---|
| $His^{44} \rightarrow Ala^{44}$ | 5' primer-TTCCGGAGCGCACAGTTTG | Seq.ID.No.49 |
| | 3' primer-CAAACTGTGGGCTCCGGAAGAGC | Seq.ID.No.50 |
| $Thr^{117} \rightarrow Ala^{117}$ | 5' primer-ATGCCAAATTGCAGTAGCAAAG | Seq.ID.No.51 |
| | 3' primer-CTTTGCTACTGCAATTTGGCAACA | Seq.ID.No.52 |
| $Asp^{110} \rightarrow Ala^{110}$ | 5' primer-ATCAGCTACTGCTAGCTGCAGA | Seq.ID.No.53 |
| | 3' primer-TCTGCAGCTAGCAGTAGCTGACT | Seq.ID.No.54 |
| $Gln^{21} \rightarrow Ala^{21}$ | 5' primer-TTACGAACCGCTTCCAGACATT | Seq.ID.No.55 |
| | 3' primer-AATGTCTGGAAGCGGTTCGTAAAAT | Seq.ID.No.56 |
| $Asp^{113} \rightarrow Ala^{113}$ | 5' primer-CTAGCAAATGCAGCTACATCTA | Seq.ID.No.57 |
| | 3' primer-TAGATGTAGCTGCATTTGCTACTAC | Seq.ID.No.58 |
| $His^{53} \rightarrow Ala^{53}$ | 5' primer-CCAAGAGAAGCACCCAGCAG | Seq.ID.No.59 |
| | 3' primer-CTGCTGGGTGCTTCTCTTGGGA | Seq.ID.No.60 |

For each analog, the following 5' flanking primer was used:
5'-CACTGGCGGTGATAATGAGC (Seq. ID. No.61)

For each analog, the following 3' flanking primer was used:
3'-GGTCATTACGGACCGGATC (Seq. ID. No.62)

1. Construction of Double Mutation

To make G-CSF analog $Gln^{12,21} \rightarrow Glu^{12,21}$, two separate DNA amplifications were conducted to create the two DNA mutations. The template DNA used was the sequence as in FIG. 1 (Seq. ID. No.1) plus certain flanking regions (from a plasmid containing the G-CSF coding region). The precise sequences are listed below. Each of the two DNA amplification reactions were carried out using a Perkin Elmer/Cetus DNA Thermal Cycler. The 40 µl reaction mix consisted of 1×PCR Buffer (Cetus), 0.2 mM each of the 4 dXTPs (Cetus), 50 pmoles of each primer oligonucleotide, 2 ng of G-CSF template DNA (on a plasmid vector), and 1 unit of Taq polymerase (Cetus). The amplification process was carried out for 30 cycles. Each cycle consisted of 1 minute at 94° C., 2 minutes at 50° C., and 3 minutes at 72° C.

DNA amplification "A" used the oligonucleotides:

5' CCACTGGCGGTGATACTGAGC 3' (Seq. ID. No.63) and

5' AGCAGAAAGCTTTCCGGCAGAGAAGAAG-CAGGA 3' (Seq. ID. No. 64)

DNA amplification "B" used the oligonucleotides:
5' GCCGCAAAGCTTTCTGCTGAAATGTCT-GAAGAGGTTCGTAAAATCCAGGGTGA 3' (Seq. ID. No.65) and
5' CTGGAATGCAGAAGCAAATGCCGGCAT-AGCACCTTCAGTCGGTTGCAGAGCTGGTGCCA 3' (Seq. ID. No.66)

From the 109 base pair double stranded DNA product obtained after DNA amplification "A", a 64 base pair XbaI to HindIII DNA fragment was cut and isolated that contained the DNA mutation $Gln^{12} \rightarrow Glu^{12}$. From the 509 base pair double stranded DNA product obtained after DNA amplification "B", a 197 base pair HindIII to BsmI DNA fragment was cut and isolated that contained the DNA mutation $Gln^{21} \rightarrow Glu^{21}$.

The "A" and "B" fragments were ligated together with a 4.8 kilo-base pair XbaI to BsmI DNA plasmid vector fragment. The ligation mix consisted of equal molar DNA restriction fragments, ligation buffer (25 mM Tris-HCl pH 7.8, 10 mM $MgCl_2$, 2 mM DTT, 0.5 mM rATP, and 100 µg/ml BSA) and T4 DNA ligase and was incubated overnight at 14° C. The ligated DNA was then transformed into *E. coli* FM5 cells by electroporation using a Bio Rad Gene Pulsar apparatus (BioRad, Richmond, Calif.). A clone was isolated and the plasmid construct verified to contain the two mutations by DNA sequencing. This "intermediate" vector also contained a deletion of a 193 base pair BsmI to BsmI DNA fragment. The final plasmid vector was constructed by ligation and transformation (as described above) of DNA fragments obtained by cutting and isolating a 2 kilo-base pair SstI to BamHI DNA fragment from the intermediate vector, a 2.8 kbp SstI to EcoRI DNA fragment from the plasmid vector, and a 360 bp BamHI to EcoRI DNA fragment from the plasmid vector. The final construct was verified by DNA sequencing the G-CSF gene. Cultures were grown, and the cells were harvested, and the G-CSF analogs were purified as set forth below.

As indicated above, any combination of mutagenesis techniques may be used to generate a G-CSF analog nucleic acid (and expression product) having one or more than one alteration. The two examples above, using M13-based mutagenesis and gene amplification-based mutagenesis, are illustrative.

E. Expression of G-CSF Analog DNA

The G-CSF analog DNAs were then placed into a plasmid vector and used to transform *E. coli* strain FM5 (ATCC#53911). The present G-CSF analog DNAs contained on plasmids and in bacterial host cells are available from the American Type Culture Collection, Rockville, Md., and the accession designations are indicated below.

One liter cultures were grown in broth containing 10 g tryptone, 5 g yeast extract and 5 g NaCl) at 30° C. until reaching a density at $A^{600}$ of 0.5, at which point they were rapidly heated to 42° C. The flasks were allowed to continue shaking at for three hours.

Other prokaryotic or eukaryotic host cells may also be used, such as other bacterial cells, strains or species, mammalian cells in culture (COS, CHO or other types) insect cells or multicellular organs or organisms, or plant cells or multicellular organs or organisms, and a skilled practitioner will recognize the appropriate host. The present G-CSF analogs and related compositions may also be prepared synthetically, as, for example, by solid phase peptide synthesis methods, or other chemical manufacturing techniques. Other cloning and expression systems will be apparent to those skilled in the art.

F. Purification of G-CSF Analog Protein

Cells were harvested by centrifugation (10,000×G, 20 minutes, 4° C.). The pellet (usually 5 grams) was resuspended in 30 ml of 1 mM DTT and passed three times through a French press cell at 10,000 psi. The broken cell suspension was centrifuged at 10,000 g for 30 minutes, the supernatant removed, and the pellet resuspended in 30–40 ml water. This was recentrifuged at 10,000×G for 30 minutes, and this pellet was dissolved in 25 ml of 2% Sarkosyl and 50 mM Tris at pH 8. Copper sulfate was added to a concentration of 40 µM, and the mixture was allowed to stir for at least 15 hours at 15–25° C. The mixture was then centrifuged at 20,000×G for 30 minutes. The resultant solubilized protein mixture was diluted four-fold with 13.3 mM Tris, pH 7.7, after which was added approximately 20 g Dowex™ (BioRad, Richmond, Calif.) equilibrated in 20 mM Tris, pH 7.7. The mixture was stirred 90 minutes at room temperature and then the Dowex™ was filtered out. The supernatant was then applied to a DEAE-cellulose (Whatman DE-52) column equilibrated in 20 mM Tris, pH 7.7. After loading and washing the column with the same buffer, the analogs were eluted with 20 mM Tris/NaCl (between 35 mM to 100 mM depending on the analog, as indicated below), pH 7.7. For most of the analogs, the eluent from the DEAE column was adjusted to a pH of 5.4, with 50% acetic acid and diluted as necessary (to obtain the proper conductivity) with 5 mM sodium acetate pH 5.4. The solution was then loaded onto a CM-sepharose column equilibrated in 20 mM sodium acetate, pH 5.4. The column was then washed with 20 mM NaAc, pH 5.4 until the absorbance at 280 nm was approximately zero. The G-CSF analog was then eluted with sodium acetate/NaCl in concentrations as described below in Table 4. The DEAE column eluents for those analogs not applied to the CM-sepharose column were dialyzed directly into 10 mM NaAc, ph 4.0 buffer. The purified G-CSF analogs were then suitably isolated for in vitro analysis. The salt concentrations used for eluting the analogs varied, as noted above. Below, the salt concentrations for the DEAE cellulose column and for the CM-sepharose column are listed:

TABLE 4

Salt Concentrations

| Analog | DEAE Cellulose | CM-Sepharose | SEQ.ID. NOS. |
|---|---|---|---|
| $Lys^{17} \rightarrow Arg^{17}$ | 35mM | 37.5mM | Seq.ID.No.67 |
| $Lys^{24} \rightarrow Arg^{24}$ | 35mM | 37.5mM | Seq.ID.No.68 |
| $Lys^{35} \rightarrow Arg^{35}$ | 35mM | 37.5mM | Seq.ID.No.69 |
| $Lys^{41} \rightarrow Arg^{41}$ | 35mM | 37.5mM | Seq.ID.No.70 |
| $Lys^{17,24,35} \rightarrow Arg^{17,24,35}$ | 35mM | 37.5mM | Seq.ID.No.71 |
| $Lys^{17,35,41} \rightarrow Arg^{17,35,41}$ | 35mM | 37.5mM | Seq.ID.No.72 |
| $Lys^{24,35,41} \rightarrow Arg^{24,35,41}$ | 35mM | 37.5mM | Seq.ID.No.73 |
| $Lys^{17,24,35,41} \rightarrow Arg^{17,24,35,41}$ | 35mM | 37.5mM | Seq.ID.No.74 |
| $Lys^{17,24,41} \rightarrow Arg^{17,24,41}$ | 35mM | 37.5mM | Seq.ID.No.75 |
| $Gln^{68} \rightarrow Glu^{68}$ | 60mM | 37.5mM | Seq.ID.No.76 |
| $Cys^{37,43} \rightarrow Ser^{37,43}$ | 40mM | 37.SmM | Seq.ID.No.77 |
| $Gln^{26} \rightarrow Ala^{26}$ | 40mM | 40mM | Seq.ID.No.78 |
| $Gln^{174} \rightarrow Ala^{174}$ | 40mM | 40mM | Seq.ID.No.79 |
| $Arg^{170} \rightarrow Ala^{170}$ | 40mM | 40mM | Seq.ID.No.80 |
| $Arg^{167} \rightarrow Ala^{167}$ | 40mM | 40mM | Seq.ID.No.81 |
| Deletion 167* | N/A | N/A | Seq.ID.No.82 |
| $Lys^{41} \rightarrow Ala^{41}$ | 160mM | 40mM | Seq.ID.No.83 |
| $His^{44} \rightarrow Lys^{44}$ | 40mM | 60mM | Seq.ID.No.84 |
| $Glu^{47} \rightarrow Ala^{47}$ | 40mM | 40mM | Seq.ID.No.85 |
| $Arg^{23} \rightarrow Ala^{23}$ | 40mM | 40mM | Seq.ID.No.86 |
| $Lys^{24} \rightarrow Ala^{24}$ | 120mM | 40mM | Seq.ID.No.87 |
| $Glu^{20} \rightarrow Ala^{20}$ | 40mM | 60mM | Seq.ID.No.88 |
| $Asp^{28} \rightarrow Ala^{28}$ | 40mM | 80mM | Seq.ID.No.89 |
| $Met^{127} \rightarrow Glu^{127}$ | 80mM | 40mM | Seq.ID.No.90 |
| $Met^{138} \rightarrow Glu^{138}$ | 80mM | 40mM | Seq.ID.No.91 |
| $Met^{127} \rightarrow Leu^{127}$ | 40mM | 40mM | Seq.ID.No.92 |
| $Met^{138} \rightarrow Leu^{138}$ | 40mM | 40mM | Seq.ID.No.93 |
| $Cys^{18} \rightarrow Ala^{18}$ | 40mM | 37.5mM | Seq.ID.No.94 |
| $Gln^{12,21} \rightarrow Gln^{12,21}$ | 60mM | 37.5mM | Seq.ID.No.95 |
| $Gln^{12,21,68} \rightarrow Glu^{12,21,68}$ | 60mM | 37.5mM | Seq.ID.No.96 |
| $Glu^{20} \rightarrow Ala^{20}; Ser^{13} \rightarrow Gly^{13}$ | 40mM | 80mM | Seq.TD.No.97 |
| $Met^{127,138} \rightarrow Leu^{127,138}$ | 40mM | 40mM | Seq.ID.No.98 |
| $Ser^{13} \rightarrow Ala^{13}$ | 40mM | 40mM | Seq.ID.No.99 |
| $Lys^{17} \rightarrow Ala^{17}$ | 80mM | 40mM | Seq.ID.No.100 |
| $Gln^{121} \rightarrow Ala^{121}$ | 40mM | 60mM | Seq.ID.No.101 |
| $Gln^{21} \rightarrow Ala^{21}$ | 50mM | Gradient 0-150mM | Seq.ID.No.102 |
| $His^{44} \rightarrow Ala^{44}**$ | 40mM | N/A | Seq.ID.No.103 |
| $His^{53} \rightarrow Ala^{53}**$ | 50mM | N/A | Seq.ID.No.104 |
| $Asp^{110} \rightarrow Ala^{110}**$ | 40mM | N/A | Seq.ID.No.105 |
| $Asp^{110} \rightarrow Ala^{110}**$ | 40mM | N/A | Seq.ID.No.106 |
| $Thr^{117} \rightarrow Ala^{117}**$ | 50mM | N/A | Seq.ID.No.107 |
| $Asp^{28} \rightarrow Ala^{28}; Asp^{110} \rightarrow Ala^{110}**$ | 50mM | N/A | Seq.ID.No.108 |
| $Glu^{124} \rightarrow Ala^{114}**$ | 40mM | 40mM | Seq.ID.No.109 |

*For Deletion 167, the data are unavailable.
**For these analogs, the DEAE cellulose column alone was use for purification.

The above purification methods are illustrative, and a skilled practitioner will recognize that other means are available for obtaining the present G-CSF analogs.

G. Biological Assays

Regardless of which methods were used to create the present G-CSF analogs, the analogs were subject to assays for biological activity. Tritiated thymidine assays were conducted to ascertain the degree of cell division. Other biological assays, however, may be used to ascertain the desired activity. Biological assays such as assaying for the ability to induce terminal differentiation in mouse WEHI-3B (D+) leukemic cell line, also provides indication of G-CSF activity. See Nicola, et al. *Blood* 54: 614–27 (1979). Other in vitro assays may be used to ascertain biological activity. See Nicola, *Ann.Rev. Biochem.* 58: 45–77 (1989). In general, the test for biological activity should provide analysis for the desired result, such as increase or decrease in biological activity (as compared to non-altered G-CSF), different biological activity (as compared to non-altered G-CSF), receptor affinity analysis, or serum half-life analysis. The list is incomplete, and those skilled in the art will recognize other assays useful for testing for the desired end result.

The $^3$H-thymidine assay was performed using standard methods. Bone marrow was obtained from sacrificed female Balb C mice. Bone marrow cells were briefly suspended, centrifuged, and resuspended in a growth medium. A 160 µl aliquot containing approximately 10,000 cells was placed into each well of a 96 well micro-titer plate. Samples of the purified G-CSF analog(as prepared above) were added to each well, and incubated for 68 hours. Tritiated thymidine was added to the wells and allowed to incubate for five additional hours. After the five hour incubation time, the cells were harvested, filtered, and thoroughly rinsed. The filters were added to a vial containing scintillation fluid. The beta emissions were counted (LKB Betaplate scintillation counter). Standards and analogs were analyzed in triplicate, and samples which fell substantially above or below the standard curve were re-assayed with the proper dilution. The results reported here are the average of the triplicate analog data relative to the unaltered recombinant human G-CSF standard results.

H. HPLC Analysis

High pressure liquid chromatography was performed on purified samples of analog. Although peak position on a reverse phase HPLC column is not a definitive indication of structural similarity between two proteins, analogs which have similar retention times may have the same type of hydrophobic interactions with the HPLC column as the non-altered molecule. This is one indication of an overall similar structure.

Samples of the analog and the non-altered recombinant human G-CSF were analyzed on a reverse phase (0.46×25 cm) Vydac 214TP54 column (Separations Group, Inc. Hesperia, Calif.). The purified analog G-CSF samples were prepared in 20 mM acetate and 40 mM NaCl solution buffered at pH 5.2 to a final concentration of 0.1 mg/ml to 5 mg/ml, depending on how the analog performed in the column. Varying amounts (depending on the concentration) were loaded onto the HPLC column, which had been equilibrated with an aqueous solution containing 1% isopropanol, 52.8% acetonitrile, and 38% trifluoro acetate (TFA). The samples were subjected to a gradient of 0.86%/minute acetonitrile, and 0.002% TFA.

I. Results

Presented below are the results of the above biological assays and HPLC analysis. Biological activity is the average of triplicate data and reported as a percentage of the control standard (non-altered G-CSF). Relative HPLC peak position is the position of the analog G-CSF relative to the control standard (non-altered G-CSF) peak. The "+" or "−" symbols indicate whether the analog HPLC peak was in advance of or followed the control standard peak (in minutes). Not all of the variants had been analyzed for relative HPLC peak, and only those so analyzed are included below. Also presented are the American Type Culture Collection designations for *E. coli* host cells containing the nucleic acids coding for the present analogs, as prepared above.

TABLE 5

| Variant | Analog | Relative HPLC Peak | ATCC No. | % Normal G-CSF Activity | SEQ. ID. NOS. |
|---|---|---|---|---|---|
| 1 | $Lys^{17}->Arg^{17}$ | N/A | 69184 | N/A | 67 |
| 2 | $Lys^{24}->Arg^{24}$ | N/A | 69185 | N/A | 68 |
| 3 | $Lys^{35}->Arg^{35}$ | N/A | 69186 | N/A | 69 |
| 4 | $Lys^{41}->Arg^{41}$ | N/A | 69187 | N/A | 70 |
| 5 | $Lys^{17,24,35}->Arg^{17,24,35}$ | N/A | 69189 | N/A | 71 |
| 6 | $Lys^{17,35,41}->Arg^{17,35,41}$ | N/A | 69192 | N/A | 72 |
| 7 | $Lys^{24,35,41}->Arg^{24,35,41}$ | N/A | 69191 | N/A | 73 |
| 8 | $Lys^{17,24,35,41}->Arg^{17,24,35,41}$ | N/A | 69193 | N/A | 74 |
| 9 | $Lys^{17,24,41}->Arg^{17,24,41}$ | N/A | 69190 | N/A | 75 |
| 10 | $Gln^{68}->Glu^{68}$ | N/A | 69196 | N/A | 76 |
| 11 | $Cys^{37,43}->Ser^{37,43}$ | N/A | 69197 | N/A | 77 |
| 12 | $Gln^{26}->Ala^{26}$ | +.96 | 69201 | 51% | 78 |
| 13 | $Gln^{174}->Ala^{174}$ | +.14 | 69202 | 100% | 79 |
| 14 | $Arg^{170}->Ala^{170}$ | +.78 | 69203 | 100% | 80 |
| 15 | $Arg^{167}->Ala^{167}$ | +.54 | 69204 | 110% | 81 |
| 16 | $Deletion^{167}$ | −.99 | 69207 | N/A | 82 |
| 17 | $Lys^{41}->Ala^{41}$ | +.25 | 69208 | 81% | 83 |
| 18 | $His^{44}->Lys^{44}$ | −1.53 | 69212 | 70% | 84 |
| 19 | $Glu^{47}->Ala^{47}$ | +.14 | 69205 | 0% | 85 |
| 20 | $Arg^{23}->Ala^{23}$ | −.03 | 69206 | 31% | 86 |
| 21 | $Lys^{24}->Ala^{24}$ | +1.95 | 69213 | 0% | 87 |
| 22 | $Glu^{20}->Ala^{20}$ | −0.07 | 69211 | 0% | 88 |
| 23 | $Asp^{28}->Ala^{28}$ | −.30 | 69210 | 147% | 89 |
| 24 | $Met^{127}->Glu^{127}$ | N/A | 69223 | N/A | 90 |
| 25 | $Met^{138}->Glu^{138}$ | N/A | 69222 | N/A | 91 |
| 26 | $Met^{127}->Leu^{127}$ | N/A | 69198 | N/A | 92 |
| 27 | $Met^{138}->Leu^{138}$ | N/A | 69199 | N/A | 93 |
| 28 | $Cys^{18}->Ala^{18}$ | N/A | 69188 | N/A | 94 |
| 29 | $Gln^{12,21}->Glu^{12,21}$ | N/A | 69194 | N/A | 95 |
| 30 | $Gln^{12,21,68}->Glu^{12,21,68}$ | N/A | 69195 | N/A | 96 |
| 31 | $Glu^{20}->Ala^{20}$; $Ser^{13}->Gly^{13}$ | +1.74 | 69209 | 0% | 97 |
| 32 | $Met^{127,138}->Leu^{127,138}$ | +1.43 | 69200 | 98% | 98 |
| 33 | $Ser^{13}->Ala^{13}$ | 0 | 69221 | 110% | 99 |
| 34 | $Lys^{17}->Ala^{17}$ | +.50 | 69226 | 70% | 100 |
| 35 | $Gln^{121}->Ala^{121}$ | +2.7 | 69225 | 100% | 101 |
| 36 | $Gln^{21}->Ala^{21}$ | +0.63 | 69217 | 9.6% | 102 |
| 37 | $His^{44}->Ala^{44}$ | +1.52 | 69215 | 10.8% | 103 |
| 38 | $His^{53}->Ala^{53}$ | +0.99 | 69219 | 8.3% | 104 |
| 39 | $Asp^{110}->Ala^{110}$ | +1.97 | 69216 | 29% | 105 |
| 40 | $Asp^{113}->Ala^{113}$ | −0.34 | 69218 | 0% | 106 |
| 41 | $Thr^{117}->Ala^{117}$ | +0.4 | 69214 | 9.7% | 107 |
| 42 | $Asp^{28}->Ala^{28}$; $Asp^{110}Ala^{110}$ | +3.2 | 69220 | 20.6% | 108 |
| 43 | $Glu^{124}->Ala^{124}$ | +0.16 | 69224 | 75% | 109 |
| 44 | $Phe^{114}->Val^{114}$, $Thr^{117}->Ala^{117}$** | +0.53 | | 0% | 110 |

**This analog was apparently a result of an inadvertent error in the oligo which was used to prepare number 41, above ($Thr^{117}->Ala^{117}$), and thus was prepared identically to the process used for that analog. "N/A" indicates data which are not available.

1. Identification of Structure-Function Relationships

The first step used to design the present analogs was to determine what moieties are necessary for structural integrity of the G-CSF molecule. This was done at the amino acid residue level, although the atomic level is also available for analysis. Modification of the residues necessary for structural integrity results in change in the overall structure of the G-CSF molecule. This may or may not be desirable, depending on the analog one wishes to produce. The working examples here were designed to maintain the overall structural integrity of the G-CSF molecule, for the purpose of maintain G-CSF receptor binding of the analog to the G-CSF receptor (as used in this section below, the "G-CSF receptor" refers to the natural G-CSF receptor, found on hematopoietic cells). It was assumed, and confirmed by the studies presented here, that G-CSF receptor binding is a necessary step for at least one biological activity, as determined by the above biological assays.

As can be seen from the figures, G-CSF (here, recombinant human met-G-CSF) is an antiparallel 4-alpha helical bundle with a left-handed twist, and with overall dimensions of 45 Å×30 Å×24 Å. The four helices within the bundle are referred to as helices A, B, C and D, and their connecting loops are known as the AB, BC and CD loops. The helix crossing angles range from −167.5° to −159.4°. Helices A, B, and C are straight, whereas helix D contains two kinds of structural characteristics, at $Gly^{150}$ and $Ser^{160}$ (of the recombinant human met-G-CSF). Overall, the G-CSF molecule is a bundle of four helices, connected in series by external loops. This structural information was then correlated with known functional information. It was known that residues (including methionine at position 1) 47, 23, 24, 20, 21, 44, 53, 113, 110, 28 and 114 may be modified, and the effect on biological activity would be substantial.

The majority of single mutations which lowered biological activity were centered around two regions of G-CSF that are separated by 30 Å, and are located on different faces of the four helix bundle. One region involves interactions between the A helix and the D helix. This is further confirmed by the presence of salt bridges in the non-altered molecule as follows:

| Atom | Helix | Atom | Helix | Distance |
|---|---|---|---|---|
| $Arg^{370}N1$ | D | $Tyr^{166}OH$ | A | 3.3 |
| $Tyr^{166}OH$ | D | $Arg^{23}N2$ | A | 3.3 |
| $Glu^{163}OE1$ | D | $Arg^{23}N1$ | A | 2.8 |
| $Arg^{23}N1$ | A | $Gln^{26}OE1$ | A | 3.1 |
| $Gln^{159}NE2$ | D | $Gln^{26}O$ | A | 3.3 |

Distances reported here were for molecule A, as indicated in FIG. 5 (wherein three G-CSF molecules crystallized together and were designated as A, B, and C). As can be seen, there is a web of salt bridges between helix A and helix D, which act to stabilize the helix A structure, and therefore affect the overall structure of the G-CSF molecule.

The area centering around residues $Glu^{20}$, $Arg^{23}$ and $Lys^{24}$ are found on the hydrophilic face of the A helix (residues 20–37). Substitution of the residues with the non-charged alanine residue at positions 20 and 23 resulted in similar HPLC retention times, indicating similarity in structure. Alteration of these sites altered the biological activity (as indicated by the present assays). Substitution at $Lys^{24}$ altered biological activity, but did not result in a similar HPLC retention time as the other two alterations.

The second site at which alteration lowered biological activity involves the AB helix. Changing glutamine at position 47 to alanine (analog no. 19, above) reduced biological activity (in the thymidine uptake assay) to zero. The AB helix is predominantly hydrophobic, except at the amino and carboxy termini; it contains one turn of a $3^{10}$ helix. There are two histadines at each termini ($His^{44}$ and $His^{56}$) and an additional glutamate at residue 46 which has the potential to form a salt bridge to $His^{44}$. The fourier transformed infra red spectrographic analysis (FTIR) of the analog suggests this analog is structurally similar to the non-altered recombinant G-CSF molecule. Further testing showed that this analog would not crystallize under the same conditions as the non-altered recombinant molecule.

Alterations at the carboxy terminus ($Gln^{174}$, $Arg^{167}$ and $Arg^{170}$) had little effect on biological activity. In contrast, deletion of the last eight residues (167–175) lowered biological activity. These results may indicate that the deletion destabilizes the overall structure which prevents the mutant from proper binding to the G-CSF receptor (and thus initiating signal transduction).

Generally, for the G-CSF internal core—the internal four helix bundle lacking the external loops —the hydrophobic internal residues are essential for structural integrity. For example, in helix A, the internal hydrophobic residues are (with methionine being position 1) $Phe^{14}$, $Cys^{18}$, $Val^{22}$, $Ile^{25}$, $Ile^{32}$ and $Leu^{36}$. Generally, for the G-CSF internal core—the internal four helix bundle lacking the external loops —the hydrophobic internal residues are essential for structural integrity. For example, in helix A, the internal hydrophobic residues are (with methionine being position 1 as in FIG. 1, Seq. ID. No.2) $Phe^{14}$, $CyS^{18}$, $Val^{22}$, $Ile^{25}$, $Ile^{32}$ and $Leu^{36}$. The other hydrophobic residues (again with the met at position 1) are: helix B $Ala^{72}$, $Leu^{76}$, $Leu^{79}$, $Leu^{83}$ $Tyr^{86}$, $Leu^{90}$ $Leu^{93}$; helix C, $Leu^{104}$, $Leu^{107}$, $Val^{111}$, $Ala^{114}$, $Ile^{118}$, $Met^{122}$; and helix D, $Val^{154}$, $Val^{158}$, $Phe^{161}$, $Val^{164}$, $Val^{168}$, $Leu^{172}$.

The above biological activity data, from the presently prepared G-CSF analogs, demonstrate that modification of the external loops interfere least with G-CSF overall structure. Preferred loops for analog preparation are the AB loop and the CD loop. The loops are relatively flexible structures as compared to the helices. The loops may contribute to the proteolysis of the molecule. G-CSF is relatively fast acting in vivo as the purpose the molecule serves is to generate a response to a biological challenge, i.e., selectively stimulate neutrophils. The G-CSF turnover rate is also relatively fast. The flexibility of the loops may provide a "handle" for proteases to attach to the molecule to inactivate the molecule. Modification of the loops to prevent protease degradation, yet have (via retention of the overall structure of non-modified G-CSF) no loss in biological activity may be accomplished.

This phenomenon is probably not limited to the G-CSF molecule but may also be common to the other molecules with known similar overall structures, as presented in FIG. 2. Alteration of the external loop of, for example hGH, Interferon β, IL-2, GM-CSF and IL-4 may provide the least change to the overall structure. The external loops on the GM-CSF molecule are not as flexible as those found on the G-CSF molecule, and this may indicate a longer serum life, consistent with the broader biological activity of GM-CSF. Thus, the external loops of GM-CSF may be modified by releasing the external loops from the beta-sheet structure, which may make the loops more flexible (similar to those G-CSF) and therefore make the molecule more susceptible to protease degradation (and thus increase the turnover rate).

Alteration of these external loops may be effected by stabilizing the loops by connection to one or more of the internal helices. Connecting means are known to those in the art, such as the formation of a beta sheet, salt bridge, disulfide bonding or hydrophobic interactions, and other means are available. Also, deletion of one or more moieties, such as one or more amino acid residues or portions thereof, to prepare an abbreviated molecule and thus eliminate certain portions of the external loops may be effected.

Thus, by alteration of the external loops, preferably the AB loop (amino acids 58–72 of r-hu-met G-CSF) or the CD loop (amino acids 119 to 145 of r-hu-met-G-CSF), and less preferably the amino terminus (amino acids 1–10), one may therefore modify the biological function without elimination of G-CSF G-CSF receptor binding. For example, one may: (1) increase half-life (or prepare an oral dosage form, for example) of the G-CSF molecule by, for example, decreasing the ability of proteases to act on the G-CSF molecule or adding chemical modifications to the G-CSF molecule, such as one or more polyethylene glycol molecules or enteric coatings for oral formulation which would act to change some characteristic of the G-CSF molecule as described above, such as increasing serum or other half-life or decreasing antigenicity; (2) prepare a hybrid molecule, such as combining G-CSF with part or all of another protein such as another cytokine or another protein which effects signal transduction via entry through the cell through a G-CSF G-CSF receptor transport mechanism; or (3) increase the biological activity as in, for example, the ability to selectively stimulate neutrophils (as compared to a non-modified G-CSF molecule). This list is not limited to the above exemplars.

Another aspect observed from the above data is that stabilizing surface interactions may affect biological activity. This is apparent from comparing analogs 23 and 40. Analog 23 contains a substitution of the charged asparagine residue at position 28 for the neutrally-charged alanine residue in that position, and such substitution resulted in a 50% increase in the biological activity (as measured by the disclosed thymidine uptake assays). The asparagine residue at position 28 has a surface interaction with the asparagine residue at position 113; both residues being negatively charged, there is a certain amount of instability (due to the repelling of like charged moieties). When, however the asparagine at position 113 is replaced with the neutrally-charged alanine, the biological activity drops to zero (in the present assay system). This indicates that the asparagine at position 113 is critical to biological activity, and elimination of the asparagine at position 28 serves to increase the effect that asparagine at position 113 possesses.

The domains required for G-CSF receptor binding were also determined based on the above analogs prepared and the G-CSF structure. The G-CSF receptor binding domain is located at residues (with methionine being position 1) 11–57 (between the A and AB helix) and 100–118 (between the B and C helices). One may also prepare abbreviated molecules capable of binding to a G-CSF receptor and initiate signal transduction for selectively stimulating neutrophils by changing the external loop structure and having the receptor binding domains remain intact.

Residues essential for biological activity and presumably G-CSF receptor binding or signal transduction have been identified. Two distinct sites are located on two different regions of the secondary structure. What is here called "Site A" is located on a helix which is constrained by salt bridge contacts between two other members of the helical bundle. The second site, "Site B" is located on a relatively more flexible helix, AB. The AB helix is potentially more sensitive to local pH changes because of the type and position of the residues at the carboxy and amino termini. The functional importance of this flexible helix may be important in a conformationally induced fit when binding to the G-CSF receptor. Additionally, the extended portion of the D helix is also indicated to be a G-CSF receptor binding domain, as ascertained by direct mutational and indirect comparative protein structure analysis. Deletion of the carboxy terminal end of r-hu-met-G-CSF reduces activity as it does for hGH, see, Cunningham et al. *Science* 244: 1081–1084 (1989). Cytokines which have similar structures, such as IL-6 and GM-CSF with predicted similar topology also center their biological activity along the carboxy end of the D helix, see Bazan *Immunology Today* 11: 350–354 (1990).

A comparison of the structures and the positions of G-CSF receptor binding determinants between G-CSF and hGH suggests both molecules have similar means of signal transduction. Two separate G-CSF receptor binding sites have been identified for hGH De Vos et al. *Science* 255: 306–32 (1991). One of these binding sites (called "Site I") is formed by residues on the exposed faces of hGH's helix 1, the connection region between helix 1 and 2, and helix 4. The second binding site (called "Site II") is formed by surface residues of helix 1 and helix 3.

The G-CSF receptor binding determinates identified for G-CSF are located in the same relative positions as those identified for hGH. The G-CSF receptor binding site located in the connecting region between helix A and B on the AB helix (Site A) is similar in position to that reported for a small piece of helix (residues 38–47) of hGH. A single point mutation in the AB helix of G-CSF significantly reduces biological activity (as ascertained in the present assays), indicating the role in a G-CSF receptor-ligand interface. Binding of the G-CSF receptor may destabilize the $3^{10}$ helical nature of this region and induce a conformation change improving the binding energy of the ligand/G-CSF receptor complex.

In the hGH receptor complex, the first helix of the bundle donates residues to both of the binding sites required to dimerize the hGH receptor. Mutational analysis of the corresponding helix of G-CSF (helix A) has identified three residues which are required for biological activity. Of these three residues, $Glu^{20}$ and $Arg^{24}$ lie on one face of the helical bundle towards helix C, whereas the side chain of $Arg^{23}$ (in two of the three molecules in the asymmetric unit) points to the face of the bundle towards helix D. The position of side chains of these biologically important residues indicates that similar to hGH, G-CSF may have a second G-CSF receptor binding site along the interface between helix A and helix C. In contrast with the hGH molecule, the amino terminus of G-CSF has a limited biological role as deletion of the first 11 residues has little effect on the biological activity.

As indicated above (see FIG. 2, for example), G-CSF has a topological similarity with other cytokines. A correlation of the structure with previous biochemical studies, mutational analysis and direct comparison of specific residues of the hGH receptor complex indicates that G-CSF has two receptor binding sites. Site A lies along the interface of the A and D helices and includes residues in the small AB helix. Site B also includes residues in the A helix but lies along the interface between helices A and C. The conservation of structure and relative positions of biologically important residues between G-CSF and hGH is one indication of a common method of signal transduction in that the receptor is bound in two places. It is therefore found that G-CSF analogs possessing altered G-CSF receptor binding domains may be prepared by alteration at either of the G-CSF receptor binding sites (residues 20–57 and 145–175).

Knowledge of the three dimensional structure and correlation of the composition of G-CSF protein makes possible a systematic, rational method for preparing G-CSF analogs. The above working examples have demonstrated that the limitations of the size and polarity of the side chains within the core of the structure dictate how much change the molecule can tolerate before the overall structure is changed.

What is claimed is:

1. A G-CSF hybrid molecule comprising a G-CSF moiety and a protein moiety, wherein:
  (a) said G-CSF moiety comprises:
    (i) a G-CSF internal core of helices A, B, C and D as set forth in FIG. 4, said internal core helices comprising corresponding amino acid residues as set forth in SEQ. ID. NO. 2;
    (ii) an external loop between helices A and B comprising corresponding amino acid residues as set forth in SEQ. ID. NO. 2;
    (iii) an external loop between helices B and C comprising corresponding amino acid residues as set forth in SEQ. ID. NO. 2;
    (iv) an external loop between helices D and A; and
    (v) an N-terminus and a C-terminus, said N-terminus being connected to helix D and said C-terminus being connected to helix C, said N-terminus and said C-terminus each comprising a portion of amino acids 120–146 of SEQ. ID. NO. 2;
  (b) said protein moiety is connected to an amino acid of subpart (v).

2. The G-CSF hybrid of claim 1, wherein said protein moiety is a cytokine or hematopoietic factor.

3. The G-CSF hybrid of claim 2, wherein said cytokine is an interleukin.

4. The G-CSF hybrid of claim 1, wherein said protein moiety of subpart (b) is connected via a linker to an amino acid of subpart (v).

5. The G-CSF hybrid of claims 1, 2, 3, or 4, wherein said hybrid molecule has an N-terminal methionyl residue.

6. The G-CSF hybrid of claims 1, 2, 3, or 4, wherein the cysteine residue at position 18 of SEQ. ID. NO. 2 of subpart (i) is altered to a scrine or alanine residue.

7. A composition comprising a G-CSF hybrid molecule according to claim 6, and a pharmaceutically acceptable carrier.

8. A G-CSF hybrid molecule comprising a G-CSF moiety and a protein moiety, wherein:
  (a) said G-CSF moiety Comprises:
    (i) a G-CSF internal core of helices A, B, C and D as set forth in FIG. 4, said internal core helices comprising corresponding amino acid residues as set forth in SEQ. ID. NO. 2;
    (ii) an external loop between helices C and D comprising corresponding amino acid residues as set forth in SEQ. ID. NO. 2;
    (iii) an external loop between helices B and C comprising corresponding amino acid residues as set forth in SEO. ID. NO. 2;
    (iv) an external loop between helices D and A; and (v) an N-terminus and a C-terminus said N-terminus being connected to helix B and said C-terminus being connected to helix A, said N-terminus and said C-terminus each comprising a portion of amino acids 39–73 of SEQ. ID. NO. 2;

b) said protein moiety is connected to an amino acid of subpart (v).

9. The G-CSF hybrid of claim 8, wherein said protein moiety is a cytokine or hematopoietic factor.

10. The G-CSF hybrid of claim 9, wherein said cytokine is an interleukin.

11. The G-CSF hybrid of claim 8, wherein said protein moiety of subpart (b) is connected via a linker to an amino acid of subpart (v).

12. The G-CSF hybrid of claims 8, 9, 10, or 11, wherein said hybrid molecule has an N-terminal methionyl residue.

13. The G-CSF hybrid of claims 8, 9, 10, or 11, wherein the cysteine residue at position 18 of SEQ. ID. NO. 2 of subpart (i) is altered to a serine or alanine residue.

14. A composition comprising a G-CSF hybrid molecule according to claim 13, and a pharmaceutically acceptable carrier.

15. A G-CSF hybrid molecule comprising a G-CSF moiety and a protein moiety, wherein:
(a) said G-CSF moiety comprises:
   (i) a G-CSF internal core of helices A, B, C and D as set forth in FIG. 4, said internal core helices comprising corresponding amino acid residues as set forth in SEQ. ID. NO. 2;
   (ii) an external loop between helices A and B comprising corresponding amino acid residues as set forth in SEQ. ID. NO. 2;
   (iii) an external loop between helices C and D comprising corresponding amino acid residues as set forth in SEQ. ID. NO. 2;
   (iv) an external loop between helices D and A; and
   (v) an N-terminus and a C-terminus, said N-terminus being connected to helix C and said C-terminus being connected to helix B, said N-terminus and said C-terminus each comprising a portion of amino acids 92–101 of SEQ. ID. NO. 2;
(b) said protein moiety is connected to an amino acid of subpart (v).

16. The G-CSF hybrid of claim 15, wherein said protein moiety is a cytokine or hematopoietic factor.

17. The G-CSF hybrid of claim 16, wherein said cytokine is an interleukin.

18. The G-CSF hybrid of claim 15, wherein said protein moiety of subpart (b) is connected via a linker to an amino acid of subpart (v).

19. The G-CSF hybrid of claims 15, 16, 17 or 18, wherein said hybrid molecule has an N-terminal methionyl residue.

20. The G-CSF hybrid of claims 15, 16, 17 or 18, wherein the cysteine residue at position 18 of SEQ. ID. NO. 2 of subpart (i) is altered to a serine or alanine residue.

21. A composition comprising a G-CSF hybrid molecule according to claim 20, and a pharmaceutically acceptable carrier.

22. A G-CSF hybrid molecule, with an N-terminal methionyl residue, comprising a G-CSF moiety and a protein moiety, wherein:
(a) said G-CSF moiety comprises:
   (i) a G-CSF internal core of helices A, B, C and D as set forth in FIG. 4, said internal core helices comprising corresponding amino acid residues as set forth in SEQ. ID. NO. 2, with the cysteine residue at position 18 altered to serine or alanine residue;
   (ii) an external loop between helices A and B comprising corresponding amino acid residues as set forth in SEQ. ID. NO. 2;
   (iii) an external loop between helices B and C comprising corresponding amino acid residues as set forth in SEQ. ID. NO. 2;
   (iv) an external loop between helices D and A; and
   (v) an N-terminus and a C-terminus, said N-terminus being connected to helix D and said C-terminus being connected to helix C, said N-terminus and said C-terminus each comprising a portion of amino acids 120–146 of SEQ. ID. NO. 2;
(b) said protein moiety is connected via a linker to an amino acid of subpart (v).

23. The G-CSF hybrid of claim 22, wherein said protein moiety is a cytokine or hematopoietic factor.

24. The G-CSF hybrid of claim 23, wherein said cytokine is an interleukin.

25. A composition comprising a G-CSF hybrid molecule according to claim 18, 15, or 22 and a pharmaceutically acceptable carrier.

\* \* \* \* \*

UNITED STATES PATENT AND TRADEMARK OFFICE
CERTIFICATE OF CORRECTION

PATENT NO. : 6,261,550 B1
DATED : July 17, 2001
INVENTOR(S) : Timothy David Osslund It is certified that error appears in the above-identified patent and that said Letters Patent is hereby corrected as shown below:→

Title page,
Item [57], ABSTRACT, replace "The present invention relates to granulocyte colony-stimulating factor ("G-CSF") analogs and compositions containing such analogs which retain the three-dimensional structure of the internal core of the four alpha helical bundle of G-CSF. In another aspect, such G-CSF analogs can also be attached with biologically active proteins to form hybrid molecules and still retain G-CSF structural integrity. Also provided are methods for determining and preparing analog or hybrid molecules and modifications." with -- The present invention relates to granulocyte colony-stimulating factor ("G-CSF") hybrid molecules which retain the internal core helices of G-CSF. Also provided are pharmaceutical compositions containing hybrid molecules. --

Column 12,
Line 4, change "(A-VV)" to -- (1-41) --.

Column 19,
Lines 46-47, change "10mM" to -- 100mM --.

Columns 23-24,
Footnote, line 3, change "$Ser^{13}Gly^{13}$" to -- $Ser^{13} \rightarrow Gly^{13}$ --.

Column 25,
Line 66, change "DNTP" to -- dNTP --.

Column 26,
Table 3, Line 9, change "5' primer - CTA..." to -- 5' primer - GTA... --.

UNITED STATES PATENT AND TRADEMARK OFFICE
CERTIFICATE OF CORRECTION

PATENT NO.    : 6,261,550 B1
DATED         : July 17, 2001
INVENTOR(S)   : Timothy David Osslund It is certified that error appears in the above-identified patent and that said Letters Patent is hereby corrected as shown below:

Column 29,
Line 29, Table 4, change "$Gln^{12,21} \rightarrow Gln^{12,21}$" to -- $Gln^{12,21} \rightarrow Glu^{12,21}$ --.
Line 41, Table 4, change "$Asp^{110} \rightarrow Ala^{110}$" to -- $Asp^{113} \rightarrow Ala^{113}$ --.
Line 44, Table 4, change "$Glu^{124} \rightarrow Ala^{114}$" to -- $Glu^{124} \rightarrow Ala^{124}$ --.

Column 33,
Line 8, change "$Arg^{370}N1$" to -- $Arg^{170}N1$ --.

Column 114
Line 50, change "scrine" to -- serine --.

Column 115,
Line 19, change "scrine" to -- serine --.

Column 116,
Line 42, change "18" to -- 1, 8, --.

Signed and Sealed this

Twenty-first Day of May, 2002

Attest:

Attesting Officer

JAMES E. ROGAN
Director of the United States Patent and Trademark Office